US011634735B2

(12) United States Patent
McBride et al.

(10) Patent No.: US 11,634,735 B2
(45) Date of Patent: *Apr. 25, 2023

(54) PRODUCTION OF PROPANOLS, ALCOHOLS, AND POLYOLS IN CONSOLIDATED BIOPROCESSING ORGANISMS

(71) Applicant: Lallemand Hungary Liquidity Management LLC, Budapest (HU)

(72) Inventors: John E. McBride, Lyme, NH (US); Vineet Rajgarhia, Dublin, CA (US); Arthur J. Shaw, IV, Grantham, NH (US); Shital A. Tripathi, Berkeley, CA (US); Elena Brevnova, Lebanon, NH (US); Nicky Caiazza, Lebanon, NH (US); Johannes Pieter Van Dijken, Schiedam (NL); Allan C. Froehlich, Lebanon, NH (US); William Ryan Sillers, Lebanon, NH (US); James H. Flatt, Del Mar, CA (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 16/918,415

(22) Filed: Jul. 1, 2020

(65) Prior Publication Data

US 2020/0325500 A1    Oct. 15, 2020

Related U.S. Application Data

(63) Continuation of application No. 15/927,126, filed on Mar. 21, 2018, now abandoned, which is a continuation of application No. 13/391,554, filed as application No. PCT/US2010/046172 on Aug. 20, 2010, now Pat. No. 9,957,530.

(60) Provisional application No. 61/298,790, filed on Jan. 27, 2010, provisional application No. 61/235,959, filed on Aug. 21, 2009.

(51) Int. Cl.
*C12P 7/18* (2006.01)
*C12P 7/04* (2006.01)
*C12P 7/36* (2006.01)

(52) U.S. Cl.
CPC .................. *C12P 7/18* (2013.01); *C12P 7/04* (2013.01); *C12P 7/36* (2013.01); *C12P 2203/00* (2013.01)

(58) Field of Classification Search
CPC ...... C12P 7/18; C12P 7/04; C12P 7/36; C12P 2203/00
See application file for complete search history.

(56) References Cited

U.S. PATENT DOCUMENTS

| 6,303,352 B1 | 10/2001 | Cameron et al. |
| 7,267,972 B2 | 9/2007 | Sarcabal et al. |
| 9,957,530 B2 | 5/2018 | McBride et al. |
| 2007/0072279 A1 | 3/2007 | Meynial-Salles et al. |
| 2008/0293125 A1 | 11/2008 | Subbian et al. |
| 2010/0159546 A1 | 6/2010 | Aristidou et al. |
| 2011/0059485 A1 | 3/2011 | Caiazza et al. |
| 2011/0281362 A1 | 11/2011 | Olson |
| 2012/0322078 A1 | 12/2012 | Mcbride et al. |
| 2013/0052646 A1 | 2/2013 | Tripathi et al. |
| 2018/0208951 A1 | 7/2018 | McBride et al. |

FOREIGN PATENT DOCUMENTS

| AU | 2010284110 B2 | 10/2015 |
| CN | 1500148 A | 5/2004 |
| CN | 1910278 A | 2/2007 |
| EP | 2467490 A1 | 6/2012 |
| NZ | 598374 A | 10/2014 |
| WO | 02/081440 A2 | 10/2002 |
| WO | 2008/098198 A2 | 8/2008 |
| WO | 2008/116848 A1 | 10/2008 |
| WO | 2008/121701 A1 | 10/2008 |
| WO | 2008/131286 A1 | 10/2008 |
| WO | 2009/035595 A1 | 3/2009 |
| WO | 2009/046375 A2 | 4/2009 |
| WO | 2009/103026 A1 | 8/2009 |

(Continued)

OTHER PUBLICATIONS

[No Author Listed] Office of Science and Office of Energy Efficiency and Renewable Energy, "Breaking the Biological Barriers to Cellulosic Ethanol: A Joint Research Agenda" U.S. Department of Energy, 216, United States (Jun. 2006).

(Continued)

*Primary Examiner* — Iqbal H Chowdhury
(74) *Attorney, Agent, or Firm* — Sterne, Kessler, Goldstein & Fox P.L.L.C.

(57) ABSTRACT

The present invention provides for novel metabolic pathways leading to propanol, alcohol or polyol formation in a consolidated bioprocessing system (CBP), where lignocellulosic biomass is efficiently converted to such products. More specifically, the invention provides for a recombinant microorganism, where the microorganism expresses one or more native and/or heterologous enzymes; where the one or more enzymes function in one or more engineered metabolic pathways to achieve: (1) conversion of a carbohydrate source to 1,2-propanediol, isopropanol, ethanol and/or glycerol; (2) conversion of a carbohydrate source to n-propanol and isopropanol; (3) conversion of a carbohydrate source to isopropanol and methanol; or (4) conversion of a carbohydrate source to propanediol and acetone; wherein the one or more native and/or heterologous enzymes is activated, upregulated or downregulated.

20 Claims, 7 Drawing Sheets

Specification includes a Sequence Listing.

(56) References Cited

FOREIGN PATENT DOCUMENTS

| WO | 2010/056450 A2 | 5/2010 |
|---|---|---|
| WO | 2011/019717 A1 | 2/2011 |
| WO | 2011022651 A1 | 2/2011 |

OTHER PUBLICATIONS

Altaras, N. E., et al., "Metabolic Engineering of a 1,2-propanediol pathway in *Escherichia coli*," Appl. Environ. Microbiol. 65(3):1180-1185, American Society for Microbiology, United States (Mar. 1999).

Altaras, N. E., and Cameron, D. C., "Enhanced Production of (R)-1,2-Propanediol by Metabolically Engineered *Escherichia coli*," Biotechnol. Prog. 16:940-946, American Chemical Society and American Institute of Chemical Engineers, United States (2000).

Altaras, N. E., et al., "Conversion of Sugars to 1,2-Propanediol by Thermoanaerobacterium thermosaccharolyticum HG-8," Biotechnol. Prog. 17:52-56, American Chemical Society and American Institute of Chemical Engineers, United States (2001).

Atsumi, et al., Metabolic engineering for advanced biofuels production from *Escherichia coli* Curr Opin Biotechnol. Oct. 2008;19(5):414-9. doi: 10.1016/j.copbio.2008.08.008. Epub Sep. 12, 2008.

Australian Office Action for Application No. 2015238904, dated Apr. 13, 2017 (9 pages).

Bakker, B.M., et al., "The Mitochondrial Alcohol Dehydrogenase Adh3p Is involved in Redox shuttle in *Saccharomyces cerevisiae*," J. Bacterial. 182(17):4730-4737, American Society for Microbiology, United States (Jun. 2000).

Bermejo, L.L., et al., "Expression of Clostridium acetobutylicum ATCC 824 genes in *Escherichia coli* for Acetone Production and Acetate Detoxification," Appl. Environ. Microbial. 64(3): 1079-1085, American Society for Microbiology, United States (Mar. 1998).

Bobik, T.A., et al., "The Propanediol Utilization (pdu) Operon Of *Salmonella enterica* Serovar Typhimurium LT2 Includes Genes Necessary for Formation of Polyhedral Organelles Involved in Coenzyme B12-Dependent 1,2-Propanediol Degradation," J. Bacterial. 181 (19):5967-5975, American Society for Microbiology, United States (Oct. 1999).

Cameron, D. C., and Cooney, C. L., "A Novel Fermentation: The Production of R(-)-1,2-Propanediol and Acetol by Clostridium thermosaccharolyticum," Bio/Technology 4(7):651-654, Nature Publishing Company, United States (Jul. 1986).

Cameron, D. C., et al., "Metabolic Engineering of Propanediol Pathways," Biotechnol. Prog. 14:116-125, American Chemical Society and American Institute of Chemical Engineers, United States (1998).

Chinese Office Action for Application No. CN 201080045752.X dated Feb. 27, 2015 (6 pages).

Chu, J., "Reinventing Cellulosic Ethanol Production," Technology Review, 2 pages, MIT, United States, accessed at <http://www.technologyreview.com/energy/22774/> (Jun. 2009).

Enebo, L., "Fermentation of Glucose by Clostridium thermobutyricum and Bacillus thermolacticus," Studies in Cellulose Decomposition by an Anaerobic Thermophilic Bacterium and two Associated Non-Cellulolytic Species, pp. 94-96, Victor Pettersons Bokindustri Aktiebolag, Stockholm, Sweden (1954).

Fasan, R., et al., Engineered alkane-hydroxylating cytochrome P450(BM3) exhibiting nativelike catalytic properties. Angew Chem Int Ed Engl. 2007;46(44):8414-8.

Hanai, T., et al., "Engineered Synthetic Pathway for Isopropanol Production in *Escherichia coli*," Applied and Environmental Microbiology 73(24):7814-7818, American Society for Microbiology, United States (Dec. 2007).

Hartmanis M. G. N., and Stadtman, T. C., "Diol Metabolism and Diol Dehydratase in Clostridium glycolicum," Arch. Biochem. Biophys. 245(1): 144 152, Academic Press, Inc., United States (Feb. 1986).

Hoffman, M.L., "Metabolic Engineering of 1,2 Propanediol Production in *Saccharomyces cerevisiae*," Ph.D. dissertation, 231 pages, University of Wisconsin—Madison, United States (Jun. 1999).

International Search Report and Written Opinion for Application No. PCT/US2010/046172 dated Feb. 2, 2011.

Jain et al. Microbial Cell Factories (2011 ), 10, 97-106.

Jones, D. T., and Woods, D. R., "Acetone-Butanol Fermentation Revisited," Microbiological Reviews 50(4):484-524, American Society for Microbiology, United States (Dec. 1986).

Ko, J., et al., "Conversion of Methylglyoxal to Acetol by *Escherichia coli* Aldo-Keto Reductases," J. Bacteriol 187(16):5782-5789 (Aug. 2005).

Lamed, R. J., and Zeikus, J. G., "Novel NADP-linked alcohol-aldehyde/ketone oxidoreductase in thermophilic ethanologenic bacteria," Biochemical J. 195:183-190, The Biochemical Society, England (Apr. 1981).

Lee, W., and Dasilva, N. A., "Application of sequential integration for metabolic engineering of 1,2-propanediol production in yeast," Metabolic Engineering 8(1):58-65, Elsevier Inc., Belgium (Jan. 2006).

Liqin, D., et al., "Construction of Recombinant Organism for Producing Glycerol," Chinese Journal of Chemistry 12:925-29, Science Press, China (2004).

Lynd, L. R., et al., "Microbial Cellulose Utilization: Fundamentals Biotechnology," Microbiology and Molecular Biology Reviews 66(3):506-577, American Society for Microbiology, United States (Sep. 2002).

Lynd, L. R., et al., "Consolidated bioprocessing of cellulosic biomass: an update," Current Opinion in Biotechnology 16:577-583, Elsevier Ltd., England (2005).

Mosier. N., et al., "Features of promising technologies for pretreatment of lignocellulosic biomass," Bioresource Technology 96:673-686, Elsevier Ltd., England (2005).

New Zealand First Examiner's Report dated May 21, 2014 for Application No. 624392, filed on Aug. 20, 2010 (3 pages).

Raynaud, C., et al., "Molecular characterization of the 1,3-propanediol (1,3-PD) operon of Clostridium butyricum," PNAS 100(9):5010-5015, National Academy of Sciences, United States (Apr. 2003).

Scott, K. P., et al,. "Whole-Genome Transcription Profiling Reveals Genes Up-Regulated by Growth on Fucose in the Human Gut Bacterium 'Roseburia inulinivorians'," J Bacteriol. 188(12):4340-4349, American Society for Microbiology, United States (Jun. 2006).

Shaw, A. J., et al., "Metabolic engineering of a thermophilic bacterium to produce ethanol at high yield," PNAS 105(37):13769-13774, National Academy of Sciences, United States (Sep. 2008).

Sriramulu, D. D., et al., "Lactobacillus reuteri DSM 20016 Produces Cobalamin-Dependent Diol Dehydratase in Metabolosomes and Metabolizes 1,2-Propanediol by Disproportionation," J. Bacteriol. 190(13):4559-4567, American Society for Microbiology, United States (Jul. 2008).

Subedi, K., et al., "Role of GldA in dihydroxyacetone and methylglyoxal metabolism of *Escherichia coli* K12," FEMS Microbiol Lett (Epub Dec. 20, 2007) 279: 180-187, 2008.

Tang, X., et al., "Microbial Conversion of Glycerol to 1,3-Propanediol by an Engineered Strain of *Escherichia coli*," Appl. Environ. Microbial. 75 (6): 1628-1634, American Society for Microbiology (Mar. 2009).

Tran-Din, K., and Gottschalk, G., "Formation of D(-)-1,2-propanediol and D(-)-lactate from glucose by Clostridium sphenoides under phosphate limitation," Arch. Microbiol. 142:87-92, Springer-Verlag, Germany (1985).

Van Maris, A. J. A., et al., "Directed Evolution of Pyruvate Decarboxylase-Negative *Saccharomyces cerevisiae*, Yielding a C2-Independent, Glucose-Tolerant, and Pyruvate-Hyperproducing Yeast," Appl. Environ. Microbiol. 70(1):159-166, American Society for Microbiology, United States (Jan. 2004).

Van Maris, A. J. A., et al., "Development of Efficient Xylose Fennentation in *Saccharomyces cerevisiae*: Xylose Isomerase as a Key Component," Adv. Biochem Engin/Biotechnol. 108: 179-204, Springer-Verlag, Germany (2007).

(56) References Cited

OTHER PUBLICATIONS

Waks, Z. and Silver, P. A., "Engineering a Synthetic Dual-Organism System for Hydrogen Production," Appl.. Env. Microbiol., 75(7):1867-1875, American Society for Microbiology, United States (Apr. 2009).

Xue, J., et al., "Exogenous or L-Rhamnose-Derived 1,2-Propanediol Is Metabolized via a pduD-Dependent Pathway in Listeria innocua," Appl. Environ. Microbial. 74(22):7073-7079, American Society for Microbiology, United States (Nov. 2008).

Yan, Y., and Liao, J. C., "Engineering metabolic systems for production of advanced fuels," J. Ind. Microbiol. Biotechnol. 36:471-479, Springer, England (Apr. 2009).

PRODUCTION OF PROPANOLS, ALCOHOLS, AND POLYOLS IN CONSOLIDATED BIOPROCESSING ORGANISMS

CROSS-REFERENCE TO RELATED APPLICATIONS

The present application is a continuation of U.S. application Ser. No. 15/927,126 filed Mar. 21, 2018, which is a continuation of U.S. application Ser. No. 13/391,554 filed Aug. 30, 2012, which is a '371 U.S. national phase application of PCT/US2010/046172, filed Aug. 20, 2010, entitled "Production of Propanols, Alcohols, and Polyols in Consolidated Bioprocessing Organisms," which claims priority to U.S. Provisional Application No. 61/235,959 filed Aug. 21, 2009, and U.S. Provisional Application No. 61/298,790 filed Jan. 27, 2010, each application of which is hereby incorporated by reference in its entirety.

REFERENCE TO SEQUENCE LISTING SUBMITTED ELECTRONICALLY VIA EFS-WTEB

The content of the electronically submitted sequence listing (Name: 1 15235-273 SeqList.txt; Size: 498,191 bytes; and Date of Creation: Jul. 1, 2020) filed with the application is incorporated herein by reference in its entirety.

BACKGROUND OF THE INVENTION

Field of the Invention

Consolidated Bio-Processing (CBP) in essence describes a mode of operation where biocatalysts produce enzymes that can breakdown inexpensive cellulose into usable sugars and then simultaneously ferment then into value added products in a single vessel. CBP, which reduces the number of unit processes, significantly lowers operating and capital costs associated with cellulosic biofuel production. Furthermore, CBP processes reduce or eliminate the need for externally-added, expensive cellulases. See Lynd el al. "Microbial cellulose utilization: Fundamentals and biotechnology," *Microbiology, and Molecular Biology Reviews* 66(3):506-577 (2002); Lynd et al., "Consolidated bioprocessing of cellulosic biomass: An update," *Current Opinion in Biotechnology* 16(5):577-583 (2005); "Breaking the Biological Barriers to Cellulosic Ethanol: A Joint Research Agenda," December 2005, Rockville, Md. Publication Date: June 2006; DOE/SC-0095. CBP is widely considered to be the "Ultimate low-cost configuration for cellulose hydrolysis and fermentation." DOE/USA Joint Research Agenda. See DOE/SC-0095 Joint Research Agenda. CBP on plant biomass, e.g., lignocellulosic biomass, also reduces the need to rely on petrochemical feedstocks to produce fermentable, value added products, such as propanols, alcohols, and polyols.

Among forms of plant biomass, lignocellulosic biomass ("biomass") is particularly well-suited for producing fermentable, value added products because of its large-scale availability, low cost, and environmentally benign production. The primary obstacle impeding the processing of biomass feedstocks is the general absence of low-cost technology for overcoming the recalcitrance of these materials to conversion into useful products. Lignocellulosic biomass contains carbohydrate fractions (e.g., cellulose and hemicellulose) that can be converted into propanols, alcohols, and polyols. In order to convert these fractions, the cellulose and hemicellulose must ultimately be converted or hydrolyzed into monosaccharides; it is the hydrolysis that has historically proven to be problematic.

Lignocellulosic feedstocks are recalcitrant to hydrolysis and subsequent release of sugars. Concentrated acid pretreatment can release sugars with some associated loss of either pentose or hexose sugars. However, the larger issue with concentrated acid use is the additional capital cost associated with those pre-treatments. The capital cost implications involve using expensive materials of construction, handling corrosive chemicals and dealing with environmental implications. In fact, a group of eminent scholars in the area of lignocellulosic pretreatment have commented that although concentrated mineral acids are effective, they are too expensive to be practical when measured against the value of the resulting sugars. Mosier el al., (2005), *Bioresource Technology* 96, 673-686.

More recently some companies have made technology claims where they have demonstrated concentrated acid recycle at laboratory scale as a means of reducing the cost associated with using concentrated acid pretreatments. A recent article on this recycling technology clarifies that they are only able to recycle 42% of the added acids and reiterates that this technology will only be tested in a pilot facility in the second half of 2010. Technology Review, Wednesday, Jun. 10, 2009 (available at technologyreview.com/energy/22774/). Additionally, the article includes caution by industry experts against the use of concentrated HCl acids for pretreatment as the plant would require expensive materials of construction. (CBP provides a viable alternative to the production of fermentable sugars from biomass.

CBP biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in CBP, which is distinguished from other less highly integrated configurations in that it does not involve a dedicated process step for cellulase and/or hemicellulase production.

Thus, CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compounds dihydroxyacetone phosphate and glyceraldehyde 3-phosphate. This process results in the net generation of ATP (biological energy supply) and the reduced cofactor NADH. From these three carbon compounds, a number of downstream value-added products can be made using the metabolic machinery of the CBP organisms, including, e.g., propanols, alcohols, and polyols.

Industrial chemicals, such as propanols, alcohols, and polyols, are traditionally derived from petrochemical feedstocks. Production of such chemicals from petrochemical feedstocks, however, has its problems, not least of which is the use of a non-renewable resource that is subject to price fluctuations and heavy regulation. Thus, there is a need in the art for the production of propanols, alcohols, and polyols from resources that allow for large-scale availability, low cost, and environmentally benign production, all of which are advantages of CBP. In particular, there is a need for engineered organisms capable of converting biomass into propanols, alcohols, and polyols as part of a CBP system.

BRIEF SUMMARY OF THE INVENTION

The present invention provides for novel metabolic pathways leading to propanol, alcohol or polyol formation in a consolidated bioprocessing system (CBP), where lignocellulosic biomass is efficiently converted to such products.

The invention therefore provides for a recombinant microorganism, where the microorganism expresses one or more native and/or heterologous enzymes; where the one or more enzymes function in one or more engineered metabolic pathways to achieve: (1) conversion of a carbohydrate source to 1,2-propanediol, isopropanol, ethanol and/or glycerol; (2) conversion of a carbohydrate source to n-propanol and isopropanol; (3) conversion of a carbohydrate source to isopropanol and methanol; or (4) conversion of a carbohydrate source to propanediol and acetone.

The engineered metabolic pathways of the invention are outlined in FIGS. 1-5 and 7. The enzymes that function at various steps along the pathways are identified in Tables 2-5. The engineered metabolic pathways of the invention are utilized to achieve high theoretical yields of products, particularly 1,2-propanediol, isopropanol, n-propanol, and methanol in bacteria and yeast.

BRIEF DESCRIPTION OF THE DRAWINGS/FIGURES

FIG. 1 shows a schematic of theoretical metabolic pathways for the production of mixed alcohols in bacterial and yeast CBP platforms. Yeast-specific branch pathways are depicted by EC numbers in dark gray boxes. Bacteria-specific branch pathways are depicted by EC numbers in light gray boxes.

Figure 4:
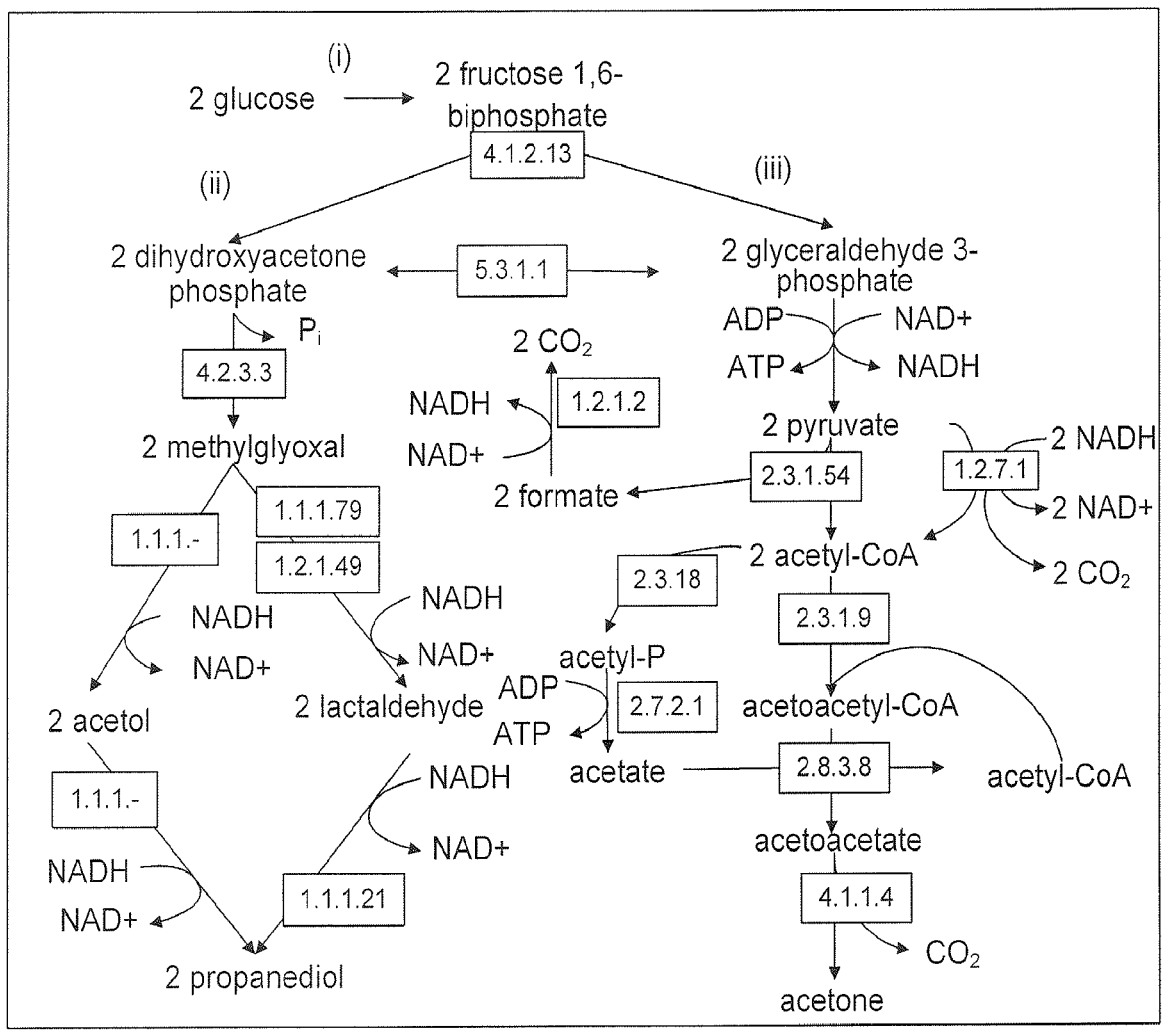

FIG. 4 shows a schematic of theoretical metabolic pathways for the anaerobic production of propanediol and acetone in bacterial and yeast CBP platforms. A yeast-specific branch pathway is depicted by EC numbers in dark gray boxes. A bacteria-specific branch pathway is depicted by the EC number in a light gray box.

Figure 5:
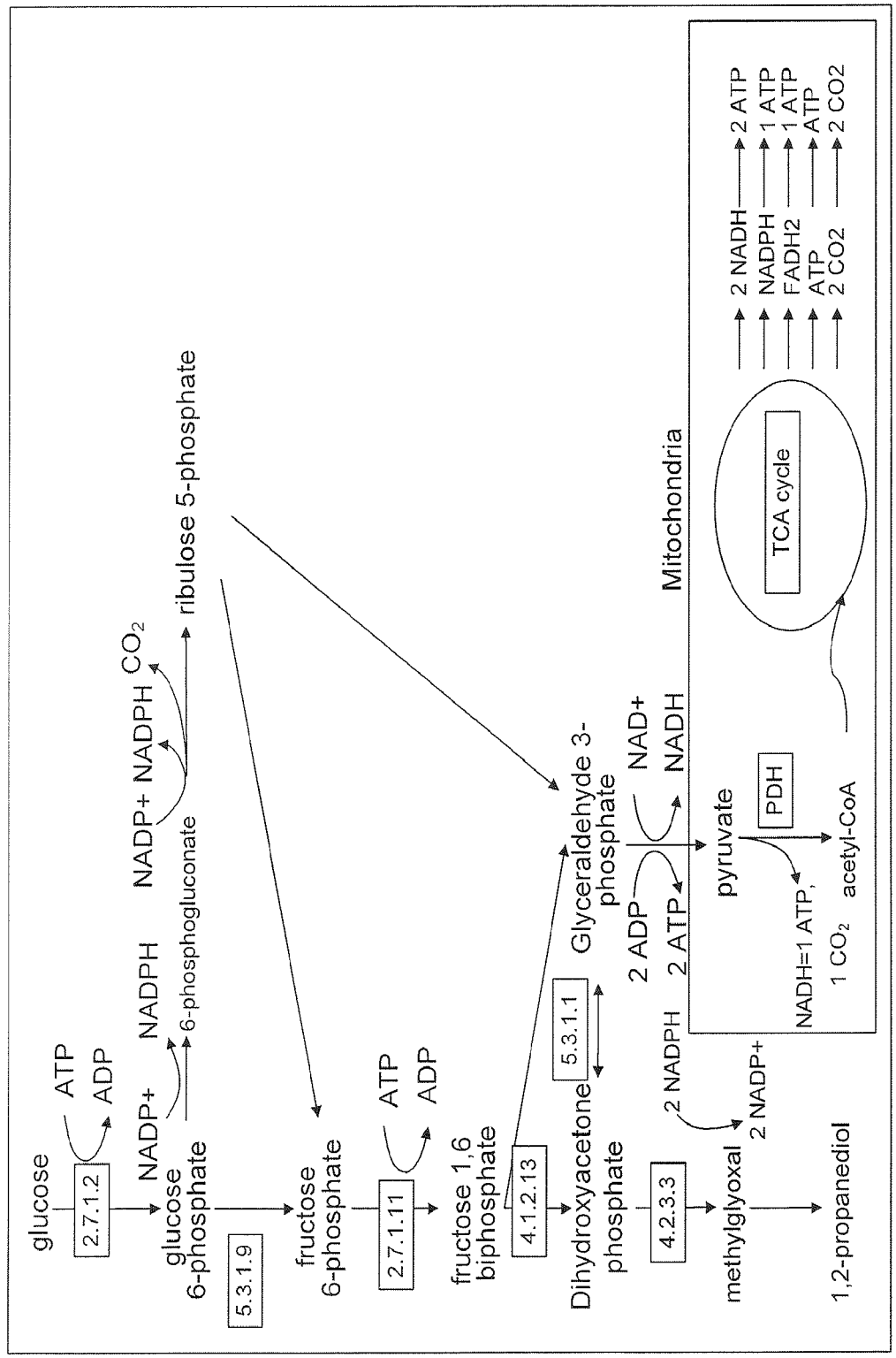

FIG. 5 shows a schematic of a theoretical metabolic pathway for the aerobic production of propanediol in yeast CBP platforms.

Figure 6:
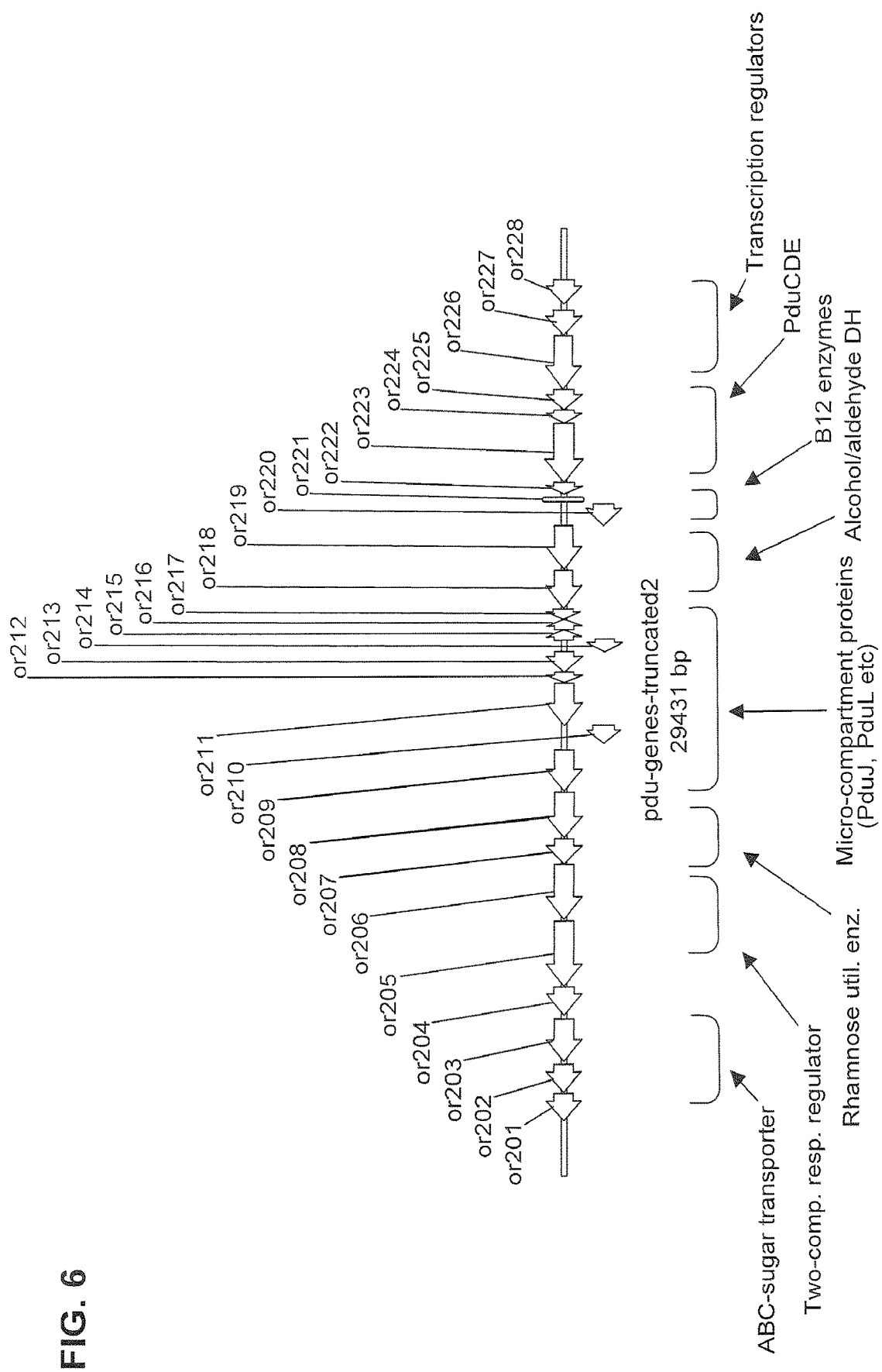

FIG. 6 shows a schematic of propanediol utilization (pdu) gene organization in *T. saccharolyticum*.

Figure 7:
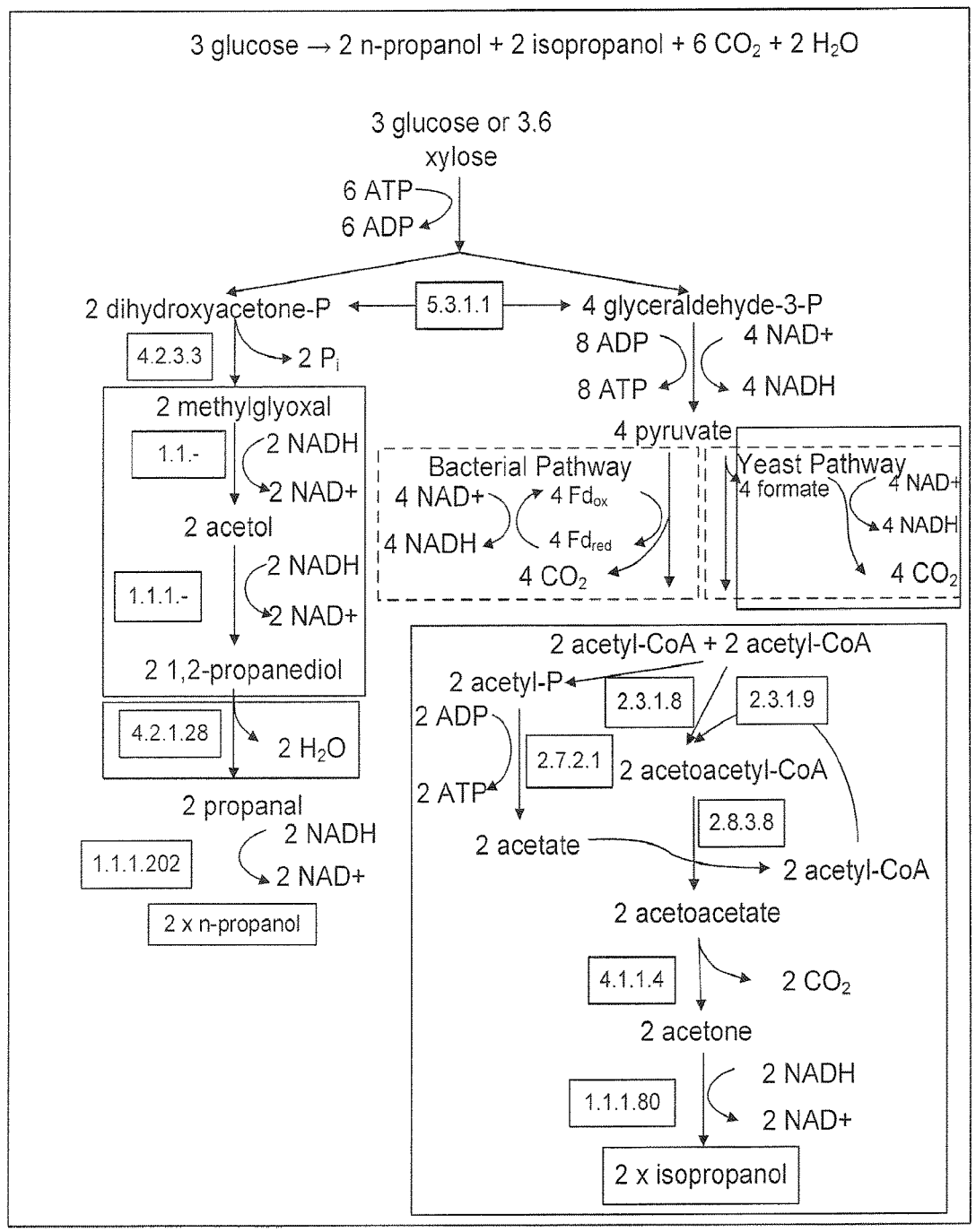

FIG. 7 shows a schematic of theoretical metabolic pathways for the production of n-propanol and isopropanol in bacterial and yeast CBP platforms.

DETAILED DESCRIPTION OF THE INVENTION

Metabolic Pathway Engineering

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl CoA), which then enters the tricarboxylic acid cycle (TCA), which in turn generates synthetic precursors, CO2 and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Most facultative anaerobes metabolize pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (ACK) with the co-production of ATP, or reduced to ethanol via acetaldehyde dehydrogenase (AcDH) and alcohol dehydrogenase (ADH). In order to maintain a balance of reducing equivalents, excess NADH produced from glycolysis is re-oxidized to NAD+ by lactate dehydrogenase (LDH) during the reduction of pyruvate to lactate. NADH can also be re-oxidized by AcDH and ADH during the reduction of acetyl-CoA to ethanol, but this is a minor reaction in cells with a functional LDH.

Ethanologenic organisms, including yeast (e.g., *Saccharomyces cerevisiae*), are capable of a second type of anaerobic fermentation, commonly referred to as alcoholic fermentation, in which pyruvate is metabolized to acetaldehyde and $CO_2$ by pyruvate decarboxylase (PDC). Acetaldehyde is then reduced to ethanol by ADH regenerating NAD+. Alcoholic fermentation results in the metabolism of one molecule of glucose to two molecules of ethanol and two molecules of $CO_2$.

The present invention is directed to the modification of traditional glycolytic pathways in bacteria and yeast, as described above, to engineer novel metabolic pathways capable of generating or increasing the yield of certain products that could not otherwise be generated by the native organism. Such products include n-propanol or isopropanol along with alcohols, propanediol, ethanol, and glycerol.

In particular embodiments, the present invention is directed to the production of mixed alcohols in CBP yeast and bacterial platforms. In other embodiments, the present invention is directed to the production of n-propanol and isopropanol in a CBP bacterial platform. In additional embodiments, the present invention is directed to production of isopropanol and methanol in a CBP bacterial platform. In certain other embodiments, the present invention is directed to the production of propanediol in a CBP yeast or bacterial platform. In further embodiments, the propanediol could be directly utilized in industrial applications or condensed to propylene or converted via a chemical or microbial based biocatalysis to propanol.

The present invention is directed to the engineering of such alternative metabolic pathways in various microorganisms, including bacteria and yeast. The term "microorganism," as used herein, refers to an organism of microscopic or submicroscopic size that can be seen only with the aid of a microscope and that typically consists of only a single cell. Microorganisms include bacteria, protozoans, and certain algae and fungi.

In certain embodiments, the bacterial microorganism is a species of the genera *Thermoanaerobacterium, Thermoanaerobacter, Clostridium, Geobacillus, Saccharococcus, Paenibacillus, Bacillus, Caldicellulosiruptor*, Anaerocellum, or *Anoxybacillus*. In certain embodiments, the microorganism is a bacterium selected from the group consisting of: *Thermoanaerobacterium* thermosulfurigenes, *Thermoanaerobacterium* aotearoense, *Thermoanaerobacterium* polysaccharolyticum, *Thermoanaerobacterium* zeae, *Thermoanaerobacterium* xylanolyticum, *Thermoanaerobacterium* saccharolyticum, *Thermoanaerobium* brockii, *Thermoanaerobacterium* thermosaccharolyticum, *Thermoanaerobacter* thermohydrosulfuricus, *Thermoanaerobacter* ethanolicus, *Thermoanaerobacter brocki, Clostridium thermocellum, Clostridium cellulolyticum, Clostridium phytofermentanrs, Clostridium* straminosolvens, *Geobacillus thermoglucosidasius, Geobacilhus stearothermophilus, Saccharococcus caldoxylosilyticus*, Saccharoccus *thermophilus, Paenibacillus campinasensis, Bacillus* flavothermus, *Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, and Anaerocellum *thermophilum*. In particular embodiments, the microorganism is *Clostridium thermocellum* or *Thermoanaerobacterium saccharolyticum*.

In certain other embodiments, the yeast microorganism is selected from the group consisting of *Saccharomyces cerevisiae, Kluyveromvces lactis, Kluyveromvces marxianus, Pichia pastoris, Yarrowia lipolytica, Hansenula* polymropha, *Phaffia rhodozyma, Candida utliis, Arxula adeninivorans, Pichia stipitis, Debaryomyces hansenii, Debaryomyces polymorphus, Schizosaccharomyces pombe, Candida albicans*, and *Schwanniomyces occidentalis*. In particular embodiments, the yeast microorganism is *Saccharomyces cerevisiae*.

In certain instances, the microorganism of the invention is cellulolytic. The term "cellulolytic" means able to hydrolyze glycosidic linkages in oligohexoses and polyhexoses. Cellulolytic activity can also include the ability to depolymerize or debranch cellulose and hemicellulose.

The term "ethanologenic" is intended to include the ability of a microorganism to produce ethanol from a carbohydrate as a fermentation product. The term is intended to include, but is not limited to, naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

By "thermophilic" is meant an organism that thrives at a temperature of about 45° C. or higher.

By "mesophilic" is meant an organism that thrives at a temperature from about 20-about 45° C.

The term "CBP organism" is intended to include microorganisms of the invention, e.g., microorganisms that have properties suitable for CBP.

Figure 1:
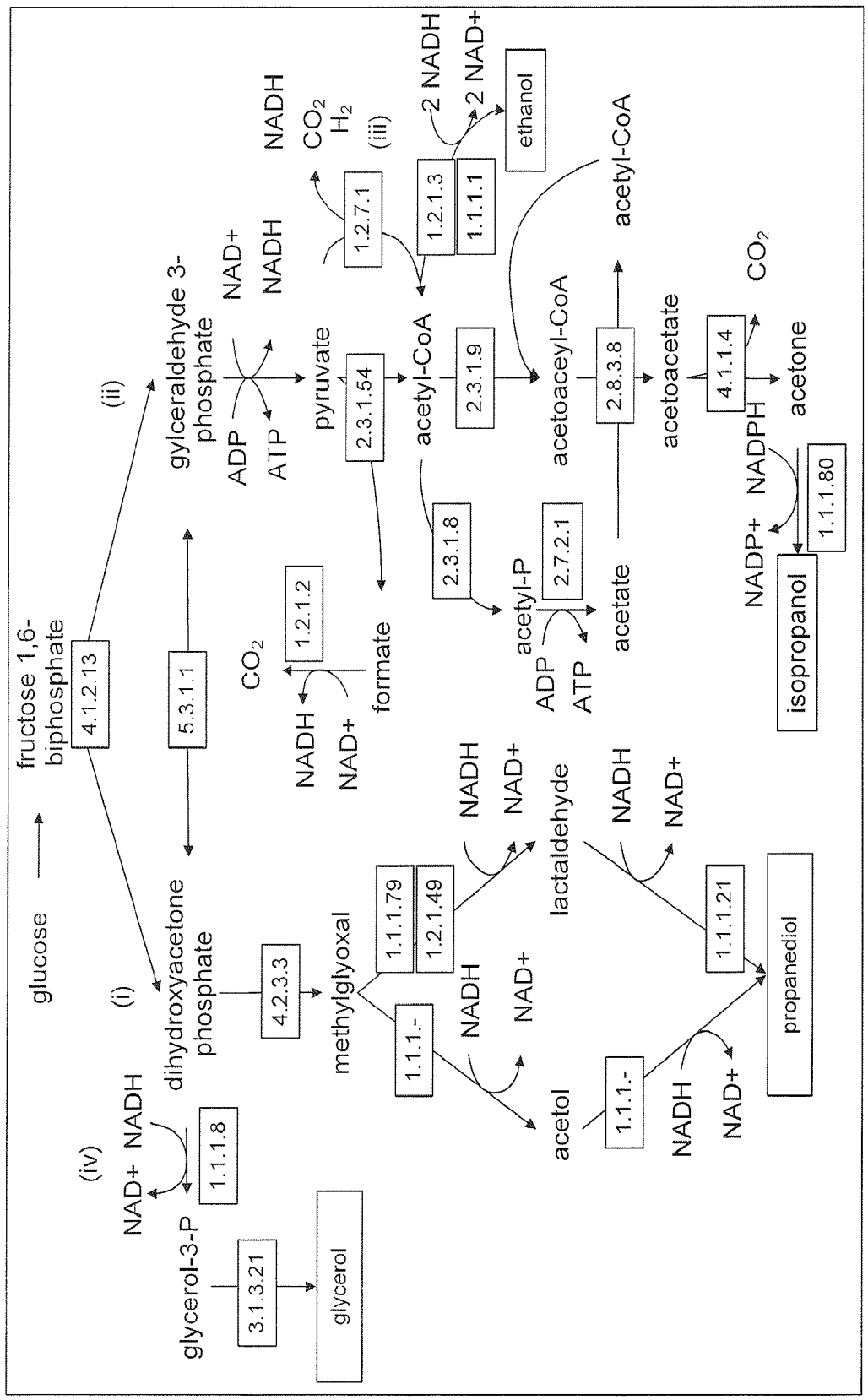

In certain embodiments of the invention, one or more metabolic engineered pathways are utilized for the combined production of propanediol and isopropanol from glucose. The metabolic pathways and the various distinct enzymes (Table 2) required for the combined production of propanediol and isopropanol are shown in FIG. 1 and described further below in Example 1. These metabolic pathways can be subdivided into the following distinct production routes: i) the conversion of dihydroxyacetone phosphate into propanediol; ii) the conversion of pyruvate into isopropanol; iii) the conversion of pyruvate into ethanol (bacterial platform only); and iv) the conversion of dihydroxyacetone phosphate into glycerol (yeast platform only).

Figure 2:
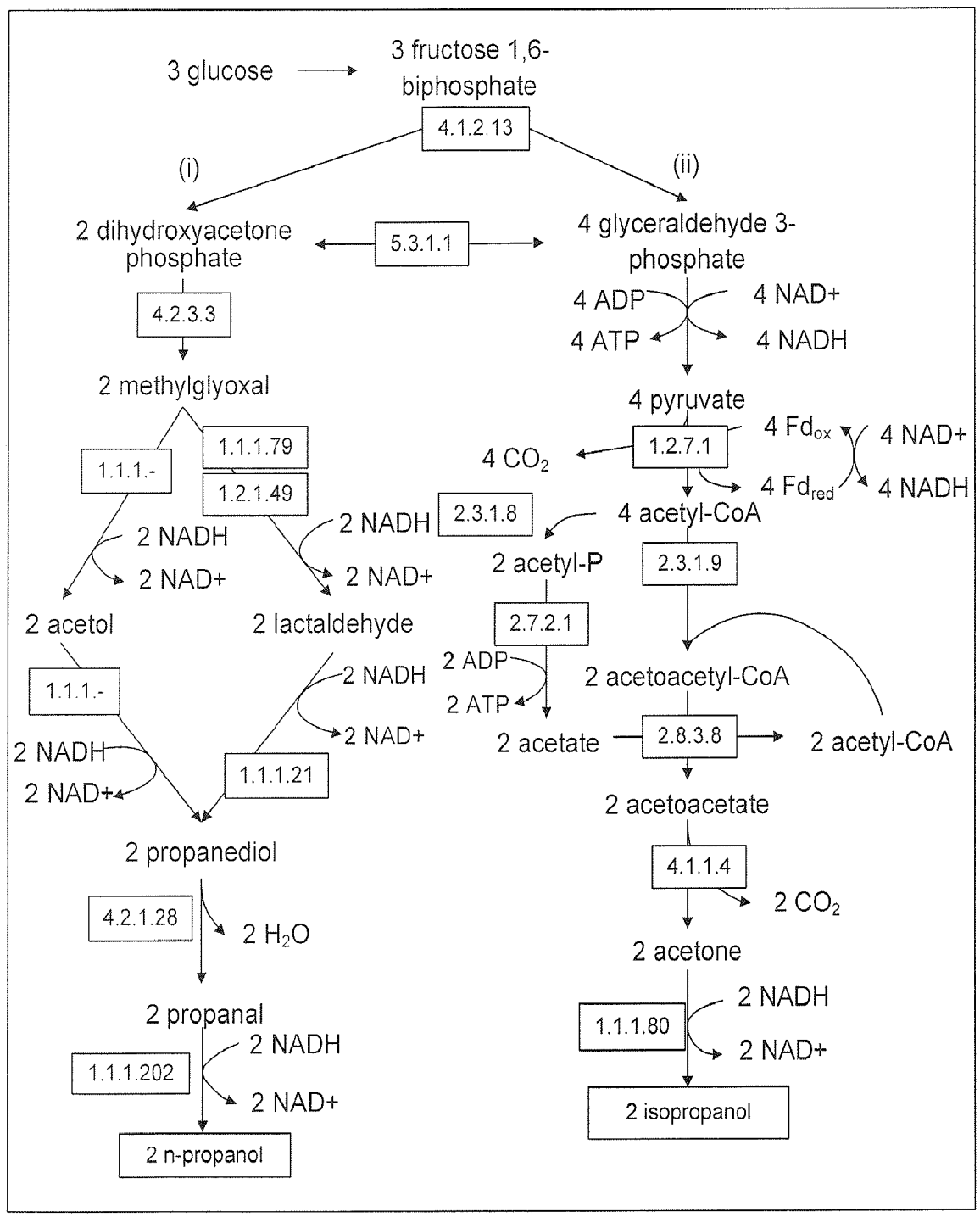
FIG. 2 shows a schematic of theoretical metabolic pathways for the production of n-propanol and isopropanol in bacterial CBP platforms.

In certain other embodiments of the invention, one or more metabolic engineered pathways are utilized for the production of n-propanol and isopropanol. The metabolic pathways and the various distinct enzymes (Table 3) required for the production of n-propanol and isopropanol are shown in FIG. 2 and described further below in Example 2. The metabolic pathways can be subdivided into two distinct production routes: i) the conversion of dihydroxyacetone phosphate into n-propanol; and ii) the conversion of pyruvate into isopropanol.

Figure 3:
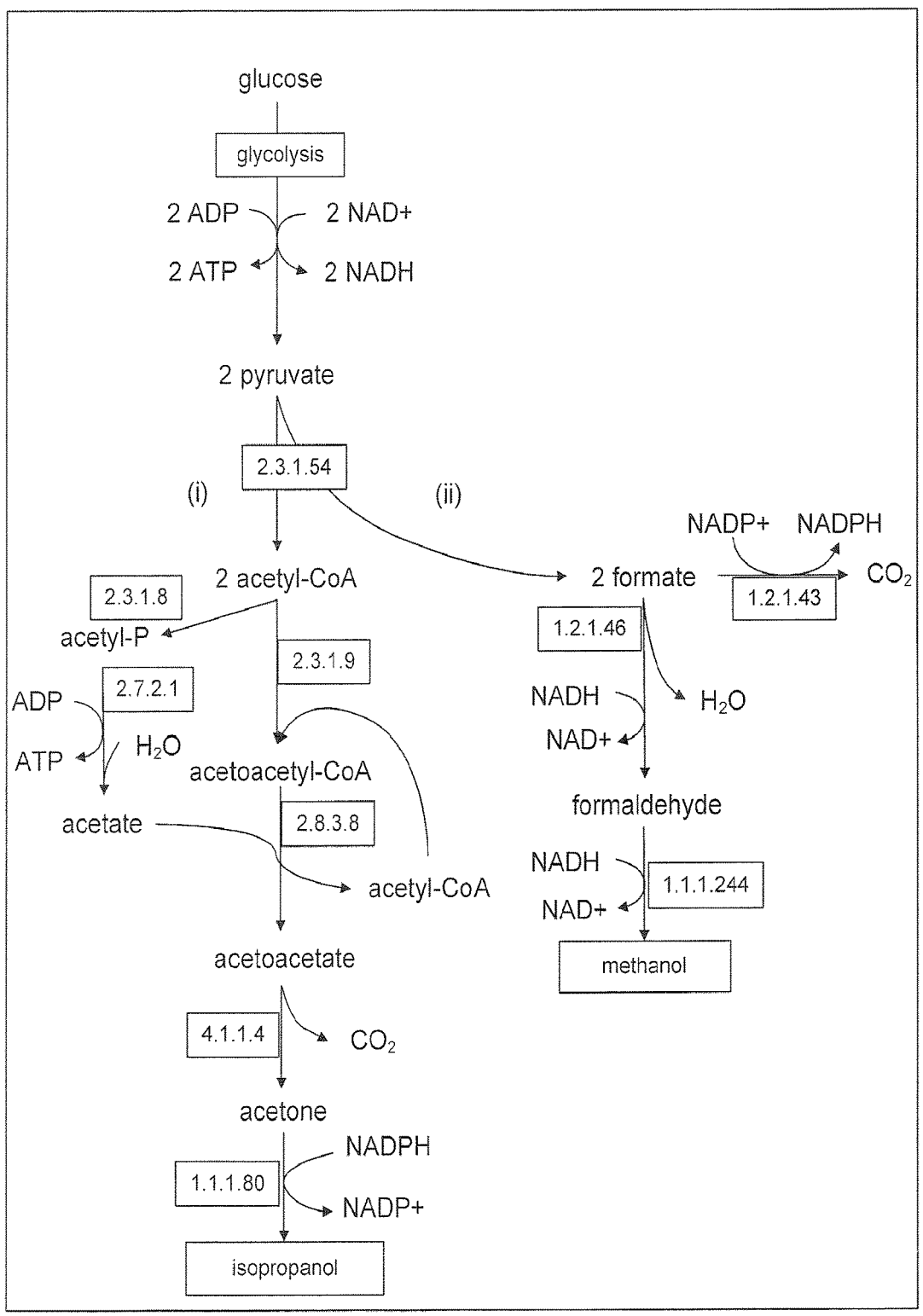
FIG. 3 shows a schematic of theoretical metabolic pathways for the production of isopropanol and methanol in bacterial CBP platforms.

In additional embodiments of the invention, one or more metabolic engineered pathways are utilized for the combined production of isopropanol and methanol from carbohydrates. The metabolic pathways and the various distinct enzymes (Table 4) required for the production of isoproponal and methanol are shown in FIG. 3 and described further below in Example 3. The metabolic pathways can be subdivided into distinct production routes: i) the conversion of pyruvate into isopropanol; and ii) the conversion of formate into $CO_2$ and methanol.

In other embodiments of the invention, one or more metabolic engineered pathways are utilized for the co-production of propanediol and acetone from hexose and pentose sugars in thermophilic clostridia and yeast, such as *S. cerevisiae*. The metabolic pathways and the various distinct enzymes (Table 5) required for the production of propanediol and acetone are shown in FIGS. 4 and 5 and described further below in Examples 4 and 5. The metabolic pathways can be subdivided as follows: i) the production of dihydroxyacetone phosphate and glyceraldehydes-3-phosphate from glucose; ii) the subsequent generation of propanediol from dihydroxyacetone phosphate; and iii) the generation of acetone from glyceraldehyde-3-phosphate.

A summary of the pathways of the present invention is provided in Table 1 as follows:

TABLE 1

Summary: Engineering of CBP biocatalysts for production of propanol

| Pathway | Theoretical yield hexose/pentose | Required Metabolic Engineering | | | | Critical Step |
|---|---|---|---|---|---|---|
| | | Gene KO EC# | Gene KO function | Gene expression EC# | Gene expression function | |
| Mixed Alcohol- Bacterial<br><br>2 glucose → 1,2-propanediol + isopropanol + ethanol + 4 CO2 + H$^+$ + 3 ATP | Hexose:<br>0.21 g/g propanediol<br>0.17 g/g propanol<br>0.13 g/g ethanol<br><br>Pentose:<br>0.21 g/g propanediol<br>0.17 g/g propanol<br>0.13 g/g ethanol | 1.1.1.27 | ldh | 4.2.3.3<br>1.1.1.-<br>2.3.1.9<br>2.8.1.8<br>4.1.1.4<br><br>1.1.1.80<br>1.1.1.202 | methylglyoxal synthase<br>aldo-keto reductase<br>thiolase<br>acetyl-CoA transferase<br>acetoacetate decarboxylase<br>Isoprop dehydoxidoreductase | pathway flux control, methylglyoxal to 1,2 propanediol |
| Mixed Alcohol - Yeast<br>2 glucose → isopropanol + propanediol + glycerol + 3 CO2 + 1 ATP | Hexose:<br>0.21 g/g propanediol<br>0.17 g/g isopropanol<br>0.26 g/g glycerol<br><br>Pentose:<br>(no tpi deletion)<br>0.21 g/g propanediol<br>0.17 g/g isopropanol<br>0.26 g/g glycerol | 4.1.1.1 | pdc1<br>pdc5<br>pdc6 | 4.2.3.3<br>1.1.1.6<br>2.3.1.54<br>2.7.2.1<br>2.3.1.8<br><br>2.8.3.8<br>4.1.1.4<br><br>1.1.1.79<br><br>1.1.1.80<br><br>1.2.1.49 | methylglyoxal synthase<br>glycerol dehydrogenase<br>pyruvate formate-lyase<br>acetate kinase<br>phosphate acetyltransferase<br>acetate CoA-transferase<br>acetoacetate decarboxylase<br>glyoxylate reductase<br>isopropanol dehydrogenase<br>methylglyoxal dehydrogenase | pathway flux control (without TPI deletion), methylglyoxal to propanol |
| n-propanol/isopropanol in bacteria | Hexose:<br>0.44 g/g propanols<br><br>Pentose:<br>0.44 g/g propanols | 1.1.1.27<br>1.12.7.2<br>1.2.1.10 | ldh<br>hyd<br>acdh | 4.2.3.3<br>1.1.1.-<br>2.3.1.9<br>2.8.1.8<br>4.1.1.4<br>1.1.1.80<br>1.1.1.202 | mgs<br>aldo-keto reduct<br>thiolase<br>acetyl-CoA trans<br>adc<br>Isoprop dehydoxidoreductase | methylglyoxal to n-propanol |
| Isopropanol/Methanol - Bacterial<br><br>2 glucose → 2 isopropanol + 2 methanol + 4 CO$_2$ + 4 ATP | Hexose:<br>0.33 g/g propanol<br>0.18 g/g methanol<br><br>Pentose:<br>0.33 g/g propanol<br>0.18 g/g ethanol | 1.1.1.27<br>1.2.1.10<br>4.2.3.3<br>1.2.7.1 | ldh<br>Acdh<br>mcs<br>pfor | 1.2.1.2<br>1.2.1.46<br>1.1.1.-<br>2.8.3.8<br>4.1.1.4<br>2.3.1.9 | formate dehyd<br>formaldehyde dehyd<br>methanol dehyd (oxidoreductase)<br>CoA transferase<br>acetoacetate decarb<br>thiolase | formate to methanol |
| 1,2-Propanediol/Acetone - Bacterial<br><br>2 glucose → 2 propanediol + acetone + 3 CO$_2$ + 1 ATP | Hexose:<br>0.42 g/g propanediol<br>0.16 g/g acetone<br><br>Pentose:<br>0.42 g/g propanediol<br>0.16 g/g acetone | 1.1.1.1<br>1.1.1.27<br>1.12.7.2 | adh<br>ldh<br>hyd | 2.3.1.9<br>2.8.3.8<br>4.1.1.4 | thiolase<br>acetate CoA-transferase<br>acetoacetate decarboxylase | methylglyoxal to propanediol |
| propanediol/Acetone - Yeast<br><br>2 glucose → 2 propanediol + acetone + 3 CO$_2$ + 1 ATP | Hexose:<br>0.42 g/g propanediol<br>0.16 g/g acetone<br><br>Pentose:<br>(no tpi deletion)<br>0.42 g/g propanediol<br>0.16 g/g acetone | 4.1.1.1<br>1.1.1.8<br>3.1.3.21 | pdc1<br>pdc5<br>pdc6<br>gpd2<br>gpp1 | 4.2.3.3<br>2.3.1.54<br>2.7.2.1<br>2.3.1.8<br>2.8.3.8<br>4.1.1.4<br>1.1.1.79<br>1.2.1.49 | methylglyoxal synthase<br>pyruvate formate-lyase<br>acetate kinase<br>phosphate acetyltransferase<br>acetate CoA-transferase<br>acetoacetate decarboxylase<br>glyoxylate reductase<br>methylglyoxal dehydrogenase | pathway flux control (without TPI deletion), methylglyoxal to propanediol |

TABLE 1-continued

Summary: Engineering of CBP biocatalysts for production of propanol

| | | Required Metabolic Engineering | | | | |
|---|---|---|---|---|---|---|
| Pathway | Theoretical yield hexose/pentose | Gene KO EC# | Gene KO function | Gene expression EC# | Gene expression function | Critical Step |
| propanediol Aerobic-Yeast | Hexose: 0.42 to 0.61 g/g propanediol | 4.1.1.1 | pdc1 pdc5 pdc6 | 4.2.3.3 1.1.1.6 1.1.1.79 | methylglyoxal synthase glycerol dehydrogenase | pathway flux control from glucose 6-phosphate to |
| 17 glucose + 6 O$_2$ → 24 propanediol + 6 H$_2$O + 30 CO$_2$ + 7 ATP | Pentose: 100% xylose could not be converted via this pathway, but glucose/xylose mixtures could, with yield similar to glucose alone | 1.1.1.8 3.1.3.21 | gpd2 gpp1 | 1.2.1.49 | glyoxylate reductase methylglyoxal dehydrogenase | PPP and propanediol, methylglyoxal to propanediol |

Metabolic Enzymes

As described above, the engineering of metabolic pathways in microorganisms requires certain enzymes to function at particular steps along the pathways, as shown in FIGS. 1-5.

The enzymes of the invention as described herein can be endogenous to the native strain of the microorganism, and can thus be understood to be referred to as "native" or "endogenous." An organism is in "a native state" if it has not been genetically engineered or otherwise manipulated by the hand of man in a manner that intentionally alters the genetic and/or phenotypic constitution of the organism. For example, wild-type organisms can be considered to be in a native state.

For example, in certain embodiments, when the host cell is a particular Thermoanaerobacter(ium) strain, one or more metabolic enzymes can be an enzyme derived from that same Thermoanaerobacter(ium) strain. Source libraries with fragments of whole genomic DNA from such a Thermoanaerobacter(ium) strain can be host-modified with promoters, terminators, replication origins, or homologous recombination targeting. Screening of these libraries can identify DNA encoding for enzymes of interest that function in one or more metabolic engineered pathways of the invention.

In other embodiments, the enzymes of the invention can be non-native or "heterologous" to the organism, and can be introduced into the organism on a vector by transformation or other methods known to one of ordinary skill in the art, as described further below.

The terms "activity," "activities," "enzymatic activity," and "enzymatic activities" are used interchangeably and are intended to include any functional activity normally attributed to a selected polypeptide. Typically, the activity of a selected polypeptide encompasses the total enzymatic activity associated with the produced polypeptide. The polypeptide produced by a host cell and having enzymatic activity can be located in the intracellular space of the cell, cell-associated, secreted into the extracellular milieu, or a combination thereof.

In certain embodiments, enzymes that function in the metabolic pathways of the invention are set forth below in Tables 2-5 and include the following: methylglyoxal synthase, aldo-keto reductase, glyoxylate reductase, methylglyoxal dehydrogenase, aldehyde reductase, pyruvate formate lyase, thiolase, CoA transferase, acetoacetate decarboxylase, isoproponal, aldehyde dehydrogenase, alcohol dehydrogenase, diol-hydrolase, dehydrogenase, phosphotransacetylase, oxidoreductase, formate dehydrogenase, formaldehyde dehydrogenase and methanol dehydrogenase.

As used herein, the term "methylglyoxal synthase" or "mgs" refers to an enzyme that catalyzes the chemical reaction glycerone phosphate ⇌ methylglyoxal+phosphate As used herein, the term "aldo-keto reductase" can refer to any number of related monomeric NADPH-dependent oxidoreductases, such as aldose reductase, prostaglandin F synthase, xylose reductase, and many others.

As used herein, the term "oxidoreductase" refers to an enzyme that catalyzes the transfer of electrons from one molecule (the reductant, also called the hydrogen or electron donor) to another (the oxidant, also called the hydrogen or electron acceptor).

As used herein, the term "glyoxylate reductase" refers to an enzyme that catalyzes the chemical reaction glycolate+ NAD$^+$ ⇌ glyoxylate+NADH+H$^+$. This enzyme belongs to the family of oxidoreductases, specifically those acting on the CH—OH group of donor with NAD+ or NADP+ as acceptor.

As used herein, the term "methylglyoxal dehydrogenase" refers to an enzyme that oxidizes methylglyoxal to pyruvate.

As used herein, the term "CoA transferase" is an enzyme, for example, such as acetyl CoA transferase that catalyzes the chemical reaction acyl-CoA+acetat ⇌ a fatty acid anion+acetyl-CoA. The term "CoA transferase" also refers an enzyme that catalyzes the chemical reaction acetoacetyl-CoA+acetate ⇌ acetoacetate+acetyl-CoA.

As used herein, the term "acetoacetate decarboxylase" or "ADC" refers to an enzyme involved in both the ketone body production pathway in humans and other mammals, and solventogenesis in certain bacteria. Its reaction involves a decarboxylation of acetoacetate, forming acetone and carbon dioxide.

As used herein, the term "aldehyde dehydrogenase" refers to an enzyme that catalyzes the oxidation (dehydrogenation) of aldehydes.

As used herein, the term "dehydrogenase" refers to an enzyme that oxidizes a substrate by transferring one or more hydrides (H$^-$) to an acceptor, usually NAD$^-$/NADP$^+$.

As used herein, the term "formate dehydrogenase" is an enzyme that catalyzes the oxidation of formate to bicarbonate or carbon dioxide, donating the electrons to a second substrate, such as NAD$^+$ in formate:NAD$^+$ oxidoreductase.

As used herein, the term "formaldehyde dehydrogenase" refers to an enzyme that catalyzes the chemical reaction formaldehyde+NAD$^+$+H$_2$O ⇌ formate+NADH+2H$^+$. This enzyme belongs to the family of oxidoreductases, specifically those acting on the aldehyde or oxo group of donor with NAD⁺ or NADP⁺ as acceptor.

As used herein, the term "methanol dehydrogenase" is an enzyme that catalyzes the chemical reaction methanol+ NAD⁺ ⇌ formaldehyde+NADH+H⁺. This enzyme also belongs to the family of oxidoreductases, specifically those acting on the aldehyde or oxo group of donor with NAD⁺ or NADP⁺ as acceptor.

As used herein, the term "pyruvate formate lyase" or "PFL" is intended to include the enzyme capable of converting pyruvate into Acetyl CoA and formate.

As used herein the term "alcohol dehydrogenase" or "ADH" is intended to include the enzyme capable of converting aldehydes, such as acetaldehyde and propionaldehyde, and ketones, such as acetone, into an alcohol, such as ethanol, n-propanol, or isopropanol.

As used herein, the term "phosphotransacetylase" or "PTA" is intended to include the enzyme capable of converting Acetyl CoA into acetyl phosphate.

As used herein, the term "diol dehydratase" is intended to include the enzyme capable of converting propanediol to propanal.

The term "upregulated" means increased in activity, e.g., increase in enzymatic activity of the enzyme as compared to activity in a native host.

The term "downregulated" means decreased in activity, e.g., decrease in enzymatic activity of the enzyme as compared to activity in a native host.

The term "activated" means expressed or metabolically functional.

The polypeptide sequences corresponding to certain of the enzymes of the present invention are as follows.

```
C. thermocellum proteins
EC 2.3.1.54 (Cthe0505; SEQ ID NO: 1)
MDAWRGFNKGNWCQEIDVRDFIIRNYTPYEGDESFLVGPTDRTRKLWEKVSELLK

KERENGGVLDVDTHTISTITSHKPGYIDKELEVIVGLQTDEPLKRAIMPFGGIRMVIKGAE

AYGHSVDPQVVEIFTKYRKTFINQGVYDVYTPEMRKAKKAGIITGLPDAYGRGRIIGDYR

RVALYGVDRLIAEKEKEMASLERDYIDYETVRDREEISEQIKSLKQLKEMALSYGEDISC

PAKDAREAFQWLYFAYLAAVKEQNGAAMSIGRISTFLDIYIERDLKEGKLTEELAQELV

DQLVIKLRIVRFLRIPEYEKLFSGDPTWVTESIGGMALDGRTLVTKSSFRFLHTLENLGH

APEPNLTVLWSVNLPEGFKKYCAKVSIHSSSIQYESDDIMRKHWGDDYGIACCVSAMRI

GKQMQFFGARCNLAKALLYAINGGKDEMTGEQIAPMFAPVETEYLDYEDVMKRFDMV

LDWVARLYMNTLNIIHYMHDKYAYEALQMALHDKDVERTMACGIAGLSVVADSLSAI

KYAKVKPIRNENNLVVDYEVEGDYPKFGNNDERVDEIAVQVVKMFMNKLRKQRAYRS

ATPTLSILTITSNVVYGKKTGNTPDGRKAGEPLAPGANPMHGRDINGALAVLNSIAKLPY

EYAQDGISYTFSIIPKALGRDEETRINNLKSMLDGYEKQGGHHINVNVFEKETLLDAMEH

PEKYPQLTIRVSGYAVNFIKLTREQQLDVINRTIHGKI

EC 2.3.1.8 (Cthe1029; SEQ ID NO: 2)
VIIYSYKYYKYSFYDNSEGIMKGEEFMSFLEQIIERAKSDVKTIVLPESTDLRVIKA

ASMIMKKGIAKVVLIGNEKEIKSLAGDIDLEGVMIEDSLNSEKLEDYANTLYELRKSKGM

TIEAARETIKDPLYYGVMMVKKGEADGMVAGAVNSTANTLRPALQILKTAPGTKLVSSF

FVMVVPNCEYGHNGTFVYADCGLVENPDADQLSEIAISASKSFEMLVGAKPQVAMLSY

SSYGSAKSELTEKVIKATQLAKEKAPHLAIDGELQVDAAIVPEVAKSKAKGSSVAGKAN

VLIFPDLDAGNIAYKLTQRLAKAEAYGPITQGLARPVNDLSRGCSAEDIVGVAAITAVQA

QYVKA

EC 2.7.2.1 (Cthe1028; SEQ ID NO: 3)
MNILVINTGSSSLKYQLIDMTNESVLAKGVCDRIGLEHSFLKHTKIGGETVVIEKD

LYNHKLAIQEVISALTDEKIGVIKSMSEISAVGHRIVHGGEKFKESAIIDEDVMKAIRDCV

ELAPLHNPSNIIGIEACKQILPDVPMVAVEDTAFHQTMPRHAYIYALPYEIYEKYKLRKY

GFHGTSHKYVAHRAAQMLGKPIESLKLITCHLGNGASICAVKGGKSVDTSMGFTPLQGL

CMGTRSGNVDPAVITYLMEKEKMNINDINNFLNKKSGVLGISGVSSDFRDVQDAAEKG

DDRAQLALDIFCYGVRKYIGKYIAVLNGVDAVVFTAGIGENNAYIRREVLKDMDFFGIKI

DLDKNEVKGKEADISAPDAKVKTLVIPTNEELEIARETLRLVKNL
```

EC 1.1.1.80 (Cthe101; SEQ ID NO: 4)
MINFVYKNPTKIIFGRGTELKVGEEVRQYSGKVLLHYGGGSIKKTGLYDRVVNSL

KQAGVEVVELGGVMPNPREGLVNEGIKICREKGIDFILAVGGGSAIDSAKAIAVGVPYDG

DVWDFFCGKAEPKEALPVGVVLTIPAAGSEASPNSVITREDGLYKRGMYSELIRPVFAIM

NPELTYTLPAYQTACGTADIMAHIMERYFTNETHTDLTDRLCEATLKTMIKNVPIALEEP

DNYNARAEIMWAGTIAHNGLLGTGRIEDWASHNIEHEISAIYDVAHGAGLAVVFPAWM

KYVYKNNLDREVQFAVRVWNVEMNFDEPERTALEGIERLKKFFKEIGLPVSLKEMNIGD

DRLEEMASKCTNGGKATIGNFVKLNREDVY NILKLAV

Cthe0394 (SEQ ID NO: 5)
MKAFNYYAPTEIIFGCGRVQEIGSITAQYGKKALLVTVPEEPEVKELYEKVKKSLR

ENGVEVVHEDGVIPNPTTDVVTEGANMAKAAGVDVVIGLGGGSSIDTAKAIAVEATHPG

TAWDYNCHTPGPTSATLPIIAIGTTAGTGSQCTQCAVITKTSEKDKSAIWHKNIFPKVAIV

DPEVTVTMPKSVTAQTGFDAFAHNFEAYLSVKTSPLVEMMAIEAIKMIKEYLPKALENP

NDIEARSKMSLADTLGGLTNSNAGVTLPHGLGMQVGGHAPHVSHGQALAIIYPQFTRYT

YAWAIEKFAKVGRIFNPALNELSDEEAAKEACVAIDDELKKIGLWIGFKDVNVTKEQIRE

IADDGQVLGDYLNNPRVATIDEMYELLMNCYERKE

Cthe0423 (SEQ ID NO: 6)
MTKIANKYEVIDNVEKLEKALKRLREAQSVYATYTQEQVDKIFFEAAMAANKM

RIPLAKMAVEFFGMGVVEDKVIKNHYASEYIYNAYKNTKTCGVIEEDPAFGEKKIAEPLG

VIAAVIPTTNPTSTAIFKTLIALKTRNAIIISPHPRAKNSTIEAAKWLEAAVKAGAPEGIIGW

IDVPSLELTNLVMREADVILATGGPGLVKAAYSSGKPAIGVGAGNTPAIIDDSADIVLAV

NSIIHSKTFDNGMICASEQSVIVLDGVYKEVKKEFEKRGCYFLNEDETEKVRKTIIINGAL

NAKIVGQKAHTIANLAGFEVPETTKILIGEVTSVDISEEFAHEKLCPVLAMYRAKDFDDA

LDKAERLVADGGEGHTSSLYIDTVTQKEKLQKFSERMKTCRILVNTPSSQGGIGDLYNEK

LAPSLTLGCGSWGGNSVSDNVGVKHLLNIKTVAERRENMLWFRTPEKIYIKRGCLPVAL

DELKNVMGKKKAFEVTDNFLYNNGYTKPFTDKLDEMGIVHKTFEDVSPDPSLASAKAGA

AEMLAFQPDTIIAVGGGSAMDAAKIMWVMYEHPEVDEMDMAMREMDIRKRVYTFPK

MGQKAYFIAIPTSAGTGSEVTPFAVITDEKTGIKYPLADYELLPDMAIVDADMMMNAPK

GLTAASGIDALTHALEAYVSMLATDYTDSLALRAIKMIFEYLPRAYENGASDPVAREKM

ANAATIAGMAFANAFLGVCHSMAFIKLGAFYHLPHGVANALMINEVIRENSSEAPTKMG

TFPQYDHPRTLERYAEIADYIGLKGKNNEEKVENLIKAIDELKEKVGIRKTIKDYDEDEKE

FLDRLDEMVEQAFDDQCTGTNPRYPLMNEIRQMYLNAYYGGAKK

Cthe2445 (SEQ ID NO: 7)
MKGKMKVCVLTGKEKLEWVERDIPQPGRGELQIKLKHVGVCGSDLHFYKEGRL

ANWELDGPLALGHEPGGIVSAIGEGVEGFEIGDKVALEPGVPCGECEDCRKGHYNLCKH

IKFMAIPHEKDGVFAEYCVHSASMCYKLPENVDTMEGGLMEPLSVALHATELSNAKIGE

TAIVLGSGCIGLCTVMALKARGVSEIYVTDVVDKRLEKALEVGATRVFNSQREDIVEFA

KTLPGGGADQVYECAGSRVTTLQTCKLIKRAGKVTLVGVSPEPVLELDIATLNAMEGTV

YSVYRYRNMYPIAIAAVSSGVIPLKKIVSHVFDFKDCIEAIEYSTNHKDEVIKSVIKF

Cthe2579 (SEQ ID NO: 8)
MNFKFKIGTKVFFGKECVKENKAVFKDFRKRALLVTGKNSAKASGAFSDVVEVL

EEYGIDYEIYDRVANNPSLENVKEGGEAARKFDADFIIGIGGGSPLDASKAVAVLATNDI

EPVDLYKNVFENKPLPIIAIPTTAGTGSEVTPYSILTRDDMKTKKSFGNEDTFPAVAFIDA

```
RYTESMSYETTVDTALDAFTHALEGYLGRRSTPVSDILAVEAIRIFGECLENLLNNKFDY

DVREKLLYMSMLGGMVISHTGTTIIHGMGYSLTYFKDIPHGRANGMLVREYLKYNYEA

AKEKTDNVLRLLKVPSIDAFGEIIDRLIPQKPVLTKEEIELYASLAMKQNSTLSNARTVVK

EDMEEIFKNTFGKG

EC 4.2.2.3 (Cthe0095; SEQ ID NO: 9)
MNIALIAHDKKKELMASFCIAYRSILKNHTLFATGTTGAIIVEATGLNVHRFLPGV

MGEQQISARAAYNELDLVIFFRDPISAKSDEPDIHSLLRECDINNIPFATNLGTAEMLIKGL

ERGDLDWRELIKK

EC 1.1.1.- (Cthe0152; SEQ ID NO: 10)
LKYCKLGNTGLEVSKLCFGGLIIGPLQANLPPETGAEIILKSFELGVNFIDTAELYG

TYSHIGKALKKTNKNIVVATKSYAYSAEGAKESLEKARKEMDIDVIDIFMLHEQESRLTL

KGHREALEYYISMKEKGIIKAVGVSTHNVEVVEACCEMPEVDVIHPIVNKAGIGIGDGTI

DDMLKAVEKAYSVGKGIYSMKPLGGGNLIKSYKEAMDFVLNIPYIHSIAVGMQSIEEVV

MNVCIFEGKEVPQDVQKSLENKKRHLHIDWWCEGCGKCVERCKQKALKLVDGKAKVE

EEKCVLCSYCASVCPVFAIKVS

Cthe0236 (SEQ ID NO: 11)
MQYRGLGKTGVKVSALGFGAMRLPQININGNTRVDEEKSIEMIHRAFELGVNYID

TAPGYCNGESEVVVGKALKGWRDKIYLSTKNPIENASGDDWRKRLENSLKKLDTDYID

FYHMWGINWETYETKIDVKGGPLEAARKAKEEGLIRHISFSEHDKPENLIKLIDTGNEET

VLCQYNLLDRSNEKAIAHAKRKGLGVIIMGPVGGGKLGEPSETIKKLLPKKTVSCAEIAL

RFVLANPNVDCALSGMSTIEMVEENVRVASNDTPLTKEELEMIRASMEENKRMEDLYC

TGCNYCMPCPVGVNIPLNFQLMNYHRVYKITDYARGQYSQIGKVEWYKGKPAHECIEC

GVCETKCPQKLEIRKQLKETARVLSVK

Cthe0283 (SEQ ID NO: 12)
MKYRKMGRTGLYISEISLGSWLTYGNSTDKETAVKVIDTAYSLGINYFDTANVY

ANGRAEVIVGEALKKYPRESYILATKAFWPMGTGPNDKGLSRKHVFEQVHASLKRLNV

DYIDIFYCHRYDPETPLEETLRTIDDLLRQGKILYVGVSEWTAAQMAQALHIADRYLLDR

IVVNQPQYNMFHRYIEKEIIPFGEKNGISQIVFSPLAQGVLTGKYKPGGNIPRDSRAADPN

SNMYIGQFLKEDKLLKVEKLKAVADEMGITLSQLAIAWVLRQPNVTSALIGASKPEQVE

ENVKASGINLSDEILNKIEAILQ

EC 5.3.1.1. (Cthe0139; SEQ ID NO: 13)
MSRKVIAAGNWKMNKTPKEAVEFVQALKGRVADADTEVVVGVPFVCLPGVVE

AAKGSNIKVAAQNMHWEEKGAFTGEVSGPMLAELGVDYVIIGHSERRQYFGETDETVN

KKVHAAFKYGLKPIICVGESLTQREQGVTAELVRYQVKIALLGLSAEQVKEAVIAYEPIW

AIGTGKTATNEQAEEVCGIIRECIKELYGQDVAEAIRIQYGGSVNAANAAELFNMPNIDG

GLVGGASLKLDDFEKIAKYNK

EC 1.2.7.1
Cthe2390 (SEQ ID NO: 14)
MGKVVEIRWHGRGGQGAKTASLLLADAAFNTGKYIQGFPEYGPERMGAPITAY

NRISDEKLTIHSNIYEPDYVVVVDDTLLTSVDVTAGLKEDGAIIVNTPKTPDEIRPLLKGY

KGKVCTIDARKISIETLGKYFPNTPMLGAVVKVSKIMDEEEFLKDMVESFKHKFANKPE

VVEGNIKALERSMQEVKGL

Cthe2391 (SEQ ID NO: 15)
MSKELRDVKPDVTWKEITSGGVIDSPGNAHLFKTGDWRSMKPVWNEEKCKQCL

LCNPVCPDSSIMVSEEGKMTGIDYDHCKGCGICSKVCPFKAIDFVEEV
```

Cthe2392 (SEQ ID NO: 16)
MGIRERLSGNEATAIAMRQINPDVVAAFPITPSTEIPQYFSSYVADGLVDTEFVAV

ESEHSAMSACIGAQAAGARAMTATSANGLAYMWEALYIAASMRLPIVLAAVNRALSGP

INIHNDHSDTMGARDSGWIQLYSENNQEAYDNMLMAHRIGEHPDVMLPVMVCQDGFIT

SHAIENIELVEDEKVKAFVGEYKPTHYLLDRENPISVGPLDLQMHYFEHKRQQAQAMEN

AKKVILEVAEEFYKLTGRKYGFFEEYKTDDADVAIVVMNSTAGTVKYVIDEYRAKGKK

VGLIKPRVFRPFPVDELAQALSKFKAVAVMDKADSFNAAGGPLFTEVTSALFTKGVFGP

KVINYKFGLGGRDVKVDDIEVVCEKLLEIASTGKVDSVYNYLGVRE

Cthe2393 (SEQ ID NO: 17)
MAYNLKEVAKKPERLTGGHRMCAGCGAPIVVRQVLKALKPEDHAVISAATGCL

EVSTFIYPYTAWKDSFIHSAFENTGATISGAEAAYKVLKKKGKIEGETKFIAFGGDGGTY

DIGLQALSGAMERGHDMVYVCYDNGAYMNTGIQRSSATPKYADTTTSPVGKKIPGKM

QPRKDLTEVLVNHRIPYVAQTAPFGNMKDLYEKAEKAIYTPGPAFLNVLAPCPRGWRY

NTPDLMELSKLAVETCFWPLYEVIDGKYIINYKPKEKVPVKEFLKLQGRFKHLFKAGNE

YMLEEIQKEVDLRWERLLKLAGEA

EC 1.1.1.27 (Cthe1053; SEQ ID NO: 18)
MNNNKVIKKVTVVGAGFVGSTTAYTLMLSGLISEIVLIDINAKKADGEVMDLNH

GMPFVRPVEIYRGDYKDCAGSDIVIITAGANQKEGETRIDLVKRNTEVFKNIINEIVKYNN

DCILLVVTNPVDILTYVTYKLSGFPKNKVIGSGTVLDTARFRYLLSEHVKVDARNVHAYI

IGEHGDTEVAAWSLANIAGIPMDRYCDECHQCEEQISRNKIYESVKNAAYEIIRNKGATY

YAVALAVRRIVEAIVRNENSILTVSSLLEGQYGLSDVCLSVPTIVGVNGIEEILNVPFNDEE

IQLLRKSGNTLKEIIKTLDI

EC 1.12.7.2
Cthe425 (SEQ ID NO: 19)
MKVSICIGSSCHLKGAKQIVEQLQSLVADYNLKEKVELGGAFCMKNCVNGVSVT

VDDKLFSVTPENVKSFFETEILKKLED

Cthe426 (SEQ ID NO: 20)
MTECLQTKKSNCKNCYKCIRHCPVKSLKFTDGQAHIVRDECVLCGECYVVCPQN

AKQIRSDVEKAKQLVLKYDVYASIAPSFVAWFHNKSIHDMEQALIKLGFKGADETAKG

AYIVKKQYEKMIEEKKSKIIISSCCHTVNTLIQRHYTGAIQYLADVVSPMLAHAQMLKKE

HKGAKVVFIGPCISKKDEAEKYKGYVELVLTFDELDEWLKSENITIESNRGSSKEGRTRS

FPVSGGIISSMDKDLGYHYMVVDGMENCINALENIERGEIDNCFIEMSACRGSCINGPPA

RRKSNNIVGAILAVNKNTGAKDFSVPMPEPEKLKKEFRFEGVHKIMPGGTAIEEILKKMG

KTSIEHELNCGSCGYDTCRDKAVAVLNGKADLTMCLPYLKEKAESFSDAIIKNTPNGVIV

LNEDLEIQQINNSAKRILNLSPSTDLLGSPVSRILDPIDYILALREGKNCYYKRKYFAEYKK

YVDETHYDKEYHVIIIIMRDVTEEEKIKALKNKQSEAAIEIADKVVEKQMRVVQEIALLL

GETAAETKIALTKLKEIMEDE

Cthe427 (SEQ ID NO: 21)
MNDLCVDLGYKSLNKFGEQLCGDMIQVVKDDDTTILVLADGLGSGVKANILSTL

TSKIISTMIAAHMGIEECVNTIMSTLPVCKVRGIAYSTFTIIKITNNTYAEIIQYDNPLVILLR

NGKKYDYPTQTKIISGKKIVESKIRLNCDDVFVVMSDGAIYAGVGQTLNYGWQRENIIEF

IESHYDKSLSANALTSLLIDTCNNLYANMPGDDTTIAAIKIRKRQVVNLMFGPPQNPEDV

-continued

HNMMSLFFAKQGRHIVCGGTTSTLAAKFLGKELETTIDYIDPRIPPIARIEGVDLVTEGVL

TISRVLEYAKDYIGKNILYNEWHSKNDGASIIARMLFEEATDINFYVGKAINPAHQNPNL

PIGFNIKMQLVEELSKILKQMGKTINLSYF

Cthe428 (SEQ ID NO: 22)
MSVTMSEAFDYSMIDNILSEHGTSETAIIAILQSIQEEYHYIPKEVFPYLSKKLKVSE

ARIFSVATFYENFSLEPKGKYIIKVCDGTACHVRKSIPIIERLRKELGLSGTKPTTDDLMFT

VETVSCLGACGLAPVITVNDKVYAEMTPDKASELIKQLREGDADA

Cthe429 (SEQ ID NO: 23)
MLKNREELRKAREMYSRYLKAEKRRVLVCAGTGCVSGGSMEIFERLSELVSKRG

MDCQVELKEEPHDNTIGMKKSGCHGFCEMGPLVRIEPEGYLYTKVKLEDCEEIVDRTIV

AGEHIERLAYKQNGVVYKKQDEIPFYKKQTRLVLEHCGQIDSTSITEYLATGGYYALEK

ALFDMTGDEIINEITEANLRGRGGGGFPAGRKWAQVKRQNAKQKYVVCNGDEGDPGAF

MDRSIMEGDPHRMIEGMIIAGIACGASEGYIYVRAEYPLAVSRLKRAIEQAKEFGLLGENI

LGSNFSFNIHINRGAGAFVCGEGSALTASIEGKRGMPRVKPPRTVEQGLFDMPTVLNNVE

TFANVPLIIKNGADWYKSIGTEKSPGTKAFALTGNIENTGLIEIPMGTTLREVIFDIGGGMR

NGADFKAVQIGGPSGGCLSEKDLDLPLDFDSLKKAGAMIGSGGLVVMDSNTCMVEVAR

FFMNFTQNESCGKCVPCREGTKRMLEILERIVEGNGQDGDIELLLELADTISATALCGLG

KAAAFPVVSTIKNFREEYEAHIYDKRCPTGNCQKLKTITIDASLCKGCSKCARSCPVGAIT

GKVKEPFVIDQSKCIKCGACIETCAFHAILEG

Cthe430 (SEQ ID NO: 24)
MDNREYMLIDGIPVEINGEKNLLELIRKAGIKLPTFCYHSELSVYGACRMCMVEN

EWGGLDAACSTPPRAGMSIKTNTERLQKYRKMILELLLANHCRDCTTCNNNGKCKLQD

LAMRYNISHIRFPNTASNPDVDDSSLCITRDRSKCILCGDCVRVCNEVQNVGAIDFAYRG

SKMTISTVFDKPIFESNCVGCGQCALACPTGAIVVKDDTQKVWKEIYDKNTRVSVQIAPA

VRVALGKELGLNDGENAIGKIVAALRRMGFDDIFDTSTGADLTVLEESAELLRRIREGKN

DMPLFTSCCPAWVNYCEKFYPELLPHVSTCRSPMQMFASIIKEEYSTSSKRLVHVAVMP

CTAKKFEAARKEFKVNGVPNVDYVLTTQELVRMIKESGIVFSELEPEAIDMPFGTYTGA

GVIFGVSGGVTEAVLRRVVSDKSPTSFRSLAYTGVRGMNGVKEASVMYGDRKLKVAV

VSGLKNAGDLIERIKAGEHYDLVEVMACPGGCINGGGQPFVQSEEREKRGKGLYSADKL

CNIKSSEENPLMMTLYKGILKGRVHELLHVDYASKKEAK

Cthe431
SEQ ID NO: 25:
MLEIKICVGSSCHLKGSYNVINEFQHLIEEKALHDKIDIKATFCMKQCQKNGVAV

EVNNEIFGVLPEAAEEFFKNVILPKV

EC 1.12.7.2
Hyd Cthe3019-24
Cthe3019 (SEQ ID NO: 26)
MSFFTMTKTLIKSIFHGPYTVRYPLEKKEPFPASRGRIEINIQDCIFCGLCARRCPTG

AINVEKPESRWSINRLRCIQCGYCSEVCPKKCLKMNNMYPAPSFENIEDVYQNARVPDN

KENNRNIAGAC

Cthe3020 (SEQ ID NO: 27)
MGKKTVIPFGPQHPVLPEPIHLDLVLEDETVVEAIPSIGYIHRGLEKLVEKKDYQQ

FVYVAERICGICSFMHGMGYCMSIENIMGVQIPERAEFLRTIWAELSRIHSHMLWLGLLA

DALGFESLFMHSWRLREQILDIFEETTGGRVIFSVCDIGGVRRDIDSEMLKKINSILDGFEK

EFSEITKVFLNDSSVKLRTQGLGVLSREEAFELGAVGPMARASGIDIDMRKSGYAAYGK

-continued

LKIEPVVETAGDCYARTSVRIREVFQSIDLIRQCISLIPDGEIKVKIVGNPSGEYFTRLEQPR

GEVLYYVKANGTKFLERFRVRTPTFANIPALLHTLKGCQLADVPVLILTIDPCISCTER

Cthe3021 (SEQ ID NO: 28)
MAQQTINTISPNELLAYALRLKNANYRLVAISCTNAENGVEMSYSFDSGSDFTNL

RITVAPGDEIESISSIYSYSFLYENEIKELFGVNITGISPDYKDKLYRISVKTPFNMKE

GDKNG

Cthe3022 (SEQ ID NO: 29)
MNFSKKSPWILHYDGSSCNGCDIEVLACLTPLYDIERFGVINTGNPKHADILLITGS

INEQNKSVVKQLYEQMADPKVVVAVGICAATGGIFSECYNVSGGVDKIIPVDVYVPGCA

ARPEAIIDGVVKALGILEERQKYARKKDK

Cthe3023 (SEQ ID NO: 30)
MSQIIRLVLYIIAIIIVAPLLGGLLTGIDRVITARMQGRKGPSVLQPFYDVLKLFQKE

SIEVNTMHRFFVYISLIFVIFTTVIMLLGGDILLALFALTLGSIFFVLGGYASNSPYSTIGSER

ELLQMMAFEPMLLLAAIGLYYGDKSFFIKDIVTARIPSIVYLPGVFLGLLYVLTFKLRKSP

FDLSMSHHGHQEIVQGITTEYSGKDLAIIQITHWYETIIALALVYLFFAFRSPFSHVIAILAC

IIAFLLEIVVDNAFARAKWEFALKSTWIVTGVLASVNLIILSFFR

Cthe3024 (SEQ ID NO: 31)
MNAILILILFPLLASVTVLSVRKDAIRNIIVRIFAFITGILTLFVVCRYFKDGISLSIEN

RNIIDMTISLAEVLIAAYIIFTGIKNKKFIVSIFAAVQTALILWFEFTQKHGINVHSDIVFDRL

SAVMVLIVGCIGSLILIYTVGYMKWYHIHHEGYKERKSFFFSVIFLFLFAMFGLIFSNNLI

WMYFCWELTTLCSYLLIGYTRTPEAVNNSFHALAINLGGGLAFASAMVYIGTNFKTLEL

SALTAMKLELAVLIPVFLLCIAALTKSAQMPFSSWLLGAMVAPTPSSALLHSATMVKAG

VYLLIRLAPLLAGTTIGKVIALLGAVTFLASSIIAISKSDAKKILAYSTISNLGLIVTCAAIGT

QESLWAAILLLIFHSISKSLLFLTGGSVEHQIGSRNVEDMDILLQVSRRLSVYMIVGIAGM

FLAPFGMLISKWVAMKAFIDSKNILTVIILGYGSATTLFYWTKWMGKLVANANRKDHIK

HTFHIDEEIPIFIHAVLVVLSCFTFPLVSRYVLVPYLSGLFGPDVPIPIGTSDVNIMLIMLSM

LLILPISFIPIYKSDRRRIVPIYMAGENTGDNESFYGAFDEKRKVELHNWYMKNFFSVKKL

TFWSNLLCAVVILVGVVLLIGGITK

Cthe342 (SEQ ID NO: 32)
MQMVNVTIDNCKIQVPANYTVLEAAKQANIDIPTLCFLKDINEVGACRMCVVEV

KGARSLQAACVYPVSEGLEVYTQTPAVREARKVTLELILSNHEKKCLTCVRSENCELQR

LAKDLNVKDIRFEGEMSNLPIDDLSPSVVRDPNKCVLCRRCVSMCKNVQTVGAIDVTER

GFRTTVSTAFNKPLSEVPCVNCGQCINVCPVGALREKDDIDKVWEALANPELHVVQTA

PAVRVALGEEFGMPIGSRVTGKMVAALSRLGFKKVFDTDTAADLTIMEEGTELINRIKN

GGKLPLITSCSPGWIKFCEHNYPEFLDNLSSCKSPHEMFGAVLKSYYAQKNGIDPSKVFV

VSIMPCTAKKFEAQRPELSSTGYPDVDVVLTTRELARMIKETGIDFNSLPDKQFDDPMGE

ASGAGVIFGATGGVMEAAIRTVGELLSGKPADKIEYTEVRGLDGIKEASIELDGFTLKAA

VAHGLGNARKLLDKIKAGEADYHFIEIMACPGGCINGGGQPIQPSSVRNWKDIRCERAK

AIYEEDESLPIRKSHENPKIKMLYEEFFGEPGSHKAHELLHTHYEKRENYPVK

Cthe430 (SEQ ID NO: 33)
MDNREYMLIDGIPVEINGEKNLLELIRKAGIKLPTFCYHSELSVYGACRMCMVEN

EWGGLDAACSTPPRAGMSIKTNTERLQKYRKMILELLLANHCRDCTTCNNNGKCKLQD

LAMRYNISHIRFPNTASNPDVDDSSLCITRDRSKCILCGDCVRVCNEVQNVGAIDFAYRG

SKMTISTVFDKPIFESNCVGCGQCALACPTGAIVVKDDTQKVWKEIYDKNTRVSVQIAPA

-continued

VRVALGKELGLNDGENAIGKIVAALRRMGFDDIFDTSTGADLTVLEESAELLRRIREGKN

DMPLFTSCCPAWVNYCEKFYPELLPHVSTCRSPMQMFASIIKEEYSTSSKRLVHVAVMP

CTAKKFEAARKEFKVNGVPNVDYVLTTQELVRMIKESGIVFSELEPEAIDMPFGTYTGA

GVIFGVSGGVTEAVLRRVVSDKSPTSFRSLAYTGVRGMNGVKEASVMYGDRKLKVAV

VSGLKNAGDLIERIKAGEHYDLVEVMACPGGCINGGGQPFVQSEEREKRGKGLYSADKL

CNIKSSEENPLMMTLYKGILKGRVHELLHVDYASKKEAK

Cthe3003 (SEQ ID NO: 34)
MDSFLMKGYIKEANIDYSCSRGSMEDLPKWEFREIPKVPRAVMPSLSLEERKNNF

NEVELGLSEEVARKEARRCLKCGCSARFTCDLRKEASNHGIVYEEPIHDRPYIPKVDDHP

FIVRDHNKCISCGRCIAACAEIEGPGVLTFYMKNGRQLVGTKSGLPLRDTDCVSCGQCVT

ACPCAALDYRRERGKVVRAINDPKKTVVGFVAPAVRSLISNTFGVSYEEASPFMAGLLK

KLGFDKVFDFTAADLTIVEETTEFLSRIQNKGVMPQFTSCCPGWINFVEKRYPEIIPHLST

CKSPQMMMGATVKNHYAKLMGINKEDLFVVSIVPCLAKKYEAARPEFIHDGIRDVDAV

LTTTEMLEMMELADIKPSEVVPQEFDEPYKQVSGAGILFGASGGVAEAALRMAVEKLTG

KVLTDHLEFEEIRGFEGVKESTIDVNGTKVRVAVVSGLKNAEPIIEKILNGVDVGYDLIEV

MACPGGCICGAGHPVPEKIDSLEKRQQVLVNIDKVSKYRKSQENPDILRLYNEFYGEPNS

PLAHELLHTHYTPKHGDSTCSPERKKGTAAFDVQEFTICMCESCMEKGAENLYNDLSSK

IRLFKMDPFVQIKRIRLKETHPGKGVYIALNGKQIEEPMLSGNIPDESESE

Cthe3004 (SEQ ID NO: 35)
MKTLENHNRIKVTVNGREIEVYDNLTILQALLQEDIHIPHLCYDIRLERSNGNCGL

CVVTLISPDGERDVKACQTPIKEGMVICTNTPKLENYRKIRLEQLLSDHNADCVAPCVMT

CPANIDIQSYLRHVGNGDFEAAIRVIKERNPFPIVCGRVCPHTCESQCRRNLVDAPVAINY

VKRFAADWDMARPEPWTPEKKPPTGKKIAIVGAGPSGLSAAYYSAIKGHDVTVFERQPH

PGGMMRYGIPEYRLPKAILDKEIEMIKKLGVKIMTEKALGIHIRLEDLSKDFDAVYLAIGS

WQATPMHIEGEKLDGVWAGINYLEQVAKNVDIPLGDNVVVIGGGNTAIDCARTALRKG

AKSVKLVYRCTREEMPAAPYEVEEAIHEGVEMIFLMAPTKIIVKDGKKKLVCIRMQLGE

PDRSGRRRPVPIEGSEVEIDADTIIGAIGQSTNTQFLYNDLPVKLNKWGDIEVNGKTLQTS

EYNIFAGGDCVTGPATVI

Cthe0349 (SEQ ID NO: 36)
MPLVTSTEMFKKAYEGKYAIGAFNVNNMEIIQGITEAAKEVNAPLILQVSAGARK

YANHTYLVKLVEAAVEETGLPICLHLDHGDSFELCKSCIDGGFTSVMIDGSHLPFEENIKL

TKQVVDYAHSKGVVVEGELGRLAGIEDDVNVSEADAAFTDPDQAEEFVKRTGVDSLAI

AIGTSHGAYKFKGEAKLRFDILEEIEKRLPGFPIVLHGASSVIPEYVDMINKYGGDMPGA

KGVPEDMLRKAASMAVCKINIDSDLRLAMTATIRKYFAENPSHFDPRQYLGPARNAIKE

LVKHKIVNVLGCDGKA

Cthe1019 (SEQ ID NO: 37)
MDIQLKKSGIGVKEKKSKNHLLYSIKQNLFAYAMLIPTFVCMMCIHFIPMLQGIYL

SLLDLNQLTMTKFLNAPFIGLKNYYEILFDEKSLIRRGFWFALRNTAIYTVVVTFATFALG

IILAMLVNREFKGRGIVRTALLMPWVVPSYVVGMTWGFLWRQDSGLINIILCDILHILPE

KPYWLVGSNQIWAIIIPTIWRGLPLSMILMLAGLQSISPDYYEAADIDGANGWQKFWHIT

LPLLKPILAINVMFSLISNIYSFNIVSMMFGNGAGIPGEWGDLLMTYIQRNTFQMWRFGP

GAAALMIVMFFVLGIVALWYTLFKDDLVVK

-continued

Cthe0390 (SEQ ID NO: 38)
VDKFTKLDLNSITSNNRMNIFNCILEAKEINRAVIAKKVGLSIPAVMSITDDLIQKG

IIYVIGKGKSSGGKRPELLAVVPDRFFFVGVDVGRTSVRVVVMNNCRDVVYKVSKPTES

VEPDELINQITEMTMESINESKFPLDRVVGIGVAMPGLIERGTGRVIFSPNFGWNNIALQD

ELKKHLPFNVLVENANRALVIGEIKNTQPNPTSCIVGVNLGYGIGSAIVLPNGLYYGVSG

TSGEIGHIIVENHGSYCSCGNYGCIESIASGEAIAREARIAIANKIQSSVFEKCEGDLKKIDA

KMVFDAAKEGDHLAQSIVEKAADYIGKGLAITINMLDPEQIILCGGLTLSGDFFIDMIKK

AVSKYQMRYAGGNVKIVVGKSGLYATAIGGAWIVANNIDFLSSN

Cthe2938 (SEQ ID NO: 39)
MYYIGIDLGGTNIAVGLVNEEGKILHKDSVPTLRERPYQEIIKDMAMLTLKVIKD

ADVSIDQVKSIGVGSPGTPNCKDGILIYNNNLNFRNVPIRSEIQKYIDLPVYLDNDANCAA

LAESVAGAAKGANTSVTITLGTGIGGGVVIDGKIYSGFNYAGGELGHTVLMMDGEPCTC

GRKGCWEAYASATALIRQARKAAEANPDSLINKLVGGDLSKIDAKIPFDAAKQGDKTGE

MVVQQYIRYIAEGLINMINIFMPEVLVIGGGVCKEGEYLLKPLRELIKQGVYSKEDIPQTE

LRTAQMGNDAGIIGAAMLGKEC

Cthe0217 (SEQ ID NO: 40)
MERIKFDYSKALPFVSEREVAYFENFVRSAHDMLHNKTGAGNDFVGWVDLPVN

YDREEFARIKAAAEKIKSDSDALVVIGIGGSYLGARAAIEMLSHSFHNLMPKSKRNAPEI

YFVGNNISSTYIADLLEVIEGKEISVNVISKSGTTTEPAIAFRIFKEYMENKYGKDGASKRI

YATTDKEKGALRKLATEEGYETFVVPDDIGGRFSVLTAVGLLPIAVAGIDIDSMMKGAA

DARELYSNPNLMENDCYKYAAVRNALYRKNKTIEIMVNYEPSLHYFTEWWKQLYGESE

GKDQKGIFPAGVDFTTDLHSMGQYIQDGLRNIFETVIRVEKPRKNIVIKEEKDNLDGLNFI

AGKDVDYVNKKAMEGTVLAHTDGGVPNLVVTVPELSAYYFGNMVYFFEKACGISGYL

LGVNPFDQPGVEAYKKNMFALLGKPG YEEQRKKLEERL

Cthe1261 (SEQ ID NO: 41)
MSSVRTIGVLTSGGDAPGMNAAIRSVVRTGLYYGFKVLGIRKGFNGLINGDIEEL

TARSVGDIIHRGGTILQTARSPQFKTEEGLKKAMSMAKVFGIDALVVIGGDGSYRGARDI

SKLGLNVIGIPGTIDNDIGCTDYTIGFDTAMNTVQDAIDKIRDTAYSHERCSVLEVMGRH

AGYIAVNVSISGGAEAVVLPEKPFDMDTDVIKPIIEGRNRGKKHYLVIVAEGGEGKAIEIA

KEITEKTGIEARATILGHIQRGGSPTVYDRVMASQMGAKAVEVLMENKRNRVIVFKDNQ

IGDMDLEEALQVKKTISEDLIQLSKILAL

*T. saccharolyticum* proteins
Reaction 6b, EC or0411 (SEQ ID NO: 42)
MSYIPNENRYEKMIYRRCGRSGIMLPAISLGLWHNFGGYDVFENMREMVKKAFD

LGITHFDLANNYGPPPGSAEENFGKILRTDLRGYRDELLISTKAGYTMWPGPYGDWGSR

KYLLSSLDQSLKRMGIDYVDIFYSHRRDPNTPLEETMSALAQAVRQGKALYVGISNYNA

EDTKKAAEILRQLGTPLLINQPSYSMFNRWIEDGLTDVLEEEGVGSIAFSPLAQGLLTDK

YLNGVPDDSRAVRKNTSLRGNLTEENINKVRELKKIADKRGQSIAQMALAWDLRKVTS

VIIGASRVSQIEENVKALDNLEFSHEELKQIDEILSK

EC4.2.3.4 or2316 (SEQ ID NO: 43)
LNIALIAHDMKKSIMVDFAIAYKEILKKCNIYATGATGQLVEEATGIKVNKFLPGP

MGGDQQIGAMIAENNMDLVIFLRDPLTAQPHEPDILALLRVCDVHSIPLATNLATAEVLI

KGLDAGFLEWRDAVK

EC5.3.1.1 or2687 (SEQ ID NO: 44)
LRRPIIAGNWKMYMTPSEAVNLVNELKPLVSGAEAEVVVIPPFVDLVDVKKAID

ASNIKLGAQNMHWEEKGAFTGEVSPIMLKEIGVEYVVIGHSERRQYFAETDETVNKKVK

SALSHGLKPIVCVGESLSQREAGEAFNVVREQTKKALDGIKSEDVLNVVIAYEPIWAIGT

GKTATSKDANDVIKVIRETIADIYSIDIANEVRIQYGGSVKPDNAKELMSESDIDGALVGG

ASLKAQDFAKIVNY

Reaction 7 (gldA) or104 (SEQ ID NO: 45)
MYMKTNFTYEMPTEIFGPGTLGKLATVKLPGKKALLVIGSGNSMRRHGYLDRVV

NYLKQNGVDYVVYDKILPNPIAEHVAEGAKVAKDNGCDFVIGLGGGSTIDSSKAIAVMA

KNPGDYWDYVSGGSGKGMEVKNGALPIVAIPTTAGTGTESDPWAVVTKTETNEKIGFG

CKYTYPTLSIVDPELMVSIPPKFTAYQGMDAFFHSVEGYLATVNQPGSDVLALQSISLITE

NLPKAVADGNNMEARTALAWASTAAGIVESLSSCISHHSLEHALSAYHPEIPHGAGLIML

SVSYFSFMASKAPERFVDIAKAMGEEIVGNTVEEQAMCFINGLKKLIRNIGMEDLSLSSF

GVTEDEATKLAKNAMDTMGGLFNVDPYKLSLDEVVSIYKNCF

EC2.3.1.54 (SEQ ID NO: 46)
VDDKKVFDHLFILTDDTGMMQHSVGSVPDPKYGYTTDDNGRALIACAMMYEK

YKDDAYINLIKKYLSFLMYAQEDDGRFRNFMSFDRKFIDEDFSEDCFGRCMWALGYLIN

SNIDERVKLPAYKMIEKSLLLVDTLNYIRGKAYTLIGLYYIYNSFKNLDKDFVRKKMDKL

AHDIVEEYEKNSSEDWQWFEDVVSYDNGVIPLSLLKYFSIAKDEEVLDIALKTIDFLDSV

CFKNGYFKAVGCKGWYRKGKDIAEYDEQPVEAYTMALMYIEAYKLTGDEKYKKRAID

CDKWFYGKNSKGLSLYDEDSGGCSDGITEDGVNSNEGAESLISIMISHCAIDQLK

EC2.3.1.8 (SEQ ID NO: 47)
MKTSELLAMVVEKGASDLHITVGVPPVLRINGQLIKLNLPQLTPQDTEEITKDLLS

SDELKKLEDMGDIDLSYSVKGLGRFRINAYKQRGTYSLAIRSVALRIPTIDELGLPEVIKE

LALKTRGLIIVTGPTGSGKSTTLASMIDLINEERNCHILTLEDPIEYLHKHKKSIVNQREIG

HDAASYASALRAALREDPDVILVGEMRDLETIQIAITAAETGHLVLSTLHTIGSAKTIDRII

DVFPPHQQQQIKVQLSNVLEGIVSQQLLPKIDNSGRVVAVEVMIATPAIRNLIREGKSFQI

QSMVQTGNKFGMVTMDMWISQLLKRNLISMDDALTYCVDRENFSRLVV

EC 2.7.2.1 (SEQ ID NO: 48)
MIKKKLGDLLVEVGLLDESQLNNAIKIQKKTGEKLGKILVKEGYLTEEQIIEALEF

QLGIPHIDMKKVFIDANVAKLIPESMAKRHVAIPIKKENNSIFVAMADPLNIFAIDDIKLVT

KLDVKPLIASEDGILKAIDRVFGKEEAERAVQDFKKELSHDSAEDDGNLLRDISEDEINN

APAVRLVNSIIEQAVKNRASDVHIEPTENDLRIRFRIDGELHEAMRVFKSTQGPVITRIKIM

ANMNIAERRIPQDGKIEMNAGGKNIDIRVSSLPTIYGEKLVLRILDKSGYIITKDKLGLGN

DDLKLFDNLLKHPNGIILLTGPTGSGKTTTLYAMLNELNKPDKNIITVEDPVEYTLEGLN

QVQVNEKAGLTFASALRSILRQDPDIIMIGEIRDRETAEIAIRSSITGHLVLSTLHTNDSAG

AITRLIDMGIEPYLVSSSVVGVIAQRLARKICDNCKIEYDASKREKIILGIDADESLKLYRS

KGCAVCNKTGYRGRVPIYEIMMMTPKIKELTNEKAPADVILNEAVSNGMSTLKESAKKL

VLSGVTTVDEMLRLTYDDAY

EC 1.2.7.1 or0047 (SEQ ID NO: 49)
MSKVMKTMDGNTAAAHVAYAFTEVAAIYPITPSSPMAEHVDEWSAHGRKNLFG

QEVKVIEMQSEAGAAGAVHGSLAAGALTTTFTASQGLLLMIPNMYKIAGELLPGVFHVS

ARALASHALSIFGDHQDVMACRQTGFALLASGSVQEVMDLGSVAHLAAIKGRVPFLHFF

DGFRTSHEYQKIEVMDYEDLRKLLDMDAVREFKKRALNPEHPVTRGTAQNPDIYFQERE

ASNRYYNAVPEIVEEYMKEISKITGREYKLFNYYGAPDAERIVIAMGSVTETIEETIDYLL

KKGEKVGVVKVHLYRPFSFKHFMDAIPKTVKKIAVLDRTKEAGAFGEPLYEDVRAAFY

DSEMKPIIVGGRYGLGSKDTTPAQIVAVFDNLKSDTPKNNFTIGIVDDVTYTSLPVGEEIE

TTAEGTISCKFWGFGSDGTVGANKSAIQIIGDNTDMYAQAYFSYDSKKSGGVTISHLRFG

KKPIRSTYLINNADFVACHKQAYVYNYDVLAGLKKGGTFLLNCTWKPEELDEKLPASM

KRYIAKNNINFYIINAVDIAKELGLGARINMIMQSAFFKLANIIPIDEAVKHLKDAIVKSYG

HKGEKIVNMNYAAVDRGIDALVKVDVPASWANAEDEAKVERNVPDFIKNIADVMNRQ

EGDKLPVSAFVGMEDGTFPMGTAAYEKRGIAVDVPEWQIDNCIQCNQCAYVCPHAAIR

PFLLNEEEVKNAPEGFTSKKAIGKGLEGLNFRIQVSVLDCTGCGVCANTCPSKEKSLIMK

PLETQLDQAKNWEYAMSLSYKENPLGTDTVKGSQFEKPLLEFSGACAGCGETPYARLV

TQLFGDRMLIANATGCSSIWGGSAPSTPYTVNKDGHGPAWANSLFEDNAEFGFGMALA

VKQQREKLADIVKEALELDLTQDLKNALKLWLDNFNSSEITKKTANIIVSLIQDYKTDDS

KVKELLNEILDRKEYLVKKSQWIFGGDGWAYDIGFGGLDHVLASGEDVNVLVFDTEVY

SNTGGQSSKATPVGAIAQFAAAGKGIGKKDLGRIAMSYGYVYVAQIAMGANQAQTIKA

LKEAESYPGPSLIIAYAPCINHGIKLGMGCSQIEEKKAVEAGYWHLYRYNPMLKAEGKN

PFILDSKAPTASYKEFIMGEVRYSSLAKTFPERAEALFEKAEELAKEKYETYKKLAEQN

EC 1.1.1.2
Or180 (SEQ ID NO: 50)
MSKVAIIGSGFVGATSAFTLALSGTVTDIVLVDLNKDKAIGDALDISHGIPLIQPVN

VYAGDYKDVKGADVIVVTAGAAQKPGETRLDLVKKNTAIFKSMIPELLKYNDKAIYLIV

TNPVDILTYVTYKISGLPWGRVFGSGTVLDSSRFRYLLSKHCNIDPRNVHGRIIGEHGDTE

FAAWSITNISGISFNEYCSICGRVCNTNFRKEVEEEVVNAAYKIIDKKGATYYAVAVAVR

RIVECILRDENSILTVSSPLNGQYGVKDVSLSLPSIVGRNGVARILDLPLSDEEVEKFRHSA

SVMADVIKQLDI

EC 2.3.1.54 (SEQ ID NO: 51)
MINEWRGFQEGKWQKTIDVQDFIQKNYTLYEGDDSFLEGPTEKTIKLWNKVLEL

MKEELKKGVLDIDTKTVSSITSHDAGYIDKDLEEIVGLQTDKPLKRAIMPYGGIRMVKKA

CEAYGYKVDPKVEEIFTKYRKTHNDGVFDAYTPEIRAARHAGIITGLPDAYGRGRIIGDY

RRVALYGIDRLIEEKEKEKLELDYDEFDEATIRLREELTEQIKALNEMKEMALKYGYDIS

KPAKNAKEAVQWTYFAFLAAIKEQNGAAMSLGRVSTFLDIYIERDLKEGTLTEKQAQEL

MDHFVMKLRMVRFLRTPDYNELFSGDPVWVTESIGGVGVDGRPLVTKNSFRILNTLYN

LGPAPEPNLTVLWSKNLPENFKRFCAKVSIDTSSIQYENDDLMRPIYNDDYSIACCVSAM

KTGEQMQFFGARANLAKALLYAINGGIDERYKTQVAPKFNPITSEYLDYDEVMAAYDN

MLEWLAKVYVKAMNIIHYMHDKYAYERSLMALHDRDIVRTMAFGIAGLSVAADSLSAI

KYAKVKAIRDENGIAIDYEVEGDFPKFGNDDDRVDSIAVDIVERFMNKLKKHKTYRNSIP

TLSVLTITSNVVYGKKTGATPDGRKAGEPFAPGANPMHGRDTKGAIASMNSSKIPYDSSL

DGISYTFTIVPNALGKDDEDKINNLVGLLDGYAFNAGHHININVLNRDMLLDAMEHPEK

YPQLTIRVSGYAVNFNKLTREQQLEVISRTFHESM

-continued

EC1.2.7.1 (following four proteins)
Or1545 (SEQ ID NO: 52)
MVITVCVGSSCHLKGSYDVINKLKEMIKNYGIEDKVELKADFCMGNCLRAVSVK

IDGGACLSIKPNSVERFFKEHVLGELK

Or1546 (SEQ ID NO: 53)
MSVINFKEANCRNCYKCIRYCPVKAIKVNDEQAEIIEYRCIACGRCLNICPQNAKT

VRSDVERVQSFLNKGEKVAFTVAPSYPALVGHDGALNFLKALKSLGAEMIVETSVGAM

LISKEYERYYNDLKYDNLITTSCPSVNYLVEKYYPDLIKCLVPVVSPMVAVGRAIKNIHG

EGVKVVFIGPCLAKKAEMSDFSCEGAIDAVLTFEEVMNLFNTNKIGVECTKENLEDVDS

ESRFKLYPIEGKTMDCMDVDLNLRKFISVSSIENVKDILNDLRAGNLHGYWIEANACDG

GCINGPAFGKLESGIAKRKEEVISYSRMKERFSGDFSGITDFSLDLSRKFIDLSDRWKMPS

EMEIKEILSKIGKFSVEDELNCGACGYDTCREKAIAVFNGMAEPYMCLPYMRGRAETLS

NIIISSTPNAIIAVNNEYEIQDMNRAFEKMFLVNSAMVKGEDLSLIFDISDFVEVIENKKSIF

NKKVSFKNYGIIALESIYYLEEYKIAIGIFTDITKMEKQKESFSKLKRENYQLAQQVIDRQ

MKVAQEIASLLGETTAETKVILTKMKDMLLNQGDDE or1547 (SEQ ID NO: 54)
MSHYIDIAHASLNKYDEELCGDSVQIIRKKDYAMAVMADGLGSGVKANILSTLT

TRIVSKMLDMGSELRDVVETVAETLPICKERNIAYSTFTVVSIYGDNAHLVEYDNPSVFY

FKNGVHKKVDRKCVEIGDKKIFESSFKLDLNDALIVVSDGVIHAGVGGILNLGWQWDN

VKQYLSKVLEVYSDASDICSQLITTCNNLYKNRPGDDTTAIVIKVNESKKVTVMVGPPIL

KNMDEWVVKKLMKSEGLKVVCGGTAAKIVSRILNKDVITSTEYIDPDIPPYAHIDGIDLV

TEGVLTLRKTVEIFKEYMNDKDSNLLRFSKKDAATRLFKILNYATDVNFLVGQAVNSAH

QNPDFPSDLRIKVRIVEELISLLERLNKNVEVNYF or1548 (SEQ ID NO: 55)
LFKFNTDVQMLKYEVLYNVAKLTLEDRLEDEYDEIPYEIIPGTKPRFRCCVYKER

AIIEQRTKVAMGKNLKRTMKHAVDGEEPIIQVLDIACEECPIKRYRVTEACRGCITHRCT

EVCPKGAITIINKKANIDYDKCIECGRCKDACPYNAISDNLRPCIRSCSAKAITMDEELKA

AINYEKCTSCGACTLACPFGAITDKSYIVDIIRAIKSGKKVYALVAPAIASQFKDVTVGQI

KSALKEFGFVDVIEVALGADFVAMEEAKEFSHKIKDIKVMTSSCCPAFVAHIKKSYPELS

QNISTTVSPMTAISKYIKKHDPMAVTVFIGPCTAKKSEVMRDDVKGITDFAMTFEEMVA

VLDAAKIDMKEQQDVEVDDATLFGRKFARSGGVLEAVVEAVKEIGADVEVNPVVCNG

LDECNKTLKIMKAGKLPNNFIEGMACIGGCIGGAGVINNNVNQAKLAVNKFGDSSYHKS

IKDRISQFDTDDVDFHVDSGEDESSETSEKEA

EC 1.2.1.43
or2328 (SEQ ID NO: 56)
MDKVRITIDGIPAEVPANYTVLQAAKYAKIEIPTLCYLEEINEIGACRLCVVEIKGV

RNLQASCVYPVSDGMEIYTNTPRVREARRSNLELILSAHDRSCLTCVRSGNCELQDLSRK

SGIDEIRFMGENIKYQKDESSPSIVRDPNKCVLCRRCVATCNNVQNVFAIGMVNRGFKTI

VAPSFGRGLNESPCISCGQCIEACPVGAIYEKDHTKIVYDALLDEKKYVVVQTAPAVRVA

LGEEFGMPYGSIVTGKMVSALKRLGFDKVFDTDFAADLTIIEEGNELLKRLNEGGKLPMI

TSCSPGWINYCERYYPEFIDNLSTCKSPHMMMGAIIKSYFAEKEGIDPKDIFVVSIMPCTA

KKYEIDRPQMIVDGMKDVDAVLTTRELARMIKQSGIDFVNLPDSEYDNPLGESSGAGVIF

-continued

```
GATGGVMEAALRTVADIVEGKDIENFEYEEVRGLEGIKEAKIDGGKEIKIAVANGTGNA

KKLLDKIKNGEAEYHFIEVMGCPGGCIMGGGQPIHNPNEKDLVRKSRLKAIYEADKDLPI

RKSHKNPMITKLYEEFLISPLGEKSHHLLHTTYSKKDLYPMND

EC 4.1.2.13
or0260 (SEQ ID NO: 57)
LNDILVKARNNKYAIGGFNFNFYDDALGIISAAYELKSPIILMASEGCVKFLGVKH

IVNFVNQLKDEYNIPIILHLDHGKDIEIIKNCIDNKFDSIMYDGSLLNFEENIKNTKFIADLC

HDKGMTIEGELGRISGAEENIENSEDVFTDPDSVAEFTERSDVDSLAVAIGNAHGLYKGR

PRLDFERLSKINKISKVPLVLHGGTGIPYEDIQKAIQLGISKVNVGTEIKIAYIKSIKKHLETI

NDNDIRHLVSMVQNDIKELVKQYLDIFGTANKYSQLQSM or0330 (SEQ ID NO: 58)
MLVTGIELLKKANEEGYAVGAFNTSNLEITQAIVEAAEEMRSPAIIQVSEGGLKY

AGIETISAIVRTLATKASVPIALHLDHGTDFNNVMKCLRNGWTSVMMDASKLPLEKNIE

VTKNVVTIAHGMGVSVEAEIGKIGGTEDNVTVDEREASMTDPDEAFKFAKETGVDYLAI

SIGTAHGPYKGEPKLDFDRLVKIKEMLKMPIVLHGASGVPEADIRKAVSLGVNKINIDTDI

RQAFAARLRELLKNDEEVYDPRKILGPCKEAMKEVIKNKM RMFGSEGRA or0272 (SEQ ID NO: 59)
MITGDQLLIKQINKSIVLNTIRKKGLISRADLANITGLNKSTVSSLVDELIKEGFVEE

EGPGESKGGRKPIMLMINSLAGCVIGVDLDVNYILVILTDILANILWQKRINLKLGESKED

IISKMLELIDEAIKNSPNTVKGILGIGIGVPGITDYKRGVVLKAPNLNWENVELKKMVEER

FNLKVYIDNEANTGAIGEKWFGGGRNAKNFVYVSAGIGIGTGIIINNELYRGSNGLAGEM

GHMTIDINDHMCSCGNRGCWENYASEKSLFRYIKERLEAGQEDDFIDSENIDSLDINDIA

GYAELGSKLAIDAINEISKNLSVGIVNIVNTFNPDLVLIGNTLSAIGDMLIDAVKEYVREK

CLVSRYNDIAIEISKLGMLERAIGAVTLVISEVFSYPGL or1389 (SEQ ID NO: 60)
MTNVLNFDYSNALNFVNEHEISYLEKQALLSLDMVLNKTAQGSDFLGWVDLPK

DYDKEEFARIKKAAEKIKSDSDALVVIGIGGSYLGARAAIEMLTHSFYNVLPQSVRKAPEI

YFAGNSISSTYLQDLLEILEGKDVSINVISKSGTTTEPAIAFRVFRDFLEKKYGKEEAKSRI

YVTTDRQKGALKKLADEEGYETFVIPDDVGGRYSVLTAVGLLPIAAAGIDIDEMMKGA

YDASIVFKKPDIKENLSMQYAVLRNALYRKGKSVEILVNYEPRLHYFSEWWKQLYGESE

GKDHKGIYPASVDFSTDLHSMGQFIQDGSRIMFETVINVEKPLKEITINEDKDNVDGLNFL

TGKTVDLVNKKAFEGTVLAHNDGGVPNLIVNVPEISAYNFGYLVYFFEMACGISGYLNG

VNPFDQPGVEAYKKNMFALLGKPGYEKEKEELEKRLKR or2875 (SEQ ID NO: 61)
MYNIQLDSPNLGDKEKDYLVKCIESGYVSTVGPFVPEFERRFAEFLNVNHCVSVQ

SGTAALYMALYELGIKDGDEVIVPAITFVATVNPIVYCGATPVFVDVDKDTWNIDPKEIE

KAITPKTKAIIPVHLYGNPCDMDKIMEIAKENNIYVIEDATESLGALYKGRMTGTIGHIGC

FSFNGNKVITTGGGGMVASNNEDWVSHIRFLVNQARDMTQGYFHTEIGFNYRMTNLEA

SLGIAQLERLAGFLEKKRMYFEIYKKIFNGIEEISLQTEYEGAKSSDWLSSVKIDCKKVGM

TIHQIQDELKRRGIPTRRIFNPIVDLPPYKKYKKGSYSNSYEIYENGLNLPSSTLNTYEDVK

YVAKTLLDILSIKKR
```

T. saccharolyticum pdu genes or228-or200
or228
SEQ ID NO: 62:
MLAIERRKRIMRLIQENQSVLVPELSKLFNVTEETIRRDLEKLEAEGLLKRTYGGA

VINENSSADIPLNIREITNIESKQAISMKVAEYIEDGDTLLLDSSSTVLQVAKQLKFKKKLT

VITNSEKIILELANAKDCKVISTGGVLKQNSMSLIGNFAEDMIKNFCVDKAIISSKGFDMT

NGITESNEMEAEIKKAMANSAEKVFLLLDHNKFDKSSFVKMFDLDKIDYLFTDRKLSLE

WEEFLKKHNIDLIYC

SEQ ID NO: 63:
ATGCTTGCGATAGAACGAAGGAAGAGGATAATGAGGCTTATACAGGAAAATC

AAAGCGTTTGGTGCCTGAGTTAAGTAAATTGTTTAATGTGACAGAGGAAACTATAAG

GAGAGATTTAGAGAAACTTGAAGCAGAAGGGCTTTTAAAGAGGACTTATGGTGGTG

CTGTTATAAATGAAAATTCAAGTGCTGATATCCCCTTAAATATAAGGGAAATAACGA

ATATAGAAAGCAAACAGGCCATAAGTATGAAGGTTGCCGAATACATTGAAGATGGT

GATACACTTTTGCTTGATTCAAGCTCTACAGTTCTTCAAGTAGCAAAGCAATTAAAA

TTCAAAAAGAAGCTTACAGTCATAACAAATTCGGAAAAGATAATATTAGAATTAGC

AAATGCGAAAGATTGCAAAGTCATTTCTACAGGAGGAGTATTGAAGCAAAATTCTAT

CTTCGCTAATTGGAAATTTCGCGGAAGATATGATAAAAAATTTCTGTGTAGATAAAGC

CATAATATCATCAAAAGGTTTTGACATGACAAATGGCATTACAGAGTCAAACGAAAT

GGAAGCTGAAATAAAAAAGCCATGGCCAACTCGGCAGAAAAAGTGTTTTTACTTC

TTGATCACAACAAATTTGACAAGTCATCGTTCGTCAAGATGTTTGACTTAGATAAAA

TCGATTATCTATTTACCGATAGAAAGCTGTCTTTAGAATGGGAAGAATTCTTGAAAA

AACACAATATTGATTTAATCTATTGTTAG or277
SEQ ID NO: 64:
VYSEYEVKKQICEIGKRIYMNGFVAANDGNITVRIGENEIITTPTGVSKGFMTPDM

LLNINLNGEVLKSSGDYKPSTEIKMHLRVYRERPDVKSVIHAHPPFGTGFAIVGIPLIKPI

MPEAVISLGCVPIAEYGTPSTEELPDAVSKYLQNYDALLLENHGALTYGPDLISAYYKME

SLEFYAKLTFISTLLGGPKELSDSQVEKLYEIRRKFGLKGRHPGDLCSTLGCSTNSAKSND

DDISELVNVITKKVLEQLKYN

SEQ ID NO: 65:
GTGTATTCTGAATATGAGGTAAAAAAACAGATCTGCGAAATAGGAAAGAGAA

TCTACATGAATGGGTTTGTGGCAGCGAATGACGGCAATATCACCGTTAGGATTGGTG

AAAATGAAATAATAACGACGCCTACCGGTGTCAGCAAAGGTTTCATGACTCCAGAC

ATGCTATTAAATATTAATTTAAACGGTGAAGTATTAAAATCTTCAGGCGACTACAAA

CCGTCCACAGAAATAAAGATGCATCTTAGAGTCTATAGAGAAAGGCCAGATGTCAA

ATCAGTCATACATGCACATCCACCATTTGGCACAGGTTTTGCTATTGTAGGGATCCC

GCTTACAAAGCCAATAATGCCAGAAGCAGTTATATCTTTAGGCTGTGTGCCGATAGC

CGAATACGGGACGCCTTCTACAGAAGAGCTGCCAGATGCCGTCTCTAAATATTTGCA

AAATTACGATGCGCTTTTATTAGAAAATCATGGTGCGTTGACATACGGTCCTGATTT

AATTAGCGCATACTACAAGATGGAATCACTTGAATTTTACGCAAAATTGACATTTAT

TTCTACACTTCTCGGAGGTCCAAAAGAATTATCAGATAGCCAAGTAGAAAAGCTTTA

-continued

```
TGAAATTAGGAGAAAATTCGGTTTAAAAGGAAGACATCCAGGCGATTTGTGCAGTA

CATTAGGATGCAGCACAAATTCTGCAAAATCGAATGATGATGACATTTCTGAACTTG

TGAATGTTATCACTAAGAAAGTATTAGAACAATTGAAATACAATTAA
``` or226
SEQ ID NO: 66:
```
MKHSKRFEVLGKRPVNQDGFINEWPEKGFIAMCSPNDPKPSIKIENDKIVEMDGK

RREDFDFIDLFIADHAINIYQAEKSMKMNSLDIAKMLVDINVERKTIIKVVSGLTPAKIME

VVNHLNVVEMMMAMQKMRARKIPANQSHITNLKDNPVQIAADAAECALRGFREEETT

VGVTKYAPFNAIALLIGSQALKRGVLTQCAVEEATELELGMRGFTTYAETISVYGTESVF

IDGDDTPYSKAFLASAYASRGLKMRFTSGTGSEVLMGNAEGKSMLYLEIRCIMVTKGAG

VQGLQNGAISCIGITSSVPSGIRAVLAENLIASMLDLEVASGNDQTFTHSDIRRTARTMMQ

FLPGTDFIFSGYSGTPNYDNMFAGSNFDAEDFDDYNVLQRDLMVDGGLRPVKEEDVVE

VRRKAAKALQDVFRELNLGVVTDEEVEAAAYAHGSKDMPERDVLSDLESIDEMMKKGI

TGIDIVKALYRSGHEDIAENILNMLKQRISGDYLQTSAILDEDFNVISAINCPNDYLGPGT

GYRIDKDRWEEIKNIPYTINPDNL
```

SEQ ID NO: 67:
```
ATGAAACATTCTAAGCGATTTGAGGTTCTCGGCAAAAGACCTGTAAATCAGG

ATGGATTTATAAATGAATGGCCAGAAAAAGGCTTCATAGCAATGTGTAGTCCCAATG

ATCCTAAGCCATCAATAAAGATTGAAAACGACAAGATCGTTGAGATGGATGGGAAG

AGAAGAGAAGACTTTGATTTTATAGATTTATTCATAGCTGATCACGCTATAAATATTT

ATCAGGCTGAGAAATCCATGAAAATGAACTCGCTTGATATAGCCAAAATGCTTGTAG

ATATAAATGTAGAGAGAAAGACTATAATAAAAGTAGTTTCGGGACTTACACCTGCC

AAAATAATGGAAGTTGTAAATCATCTTAATGTCGTTGAAATGATGATGGCTATGCAG

AAAATGCGAGCAAGAAAGATTCCGGCTAATCAATCACATATTACAAATCTTAAAGA

TAATCCTGTGCAGATTGCAGCGGATGCTGCCGAATGTGCTTTAAGAGGTTTTAGGGA

AGAAGAGACCACCGTAGGAGTGACAAAATATGCTCCGTTTAATGCAATAGCGTTATT

GATAGGGTCTCAGGCATTAAAAAGAGGCGTGCTTACTCAATGTGCTGTTGAGGAGGC

GACGGAACTTGAATTAGGCATGAGGGGATTTACCACATACGCTGAGACTATATCTGT

TTATGGAACTGAAAGTGTTTTTATAGATGGTGACGATACACCTTACTCCAAAGCATT

CCTTGCTTCTGCTTATGCGTCAAGAGGATTGAAAATGAGGTTTACGTCAGGTACAGG

TTCAGAAGTTCTTATGGGAAATGCAGAGGGTAAATCGATGTTGTACCTGGAAATCAG

GTGCATCATGGTTACAAAAGGTGCAGGAGTGCAGGGGCTTCAAAATGGTGCAATAA

GCTGTATAGGCATAACTAGCTCAGTTCCTTCAGGTATAAGGGCGGTGCTGGCTGAAA

ACCTTATAGCATCTATGCTTGATTTAGAGGTAGCATCAGGCAATGATCAGACTTTTA

CACATTCAGACATAAGAAGGACAGCAAGGACTATGATGCAGTTTTTACCCGGTACTG

ATTTCATATTTTCAGGTTACAGTGGAACGCCTAATTATGACAATATGTTTGCAGGTTC

CAATTTTGATGCAGAAGATTTTGATGACTACAATGTACTGCAAAGGGATTTAATGGT

AGATGGAGGGTTAAGGCCTGTAAAAGAAGAAGATGTGGTAGAAGTGAGGCGAAAG

GCAGCTAAAGCTTTGCAGGATGTATTTAGAGAGTTAAATCTTGGAGTAGTTACAGAT

GAAGAAGTAGAAGCAGCAGCATATGCACACGGCAGCAAAGATATGCCTGAAAGAG

ATGTTTTGTCTGACCTTGAATCAATCGATGAGATGATGAAAAGAGGGATTACAGGCA

TTGACATCGTAAAGGCTTTATATAGATCTGGACATGAGGATATAGCGGAAAACATTT
```

```
-continued
TAAACATGTTAAAACAGCGCATATCTGGAGACTATTTGCAGACATCAGCTATTCTTG

ATGAAGATTTTAATGTTATAAGCGCCATAAATTGTCCAAATGATTACTTAGGACCTG

GAACAGGATATAGGATTGATAAAGATAGATGGGAAGAGATAAAGAATATTCCTTAC

ACCATTAATCCTGACAATTTGTAA or225
SEQ ID NO: 68:
MYVDEELLKEITKRVIEELNNKHKTDNVPSYFIENGVAYKGKNIEEVVIGVGPAF

GKHIKKTINGLDHRDVIKEIIAGIEEEGMVHRIVRVLKTSDVAFIGKEAALLSGSGIGIGIQ

SKGTTVIHQKDLYPLSNLELFPQAPLLNLELYREIGKNAARYAKGMMVKPILIQNDYMV

RPKYQVKAAIMHIKETEKILKNAQSIQLTIDL

SEQ ID NO: 69:
ATGTACGTAGATGAAGAACTGTTAAAAGAAATTACTAAACGTGTTATAGAAG

AATTAAATAATAAGCATAAAACTGATAATGTGCCTTCGTATTTTATTGAAAATGGAG

TTGCCTATAAGGGTAAAAATATAGAGGAAGTCGTCATTGGTGTTGGGCCTGCATTTG

GAAAGCATATAAAAAAGACTATAAATGGCCTTGACCATAGAGATGTCATAAAAGAA

ATAATTGCAGGCATCGAAGAAGAAGGTATGGTTCATAGAATTGTAAGAGTTCTAAA

GACTTCTGATGTGGCGTTCATAGGCAAAGAAGCTGCTTTATTAAGCGGATCGGGAAT

AGGCATAGGCATACAATCAAAAGGTACTACAGTGATTCATCAAAAGATTTATATCC

TTTAAGCAATTTAGAACTGTTTCCACAAGCTCCACTGCTAAATTTAGAATTATACAG

GGAAATAGGCAAAAATGCGGCGAGATATGCTAAAGGCATGATGGTAAAGCCTATTT

TGATTCAAAATGATTACATGGTGAGACCTAAATACCAAGTGAAAGCTGCTATAATGC

ATATAAAAGAGACGGAAAAGATATTGAAAAATGCTCAATCAATCCAATTGACGATA

GACTTGTAA or224
SEQ ID NO: 70:
MEEYPLSKSAFDKLVTKTGKHLNEINIENVMKGNVKPDDIKISKEVLLMQGQIAE

RYGRHQMKENFTRASELTDVPDEKILEIYESLRPFRSTKEELINLAYELRDKYNAINCANL

ILEAAEVYEKRNILKT

SEQ ID NO: 71:
ATGGAAGAATATCCGCTATCAAAAAGTGCTTTTGATAAATTGGTGACAAAAA

CAGGCAAACATTTGAATGAAATAAATATTGAAAATGTAATGAAGGGAAACGTAAAA

CCCGATGATATCAAGATATCCAAAGAAGTGCTTTTAATGCAAGGGCAAATTGCAGA

AAGATACGGCAGGCATCAGATGAAGGAGAATTTCACAAGAGCATCGGAGCTTACAG

ATGTTCCAGATGAAAAGATTTTGGAAATATATGAGAGCTTAAGGCCGTTTAGATCTA

CAAAGGAAGAGCTTATAAATCTTGCCTATGAATTAAGAGATAAGTACAATGCCATTA

ACTGTGCAAACTTGATACTTGAGGCTGCTGAAGTATATGAAAAAAGAAATATTTTGA

AAACTTAA or223
SEQ ID NO: 72:
MKLIAGVDIGNSTTEVCIAAIKDDNTLEFLSSSLTATTGVKGTVDNVTGVINGLTE

ALKKIGKNIRDLSLIRINEAAPVVCGAAMETITETVITGSTMIGHNPSTPGGVGLGVGEIIH

INDLADATKGKNYIVVIPKEIGYEEASIMINKSFENDIDVKAAIVQSDEAVLINNRLKKIIPI

VDEVRQIEKIPSGVVAAVEVAPEGKSISTLSNPYGIATIFDLTPEETKYVIPISKSLMGKKS

AVVIKTPRGQVKERIIPAGNLLIMGPTMSSKVSVDSGAEAIMESVEEVGTIDDVEGEENT

NVGNMIKNLKNKMANITGQKVDKIKIKDIFAVDTTVPVKVEGGLAGETSMEKAVVLAA
```

-continued

MVKTDTLPMIEIAEKLQRKLGVFVKIAGVEAVMATLGALTTPGTKLPLAILDIGGGSTDA

ALIDEKGIVKSIHMAGAGELVTMLIDSELGLNDRYLSEEIKRNPIGKVESLFHIRMENREI

KFFDKPLNPRYYGRIVILKENDMIPVFKEDLTMEKIIYVRRQAKDKVFVKNAIRALKKIA

PENNLRRIPNVVLVGGSALDFEIPEMILSELSKYKIIAGRGNIRKIEGPRNAVATGLVMSY

LG

SEQ ID NO:73:
ATGAAACTCATAGCAGGTGTTGATATTGGCAATTCTACAACAGAAGTGTGTAT

AGCCGCTATTAAAGATGACAATACATTAGAATTTTTAAGCAGTTCCTTGACAGCTAC

GACAGGTGTAAAAGGCACTGTGGATAATGTGACAGGGGTTATTAATGGATTGACTG

AGGCACTAAAAAAAATTGGCAAGAATATTAGGGATTTAAGCCTCATTAGAATCAAT

GAAGCCGCCCCAGTTGTCTGTGGTGCTGCTATGGAGACAATAACGGAAACTGTTATC

ACTGGTTCGACTATGATAGGTCATAATCCATCCACGCCGGGTGGTGTCGGACTTGGA

GTAGGCGAGATAATACATATAAATGATTTAGCTGATGCTACTAAAGGCAAAAATTAC

ATTGTGGTTATACCTAAGGAGATTGGCTATGAAGAAGCTTCAATAATGATAAACAAA

TCTTTTGAAAACGATATTGATGTAAAAGCTGCTATAGTTCAAAGCGATGAAGCAGTT

TTAATCAACAACAGGCTTAAAAAGATTATACCAATTGTTGACGAAGTAAGGCAGAT

AGAAAAGATTCCATCGGGTGTTGTAGCGGCTGTAGAGGTGGCACCAGAAGGCAAGT

CCATAAGCACGTTATCAAATCCTTATGGTATCGCAACAATATTTGACTTAACTCCAG

AAGAGACAAAGTATGTCATACCGATTTCGAAAAGTTTGATGGGGAAAAAGTCAGCA

GTTGTCATAAAAACACCGAGGGGACAAGTGAAAGAAAGAATAATTCCGGCTGGTAA

TCTCTTAATCATGGGGCCTACTATGTCATCAAAAGTAAGTGTTGATTCTGGTGCTGAA

GCTATAATGGAATCAGTTGAAGAAGTCGGCACAATTGATGACGTAGAAGGTGAAGA

AAATACAAATGTTGGGAATATGATAAAAAATCTAAAAAACAAGATGGCAAATATAA

CTGGGCAAAAAGTAGATAAGATAAAGATTAAAGATATCTTCGCTGTTGATACGACA

GTCCCTGTTAAAGTAGAGGGCGGACTTGCTGGTGAGACTTCAATGGAAAAAGCAGT

CGTGTTGGCGGCTATGGTAAAGACAGATACGCTTCGATGATAGAAATTGCAGAAAA

GCTTCAAAGAAAGTTGGGTGTATTTGTAAAAATAGCTGGAGTAGAAGCTGTGATGGC

TACATTAGGTGCGCTTACAACTCCAGGCACAAAGTTGCCACTTGCAATACTGGATAT

CGGTGGGGGTTCTACAGATGCAGCTTTGATTGATGAAAAAGGCATTGTAAAATCTAT

ACACATGGCAGGTGCTGGAGAATTAGTCACAATGCTTATTGATTCAGAATTAGGGTT

AAATGATAGATATTTGTCTGAAGAAATAAAGAGAAATCCGATTGGAAAAGTTGAAA

GCCTATTTCACATAAGAATGGAAAATAGGGAGATAAAGTTTTTTGACAAACCTTTAA

ATCCTCGATATTACGGTAGGATCGTAATTTTAAAAGAAAATGACATGATCCCTGTAT

TTAAAGAAGATTTGACAATGGAAAAGATTATTTACGTGCGAAGACAAGCGAAGGAT

AAAGTTTTCGTTAAAAATGCTATTAGAGCTTTGAAAAAAATTGCTCCGGAAAATAAT

TTAAGGCGAATACCAAATGTAGTCTTGGTTGGCGGTTCTGCTTTGGACTTTGAAATTC

CAGAGATGATTTTATCAGAGCTATCAAAATACAAATCATAGCAGGCAGAGGGAAT

ATAAGAAAAATCGAAGGGCCAAGAAATGCTGTAGCGACAGGTCTTGTGATGTCTTA

TTTAGGGTGA or222
SEQ ID NO: 74:
MEFIKPQIVIFANTENKYIINEVIAGIEEEGALYRLSYNECADVMKMAYDAAKAS

VLGIGIGISGDLVCLHSKNLEINTPLILSKTSENFDPRLVGCNAAKYVKGLPLKYLD

SEQ ID NO: 75:
ATGGAATTTATAAAGCCTCAAATAGTGATTTTTGCAAATACAGAAAACAAAT

ATATAATAAACGAGGTTATAGCTGGCATTGAAGAAGAAGGTGCATTATATAGATTAT

CTTACAATGAATGTGCTGATGTTATGAAAATGGCTTATGATGCAGCAAAAGCATCTG

TATTAGGTATCGGAATAGGCATATCTGGAGATTTAGTGTGTTTGCACTCTAAAAACT

TGGAAATCAATACACCTTTGATTCTTTCAAAGACAAGTGAAAACTTTGATCCACGAC

TCGTTGGATGCAATGCTGCAAAATATGTAAAGGGTTTGCCACTTAAATACTTAGATT

AG or221
SEQ ID NO: 76:
MSVYTKTGDDGYTLLLNGERIPKDDLRIETLGNLDELTSYLGFAKAQINDDSIKK

R

SEQ ID NO: 77:
ATGAGTGTTTATACTAAAACTGGTGATGATGGTTACACGTTGCTATTAAATGG

AGAAAGAATTCCAAAGGACGATTTGAGAATAGAGACATTGGGAAATTTGGATGAAT

TGACAAGCTATTTAGGATTTGCAAAAGCTCAAATAAATGATGATTCCATAAAAAGA

GATAG or220
SEQ ID NO: 78:
MVKIKNGFVIPGKNQISALLDIVRTITRKTERSLIKVDKKYPVNINSKVYINRLSDY

LFVLARYMEIRTEIEEKVKDVIRKHYGKNKGEIKLNLDIAKNLMAKVEKKAESINLPVAI

AIVDMHGNLIAAHFMDGTLLESMNLAINKAYTSVVLKMSTQELSKLAQPGQPLYGINTT

DNRIVVFGGGCPIKHQGEIVGGIGVSGGTVEQDIELSIYGADVFEEVIS

SEQ ID NO: 79:
ATGGTAAAGATTAAAAATGGTTTTGTAATACCTGGTAAAAACCAAATCTCAG

CATTATTAGATATTGTAAGGACTATAACGAGAAAAACTGAGAGAAGCTTAATCAAA

GTTGACAAGAAATATCCTGTAAATATTAATTCGAAAGTTTACATCAATAGATTGTCT

GATTATTTGTTTGTTTTAGCAAGGTATATGGAAATAAGAACGGAAATAGAAGAAAA

AGTAAAAGACGTGATAAGAAAGCATTATGGAAAGAACAAAGGCGAAATAAAGCTA

AATTTAGATATAGCAAAAAATTTAATGGCTAAGGTAGAAAAGAAGGCAGAAAGCAT

TAATCTACCGGTTGCTATTGCAATAGTTGACATGCATGGCAATTTGATAGCGGCTCA

TTTTATGGATGGTACACTTCTTGAAAGCATGAATCTAGCTATAAATAAAGCTTATAC

ATCAGTGGTGCTTAAAATGTCGACGCAAGAGTTATCAAAACTTGCACAACCAGGGC

AGCCTCTTTACGGGATAAATACAACTGATAATAGAATCGTAGTGTTTGGAGGTGGGT

GCCCTATAAAACATCAAGGTGAAATAGTTGGTGGAATTGGAGTTAGCGGTGGTACA

GTAGAACAAGATATAGAACTTTCTATTTATGGTGCAGATGTATTTGAGGAGGTTATA

TCATGA or 219
SEQ ID NO: 80:
MKVKEEDIEAIVKKVLSEFNFEKNTKSFRDFGVFQDMNDAIRAAKDAQKKLRNM

SMESREKIIQNIRKKIMENKKILAEMGVSETGMGKVEHKIIKHELVALKTPGTEDIVTTA

WSGDKGLTLVEMGPFGVIGTITPSTNPSETVLCNSIGMIAAGNSVVFNPHPGAVNVSNYA

-continued

```
VKLVNEAVMEAGGPENLVASVEKPTLETGNIMFKSPDVSLLVATGGPGVVTSVLSSGKR

AIGAGAGNPPVVVDETADIKKAAKDIVDGATFDNNLPCIAEKEVVSVDKITDELIYYMQ

QNGCYKIEGREIEKLIELVLDHKGGKITLNRKWVGKDAHLILKAIGIDADESVRCIIFEAE

KDNPLVVEELMMPILGIVRAKNVDEAIMIATELEHGNRHSAHMHSKNVDNLTKFGKIID

TAIFVKNAPSYAALGYGGEGYCTFTIASRTGEGLTSARTFTKSRRCVLADGLSIR

SEQ ID NO: 81:
ATGAAAGTTAAAGAGGAAGATATTGAAGCGATCGTCAAAAAAGTCTTATCGG

AATTTAATTTTGAAAAAAATACTAAAAGTTTCAGAGATTTTGGCGTATTTCAAGATA

TGAATGATGCTATTCGTGCTGCAAAAGATGCCCAGAAAAAATTGAGAAATATGTCCA

TGGAGTCGAGAGAAAAGATTATACAGAATATAAGAAAAAAGATTATGGAGAATAAA

AAAATACTTGCAGAGATGGGCGTCAGTGAAACTGGCATGGGGAAAGTAGAGCACAA

AATAATAAAACATGAGCTTGTAGCACTTAAGACACCTGGTACCGAAGATATAGTGA

CAACAGCATGGTCTGGCGATAAGGGACTGACATTGGTTGAAATGGGGCCATTTGGTG

TAATAGGTACGATTACTCCTTCGACAAATCCAAGTGAAACCGTCCTTTGCAATAGCA

TAGGTATGATAGCCGCAGGTAATTCAGTCGTATTTAATCCACATCCAGGTGCGGTAA

ATGTATCTAATTACGCTGTCAAGTTAGTAAATGAAGCGGTGATGGAAGCTGGCGGCC

CTGAGAATTTAGTCGCATCTGTTGAAAAACCTACACTTGAAACTGGAAATATTATGT

TCAAGAGTCCTGATGTTTCGCTATTAGTAGCGACAGGCGGACCTGGTGTAGTAACAT

CGGTTCTCTCATCTGGCAAAGGGCAATAGGAGCAGGAGCAGGAAATCCACCAGTT

GTAGTTGATGAAACGGCAGATATAAAAAAAGCTGCGAAAGATATAGTCGATGGTGC

TACATTTGACAACAATTTGCCTTGTATTGCTGAAAAGGAAGTAGTTTCTGTAGATAA

AATAACAGATGAACTGATTTACTACATGCAACAGAATGGCTGCTACAAGATTGAGG

GGCGAGAAATTGAAAAGCTCATTGAACTTGTATTGGATCACAAAGGTGGCAAGATA

ACATTAAACAGGAAATGGGTTGGCAAAGATGCTCATTTAATACTAAAAGCTATAGG

CATAGATGCTGATGAAAGCGTAAGGTGCATAATTTTTGAGGCGGAAAAAGACAATC

CGTTAGTGGTAGAAGAGCTGATGATGCCTATTTTAGGAATAGTAAGAGCCAAAAAT

GTAGATGAAGCGATAATGATTGCGACAGAGTTAGAACATGGCAATAGGCATTCAGC

ACATATGCATTCTAAAAACGTTGATAATTTAACAAAGTTTGGAAAAATAATTGACAC

TGCTATATTTGTAAAAAATGCTCCATCGTATGCCGCGTTAGGATATGGTGGTGAAGG

TTATTGCACATTTACGATTGCAAGCAGAACAGGTGAAGGATTGACATCTGCAAGGAC

TTTTACTAAAAGTCGTAGATGTGTCTTGGCAGATGGATTATCAATAAGATAG or218
SEQ ID NO: 82:
MEVNQIDIEEIVKKILNDLRNEPKENIKESNSKIPSICRAAVLTDVKKIEVKEFNIPEI

NDDEMLVKVEGCGVCGTDVHEYKGDPFGLIPLVLGHEGTGEIVKLGKNVRRDSAGKEI

KEGDKIVTSVVPCGECDICLNHPDKTNLCENSKIYGLISDDNYHLNGWFSEYIVIRKGSTF

YKVNDINLNLRLLVEPAAVVVHAVERAKSTGLMKFNSKVLVQGCGPIGLLLLSVVKTL

GVENIIAVDGDENRLNMAKRLGATALINFTKYSNIDELVDAVKKASDGIGADFAFQCTG

VPSAASNIWKFVRRGGGLCEVGFFVNNGDCKINPHYDICNKEITAVGSWTYTPQDYLTT

FDFLKRAKEIGLPIEELITHRFSLDKMNEAMEVNMKQEGIKVVYINDRF

SEQ ID NO: 83:
ATGGAAGTCAATCAGATAGACATTGAGGAGATAGTTAAGAAAATATTAAATG

ATTTAAGAAATGAGCCTAAAGAAAACATTAAAGAGAGCAATTCAAAAATACCATCT
```

-continued

```
ATCTGCAGAGCTGCTGTACTTACAGATGTTAAAAAAATAGAAGTAAAAGAATTTAAT

ATTCCAGAAATAAATGATGATGAAATGCTTGTCAAGGTGGAAGGCTGTGGCGTTTGC

GGTACTGATGTTCATGAATACAAAGGAGATCCTTTTGGACTTATACCATTGGTTTTAG

GACACGAAGGTACAGGTGAGATAGTCAAGCTGGGGAAAAACGTGAGACGAGATTCT

GCTGGTAAAGAAATCAAAGAAGGCGATAAGATTGTTACATCTGTCGTTCCGTGCGGT

GAATGCGATATATGTTTGAATCATCCAGACAAGACAAATTTGTGTGAAAACTCAAAG

ATTTACGGCTTAATATCCGATGATAATTACCATTTAAATGGTTGGTTCTCAGAGTACA

TCGTCATAAGGAAAGGCTCAACATTTTATAAGGTCAATGATATAAACCTTAATTTGA

GGCTTTTGGTAGAACCGGCTGCAGTAGTCGTACATGCAGTAGAGCGCGCAAAATCCA

CAGGTCTTATGAAATTCAACAGTAAAGTTCTCGTACAAGGCTGTGGCCCTATAGGAT

TACTGCTATTGTCGGTTGTAAAGACGCTTGGAGTAGAAAATATCATAGCCGTCGACG

GCGATGAGAATAGACTCAACATGGCTAAAAGATTAGGTGCTACAGCACTCATTAATT

TTACTAAATACAGCAATATTGATGAGCTTGTTGATGCTGTTAAAAAAGCAAGCGATG

GAATTGGCGCAGATTTTGCATTTCAATGTACAGGCGTTCCTTCTGCAGCGTCTAATAT

TTGGAAGTTTGTAAGGCGGGGAGGTGGTTTATGCGAAGTTGGATTTTTTGTAAATAA

TGGTGATTGTAAGATAAACCCCCATTATGATATTTGCAATAAGGAGATAACAGCAGT

TGGCTCATGGACTTACACTCCTCAAGACTATTTGACAACTTTTGATTTTCTCAAAAGA

GCTAAAGAAATAGGACTTCCAATTGAAGAGCTGATAACACATAGATTTTCACTTGAT

AAAATGAATGAAGCTATGGAAGTTAATATGAAGCAGGAAGGGATAAAAGTAGTGTA

TATAAATGACAGATTTTAG or217
SEQ ID NO: 84:
MQAVGLIEVYGLVAAFVAADAACKKANVVIESFDNNKPLNAEALPVPLIIVVKL

RGDLEDVKIAVDAAVDAANKISGVVATNIIAKPEEDTEKLLKLNCLK

SEQ ID NO: 85:
ATGCAGGCTGTTGGATTGATTGAAGTTTATGGATTAGTAGCGGCATTTGTGGC

AGCAGATGCTGCATGCAAAAAAGCGAATGTCGTAATAGAGTCTTTTGACAACAATA

AGCCATTAAATGCTGAAGCATTGCCAGTTCCATTGATAATAGTCGTTAAGCTCAGAG

GAGATCTTGAGGATGTAAAAATAGCGGTAGATGCTGCAGTTGATGCAGCTAATAAA

ATATCTGGTGTAGTTGCTACAAATATAATAGCAAAACCAGAAGAAGATACTGAAAA

GCTATTAAAGCTAAATTGTCTTAAATAA or216
SEQ ID NO: 86:
MVQEALGMVETRGLVAAIEAADAMVKAADVTLIGTEKIGSGLVTVMVRGDVG

AVKAATEVGASAASKLGELVAVHVIPRPHTDVEKILPTIK

SEQ ID NO: 87:
ATGGTACAAGAAGCATTGGGAATGGTAGAAACGAGAGGATTGGTAGCAGCA

ATAGAAGCAGCAGATGCTATGGTAAAGGCTGCGGATGTCACTTTGATAGGAACTGA

AAAAATAGGTTCAGGACTTGTAACAGTCATGGTAAGAGGAGATGTCGGTGCAGTAA

AAGCAGCGACAGAAGTTGGCGCAAGTGCAGCTTCAAAATTGGGAGAGTTAGTGGCT

GTTCACGTAATACCAAGGCCTCATACTGATGTTGAAAAGATACTGCCGACAATTAAA

TAA
``` or215
SEQ ID NO: 88:
MYAIGLIEVNGFVTAVETLDAMLKTANVEFVTWEKKLGGRLVTIIIKGDVSAVEE

AILTGKIEADKITRTVAYAVIPNPHPETIKMVNISAGKLFKADGGEINEF

SEQ ID NO: 89:
ATGTATGCAATTGGACTTATTGAAGTAAATGGGTTTGTCACAGCGGTTGAAAC

ACTGGATGCAATGTTGAAAACAGCCAATGTAGAGTTTGTAACATGGGAGAAAAAAC

TTGGAGGCAGACTTGTGACAATCATTATTAAAGGAGATGTTTCAGCAGTTGAAGAAG

CAATTTTAACTGGAAAGATTGAAGCTGACAAGATTACACGGACAGTAGCATACGCA

GTTATTCCAAATCCACATCCAGAAACTATAAAGATGGTAAATATTAGTGCAGGAAAG

CTATTTAAAGCAGATGGTGGTGAAATAAATGAGTTCTGA or214
SEQ ID NO: 90:
MSSEEKDTNAKDVKVEKQKNNLTKTSNKEFKEELIMEQQALGMVETRGLVAAIE

AADAMVKAANVTLIGTEKIGSGLVTVMVRGDVGAVKAATETGANAAKKLGELVAVH

VIPRPHADVEKILPTIK

SEQ ID NO: 91:
ATGAGTTCTGAAGAAAAGGATACGAATGCAAAAGATGTTAAAGTCGAAAAG

CAGAAAAATAATTTAACGAAAACATCAAATAAAGAATTTAAGGAGGAATTGATTAT

GGAACAACAAGCATTAGGAATGGTAGAGACGAGAGGATTGGTAGCAGCGATAGAA

GCTGCTGATGCAATGGTAAAGGCTGCTAATGTCACGTTAATAGGAACTGAAAAAAT

AGGTTCAGGACTTGTAACAGTCATGGTAAGAGGAGATGTTGGTGCAGTAAAAGCAG

CGACAGAGACTGGAGCAAATGCAGCTAAAAAGTTAGGGGAGTTAGTAGCTGTTCAC

GTAATACCAAGACCTCATGCAGATGTAGAGAAAATACTGCCTACGATAAAGTAG or213
SEQ ID NO: 92:
VITVNEKLIEIISKTIADTISERNSLKIPVGVSARHVHLTKEHLDILFGKDYILKKKK

ELMGGQFAAEECVTIIGFKLNAIEKVRVLGPLRDKTQVEISKTDAISLGLNPPIRESGDIKG

SSPITIVGPRGAISLKEGCIIAKRHIHMSPEDSKRFNVKDDDIISVKINGQRGGILENVQIRV

DEKYTLEMHIDTDEANCMGLKSGDFVEIVRDNRS

SEQ ID NO: 93:
GTGATAACAGTGAACGAAAAATTGATAGAGATTATATCAAAAACTATAGCGG

ATACGATTAGTGAAAGGAATTCGCTTAAGATACCAGTAGGCGTATCAGCCCGACATG

TACATCTGACTAAAGAACATTTGGATATATTATTTGGAAAAGATTATATCCTTAAAA

AGAAAAAGGAATTGATGGGTGGACAGTTCGCAGCAGAGGAATGTGTGACAATTATC

GGATTTAAATTAAATGCTATTGAGAAAGTGAGAGTTTTGGGTCCTTTAAGAGATAAA

ACGCAGGTAGAAATATCGAAGACCGATGCAATAAGTTTAGGGTTAAACCCTCCTATA

CGGGAATCAGGTGATATAAAAGGTTCATCGCCAATTACAATTGTAGGGCCGAGAGG

AGCAATATCATTAAAAGAAGGATGTATAATAGCAAAACGACATATTCACATGTCAC

CGGAAGATTCCAAAAGATTCAATGTTAAAGACGACGATATAATATCAGTAAAAATA

AATGGTCAGCGAGGCGGAATTTTAGAAAATGTACAGATTAGAGTTGACGAAAGTA

TACACTTGAGATGCATATTGACACAGATGAAGCTAATTGCATGGGACTAAAAAGCG

GCGATTTTGTTGAAATAGTAAGAGATAATAGGAGTTGA or212
SEQ ID NO: 94:
LIIAKVVGTVISTRKNQNLIGNKFLIVEPVSEMNYDSKNRVVAIDNVGAGVGEIVL

VTFGSSARIGCMPDSPVDAAIVGIVDSIKDIIIDD

SEQ ID NO: 95:
TTGATAATAGCTAAAGTTGTTGGTACTGTTATTTCTACCCGCAAGAATCAAAA

TTTAATAGGCAATAAATTTTTAATAGTAGAACCAGTAAGTGAAATGAATTATGACAG

TAAAAATAGGGTTGTTGCAATAGATAATGTAGGTGCAGGTGTAGGAGAGATAGTAT

TAGTTACCTTTGGAAGTTCAGCAAGAATCGGTTGTGGTATGCCAGATTCGCCTGTAG

ATGCGGCAATTGTCGGAATTGTTGATAGCATAAAAGATATTATCATTGATGATTAG or211
SEQ ID NO: 96:
MMNIDELKNIVFENGIVGAGGAGFPTHAKLTTGIDTIILNGAECEPLLRVDRQLLA

IYTDEILMTLSFIVDTLGAKRGIVAIKSAYKTAISSVKNLIGNYKNLELKVLPDVYPAGDE

VVLIYETTGRIVPEGSIPISVGTLVMNVETVLNVYNAIYLKHPVTEKYVTVTGDVKYPSTF

KAKVGTSVARLIEKAGGCLEKDCEVIMGGPMTGKIVDVKTPITKTTKAIIVLPKDHPVIT

KRKTNIRIGLKRAMSVCSQCQMCTDLCPRNLLGHSIKPHKVMNAVANSIIDDTAAYTMT

MLCSECGLCEMYSCHQSLSPRKIISQIKIKLRQNGVKNPHNKRPETANVMRDERLVPME

RLISRLSLKKYDVDAPMNFDTVIPSHHVVMQLSQHVGAKAIPVVKVGDIVKEGDLIGDV

PNNKLGAKLHASIDGIIIDVTDDSIVIKPRGDFDGQSDRIG

SEQ ID NO: 97:
ATGATGAATATTGATGAACTTAAAAATATCGTATTTGAAAATGGAATAGTCG

GTGCAGGCGGAGCTGGATTTCCTACACATGCAAAACTTACTACAGGTATAGATACAA

TCATATTAAATGGCGCTGAATGTGAACCGCTTTTAAGAGTAGATAGGCAGCTACTTG

CAATATATACTGATGAAATATTGATGACTTTATCATTCATAGTTGATACTTTAGGAGC

CAAACGTGGCATTGTAGCAATAAAATCAGCATACAAAACTGCCATCAGCTCAGTTAA

GAATTTGATTGGTAATTATAAAAACTTGGAGTTAAAGGTATTGCCAGACGTTTATCC

TGCTGGTGATGAAGTTGTATTAATATATGAAACGACTGGAAGAATTGTGCCAGAAGG

TTCTATACCTATTTCTGTTGGCACGTTGGTAATGAATGTGGAAACTGTGCTTAATGTT

TATAATGCTATTTATTTAAAACATCCAGTCACAGAAAAGTATGTAACAGTAACGGGA

GATGTCAAATATCCCAGCACATTTAAAGCAAAAGTAGGAACATCTGTAGCTCGTCTT

ATTGAAAAAGCAGGAGGATGCTTAGAAAAAGATTGTGAAGTGATAATGGGTGGTCC

TATGACTGGGAAAATAGTTGATGTAAAGACTCCAATAACAAAAACTACAAAAGCTA

TTATCGTTCTCCCAAAAGACCACCCTGTGATAACAAAGAGAAAGACAAACATAAGG

ATAGGGTTAAAACGAGCAATGTCTGTTTGCTCTCAATGCCAAATGTGCACAGATCTA

TGTCCTAGAAATTTATTAGGTCATTCCATCAAACCTCATAAAGTCATGAATGCAGTT

GCAAATAGTATTATTGATGATACCGCTGCATATACGATGACAATGTTATGTTCTGAA

TGTGGATTGTGCGAGATGTATTCATGTCATCAAAGTTTGTCGCCGAGAAAGATAATA

AGCCAGATAAAGATAAAATTAAGGCAAAATGGTGTAAAAAATCCACACAACAAAAG

ACCAGAAACAGCAAATGTCATGCGAGATGAGAGATTAGTGCCGATGGAAAGGCTTA

TTTCAAGACTTTCGCTCAAAAAATACGATGTAGATGCTCCGATGAATTTTGATACTGT

TATTCCTTCACATCACGTTGTCATGCAACTAAGTCAGCATGTTGGTGCCAAAGCGAT

ACCTGTAGTAAAGGTAGGAGATATTGTGAAAGAAGGAGATCTGATAGGCGATGTGC

CTAATAATAAGCTGGGTGCTAAATTGCATGCCAGTATTGACGGCATTATAATAGATG

TAACTGATGACAGTATTGTTATCAAACCAAGAGGTGATTTTGATGGACAAAGCGATA

GGATTGGTTGA or210
SEQ ID NO: 98:
MDKAIGLVEYKSVATGITAADDMAKTADVEIIEAYTVCPGKYIVLLAGKLSAVN

SAIEKGINQYSENVIDSFILGNPHETIYKAMSGTSVIEDVEALGIIETFSAASIILAADTAAK

AAKVNLVEIRIARGMCGKSYLLLTGELAAVEASINAGCKALERTGMLLNKSIIPNPDRAI

WDKII

SEQ ID NO: 99:
ATGGACAAAGCGATAGGATTGGTTGAATACAAATCAGTTGCTACAGGTATAA

CTGCTGCTGATGACATGGCTAAAACTGCTGATGTGGAAATAATAGAAGCATATACAG

TATGTCCGGGGAAATACATTGTTCTGTTAGCTGGGAAATTAAGTGCAGTTAATTCGG

CGATAGAAAAGGGCATAAATCAGTATTCGGAAAATGTCATTGATAGCTTTATATTGG

GAAATCCGCATGAAACAATATATAAAGCTATGAGTGGCACGTCTGTAATTGAAGAT

GTAGAAGCACTTGGTATCATAGAGACATTTTCTGCAGCATCAATAATACTTGCAGCA

GATACGGCTGCAAAAGCTGCAAAAGTGAATCTGGTAGAGATAAGAATAGCCAGAGG

TATGTGCGGCAAGTCATATCTACTGCTTACAGGAGAACTTGCTGCTGTTGAAGCATC

TATAAATGCAGGATGCAAAGCTTTGGAGAGAACGGGTATGCTTTTAAATAAGTCTAT

AATACCCAATCCAGATAGAGCTATTTGGGATAAGATAATTTAA or209
SEQ ID NO: 100:
MYEAEKDKILNDYYNAKEIYAKFDIDIDKVLDKMKKIRISLHCWQGDDVTGFEK

SANGLSGGGILATGNWPGRARNGEELRQDIEKALSLIPGKHKINLHAIYAETDGEFVDRD

EINVEHFRKWIYWAKENGLGLDFNPTFFSHPKANDGYTLSSKDENIRKFWIQHGKRCREI

ANEIGRELKTQCVNNVWIPDGSKDLPANRIEHRKILKESLDEIFSVKYDKSNIVDSVESKL

FGIGSESYVVGSHEFYMNYASRNDVMLCLDMGHFHPTENIADKISSILTFNDNLLIHVSR

GVRWDSDHVVILNEDLLSLAKEIRRCDAYDKVYIALDFFDASINRIMAWVIGARATLKAI

LISLLEPVHLLMEEENKGNFGARLALMEEFKTLPFYSVWNKYCMDENVPIGTSWIDDVK

EYEKEIVKNRA

SEQ ID NO: 101:
ATGTATGAAGCAGAAAAAGATAAAATTTTAAATGATTATTATAATGCAAAG

AGATTTATGCAAAGTTTGACATAGATATTGATAAAGTATTAGATAAAATGAAGAAG

ATTCGTATTTCACTTCACTGCTGGCAAGGCGATGATGTAACTGGATTCGAAAAAGT

GCCAATGGATTAAGCGGTGGAGGTATTTTGGCGACAGGAAACTGGCCTGGTAGAGC

AAGAAATGGTGAAGAATTAAGGCAAGACATTGAAAAAGCCTTAAGCCTTATACCAG

GCAAACACAAAATCAATTTACATGCCATTTACGCAGAAACGGATGGTGAATTTGTAG

ACAGAGATGAAATAAACGTGGAGCATTTCAGGAAATGGATTTACTGGGCAAAGAA

AATGGCCTTGGCCTTGACTTCAATCCTACGTTTTTTTCGCATCCTAAAGCAAATGATG

GCTATACGCTTTCAAGCAAAGATGAAAACATAAGAAAATTTTGGATCCAACATGGTA

AAAGATGCCGTGAAATCGCAAATGAAATAGGAAGAGAGCTAAAAACTCAATGTGTG

AATAATGTTTGGATTCCTGATGGTTCAAAAGATTTGCCTGCTAATAGGATTGAACAC

AGAAAAATACTTAAAGAATCTTTAGATGAGATATTTTCAGTAAAATATGACAAATCA

AATATCGTTGATTCTGTTGAAAGCAAATTATTTGGCATTGGATCTGAAAGCTATGTG

-continued

```
GTTGGTTCACATGAGTTTTATATGAACTATGCGTCGAGAAATGATGTAATGCTGTGC

CTTGATATGGGACATTTTCATCCTACTGAGAATATTGCTGATAAGATATCATCAATAC

TTACATTCAATGACAATTTGTTGATTCATGTAAGCCGTGGTGTCCGGTGGGATAGCG

ACCATGTAGTCATTTTAAATGAAGATTTGCTTTCATTAGCAAAAGAAATAAGAAGAT

GTGATGCTTATGACAAAGTGTATATTGCATTAGATTTCTTTGATGCAAGCATAAATA

GGATAATGGCATGGGTAATAGGTGCAAGAGCGACGCTAAAAGCCATATTAATATCA

CTATTAGAGCCTGTGCATCTACTTATGGAAGAGGAGAATAAAGGAAATTTTGGTGCA

AGACTTGCTTTGATGGAGGAATTCAAAACATTGCCATTTTACTCTGTTTGGAACAAA

TACTGCATGGACGAAAATGTGCCTATTGGTACATCGTGGATTGATGATGTTAAAGAA

TATGAAAAGAAATTGTAAAAAATAGGGCTTAA or208
SEQ ID NO: 102:
MKDIVYNLAFDFGASSGRLMLSAFDGEKITIEEIYRFPNEPVKLGQSFYWDFLRLF

HELKNGLKIASKRKIKISGIGIDTWGVDYGLLDKNDQLISNPFHYRDKRTDGIIKDFENM

ALLEEIYNVTGIQFMEFNTIFQLYCDYKKRPELLDNAKTLLFIPDLFNFYLTNEKYNEYTV

ASTSQMLDANKKDWANDLIEKLNLPEGIFQKILMPGNTIGYLTKEIQEETGLSEVPVISVG

SHDTASAVAGTPIENGSSAYLICGTWSLLGVESEKPIINENTKKYNFTNEGGVEGLIRLLK

NINGLWIIQQLKQSWNSNGIKIGFPEISQMASKAEHEEFIINPDDKLFIAPDDMAEAIRQYC

TKTGQGLPQNIGDIARAAYNGIVEQYKNCLNNLEDIVGQEIDNIHMVGGGIQDKFLCKLT

ADVTGKKVITGPVEASIYGNVIVQLMALGYIKDLREGRKIIKNSIENDEEMFAK

SEQ ID NO: 103:
ATGAAAGATATTGTGTATAATCTGGCTTTTGATTTTGGAGCTTCAAGTGGCCG

TCTTATGCTATCCGCGTTTGATGGCGAAAAAATCACAATTGAAGAGATTTATAGATT

TCCAAATGAGCCAGTCAAGCTGGGACAATCATTTTATTGGGATTTTTTAAGGCTTTTT

CACGAATTAAAAAACGGATTAAAAATAGCATCAAAGAGGAAAATCAAATATCCGG

CATTGGTATAGACACTTGGGGTGTCGATTATGGATTGCTTGATAAAAATGATCAATT

GATTTCAAATCCTTTTCATTACAGAGATAAAAGAACGGATGGCATAATAAAAGATTT

TGAAAATATGGCGTTACTGGAGGAAATCTACAACGTAACTGGTATACAGTTTATGGA

ATTTAATACAATATTCCAATTGTATTGCGATTATAAAAAGCGTCCAGAATTATTGGA

TAATGCAAAGACATTGTTGTTTATTCCAGATTTATTTAACTTTTATTTGACAAATGAG

AAATACAATGAATATACTGTTGCATCCACATCGCAAATGTTGGATGCTAACAAGAAA

GATTGGGCAAATGATCTTATAGAAAAGTTAAATTTGCCAGAAGGTATTTTTCAAAAG

ATACTGATGCCAGGAAATACAATTGGTTATCTAACAAAAGAAATTCAAGAAGAAAC

AGGATTGTCTGAAGTTCCCGTGATTTCTGTTGGCAGCCATGATACGGCATCAGCAGT

TGCAGGTACACCTATTGAAAACGGTTCAAGTGCTTATTTGATTTGTGGTACTTGGTCA

TTATTAGGTGTTGAAAGTGAAAAACCTATAATAAATGAAAATACAAAGAAGTACAA

TTTTACAAATGAAGGCGGTGTCGAAGGCCTTATAAGGCTACTTAAAAATATTAATGG

TCTGTGGATAATTCAGCAATTAAAACAAAGTTGGAATTCAAATGGCATTAAAATAGG

ATTTCCAGAAATCAGCCAGATGGCATCTAAAGCAGAGCACGAAGAATTTATCATAA

ATCCTGATGACAAATTGTTTATAGCTCCAGATGATATGGCTGAGGCGATAAGGCAAT

ATTGTACAAAAACAGGACAGGGTTTGCCGCAGAATATTGGCGACATAGCAAGAGCC

GCTTACAATGGTATAGTTGAACAATACAAAAATTGCTTAAACAATTTAGAAGATATT
```

-continued

```
GTAGGGCAAGAAATAGATAATATTCACATGGTTGGTGGTGGGATACAGGATAAGTT

CCTGTGCAAGCTGACTGCAGATGTTACAGGGAAAAAAGTCATAACAGGCCCTGTAG

AAGCTTCAATCTATGGCAATGTGATAGTCCAGCTTATGGCATTGGGATATATAAAAG

ACTTGAGAGAAGGAAGAAAGATAATAAAGAATTCTATAGAGAATGATGAAGAGATG

TTTGCTAAATAG
``` or207
SEQ ID NO: 104:
VSNIYTLVVVEDEYEIRTGLVNCFPWNKMGFVVAEEFENGGECFEYLCKNKVDT

ILCDIKMPVMSGIELAKKIFESNISTKIVIISGYTDFEYARQALRYGVKDYIVKPTKYNEIID

VFSRIKKELDNENTKEILNNSCNNEIDQYSSIISIIEKYVDEHYRDVTLEDVAKVVYMNPY

YLSKYFKQKTGMNFSDYITEVRMKKAVEFLKNPLYKTYEISYMIGYKNPKNFTRAFKKY

YKKSPREFVNSAINFKE

SEQ ID NO:105:
```
GTGTCTAATATTTATACGCTTGTAGTAGTAGAAGATGAATATGAGATAAGAA

CAGGATTAGTTAACTGCTTTCCATGGAACAAAATGGGTTTTGTTGTTGCAGAAGAAT

TTGAAAATGGAGGAGAATGTTTTGAGTATTTGTGTAAAAATAAGGTTGATACAATTT

TATGTGATATAAAAATGCCAGTTATGTCTGGTATAGAGTTGGCAAAGAAAATTTTTG

AAAGTAATATAAGCACTAAAATAGTTATAATCAGTGGTTATACTGATTTTGAATATG

CCAGACAGGCGTTAAGATATGGTGTTAAAGATTATATAGTAAAACCTACTAAATATA

ATGAAATAATTGATGTTTTCAGCAGAATAAAAAAAGAATTAGACAATGAAAATACA

AAGGAAATATTGAATAACTCATGTAACAATGAAATTGATCAGTACAGCAGCATAATT

TCAATCATAGAAAAATATGTTGATGAACATTACAGAGATGTGACATTGGAAGATGTA

GCTAAAGTAGTTTATATGAATCCGTATTATTTAAGCAAATATTTTAAACAAAAACC

GGTATGAATTTTTCTGATTATATAACTGAGGTCAGAATGAAAAAAGCTGTAGAGTTT

CTAAAAAATCCTTTGTATAAAACTTATGAAATAAGTTATATGATTGGATATAAAAAT

CCAAAAAATTTTACTAGAGCATTTAAAAAATATTATAAAAAATCCCCAAGAGAATTT

GTAAATTCAGCAATAAATTTTAAGGAATGA
``` or206
SEQ ID NO: 106:
MRELNNKFFYKNLFVLALPLILIVIVLGSFSILITERYVRDEIYKNSREILKQSSNDL

SILFNDINKIYLTFGTNKDVTLYLERILNTNKYSLDDMWHLSMIESLFDSTSFSEPYIQSIY

LYFNNPNKNFLVTGNGINSVTNYIDNKWYDSFLNAPKDEISWIEVRNLKMYSFDKKGIK

VLSIYKKIANFNGDKIDGVLVLNIYLDYIENLLNTSTIFPDQKILILDAHDNLICQNINGNFT

GKIDLDNYSKANIITKLESPNYNIKYVSIVPKKYLYEVPIKLLKMTLVLLLTSIFFVILITFRI

TKRNYENVNKILKIIEAEKTNEIFPEIPVESRDEYSYIIYNIINSYIEKSQLKMELAEKKYKM

KAMELLALQSQISPHFLSNALEIIYLRALSYTNGPNDVTKMIENLSQILKYLLSNPNETVT

VKEEIENTKAYIQILKVRYRDKFKVNLIYDESILSCLMMKLMLQHLIENSIKHGLKKKNY

EGSIKIKIKAVDKKKIKISVIDNGIGMSKERLNYVKRILDSDFDFYEHIGLMNTNERLKLL

YGKDCEILIRSKLNIGTAV YIIFPYQLKNQNNDDYNK

SEQ ID NO: 107:
```
ATGAGAGAATTAAACAATAAATTTTTTTATAAAAATCTTTTTGTTTTGGCATT

GCCATTAATTTTAATTGTTATTGTATTAGGTTCATTTTCAATATTAATAACAGAAAGA

TATGTTAGAGATGAAATATACAAAAATAGTAGAGAAATATTAAAGCAAAGCAGTAA

TGATTTGTCAATTTTATTTAATGATATAAATAAAATTTATTTAACATTTGGAACAAAC
```

-continued

```
AAAGATGTGACATTGTATTTGGAAAGGATCTTAAATACAAATAAATATTCTTTAGAT

GATATGTGGCATCTTAGCATGATAGAAAGTTTATTTGATTCTACGTCGTTTTCAGAAC

CTTATATACAATCAATTTATTTGTATTTTAACAATCCTAATAAAAATTTTTTAGTGAC

AGGAAATGGTATTAATTCTGTAACAAATTATATTGATAATAAATGGTATGACAGCTT

TTTAAATGCACCAAAAGATGAGATTTCTTGGATAGAGGTTAGAAATTTAAAAATGTA

TAGTTTCGATAAAAAGGGGATAAAAGTCCTAAGTATATACAAAAAAATTGCAAACT

TTAACGGGGATAAAATTGATGGTGTGCTTGTACTAAATATATATTTGGACTATATTG

AAAATTTGCTAAATACTTCAACAATATTTCCTGACCAAAAAATTCTTATATTAGATGC

CCACGACAATTTAATATGTCAAAATATTAATGGGAATTTCACTGGGAAGATAGACTT

AGATAATTATAGCAAAGCAAACATCATAACAAAATTAGAATCTCCAAATTATAATAT

AAAATATGTATCTATTGTTCCTAAAAAATACCTTTATGAAGTTCCTATAAAGCTTTTA

AAGATGACTTTAGTTTTACTTTTGACGTCAATTTTTTTTGTGATATTGATAACATTTAG

AATCACTAAACGAAATTACGAAAATGTAAATAAAATATTAAAGATTATAGAGGCAG

AAAAGACAAATGAGATATTTCCAGAAATTCCAGTAGAAAGTAGAGATGAGTACAGC

TATATAATTTACAACATTATTAATAGTTATATTGAAAAAAGTCAATTGAAAATGGAA

TTAGCAGAAAAGAAGTATAAAATGAAAGCAATGGAGTTATTAGCACTGCAATCGCA

AATTAGTCCTCATTTTTTGTCTAATGCGTTGGAGATTATTTATCTTAGGGCATTGTCA

TACACAAACGGTCCTAATGATGTCACAAAAATGATTGAAAATTTGTCACAGATTTTA

AAGTATTTGTTAAGTAATCCAAATGAAACAGTAACTGTAAAAGAAGAAATTGAAAA

TACAAAGGCATATATACAAATATTGAAGGTCAGGTATAGAGATAAATTTAAAGTAA

ATCTAATTTATGATGAAAGTATTTTATCATGTCTCATGATGAAACTGATGCTGCAACA

TTTAATAGAAAATTCTATAAAACATGGGCTTAAGAAGAAAAATTATGAAGGATCAA

TAAAAATCAAAATAAAAGCAGTTGATAAAAAGAAAATAAAAATTTCAGTAATCGAT

AATGGCATAGGAATGTCCAAAGAGAGGCTAAATTATGTAAAAAGAATTCTTGACTCT

GACTTCGATTTTTATGAACATATTGGACTAATGAATACAAATGAACGGTTAAAACTT

CTCTATGGGAAAGATTGTGAAATATTAATAAGAAGTAAATTGAATATTGGTACTGCC

GTATATATAATTTTTCCATATCAATTAAAAAATCAGAATAATGATGATTATAATAAG

TGA
``` or205
SEQ ID NO: 108:

```
MGINRYDLVKRHNVILEKADIENPLSVGNGEIAFTADITGMQTFIDDYKSIPLCTM

SQWGFHTTPAQNDKGYYTLEDLNLKYYDAFDRKVGYVTSAENQENVFNWLRSNPHRI

NLGNIGLNIILDDGTKAELKDIFEIHQVLDLWNGILISDFKVEKVPVHVETFCHPYEDMIN

FSVESELLKQNKIYIEVKFPYGAANISGSDWDRNDRHDTNVVDYGRDFVELLRIVDEDV

YFVKIEYSKGVYLNRIGENHFALKQKEYNGRIEFSCLFSKQKPLKCLHSFSESKRMCKEY

WNSFWRGGGAIDFSKCEDKRAFELERRVILSQYLTAIQCSGSMPPQETGLTCNSWYGKF

HLEMHWWHAVHFALWGRMPLLSRSIWWYRSIFNVSRDIARKQGYKGVRWPKMVGPD

GRDSPSPIGPLLVWQQPHLIYYSELFFRENPTEETLDMFKDIVINTADFIASFVAYDRKND

RYILAPPLIPAQENHDPNVTLNPVFELEYFSFALEIAVKWIERLGLNVNQEWNEIRFKLAN
```

-continued

LPSKDGVYISHEKCINTYEKFNFDHPSMLAALGMLPGRKVDKETMRRTLHRVLKEWKF

EEMWGWDFPMMAMTATRLGEPETAINILLMDSPKNTYMVNGHNNQIPNKELPVYLPG

NGGLLAAM ALMTAGWDGNSQSTPGFPKNGMWNVEWEGLKAMI

SEQ ID NO: 109
ATGGGAATTAACAGATATGATCTTGTAAAAAGGCATAATGTAATTTTGGAAA

AAGCAGATATCGAAAATCCATTGTCAGTAGGTAATGGAGAAATTGCTTTTACAGCTG

ATATAACGGGAATGCAAACTTTTATTGATGACTATAAGAGCATTCCTTTATGTACCA

TGTCACAGTGGGGGTTTCATACTACGCCGGCACAGAATGATAAGGGCTATTATACTT

TGGAAGATTTGAACCTCAAGTATTACGATGCATTTGACCGAAAGGTTGGATATGTAA

CATCAGCAGAAAATCAAGAGAATGTATTTAATTGGTTGAGGAGTAATCCTCATAGAA

TTAATTTAGGTAATATAGGATTAAATATAATTCTTGATGATGGCACAAAAGCAGAAT

TGAAAGATATTTTCGAAATACACCAAGTATTAGATTTGTGGAACGGAATATTGATAA

GTGACTTTAAAGTCGAAAAAGTCCCTGTTCACGTTGAGACTTTTTGCCATCCATATGA

AGATATGATAAATTTTTCTGTTGAATCAGAACTGCTAAAACAAATAAAATTTATAT

TGAAGTAAAATTTCCATATGGTGCGGCCAATATATCAGGCTCCGATTGGGATAGAAA

TGATAGACATGATACAAATGTGGTTGATTATGGCAGAGATTTTGTCGAATTATTGAG

AACTGTCGATGAAGATGTTTATTTTGTAAAAATAGAGTACTCAAAAGGCGTTTATTT

AAATAGAATCGGGGAAAATCATTTTGCATTAAAGCAAAAAGAGTATAATGGGAGAA

TAGAATTTTCGTGCTTGTTTTCGAAGCAAAAACCTCTTAAGTGCTTGCATTCATTTAG

TGAAAGCAAAAGGATGTGTAAAGAATATTGGAATAGCTTTTGGAGAGGAGGTGGTG

CAATAGATTTTTCAAAGTGTGAGGATAAAAGAGCTTTTGAATTGGAGAGAAGGGTA

ATACTTTCGCAATATCTTACAGCTATTCAATGTTCGGGTTCTATGCCGCCGCAAGAAA

CAGGGCTCACCTGTAATAGCTGGTATGGTAAATTTCATTTGGAAATGCATTGGTGGC

ATGCTGTACATTTTGCTTTATGGGTAGAATGCCTTTGCTGAGTAGAAGTATATGGTG

GTACAGGAGCATTTTCAATGTATCACGTGACATTGCGAGAAAGCAAGGATACAAAG

GTGTACGCTGGCCTAAAATGGTTGGACCAGATGGAAGGGATAGCCCTTCTCCGATAG

GACCATTGCTTGTTTGGCAGCAGCCTCATCTTATATATTACAGTGAACTGTTTTTTAG

AGAAAATCCTACGGAAGAAACATTAGATATGTTTAAAGACATAGTAATTAATACTGC

TGATTTTATTGCATCATTTGTTGCATATGATAGAAAAAATGATAGATATATACTTGCG

CCACCTTTGATTCCAGCACAAGAAAATCATGATCCTAACGTTACATTAAATCCGGTA

TTTGAATTGGAGTATTTTTCGTTTGCGCTGGAAATAGCAGTTAAATGGATTGAAAGG

TTAGGACTAAATGTGAACCAAGAGTGGAATGAAATACGTTTTAAATTAGCTAATTTA

CCTTCAAAAGACGGTGTATATATATCGCATGAAAATGTATTAACACTTATGAGAAA

TTTAATTTTGACCATCCATCTATGCTTGCAGCATTGGGGATGCTACCAGGCCGCAAG

GTTGATAAAGAAACTATGAGAAGGACTTTACATAGAGTATTAAAAGAGTGGAAATT

TGAGGAAATGTGGGGTTGGGATTTTCCGATGATGGCTATGACTGCAACAAGATTAGG

CGAACCGGAGACAGCAATAAATATTCTTTTGATGGATTCACCAAAAAATACTTATAT

GGTAAATGGCCATAATAACCAAATACCGAATAAAGAACTACCAGTATATTTGCCTGG

AAATGGTGGACTATTGGCGGCAATGGCCCTCATGACAGCTGGTTGGGATGGGAATA

GCCAAAGCACACCTGGATTTCCTAAAAATGGGATGTGGAATGTTGAATGGGAAGGG

TTAAAAGCGATGATATGA or204
SEQ ID NO: 110:
MIKRKDLYIRDPFVVPVPNEKIYYMFGTTDINCWNDEKATGFDYYKSSDLENFEG

PFIAFRPDKNFIWDKNFWAPEVHKYNDMYYMFATFFADGRNRGTQILVSEKISGPYRPW

SIEPVTPKDWMCLDGTFYVDENGEPWMIFCHEWVQIYDGEICAVRLSKDLKTTIGNPITL

FKASSANWTRSIKKIKDHECYVTDGPFIYRSEEGKLYMLWSSFIENNIYAVGISLSRTGKI

TGPWVHSENPIFAGDGGHGMIFKTFEGNLTLAVHTPNKRKEERPLFITLEKSVLNDTL

SEQ ID NO: 111:
ATGATAAAACGAAAGGATCTTTATATACGTGATCCATTTGTAGTTCCAGTACC

GAATGAAAAATATATTATATGTTTGGAACTACTGATATAAATTGCTGGAATGATGA

GAAAGCAACTGGATTTGATTACTATAAATCATCTGATTTAGAAAATTTTGAAGGACC

TTTTATTGCATTTAGACCAGATAAAAACTTTATTTGGGATAAAAATTTTTGGGCTCCA

GAAGTGCACAAATACAATGACATGTATTATATGTTTGCTACATTTTTCGCTGATGGC

AGAAATAGAGGAACGCAAATTTTAGTATCTGAAAAAATAAGTGGGCCATATAGACC

ATGGAGTATTGAACCGGTGACGCCGAAGGATTGGATGTGTTTAGATGGGACTTTTTA

TGTAGATGAGAATGGGGAACCCTGGATGATATTTTGCCATGAATGGGTACAAATATA

TGATGGGAAATTTGTGCTGTAAGATTGTCGAAAGATTTAAAAACAACGATAGGAA

ATCCTATTACACTTTTTAAAGCTTCCAGTGCTAATTGGACAAGAAGTATTAAAAAGA

TTAAAGATCATGAATGCTACGTTACGGATGGCCCTTTTATTTATAGGTCTGAAGAGG

GAAAGCTTTATATGTTGTGGTCCAGTTTTATTGAAAACAATATATACGCTGTTGGTAT

ATCATTATCGAGAACAGGCAAAATAACCGGCCCGTGGGTACACAGTGAAAATCCAA

TTTTCGCAGGTGATGGTGGGCATGGTATGATATTTAAGACCTTTGAAGGGAATCTAA

CATTGGCAGTACACACACCTAATAAAAGGAAAGAAGAACGGCCCCTTTTTATAACTT

TAGAAAAATCTGTGCTTAATGATACCTTATAA or203
SEQ ID NO: 112:
MFKKITSLLISLLLIISLVTGCSSSSNSSSSSKNSSENNTSPKTVTLRFMWWGGDAR

HKATLDAISLYEKEHPNVKINAEYGGVTDYLQKLITQLSSGTAPDLIQIDVTWLQQLFSQ

GDFFADLSKLKDINVNAFDQNFLKNYCYVNNKLIGLPTGINNSAMYINKDFFNKFGIDD

KTVWTWDNLLQTAKMVHEKDKNAYLLDADSTICDYILVTYVGQKTGNQWVKDDYTL

GFDKQTLTEAFKYLNDLFEVGAIEPFSQSAPYEGKPDQNPMWLNGQTGMLWNWSSIYA

GVKANIKNLSLALPPIDPNAKQTGIVVRPSQLIAINKDSKNIDEAAKFLNWFFTNTDAIKT

LKDVRGVPATADARKILSENNLLDSTLTDNANQAMEKMAPPENGISGNQELEKINTDIIQ

ELAYKKITPEQAADELINTYKQKLPELKSQQ

SEQ ID NO: 113:
ATGTTTAAAAAAATTACATCTCTGTTAATATCGCTTCTTTTGATAATTTCATTA

GTTACAGGATGTAGCAGTTCTTCGAATTCTTCGAGTTCATCGAAAAATAGTTCTGAA

AATAATACCAGCCCAAAAACCGTAACATTAAGATTTATGTGGTGGGGTGGAGATGC

CAGACATAAAGCAACACTTGATGCCATAAGTCTTTATGAAAAAGAACATCCCAATGT

AAAGATTAATGCTGAATATGGCGGCGTTACTGACTATCTCCAAAAGCTGATAACTCA

ATTAAGCAGTGGTACAGCACCTGATCTTATACAAATAGATGTAACATGGTTGCAGCA

ACTTTTTAGCCAAGGTGATTTTTTTGCAGATTTAAGTAAGTTAAAAGATATCAATGTG

AATGCATTTGATCAAAATTTTCTTAAAAATTATTGCTATGTCAACAATAAGTTGATAG

GTTTGCCTACAGGAATAAACAATTCGGCAATGTATATTAACAAAGACTTTTTTAATA

```
AATTTGGCATAGACGATAAGACGGTTTGGACATGGGATAATCTCTTGCAAACCGCTA

AGATGGTGCATGAAAAGGATAAAAATGCTTATCTTTTAGATGCTGATTCTACTATTT

GTGATTATATATTGGTCACATACGTGGGGCAAAAAACTGGAAATCAGTGGGTGAAA

GATGATTACACTTTAGGTTTTGATAAACAAACATTGACAGAGGCATTCAAATATTTA

AACGATTTGTTCGAAGTAGGCGCTATAGAGCCATTTTCTCAAAGTGCTCCATACGAA

GGAAAACCTGATCAAAATCCTATGTGGCTTAATGGTCAAACGGGTATGCTTTGGAAC

TGGTCATCTATATATGCTGGTGTAAAAGCAAACATAAAGAACCTGTCATTGGCATTG

CCACCTATTGACCCTAATGCAAACAGACAGGCATAGTTGTAAGACCATCACAGCTT

ATTGCTATTAACAAGGATTCTAAAAATATCGATGAAGCAGCAAAATTTTTAAATTGG

TTCTTTACGAATACAGATGCTATAAAAACACTTAAAGATGTCAGAGGAGTTCCAGCT

ACCGCAGATGCACGCAAAATTTTATCAGAAATAATTTGTTGGATTCGACTTTAACT

GATAATGCAAATCAAGCTATGGAAAAGATGGCACCTCCTGAAAACGGTATAAGTGG

TAATCAAGAGTTAGAAAAGATAAATACTGATATCATACAAGAACTGGCTTATAAAA

AGATAACGCCAGAGCAGGCTGCTGATGAATTGATAAATACTTATAAACAGAAACTT

CCAGAATTAAAAAGCCAGCAATAA or202
SEQ ID NO: 114:
MSYNKKRNLMGYLYISPWIIGFLIFTLYPFAMTFIYSFCNYSITKSPVFIGLGNYIT

MFTKDMYFWPSLINTIKYVLMTVPLKLCFALFVAMILNIDIKGVNVFRTTYYLPSIFGGS

VALSVIWKFLFMDNGIMNKFLSYFHIHGPSWLGNPHISLFTISLLSVWEFGSSMVIFLAAL

KQVPNELYEASMLDGASKIRRFFSITLPMISPVLLFNLVMQTINAFQEFTGPYVITGGGPM

NSTYVYSMLIYDNAFRYFRMGYSSALSWILFLLILIVTVIIFKSSNTWVYYENGGR

SEQ ID NO: 115:
ATGAGTTATAATAAAAAGAGAAATTTGATGGGGTATTTATATATTAGTCCATG

GATTATAGGCTTTTTAATATTTACTCTGTATCCATTTGCTATGACTTTTATCTATTCAT

TTTGTAACTACAGTATTACAAAATCACCTGTATTTATTGGATTAGGCAATTATATAAC

TATGTTTACTAAAGATATGTATTTTTGGCCATCTTTAATTAATACTATAAAATATGTA

TTAATGACAGTTCCTTTAAAATTATGTTTTGCACTTTTTGTTGCAATGATCTTAAATAT

TGATATTAAAGGAGTTAATGTGTTTAGAACAACTTATTATCTGCCTTCTATTTTTGGA

GGAAGTGTTGCTTTATCTGTTATATGGAAATTTTTATTCATGGATAATGGTATTATGA

ATAAATTTCTTTCATACTTTCATATACACGGGCCAAGTTGGCTTGGAAACCCACACAT

ATCATTATTTACTATAAGTTTATTGTCAGTGTGGGAATTTGGGTCTTCTATGGTAATA

TTTTTGGCAGCCCTAAAACAGGTCCCGAATGAGTTGTATGAAGCATCTATGTTAGAT

GGTGCAAGCAAAATAAGAAGGTTTTTCTCAATAACTTTACCTATGATATCGCCTGTG

CTATTATTTAATTTGGTTATGCAGACTATAAATGCTTTTCAGGAATTTACAGGTCCAT

ACGTGATAACTGGTGGAGGACCGATGAACTCTACTTATGTGTACAGTATGTTGATTT

ATGATAATGCGTTTAGGTATTTTAGGATGGGTTATTCATCTGCCTTGTCTTGGATTTT

ATTTTTGTTAATATTGATTGTTACAGTTATAATATTTAAATCTTCAAATACATGGGTG

TATTACGAAAATGGAGGTAGATGA or201
SEQ ID NO: 116:
MKAKNSQNNDIIRKVFIYVFLVAFGIFMIYPLLWVFASSFKSNDEIFKSISLIPKHIV

TNSYFEGWKGTGQYSFGTFILNSITLVVPVVVFTAISSTIVAYGFARFEFPLKTILFTLMIST
```

```
MMLPGTAVLIPRYILFNWLGWINTYKPFIVPALFGTTPFFIFMMVQFLRGLPKELEESATI
DGCNSFQILMKILIPLCKPAIISMCIFQFIWTWNDFFNPLIYINSVEKYTVSLGLNMTIDGTS
VVNWNQIMAMTIISMIPSIIIFFSAQKYFVEGIATTGLKN

SEQ ID NO: 117:
ATGAAAGCAAAGAATAGTCAAAATAACGATATAATCAGAAAAGTATTTATAT
ATGTTTTCTTGGTGGCTTTTGGTATTTTCATGATATATCCTTTACTTTGGGTTTTTGCA
TCATCATTTAAATCAAATGATGAAATCTTTAAATCGATAAGCCTTATACCAAACAC
ATTGTGACAAATTCATATTTTGAAGGATGGAAAGGTACGGGACAATACTCTTTTGGT
ACATTTATTTTAAACAGCATTACGCTTGTTGTACCTGTTGTTGTATTTACTGCTATATC
ATCAACAATTGTAGCCTATGGATTTGCAAGATTTGAGTTTCCGCTTAAAACTATTTTG
TTTACTTTGATGATATCTACTATGATGTTGCCGGGCACTGCAGTTTTGATACCAAGAT
ATATATTGTTTAATTGGTTAGGCTGGATAAACACTTATAAACCATTTATTGTTCCCGC
TTTGTTCGGAACAACGCCTTTTTTCATTTTTATGATGGTTCAATTTTTGAGAGGTCTTC
CTAAAGAATTAGAAGAATCGGCTACAATTGATGGTTGCAATTCATTTCAAATACTTA
TGAAGATTTTAATACCATTGTGTAAACCTGCAATTATTTCTATGTGTATATTTCAGTT
CATTTGGACTTGGAATGACTTTTTTAATCCATTGATATATATCAACAGTGTAGAAAA
ATATACAGTTTCTCTCGGGCTTAATATGACAATTGATGGGACTTCAGTTGTAAATTGG
AACCAAATAATGGCAATGACAATTATTTCAATGATACCGAGCATCATAATATTTTTT
TCAGCGCAAAAATACTTCGTTGAAGGTATTGCAACAACTGGATTAAAGAACTAA or200
SEQ ID NO: 118:
MRYTDGKVHDITIAYIGGGSRGWAWNLMTDLAKEESISGTVKLYDIDYDAAHD
NEIIGNALSMRQDVKGKWLYKACETLEESLKGADFVIISILPGTFDEMESDVHAPEKYGI
YQSVGDTVGPGGIVRALRTIPMFVDIANAIKEHCPDAWVINYTNPMTLCVRTLYEIFPQI
KAFGCCHEVFGTQKLLSRALQDIEGIENVPREEIKINVLGINHFTWIDNARYKDIDLMYV
YKQFVNKYYESGFVSDANNNWMNNSFVSAERVKFDLFLRYGVIAAAGDRHLAEFVPG
YWYLKDPETVREWMFGLTTVSWRKEDLKRRLERSKRLKTGEEKFELKETGEEGVRQIK
ALLGLGDLVTNVNMPNHGQIEGIPYGAVVETNALFSGNKLKPVLSGKLPDNVNSLVLRQ
VYNQETTLKAALKRDFDLAFSAFVNDPLVTISLKDAKKLFKEMLENTKKYLDGWKIKA

SEQ ID NO: 119:
ATGAGATATACAGATGGAAAGGTTCATGACATTACTATTGCTTATATCGGTGG
TGGTTCAAGAGGATGGGCGTGGAATTTAATGACTGACTTAGCAAAAGAGGAAAGTA
TTTCTGGTACAGTAAAGTTATACGACATAGATTACGATGCGGCACATGACAATGAGA
TAATAGGCAATGCTTTATCAATGAGACAGGATGTTAAAGGCAAATGGCTTTATAAAG
CTTGTGAGACGTTAGAAGAGTCACTAAAAGGTGCTGATTTTGTCATAATATCTATTTT
GCCAGGTACGTTCGACGAGATGGAATCTGATGTTCATGCACCAGAAAAGTATGGCAT
TTATCAGTCAGTAGGTGATACAGTAGGACCTGGTGGAATAGTCAGAGCTTTAAGGAC
GATTCCGATGTTTGTGGACATTGCCAATGCGATTAAAGAGCATTGTCCAGATGCATG
GGTCATAAATTATACAAATCCTATGACACTTTGTGTAAGGACATTGTATGAAATTTTC
CCTCAAATTAAAGCATTTGGATGCTGCCATGAAGTTTTTGGCACACAGAAGCTATTA
TCTCGTGCTCTGCAGGATATAGAAGGCATTGAAAATGTTCCGAGGGAAGAGATAAA
GATAAATGTTTTAGGTATAAATCATTTTACGTGGATCGACAATGCAAGGTACAAAGA
```

-continued

```
CATAGATTTAATGTATGTTTATAAACAATTTGTGAATAAGTACTATGAAAGCGGATT

TGTCAGCGATGCTAACAATAATTGGATGAACAATTCATTTGTATCTGCAGAGAGAGT

AAAGTTTGATCTGTTTTTGAGGTATGGAGTAATAGCTGCAGCGGGAGATAGACATCT

GGCGGAATTTGTGCCGGGATATTGGTATTTAAAAGATCCAGAGACAGTCAGAGAAT

GGATGTTTGGCTTAACGACTGTAAGTTGGAGAAAAGAAGACTTAAAACGCAGGCTT

GAAAGAAGTAAAAGGCTTAAGACAGGTGAGGAAAAATTTGAGTTAAAGGAAACAG

GCGAAGAAGGTGTTAGGCAAATTAAAGCACTATTAGGCTTAGGCGATTTAGTGACTA

ATGTCAACATGCCGAACCATGGACAGATTGAAGGAATACCATACGGTGCGGTAGTT

GAAACAAACGCTTTATTTTCAGGTAATAAACTAAAGCCTGTATTATCAGGAAAATTG

CCTGACAATGTAAACAGCCTCGTGTTAAGGCAAGTATACAACCAAGAAACGACGTT

GAAAGCTGCTTTAAAGAGAGATTTTGATTTGGCTTTTAGTGCTTTTGTAAATGATCCA

CTTGTTACAATATCTTTAAAAGATGCAAAAAAATTATTTAAGGAAATGCTTGAAAAT

ACGAAGAAATATCTAGATGGATGGAAAATAAAAGCTTGA
```

```
Non-Native proteins
EC 2.3.1.9
C. acetobutylicum ThlA (SEQ ID NO: 120)
MKEVVIASAVRTAIGSYGKSLKDVPAVDLGATAIKEAVKKAGIKPEDVNEVILGN

VLQAGLGQNPARQASFKAGLPVEIPAMTINKVCGSGLRTVSLAAQIIKAGDADVIIAGGM

ENMSRAPYLANNARWGYRMGNAKFVDEMITDGLWDAFNDYHMGITAENIAERWNISR

EEQDEFALASQKKAEEAIKSGQFKDEIVPVVIKGRKGETVVDTDEHPRFGSTIEGLAKLK

PAFKKDGTVTAGNASGLNDCAAVLVIMSAEKAKELGVKPLAKIVSYGSAGVDPAIMGY

GPFYATKAAIEKAGWTVDELDLIESNEAFAAQSLAVAKDLKFDMNKVNVNGGAIALGH

PIGASGARILVTLVHAMQKRDAKKGLATLCIGGGQGTAILLEKC

EC 2.8.3.8
C. acetobutylicum CtfAB
CtfA (SEQ ID NO: 121)
MNSKIIRFENLRSFFKDGMTIMIGGFLNCGTPTKLIDFLVNLNIKNLTIISNDTCYPN

TGIGKLISNNQVKKLIASYIGSNPDTGKKLFNNELEVELSPQGTLVERIRAGGSGLGGVLT

KTGLGTLIEKGKKKISINGTEYLLELPLTADVALIKGSIVDEAGNTFYKGTTKNFNPYMA

MAAKTVIVEAENLVSCEKLEKEKAMTPGVLINYIVKEPA

CtfB (SEQ ID NO: 122)
MINDKNLAKEIIAKRVARELKNGQLVNLGVGLPTMVADYIPKNFKITFQSENGIV

GMGASPKINEADKDVVNAGGDYTTVLPDGTFFDSSVSFSLIRGGHVDVTVLGALQVDE

KGNIANWIVPGKMLSGMGGAMDLVNGAKKVIIAMRHTNKGQPKILKKCTLPLTAKSQA

NLIVTELGVIEVINDGLLLTEINKNTTIDEIRSLTAADLLISNELRPMAV

EC 4.1.1.4
C. acetobutylicum Adc, Aad
Adc (SEQ ID NO: 123)
MLKDEVIKQISTPLTSPAFPRGPYKFHNREYFNIVYRTDMDALRKVVPEPLEIDEP

LVRFEIMAMHDTSGLGCYTESGQAIPVSFNGVKGDYLHMMYLDNEPAIAVGRELSAYP

KKLGYPKLFVDSDTLVGTLDYGKLRVATATMGYKHKALDANEAKDQICRPNYMLKIIP

NYDGSPRICELINAKITDVTVHEAWTGPTRLQLFDHAMAPLNDLPVKEIVSSSHILADIILP

RAEVIYDYLK

Aad (SEQ ID NO: 124)
MLKDEVIKQISTPLTSPAFPRGPYKFHNREYFNIVYRTDMDALRKVVPEPLEIDEP

LVRFEIMAMHDTSGLGCYTESGQAIPVSFNGVKGDYLHMMYLDNEPAIAVGRELSAYP
```

-continued

KKLGYPKLFVDSDTLVGTLDYGKLRVATATMGYKHKALDANEAKDQICRPNYMLKIIP

NYDGSPRICELINAKITDVTVHEAWTGPTRLQLFDHAMAPLNDLPVKEIVSSSHILADIILP

RAEVIYDYLK

EC 1.2.1.43 Formate dehydrogenase (*M. thermoacetica*) Moth_2312
(SEQ ID NO: 125)
MVNLTIDGQRVTAPEGMTILEVARENGIHIPTLCHHPKLRPLGYCRLCLVDIEGAA

KPMTACNTPVAEGMVIRTSTPVIEEMRKGIIEMLLSLHPEDCLTCEKAGNCQLQDCAYT

YGVKHGELPVKREELPVLKENPFIVRDYNKCIVCGRCVRACQEVQVQRVVDLVGKGSA

ARVGATKAGAEVSLEEGGCVFCGNCVQVCPVGALTEKAGLGQGREWEFKKVRSICSYC

GVGCNLTLYVKDGKVVKVRGYENPEVNNGWLCVKGRFGFDYIHNPDRITRPLIREGDR

EKGYFREASWEEALALVSQKLTQIKGSYGSEALGFLCSAKCTNEENYLLQKLARGVLGT

NNVDHCARLHSSTVAGLATTFGSGAMTNSIADIASADCIFVIGSNTTENHPVIALKVKEA

VRRGARLIVADPRRIELVNFSYLWLRQKPGTDLALLNGLLHVIIKEELYDKEFIAQRTEGF

EALKLAVEEYTPAKVSEVTGVPAGDIIEAARTYARGPSSTILYAMGITQHITGTANVMAL

ANLAMACGQVGKEGSGVNPLRGQSNVQGACDMGGLPNVLPGYQPVTDPGVRHKFSEA

WGVPDLPGEPGLTLMEMMAAAQEGKLKGMYILGENPVLTDPDVSHVKEALKNLEFLV

VQDIFLTETARMADVVLPGASFAEKEGTFTSTERRVQLLHKAIEPPGEARPDWLILNDLL

LLMGYPRKYSSPGEIMQEIAGLTPSYAGITYERLEDKGLQWPVLSLEHPGTPVLHREKFS

RGYGQFQVVHYRPPAEEPDEEYPFLFTTGRNLYHYHTVISRKSRGLEEMCPAPVVEINDN

DAARLGIREGEMIEIVSRRGKVRVKALVTDRIPRGQVFMNFHFHEAAANLLTIAALDPVA

KIPEYKTCAVAIKVKK

Proteins sequences for *Saccharomyces cerevisae* engineering
EC 4.2.3.3
*Oryza sativa*-mgs (SEQ ID NO: 126)
MELTTRTIAERKHIALVAHDHRKQALLEWVESHKTILAQHQLYATGTTGNLIQR

ASGIPVTSMLSGPMGGDQQVGALIAEGKIDMLIFFWDPLNAVPHDPDVKALLRLATVW

NIPVATNRSTADFLIDSPLFKSEVAIAIPDYQRYLQDRLK

EC 2.3.1.8
*T. saccharolyticum*-or1741 (SEQ ID NO: 127)
MKTSELLAMVVEKGASDLHITVGVPPVLRINGQLIKLNLPQLTPQDTEEITKDLLS

SDELKKLEDMGDIDLSYSVKGLGRFRINAYKQRGTYSLAIRSVALRIPTIDELGLPEVIKE

LALKTRGLIIVTGPTGSGKSTTLASMIDLINEERNCHILTLEDPIEYLHKHKKSIVNQREIG

HDAASYASALRAALREDPDVILVGEMRDLETIQIAITAAETGHLVLSTLHTIGSAKTIDRII

DVFPPHQQQQIKVQLSNVLEGIVSQQLLPKIDNSGRVVAVEVMIATPAIRNLIREGKSFQI

QSMVQTGNKFGMVTMDMWISQLLKRNLISMDDALTYCVDRENFSRLVV

EC 1.1.1.6
*Pseudomonas putida* gldA (SEQ ID NO: 128)
MDRAIQSPGKYVQGADALQRLGDYLKPLADSWLVIADKFVLGFAEDTIRQSLSK

AGLAMDIVAFNGECSQGEVDRLCQLATQNGRSAIVGIGGGKTLDTAKAVAFFQKVPVA

VAPTIASTDAPCSALSVLYTDEGEFDRYLMLPTNPALVVVDTAIVARAPARLLAAGIGDA

LATWFEARAASRSSAATMAGGPATQTALNLARFCYDTLLEEGEKAMLAVQAQVVTPA

LERIVEANTYLSGVGFESGGVAAAHAVHNGLTAVAETHHFYHGEKVAFGVLVQLALEN

ASNAEMQEVMSLCHAVGLPITLAQLDITEDIPTKMRAVAELACAPGETIHNMPGGVTVE

QVYGALLVADQLGQHFLEF

EC 2.7.2.1
*T. saccharolyticum* or1742 (SEQ ID NO: 129)
MIKKKLGDLLVEVGLLDESQLNNAIKIQKKTGEKLGKILVKEGYLTEEQIIEALEF

QLGIPHIDMKKVFIDANVAKLIPESMAKRHVAIPIKKENNSIFVAMADPLNIFAIDDIKLVT

KLDVKPLIASEDGILKAIDRVFGKEEAERAVQDFKKELSHDSAEDDGNLLRDISEDEINN

APAVRLVNSIIEQAVKNRASDVHIEPTENDLRIRFRIDGELHEAMRVFKSTQGPVITRIKIM

ANMNIAERRIPQDGKIEMNAGGKNIDIRVSSLPTIYGEKLVLRILDKSGYIITKDKLGLGN

DDLKLFDNLLKHPNGIILLTGPTGSGKTTTLYAMLNELNKPDKNIITVEDPVEYTLEGLN

QVQVNEKAGLTFASALRSILRQDPDIIMIGEIRDRETAEIAIRSSITGHLVLSTLHTNDSAG

AITRLIDMGIEPYLVSSSVVGVIAQRLARKICDNCKIEYDASKREKIILGIDADESLKLYRS

KGCAVCNKTGYRGRVPIYEIMMMTPKIKELTNEKAPADVILNEAVSNGMSTLKESAKKL

VLSGVTTVDEMLRLTYDDAY

EC 2.8.3.8
*C. acetobutylicum* CtfAB
CtfA (SEQ ID NO: 130)
MNSKIIRFENLRSFFKDGMTIMIGGFLNCGTPTKLIDFLVNLNIKNLTIISNDTCYPN

TGIGKLISNNQVKKLIASYIGSNPDTGKKLFNNELEVELSPQGTLVERIRAGGSGLGGVLT

KTGLGTLIEKGKKKISINGTEYLLELPLTADVALIKGSIVDEAGNTFYKGTTKNFNPYMA

MAAKTVIVEAENLVSCEKLEKEKAMTPGVLINYIVKEPA

CtfB (SEQ ID NO: 131)
MINDKNLAKEIIAKRVARELKNGQLVNLGVGLPTMVADYIPKNFKITFQSENGIV

GMGASPKINEADKDVVNAGGDYTTVLPDGTFFDSSVSFSLIRGGHVDVTVLGALQVDE

KGNIANWIVPGKMLSGMGGAMDLVNGAKKVIIAMRHTNKGQPKILKKCTLPLTAKSQA

NLIVTELGVIEVINDGLLLTEINKNTTIDEIRSLTAADLLISNELRPMAV

EC 4.1.1.4
*C. acetobutylicum*-Adc (SEQ ID NO: 132)
MLKDEVIKQISTPLTSPAFPRGPYKFHNREYFNIVYRTDMDALRKVVPEPLEIDEP

LVRFEIMAMHDTSGLGCYTESGQAIPVSFNGVKGDYLHMMYLDNEPAIAVGRELSAYP

KKLGYPKLFVDSDTLVGTLDYGKLRVATATMGYKHKALDANEAKDQICRPNYMLKIIP

NYDGSPRICELINAKITDVTVHEAWTGPTRLQLFDHAMAPLNDLPVKEIVSSSHILADIILP

RAEVIYDYLK

EC 2.3.1.54
*Escherichia coli*-pflA (SEQ ID NO: 133)
MSVIGRIHSFESCGTVDGPGIRFITFFQGCLMRCLYCHNRDTWDTHGGKEVTVED

LMKEVVTYRHFMNASGGGVTASGGEAILQAEFVRDWFRACKKEGIHTCLDTNGFVRRY

DPVIDELLEVTDLVMLDLKQMNDEIHQNLVGVSNHRTLEFAKYLANKNVKVWIRYVVV

PGWSDDDDSAHRLGEFTRDMGNVEKIELLPYHELGKHKWVAMGEEYKLDGVKPPKKE

TMERVKGILEQYGHKVMF

EC 2.3.1.54
*Escherichia coli*-pflB (SEQ ID NO: 134)
MSELNEKLATAWEGFTKGDWQNEVNVRDFIQKNYTPYEGDESFLAGATEATTT

LWDKVMEGVKLENRTHAPVDFDTAVASTITSHDAGYINKQLEKIVGLQTEAPLKRALIP

FGGIKMIEGSCKAYNRELDPMIKKIFTEYRKTHNQGVFDVYTPDILRCRKSGVLTGLPDA

YGRGRIIGDYRRVALYGIDYLMKDKLAQFTSLQADLENGVNLEQTIRLREEIAEQHRAL

GQMKEMAAKYGYDISGPATNAQEAIQWTYFGYLAAVKSQNGAAMSFGRTSTFLDVYIE

RDLKAGKITEQEAQEMVDHLVMKLRMVRFLRTPEYDELFSGDPIWATESIGGMGLDGR

TLVTKNSFRFLNTLYTMGPSPEPNMTILWSEKLPLNFKKFAAKVSIDTSSLQYENDDLMR

-continued

PDFNNDDYAIACCVSPMIVGKQMQFFGARANLAKTMLYAINGGVDEKLKMQVGPKSEP

IKGDVLNYDEVMERMDHFMDWLAKQYITALNIIHYMHDKYSYEASLMALHDRDVIRT

MACGIAGLSVAADSLSAIKYAKVKPIRDEDGLAIDFEIEGEYPQFGNNDPRVDDLAVDLV

ERFMKKIQKLHTYRDAIPTQSVLTITSNVVYGKKTGNTPDGRRAGAPFGPGANPMHGRD

QKGAVASLTSVAKLPFAYAKDGISYTFSIVPNALGKDDEVRKTNLAGLMDGYFHHEASI

EGGQHLNVNVMNREMLLDAMENPEKYPQLTIRVSGYAVRFNSLTKEQQQDVITRTFTQ

SM

EC 2.3.1.9
Saccharomyces cerevisiae ERG10 (SEQ ID NO: 135)
MSQNVYIVSTARTPIGSFQGSLSSKTAVELGAVALKGALAKVPELDASKDFDEIIF

GNVLSANLGQAPARQVALAAGLSNHIVASTVNKVCASAMKAIILGAQSIKCGNADVVV

AGGCESMTNAPYYMPAARAGAKFGQTVLVDGVERDGLNDAYDGLAMGVHAEKCARD

WDITREQQDNFAIESYQKSQKSQKEGKFDNEIVPVTIKGFRGKPDTQVTKDEEPARLHVE

KLRSARTVFQKENGTVTAANASPINDGAAAVILVSEKVLKEKNLKPLAIIKGWGEAAHQ

PADFTWAPSLAVPKALKHAGIEDINSVDYFEFNEAFSVVGLVNTKILKLDPSKVNVYGG

AVALGHPLGCSGARVVVTLLSILQQEGGKIGVAAICNGGGGASSIVIEKI

EC 1.1.1.1
Saccharomyces cerevisiae ADH1 (SEQ ID NO: 136)
MSIPETQKGVIFYESHGKLEYKDIPVPKPKANELLINVKYSGVCHTDLHAWHGD

WPLPVKLPLVGGHEGAGVVVGMGENVKGWKIGDYAGIKWLNGSCMACEYCELGNES

NCPHADLSGYTHDGSFQQYATADAVQAAHIPQGTDLAQVAPILCAGITVYKALKSANL

MAGHWVAISGAAGGLGSLAVQYAKAMGYRVLGIDGGEGKEELFRSIGGEVFIDFTKEK

DIVGAVLKATDGGAHGVINVSVSEAAIEASTRYVRANGTTVLVGMPAGAKCCSDVFNQ

VVKSISIVGSYVGNRADTREALDFFARGLVKSPIKVVGLSTLPEIYEKMEKGQIVGRYVV

DTSK

EC 1.1.1.1
Saccharomyces cerevisiae ADH2 (SEQ ID NO: 137)
MSIPETQKAIIFYESNGKLEHKDIPVPKPKPNELLINVKYSGVCHTDLHAWHGDW

PLPTKLPLVGGHEGAGVVVGMGENVKGWKIGDYAGIKWLNGSCMACEYCELGNESNC

PHADLSGYTHDGSFQEYATADAVQAAHIPQGTDLAEVAPILCAGITVYKALKSANLRAG

HWAAISGAAGGLGSLAVQYAKAMGYRVLGIDGGPGKEELFTSLGGEVFIDFTKEKDIVS

AVVKATNGGAHGIINVSVSEAAIEASTRYCRANGTVVLVGLPAGAKCSSDVFNHVVKSI

SIVGSYVGNRADTREALDFFARGLVKSPIKVVGLSSLPEIYEKMEKGQIAGRYVVDTSK

EC 1.1.1.1
Saccharomyces cerevisiae ADH3 (SEQ ID NO: 138)
MLRTSTLFTRRVQPSLFSRNILRLQSTAAIPKTQKGVIFYENKGKLHYKDIPVPEPK

PNEILINVKYSGVCHTDLHAWHGDWPLPVKLPLVGGHEGAGVVVKLGSNVKGWKVGD

LAGIKWLNGSCMTCEFCESGHESNCPDADLSGYTHDGSFQQFATADAIQAAKIQQGTDL

AEVAPILCAGVTVYKALKEADLKAGDWVAISGAAGGLGSLAVQYATAMGYRVLGIDA

GEEKEKLFKKLGGEVFIDFTKTKNMVSDIQEATKGGPHGVINVSVSEAAISLSTEYVRPC

GTVVLVGLPANAYVKSEVFSHVVKSINIKGSYVGNRADTREALDFFSRGLIKSPIKIVGLS

ELPKVYDLMEKGKILGRYVVDTSK

EC 1.1.1.1
*Saccharomyces cerevisiae* ADH4 (SEQ ID NO: 139)
MSSVTGFYIPPISFFGEGALEETADYIKNKDYKKALIVTDPGIAAIGLSGRVQKML

EERDLNVAIYDKTQPNPNIANVTAGLKVLKEQNSEIVVSIGGGSAHDNAKAIALLATNG

GEIGDYEGVNQSKKAALPLFAINTTAGTASEMTRFTIISNEEKKIKMAIIDNNVTPAVAVN

DPSTMFGLPPALTAATGLDALTHCIEAYVSTASNPITDACALKGIDLINESLVAAYKDGK

DKKARTDMCYAEYLAGMAFNNASLGYVHALAHQLGGFYHLPHGVCNAVLLPHVQEA

NMQCPKAKKRLGEIALHFGASQEDPEETIKALHVLNRTMNIPRNLKELGVKTEDFEILAE

HAMHDACHLTNPVQFTKEQVVAIIKKAYEY

EC 1.1.1.1
*Saccharomyces cerevisiae* ADH5 (SEQ ID NO: 140)
MPSQVIPEKQKAIVFYETDGKLEYKDVTVPEPKPNEILVHVKYSGVCHSDLHAW

HGDWPFQLKFPLIGGHEGAGVVVKLGSNVKGWKVGDFAGIKWLNGTCMSCEYCEVGN

ESQCPYLDGTGFTHDGTFQEYATADAVQAAHIPPNVNLAEVAPILCAGITVYKALKRAN

VIPGQWVTISGACGGLGSLAIQYALAMGYRVIGIDGGNAKRKLFEQLGGEIFIDFTEEKDI

VGAIIKATNGGSHGVINVSVSEAAIEASTRYCRPNGTVVLVGMPAHAYCNSDVFNQVVK

SISIVGSCVGNRADTREALDFFARGLIKSPIHLAGLSDVPEIFAKMEKGEIVGRYVVETSK

EC 1.1.1.1
*Saccharomyces cerevisiae* ADH6 (SEQ ID NO: 141)
MSYPEKFEGIAIQSHEDWKNPKKTKYDPKPFYDHDIDIKIEACGVCGSDIHCAAG

HWGNMKMPLVVGHEIVGKVVKLGPKSNSGLKVGQRVGVGAQVFSCLECDRCKNDNEP

YCTKFVTTYSQPYEDGYVSQGGYANYVRVHEHFVVPIPENIPSHLAAPLLCGGLTVYSPL

VRNGCGPGKKVGIVGLGGIGSMGTLISKAMGAETYVISRSSRKREDAMKMGADHYIAT

LEEGDWGEKYFDTFDLIVVCASSLTDIDFNIMPKAMKVGGRIVSISIPEQHEMLSLKPYGL

KAVSISYSALGSIKELNQLLKLVSEKDIKIWVETLPVGEAGVHEAFERMEKGDVRYRFTL

VGYDKEFSD

EC 1.1.1.1
*Saccharomyces cerevisiae* ADH7 (SEQ ID NO: 142)
MLYPEKFQGIGISNAKDWKHPKLVSFDPKPFGDHDVDVEIEACGICGSDFHIAVG

NWGPVPENQILGHEIIGRVVKVGSKCHTGVKIGDRVGVGAQALACFECERCKSDNEQYC

TNDHVLTMWTPYKDGYISQGGFASHVRLHEHFAIQIPENIPSPLAAPLLCGGITVFSPLLR

NGCGPGKRVGIVGIGGIGHMGILLAKAMGAEVYAFSRGHSKREDSMKLGADHYIAMLE

DKGWTEQYSNALDLLVVCSSSLSKVNFDSIVKIMKIGGSIVSIAAPEVNEKLVLKPLGLM

GVSISSSAIGSRKEIEQLLKLVSEKNVKIWVEKLPISEEGVSHAFTRMESGDVKYRFTLVD

YDKKFHK

EC 1.1.1.1
*Saccharomyces cerevisiae* BDH2 (SEQ ID NO: 143)
MRALAYFGKGNIRFTNHLKEPHIVAPDELVIDIEWCGICGTDLHEYTDGPIFFPED

GHTHEISHNPLPQAMGHEMAGTVLEVGPGVKNLKVGDKVVVEPTGTCRDRYRWPLSP

NVDKEWCAACKKGYYNICSYLGLCGAGVQSGGFAERVVMNESHCYKVPDFVPLDVAA

LIQPLAVCWHAIRVCEFKAGSTALIIGAGPIGLGTILALNAAGCKDIVVSEPAKVRRELAE

KMGARVYDPTAHAAKESIDYLRSIADGGDGFDYTFDCSGLEVTLNAAIQCLTFRGTAVN

LAMWGHHKIQFSPMDITLHERKYTGSMCYTHHDFEAVIEALEEGRIDIDRARHMITGRV

NIEDGLDGAIMKLINEKESTIKIILTPNNHGELNREADNEKKEISELSSRKDQERLRESINE

AKLRHT

-continued

EC 1.1.1.1
*Saccharomyces cerevisiae* SFA1 (SEQ ID NO: 144)
MSAATVGKPIKCIAAVAYDAKKPLSVEEITVDAPKAHEVRIKIEYTAVCHTDAYT

LSGSDPEGLFPCVLGHEGAGIVESVGDDVITVKPGDHVIALYTAECGKCKFCTSGKTNLC

GAVRATQGKGVMPDGTTRFHNAKGEDIYHFMGCSTFSEYTVVADVSVVAIDPKAPLDA

ACLLGCGVTTGFGAALKTANVQKGDTVAVFGCGTVGLSVIQGAKLRGASKIIAIDINNK

KKQYCSQFGATDFVNPKEDLAKDQTIVEKLIEMTDGGLDFTFDCTGNTKIMRDALEACH

KGWGQSIIIGVAAAGEEISTRPFQLVTGRVWKGSAFGGIKGRSEMGGLIKDYQKGALKV

EEFITHRRPFKEINQAFEDLHNGDCLRTVLKSDEIK

EC 1.1.1.1
*Saccharomyces cerevisiae* YPL088W (SEQ ID NO: 145)
MVLVKQVRLGNSGLKISPIVIGCMSYGSKKWADWVIEDKTQIFKIMKHCYDKGL

RTFDTADFYSNGLSERIIKEFLEYYSIKRETVVIMTKIYFPVDETLDLHHNFTLNEFEELDL

SNQRGLSRKHIIAGVENSVKRLGTYIDLLQIHRLDHETPMKEIMKALNDVVEAGHVRYIG

ASSMLATEFAELQFTADKYGWFQFISSQSYYNLLYREDERELIPFAKRHNIGLLPWSPNA

RGMLTRPLNQSTDRIKSDPTFKSLHLDNLEEEQKEIINRVEKVSKDKKVSMAMLSIAWVL

HKGCHPIVGLNTTARVDEAIAALQVTLTEEEIKYLEEPYKPQRQRC*

EC 4.1.2.13
*Saccharomyces cerevisiae* FBA1 (SEQ ID NO: 146)
MGVEQILKRKTGVIVGEDVHNLFTYAKEHKFAIPAINVTSSSTAVAALEAARDSK

SPIILQTSNGGAAYFAGKGISNEGQNASIKGAIAAAHYIRSIAPAYGIPVVLHSDHCAKKL

LPWFDGMLEADEAYFKEHGEPLFSSHMLDLSEETDEENISTCVKYFKRMAAMDQWLEM

EIGITGGEEDGVNNENADKEDLYTKPEQVYNVYKALHPISPNFSIAAAFGNCHGLYAGDI

ALRPEILAEHQKYTREQVGCKEEKPLFLVFHGGSGSTVQEFHTGIDNGVVKVNLDTDCQ

YAYLTGIRDYVLNKKDYIMSPVGNPEGPEKPNKKFFDPRVWVREGEKTMGAKITKSLET

FRTTNTL

EC 5.3.1.1
*Saccharomyces cerevisiae* TPI1 (SEQ ID NO: 147)
MARTFFVGGNFKLNGSKQSIKEIVERLNTASIPENVEVVICPPATYLDYSVSLVKK

PQVTVGAQNAYLKASGAFTGENSVDQIKDVGAKWVILGHSERRSYFHEDDKFIADKTK

FALGQGVGVILCIGETLEEKKAGKTLDVVERQLNAVLEEVKDWTNVVVAYEPVWAIGT

GLAATPEDAQDIHASIRKFLASKLGDKAASELRILYGGSANGSNAVTFKDKADVDGFLV

GGASLKPEFVDIINSRN

EC 1.2.1.2
*Saccharomyces cerevisiae* FDH1 (SEQ ID NO: 148)
MSKGKVLLVLYEGGKHAEEQEKLLGCIENELGIRNFIEEQGYELVTTIDKDPEPTS

TVDRELKDAEIVITTPFFPAYISRNRIAEAPNLKLCVTAGVGSDHVDLEAANERKITVTEV

TGSNVVSVAEHVMATILVLIRNYNGGHQQAINGEWDIAGVAKNEYDLEDKIISTVGAGR

IGYRVLERLVAFNPKKLLYYDYQELPAEAINRLNEASKLFNGRGDIVQRVEKLEDMVAQ

SDVVTINCPLHKDSRGLFNKKLISHMKDGAYLVNTARGAICVAEDVAEAVKSGKLAGY

GGDVWDKQPAPKDHPWRTMDNKDHVGNAMTVHISGTSLDAQKRYAQGVKNILNSYF

SKKFDYRPQDIIVQNGSYATRAYGQKK

EC 1.1.1.21
*Saccharomyces cerevisiae* GRE3 (SEQ ID NO: 149)
MSSLVTLNNGLKMPLVGLGCWKIDKKVCANQIYEAIKLGYRLFDGACDYGNEK

EVGEGIRKAISEGLVSRKDIFVVSKLWNNFHHPDHVKLALKKTLSDMGLDYLDLYYIHF

PIAFKYVPFEEKYPPGFYTGADDEKKGHITEAHVPIIDTYRALEECVDEGLIKSIGVSNFQ

```
GSLIQDLLRGCRIKPVALQIEHHPYLTQEHLVEFCKLHDIQVVAYSSFGPQSFIEMDLQLA

KTTPTLFENDVIKKVSQNHPGSTTSQVLLRWATQRGIAVIPKSSKKERLLGNLEIEKKFTL

TEQELKDISALNANIRFNDPWTWLDGKFPTFA

EC 1.1.1.79
Saccharomyces cerevisiae GOR1 (SEQ ID NO: 150)
MSKKPIVLKLGKDAFGDQAWGELEKIADVITIPESTTREQFLREVKDPQNKLSQV

QVITRTARSVKNTGRFDEELALALPSSVVAVCHTGAGYDQIDVEPFKKRHIQVANVPDL

VSNATADTHVFLLLGALRNFGIGNRRLIEGNWPEAGPACGSPFGYDPEGKTVGILGLGRI

GRCILERLKPFGFENFIYHNRHQLPSEEEHGCEYVGFEEFLKRSDIVSVNVPLNHNTHHLI

NAETIEKMKDGVVIVNTARGAVIDEQAMTDALRSGKIRSAGLDVFEYEPKISKELLSMSQ

VLGLPHMGTHSVETRKKMEELVVENAKNVILTGKVLTIVPELQNEDWPNESKPLV

EC 1.1.1.79
Saccharomyces cerevisiae YPL113C (SEQ ID NO: 151)
MITSIDIADVTYSAKPRILVPYKTQWEVASHLPEYRKLAERVEFYKYEMSTKDDF

VKFLETHRINGFWLTEEFFTVLGNPSSYIEFFPASLKVILVPWVGCDFIDGKLLRSKGITLC

NIGPHAADHVTELAIFLAISCFRMTSFWEYCFKYVENGNVEQCKKYISSDSYEIVTDSYH

GQEMKFPSRTDKCKPNKDRKVVHLAEKYTVGGKKMESPMNKKVLILGFGSIGQNIGSN

LHKVFNMSIEYYKRTGPVQKSLLDYNAKYHSDLDDPNTWKNADLIILALPSTASTNNIIN

RKSLAWCKDGVRIVNVGRGTCIDEDVLLDALESGKVASCGLDVFKNEETRVKQELLRR

WDVTALPHIGSTVADMVIKQTLITLENVQDIFVEGGDGKYVLN

EC 1.2.1.49
Saccharomyces cerevisiae GCY1 (SEQ ID NO: 152)
MPATLHDSTKILSLNTGAQIPQIGLGTWQSKENDAYKAVLTALKDGYRHIDTAAI

YRNEDQVGQAIKDSGVPREEIFVTTKLWCTQHHEPEVALDQSLKRLGLDYVDLYLMHW

PARLDPAYIKNEDILSVPTKKDGSRAVDITNWNFIKTWELMQELPKTGKTKAVGVSNFSI

NNLKDLLASQGNKLTPAANQVEIHPLLPQDELINFCKSKGIVVEAYSPLGSTDAPLLKEP

VILEIAKKNNVQPGHVVISWHVQRGYVVLPKSVNPDRIKTNRKIFTLSTEDFEAINNISKE

KGEKRVVHPNWSPFEVFK

EC 1.2.1.49
Saccharomyces cerevisiae ALD2 (SEQ ID NO: 153)
MPTLYTDIEIPQLKISLKQPLGLFINNEFCPSSDGKTIETVNPATGEPITSFQAANEK

DVDKAVKAARAAFDNVWSKTSSEQRGIYLSNLLKLIEEEQDTLAALETLDAGKPYSNAK

GDLAQILQLTRYFAGSADKFDKGATIPLTFNKFAYTLKVPFGVVAQIVPWNYPLAMAC

WKLQGALAAGNTVIIKPAENTSLSLLYFATLIKKAGFPPGVVNIVPGYGSLVGQALASH

MDIDKISFTGSTKVGGFVLEASGQSNLKDVTLECGGKSPALVFEDADLDKAIDWIAAGIF

YNSGQNCTANSRVYVQSSIYDKFVEKFKETAKKEWDVAGKFDPFDEKCIVGPVISSTQY

DRIKSYIERGKREEKLDMFQTSEFPIGGAKGYFIPPTIFTDVPQTSKLLQDEIFGPVVVVSK

FTNYDDALKLANDTCYGLASAVFTKDVKKAHMFARDIKAGTVWINSSNDEDVTVPFGG

FKMSGIGRELGQSGVDTYLQTKAVHINLSLDN

EC 1.2.1.49
Saccharomyces cerevisiae ALD3 (SEQ ID NO: 154)
MPTLYTDIEIPQLKISLKQPLGLFINNEFCPSSDGKTIETVNPATGEPITSFQAANEK

DVDKAVKAARAAFDNVWSKTSSEQRGIYLSNLLKLIEEEQDTLAALETLDAGKPFHSNA

KQDLAQIIELTRYYAGAVDKFNMGETIPLTFNKFAYTLKVPFGVVAQIVPWNYPLAMAC

RKMQGALAAGNTVIIKPAENTSLSLLYFATLIKKAGFPPGVVNVIPGYGSVVGKALGTH
```

```
MDIDKISFTGSTKVGGSVLEASGQSNLKDITLECGGKSPALVFEDADLDKAIEWVANGIF

FNSGQICTANSRVYVQSSIYDKFVEKFKETAKKEWDVAGKFDPFDEKCIVGPVISSTQYD

RIKSYIERGKKEEKLDMFQTSEFPIGGAKGYFIPPTIFTDVPETSKLLRDEIFGPVVVSKFT

NYDDALKLANDTCYGLASAVFTKDVKKAHMFARDIKAGTVWINQTNQEEAKVPFGGF

KMSGIGRESGDTGVDNYLQIKSVHVDLSLDK
```

EC 1.2.1.49
*Saccharomyces cerevisiae* ALD4 (SEQ ID NO: 155)
```
MFSRSTLCLKTSASSIGRLQLRYFSHLPMTVPIKLPNGLEYEQPTGLFINNKFVPSK

QNKTFEVINPSTEEEICHIYEGREDDVEEAVQAADRAFSNGSWNGIDPIDRGKALYRLAE

LIEQDKDVIASIETLDNGKAISSSRGDVDLVINYLKSSAGFADKIDGRMIDTGRTHFSYTK

RQPLGVCGQIIPWNFPLLMWAWKIAPALVTGNTVVLKTAESTPLSALYVSKYIPQAGIPP

GVINIVSGEGKIVGEAITNHPKIKKVAFTGSTATGRHIYQSAAAGLKKVTLELGGKSPNIV

FADAELKKAVQNIILGIYYNSGEVCCAGSRVYVEESIYDKFIEEFKAASESIKVGDPFDES

TFQGAQTSQMQLNKILKYVDIGKNEGATLITGGERLGSKGYFIKPTVFGDVKEDMRIVK

EEIFGPVVTVTKFKSADEVINMANDSEYGLAAGIHTSNINTALKVADRVNAGTVWINTY

NDFHHAVPFGGFNASGLGREMSVDALQNYLQVKAVRAKLDE
```

EC 1.2.1.49
*Saccharomyces cerevisiae* ALD5 (SEQ ID NO: 156)
```
MLSRTRAAAPNSRIFTRSLLRLYSQAPLRVPITLPNGFTYEQPTGLFINGEFVASKQ

KKTFDVINPSNEEKITTVYKAMEDDVDEAVAAAKKAFETKWSIVEPEVRAKALFNLADL

VEKHQETLAAIESMDNGKSLFCARGDVALVSKYLRSCGGWADKIYGNVIDTGKNHFTY

SIKEPLGVCGQIIPWNFPLLMWSWKIGPALATGNTVVLKPAETTPLSALFASQLCQEAGIP

AGVVNILPGSGRVVGERLSAHPDVKKIAFTGSTATGRHIMKVAADTVKKVTLELGGKSP

NIVFADADLDKAVKNIAFGIFYNSGEVCCAGSRIYIQDTVYEEVLQKLKDYTESLKVGDP

FDEEVFQGAQTSDKQLHKILDYVDVAKSEGARLVTGGARHGSKGYFVKPTVFADVKGD

MRIVKEEVFGPIVTVSKFSTVDEVIAMANDSQYGLAAGIHTNDINKAVDVSKRVKAGTV

WINTYNNFHQNVPFGGFGQSGIGREMGEAALSNYTQTKSVRIAIDKPIR
```

EC 1.2.1.49
*Saccharomyces cerevisiae* ALD6 (SEQ ID NO: 157)
```
MTKLHFDTAEPVKITLPNGLTYEQPTGLFINNKFMKAQDGKTYPVEDPSTENTVC

EVSSATTEDVEYAIECADRAFHDTEWATQDPRERGRLLSKLADELESQIDLVSSIEALDN

GKTLALARGDVTIAINCLRDAAAYADKVNGRTINTGDGYMNFTTLEPIGVCGQIIPWNFP

IMMLAWKIAPALAMGNVCILKPAAVTPLNALYFASLCKKVGIPAGVVNIVPGPGRTVGA

ALTNDPRIRKLAFTGSTEVGKSVAVDSSESNLKKITLELGGKSAHLVFDDANIKKILPNL

VNGIFKNAGQICSSGSRIYVQEGIYDELLAAFKAYLETEIKVGNPFDKANFQGAITNRQQF

DTIMNYIDIGKKEGAKILTGGEKVGDKGYFIRPTVFYDVNEDMRIVKEEIFGPVVTVAKF

KTLEEGVEMANSSEFGLGSGIETESLSTGLKVAKMLKAGTVWINTYNDFDSRVPFGGVK

QSGYGREMGEEVYHAYTEVKAVRIKL
```

EC 1.2.1.49
*Saccharomyces cerevisiae* HFD1 (SEQ ID NO: 158)
```
MSNDGSKILNYTPVSKIDEIVEISRNFFFEKQLKLSHENNPRKKDLEFRQLQLKKL

YYAVKDHEEELIDAMYKDFHRNKIESVLNETTKLMNDILHLIEILPKLIKPRRVSDSSPPF

MFGKTIVEKISRGSVLIIAPFNFPLLLAFAPLAAALAAGNTIVLKPSELTPHTAVVMENLLT

TAGFPDGLIQVVQGAIDETTRLLDCGKFDLIFYTGSPRVGSIVAEKAAKSLTPCVLELGGK

SPTFITENFKASNIKIALKRIFFGAFGNSGQICVSPDYLLVHKSIYPKVIKECESVLNEFYPS
```

FDEQTDFTRMIHEPAYKKAVASINSTNGSKIVPSKISINSDTEDLCLVPPTIVYNIGWDDPL

MKQENFAPVLPIIEYEDLDETINKIIEEHDTPLVQYIFSDSQTEINRILTRLRSGDCVVGDTV

IHVGITDAPFGGIGTSGYGNYGGYYGFNTFSHERTIFKQPYWNDFTLFMRYPPNSAQKEK

LVRFAMERKPWFDRNGNNKWGLRQYFSLSAAVILISTIYAHCSS

EC 2.7.1.2
*Saccharomyces cerevisiae* GLK1 (SEQ ID NO: 159)
MSFDDLHKATERAVIQAVDQICDDFEVTPEKLDELTAYFIEQMEKGLAPPKEGHT

LASDKGLPMIPAFVTGSPNGTERGVLLAADLGGTNFRICSVNLHGDHTFSMEQMKSKIP

DDLLDDENVTSDDLFGFLARRTLAFMKKYHPDELAKGKDAKPMKLGFTFSYPVDQTSL

NSGTLIRWTKGFRIADTVGKDVVQLYQEQLSAQGMPMIKVVALTNDTVGTYLSHCYTS

DNTDSMTSGEISEPVIGCIFGTGTNGCYMEEINKITKLPQELRDKLIKEGKTHMIINVEWG

SFDNELKHLPTTKYDVVIDQKLSTNPGFHLFEKRVSGMFLGEVLRNILVDLHSQGLLLQQ

YRSKEQLPRHLTTPFQLSSEVLSHIEIDDSTGLRETELSLLQSLRLPTTPTERVQIQKLVRAI

SRRSAYLAAVPLAAILIKTNALNKRYHGEVEIGCDGSVVEYYPGFRSMLRHALALSPLG

AEGERKVHLKIAKDGSGVGAALCALVA

EC 5.3.1.9
*Saccharomyces cerevisiae* PGI1 (SEQ ID NO: 160)
MSNNSFTNFKLATELPAWSKLQKIYESQGKTLSVKQEFQKDAKRFEKLNKTFTN

YDGSKILFDYSKNLVNDEIIAALIELAKEANVTGLRDAMFKGEHINSTEDRAVYHVALRN

RANKPMYVDGVNVAPEVDSVLKHMKEFSEQVRSGEWKGYTGKKITDVVNIGIGGSDLG

PVMVTEALKHYAGVLDVHFVSNIDGTHIAETLKVVDPETTLFLIASKTFTTAETITNANT

AKNWFLSKTGNDPSHIAKHFAALSTNETEVAKFGIDTKNMFGFESWVGGRYSVWSAIGL

SVALYIGYDNFEAFLKGAEAVDNHFTQTPLEDNIPLLGGLLSVWYNNFFGAQTHLVAPF

DQYLHRFPAYLQQLSMESNGKSVTRGNVFTDYSTGSILFGEPATNAQHSFFQLVHQGTK

LIPSDFILAAQSHNPIENKLHQKMLASNFFAQAEALMVGKDEEQVKAEGATGGLVPHKV

FSGNRPTTSILAQKITPATLGALIAYYEHVTFTEGAIWNINSFDQWGVELGKVLAKVIGKE

LDNSSTISTHDASTNGLINQFKEWM

EC 2.7.1.11
*Saccharomyces cerevisiae* PFK1 (SEQ ID NO: 161)
MQSQDSCYGVAFRSIITNDEALFKKTIHFYHTLGFATVKDFNKFKHGENSLLSSGT

SQDSLREVWLESFKLSEVDASGFRIPQQEATNKAQSQGALLKIRLVMSAPIDETFDTNET

ATITYFSTDLNKIVEKFPKQAEKLSDTLVFLKDPMGNNITFSGLANATDSAPTSKDAFLEA

TSEDEIISRASSDASDLLRQTLGSSQKKKKIAVMTSGGDSPGMNAAVRAVVRTGIHFGCD

VFAVYEGYEGLLRGGKYLKKMAWEDVRGWLSEGGTLIGTARSMEFRKREGRRQAAGN

LISQGIDALVVCGGDGSLTGADLFRHEWPSLVDELVAEGRFTKEEVAPYKNLSIVGLVGS

IDNDMSGTDSTIGAYSALERICEMVDYIDATAKSHSRAFVVEVMGRHCGWLALMAGIA

TGADYIFIPERAVPHGKWQDELKEVCQRHRSKGRRNNTIIVAEGALDDQLNPVTANDVK

DALIELGLDTKVTILGHVQRGGTAVAHDRWLATLQGVDAVKAVLEFTPETPSPLIGILEN

KIIRMPLVESVKLTKSVATAIENKDFDKAISLRDTEFIELYENFLSTTVKDDGSELLPVSDR

LNIGIVHVGAPSAALNAATRAATLYCLSHGHKPYAIMNGFSGLIQTGEVKELSWIDVEN

WHNLGGSEIGTNRSVASEDLGTIAYYFQKNKLDGLIILGGFEGFRSLKQLRDGRTQHPIF

NIPMCLIPATVSNNVPGTEYSLGVDTCLNALVNYTDDIKQSASATRRRVFVCEVQGGHS

GYIASFTGLITGAVSVYTPEKKIDLASIREDITLLKENFRHDKGENRNGKLLVRNEQASSV

-continued

YSTQLLADIISEASKGKFGVRTAIPGHVQQGGVPSSKDRVTASRFAVKCIKFIEQWNKKN

EASPNTDAKVLRFKFDTHGEKVPTVEHEDDSAAVICVNGSHVSFKPIANLWENETNVEL

RKGFEVHWAEYNKIGDILSGRLKLRAEVAALAAENK

EC 2.7.1.11
*Saccharomyces cerevisiae* PFK2 (SEQ ID NO: 162)
MTVTTPFVNGTSYCTVTAYSVQSYKAAIDFYTKFLSLENRSSPDENSTLLSNDSIS

LKILLRPDEKINKNVEAHLKELNSITKTQDWRSHATQSLVFNTSDILAVKDTLNAMNAPL

QGYPTELFPMQLYTLDPLGNVVGVTSTKNAVSTKPTPPPAPEASAESGLSSKVHSYTDLA

YRMKTTDTYPSLPKPLNRPQKAIAVMTSGGDAPGMNSNVRAIVRSAIFKGCRAFVVME

GYEGLVRGGPEYIKEFHWEDVRGWSAEGGTNIGTARCMEFKKREGRLLGAQHLIEAGV

DALIVCGGDGSLTGADLFRSEWPSLIEELLKTNRISNEQYERMKHLNICGTVGSIDNDMS

TTDATIGAYSALDRICKAIDYVEATANSHSRAFVVEVMGRNCGWLALLAGIATSADYIFI

PEKPATSSEWQDQMCDIVSKHRSRGKRTTIVVVAEGAIAADLTPISPSDVHKVLVDRLGL

DTRITTLGHVQRGGTAVAYDRILATLQGLEAVNAVLESTPDTPSPLIAVNENKIVRKPLM

ESVKLTKAVAEAIQAKDFKRAMSLRDTEFIEHLNNFMAINSADHNEPKLPKDKRLKIAIV

NVGAPAGGINSAVYSMATYCMSQGHRPYAIYNGWSGLARHESVRSLNWKDMLGWQS

RGGSEIGTNRVTPEEADLGMIAYYFQKYEFDGLIIVGGFEAFESLHQLERARESYPAFRIP

MVLIPATLSNNVPGTEYSLGSDTALNALMEYCDVVKQSASSTRGRAFVVDCQGGNSGY

LATYASLAVGAQVSYVPEEGISLEQLSEDIEYLAQSFEKAEGRGRFGKLILKSTNASKALS

ATKLAEVITAEADGRFDAKPAYPGHVQQGGLPSPIDRTRATRMAIKAVGFIKDNQAAIA

EARAAEENFNADDKTISDTAAVVGVKGSHVVYNSIRQLYDYETEVSMRMPKVIHWQAT

RLIADHLVGRKRVD

EC 4.1.1.1
*Saccharomyces cerevisiae* PDC1 (SEQ ID NO: 163)
MSEITLGKYLFERLKQVNVNTVFGLPGDFNLSLLDKIYEVEGMRWAGNANELNA

AYAADGYARIKGMSCIITTFGVGELSALNGIAGSYAEHVGVLHVVGVPSISAQAKQLLL

HHTLGNGDFTVFHRMSANISETTAMITDIATAPAEIDRCIRTTYVTQRPVYLGLPANLVD

LNVPAKLLQTPIDMSLKPNDAESEKEVIDTILALVKDAKNPVILADACCSRHDVKAETKK

LIDLTQFPAFVTPMGKGSIDEQHPRYGGVYVGTLSKPEVKEAVESADLILSVGALLSDFN

TGSFSYSYKTKNIVEFHSDHMKIRNATFPGVQMKFVLQKLLTTIADAAKGYKPVAVPAR

TPANAAVPASTPLKQEWMWNQLGNFLQEGDVVIAETGTSAFGINQTTFPNNTYGISQVL

WGSIGFTTGATLGAAFAAEEIDPKKRVILFIGDGSLQLTVQEISTMIRWGLKPYLFVLNND

GYTIEKLIHGPKAQYNEIQGWDHLSLLPTFGAKDYETHRVATTGEWDKLTQDKSFNDNS

KIRMIEIMLPVFDAPQNLVEQAKLTAATNAKQ

EC 4.1.1.1
*Saccharomyces cerevisiae* PDC5 (SEQ ID NO: 164)
MSEITLGKYLFERLSQVNCNTVFGLPGDFNLSLLDKLYEVKGMRWAGNANELN

AAYAADGYARIKGMSCIITTFGVGELSALNGIAGSYAEHVGVLHVVGVPSISSQAKQLLL

HHTLGNGDFTVFHRMSANISETTAMITDIANAPAEIDRCIRTTYTTQRPVYLGLPANLVD

LNVPAKLLETPIDLSLKPNDAEAEAEVVRTVVELIKDAKNPVILADACASRHDVKAETK

KLMDLTQFPVYVTPMGKGAIDEQHPRYGGVYVGTLSRPEVKKAVESADLILSIGALLSD

FNTGSFSYSYKTKNIVEFHSDHIKIRNATFPGVQMKFALQKLLDAIPEVVKDYKPVAVPA

RVPITKSTPANTPMKQEWMWNHLGNFLREGDIVIAETGTSAFGINQTTFPTDVYAIVQVL

WGSIGFTVGALLGATMAAEELDPKKRVILFIGDGSLQLTVQEISTMIRWGLKPYIFVLNN

-continued

```
NGYTIEKLIHGPHAEYNEIQGWDHLALLPTFGARNYETHRVATTGEWEKLTQDKDFQD

NSKIRMIEVMLPVFDAPQNLVKQAQLTAATNAKQ

EC 4.1.1.1
Saccharomyces cerevisiae PDC6 (SEQ ID NO: 165)
MSEITLGKYLFERLKQVNVNTIFGLPGDFNLSLLDKIYEVDGLRWAGNANELNA

AYAADGYARIKGLSVLVTTFGVGELSALNGIAGSYAEHVGVLHVVGVPSISAQAKQLLL

HHTLGNGDFTVFHRMSANISETTSMITDIATAPSEIDRLIRTTFITQRPSYLGLPANLVDLK

VPGSLLEKPIDLSLKPNDPEAEKEVIDTVLELIQNSKNPVILSDACASRHNVKKETQKLID

LTQFPAFVTPLGKGSIDEQHPRYGGVYVGTLSKQDVKQAVESADLILSVGALLSDFNTGS

FSYSYKTKNVVEFHSDYVKVKNATFLGVQMKFALQNLLKVIPDVVKGYKSVPVPTKTP

ANKGVPASTPLKQEWLWNELSKFLQEGDVIISETGTSAFGINQTIFPKDAYGISQVLWGSI

GFTTGATLGAAFAAEEIDPNKRVILFIGDGSLQLTVQEISTMIRWGLKPYLFVLNNDGYTI

EKLIHGPHAEYNEIQTWDHLALLPAFGAKKYENHKIATTGEWDALTTDSEFQKNSVIRLI

ELKLPVFDAPESLIKQAQLTAATNAKQ

EC 1.1.1.8
Saccharomyces cerevisiae GPD2 (SEQ ID NO: 166)
MLAVRRLTRYTFLKRTHPVLYTRRAYKILPSRSTFLRRSLLQTQLHSKMTAHTNI

KQHKHCHEDHPIRRSDSAVSIVHLKRAPFKVTVIGSGNWGTTIAKVIAENTELHSHIFEPE

VRMWVFDEKIGDENLTDIINTRHQNVKYLPNIDLPHNLVADPDLLHSIKGADILVFNIPH

QFLPNIVKQLQGHVAPHVRAISCLKGFELGSKGVQLLSSYVTDELGIQCGALSGANLAPE

VAKEHWSETTVAYQLPKDYQGDGKDVDHKILKLLFHRPYFHVNVIDDVAGISIAGALK

NVVALACGFVEGMGWGNNASAAIQRLGLGEIIKFGRMFFPESKVETYYQESAGVADLIT

TCSGGRNVKVATYMAKTGKSALEAEKELLNGQSAQGIITCREVHEWLQTCELTQEFPLF

EAVYQIVYNNVRMEDLPEMIEELDIDDE

EC 3.1.3.21
Saccharomyces cerevisiae GPP1 (SEQ ID NO: 167)
MPLTTKPLSLKINAALFDVDGTIIISQPAIAAFWRDFGKDKPYFDAEHVIHISHGW

RTYDAIAKFAPDFADEEYVNKLEGEIPEKYGEHSIEVPGAVKLCNALNALPKEKWAVAT

SGTRDMAKKWFDILKIKRPEYFITANDVKQGKPHPEPYLKGRNGLGFPINEQDPSKSKVV

VFEDAPAGIAAGKAAGCKIVGIATTFDLDFLKEKGCDIIVKNHESIRVGEYNAETDEVELI

FDDYLYAKDDLLKW
```

In certain embodiments, an enzyme of the present invention includes any enzyme that is at least about 70%, 80%, 90%, 95%, 99% identical, or sharing at least about 60%, 70%, 80%, 90%, 95% sequence identity to any of the enzymes of the metabolic engineered pathways as described above. These enzymes sharing the requisite sequence identity or similarity can be wild-type enzymes from a different organism, or can be artificial, i.e., recombinant, enzymes.

In certain embodiments, any genes encoding for enzymes with the same activity as any of the enzymes of the metabolically engineered pathways as described above may be used in place of the enzymes. These enzymes may be wild-type enzymes from a different organism, or may be artificial, recombinant or engineered enzymes.

Additionally, due to the inherent degeneracy of the genetic code, other nucleic acid sequences which encode substantially the same or a functionally equivalent amino acid sequence can also be used to express the polynucleotide encoding such enzymes. As will be understood by those of skill in the art, it can be advantageous to modify a coding sequence to enhance its expression in a particular host. The codons that are utilized most often in a species are called "optimal codons", and those not utilized very often are classified as "rare or low-usage codons". Codons can be substituted to reflect the preferred codon usage of the host, a process sometimes called "codon optimization" or "controlling for species codon bias." Methodology for optimizing a nucleotide sequence for expression in, e.g. *Saccharomyces cerevisiae*, are known to one of ordinary skill in the art.

Modified Strains

The present invention further provides for knockout strains in which the metabolic engineered pathways of the invention are carried out. Such a genetically modified microorganism would have an increased ability to produce lactate or acetate as a fermentation product. "Knock out" of the genes means partial, substantial, or complete deletion, silencing, inactivation, or down-regulation.

Thus, certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences can be understood to encompass "genetic modification(s)" or "transformation(s)" such that the resulting strains of said thermophilic or mesophilic microorganisms can be understood to be "genetically modified" or "transformed." In certain embodiments, strains can be of bacterial, fungal, or yeast origin.

A genetically modified strain that is a knockout strain can have the advantage of eliminating the production of certain organic acids or products that interfere with the ability of the strain to generate a high yield of an alternative product, such as isopropanol or propanediol.

For example, if the conversion of pyruvate to lactate (the salt form of lactic acid) by the action of LDH was not available in the early stages of the glycolytic pathway, then the pyruvate could be more efficiently converted to acetyl CoA by the action of pyruvate dehydrogenase or pyruvate-ferredoxin oxidoreductase.

Genes to be targeted for knockout for the present invention include lactate dehydrogenase (ldh), hydrogenase (hyd), acetaldehyde dehydrogenase (acdh), acetate kinase (ack), pyruvate-ferredoxin oxidoreductase (por) or pyruvate decarboxylase (pdc).

As used herein, the term "lactate dehydrogenase" or "LDH" is intended to include the enzyme capable of converting pyruvate into lactate. It is understood that LDH can also catalyze the oxidation of hydroxybutyrate.

As used herein, the term "acetate kinase" or "ACK" is intended to include the enzyme capable of converting acetyl phosphate into acetate.

As used herein, the term "pyruvate-ferredoxin oxidoreductase" or "POR" is intended to include the enzyme capable of converting pyruvate into acetyl CoA, carbon dioxide, and reduced ferredoxin.

The term "pyruvate decarboxylase activity" is intended to include the ability of a polypeptide to enzymatically convert pyruvate into acetaldehyde (e.g., "pyruvate decarboxylase" or "PDC"). Typically, the activity of a selected polypeptide encompasses the total enzymatic activity associated with the produced polypeptide, comprising, e.g., the superior substrate affinity of the enzyme, thermostability, stability at different pHs, or a combination of these attributes.

Certain embodiments of the present invention, alternatively, provide for the "insertion," (e.g., the addition, integration, incorporation, or introduction) of certain genes or particular polynucleotide sequences within thermophilic or mesophilic microorganisms, which insertion of genes or particular polynucleotide sequences can be understood to encompass "genetic modification(s)" or "transformation(s)" such that the resulting strains of said thermophilic or mesophilic microorganisms can be understood to be "genetically modified" or "transformed." In certain embodiments, strains can be of bacterial, fungal, or yeast origin.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, can be added to a mesophilic or thermophilic organism. In certain embodiments of the invention, the enzyme can confer the ability to metabolize a pentose sugar and be involved, for example, in the D-xylose pathway and/or L-arabinose pathway.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest can be engineered by site directed homologous recombination to knockout the production of organic acids. In still other embodiments, RNAi or antisense DNA (asDNA) can be used to partially, substantially, or completely silence, inactivate, or down-regulate a particular gene of interest.

Vectors and Host Cells

The present invention also relates to vectors which include genes encoding for enzymes of the present invention, as described above, as well as host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The DNA sequence in the expression vector is operatively associated with an appropriate expression control sequence(s) (promoter) to direct mRNA synthesis. Any suitable promoter to drive gene expression in the host cells of the invention can be used. Additionally, promoters known to control expression of genes in prokaryotic or lower eukaryotic cells can be used. The expression vector also contains a ribosome binding site for translation initiation and a transcription terminator. The vector can also include appropriate sequences for amplifying expression, or can include additional regulatory regions.

The vector containing the appropriate selectable marker sequence as used herein, as well as an appropriate promoter or control sequence, can be employed to transform an appropriate thermophilic host to permit the host to express the protein.

The terms "promoter" or "surrogate promoter" is intended to include a polynucleotide segment that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter can be used to replace the natural promoter, or can be used in addition to the natural promoter. A surrogate promoter can be endogenous with regard to the host cell in which it is used, or it can be a heterologous polynucleotide sequence introduced into the host cell, e.g., exogenous with regard to the host cell in which it is used.

The terms "gene(s)" or "polynucleotide segment" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In addition to the plasmid form, a gene can, for example, be in the form of linear DNA. In certain embodiments, the gene encodes a polypeptide, such as an enzyme of the present invention. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more gene is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof.

In certain aspects, the present invention relates to host cells containing the above-described constructs. The host cell can be an anaerobic thermophilic bacterial cell, including an anaerobic xylanolytic and/or cellulolytic host cell. The selection of an appropriate host is deemed to be within the scope of those skilled in the art from the teachings herein.

The present invention also includes recombinant constructs comprising one or more of the selectable marker sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available. The following vectors are provided by way of example only.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

Introduction of the construct in host cells can be done using methods known in the art. Introduction can also be effected by electroporation methods as described in U.S. Prov. Appl. No. 61/109,642, filed Oct. 30, 2008, the contents of which are herein incorporated by reference.

Furthermore, the use of positive and/or negative selection markers, genetic tools, and homologous recombination-based genome integration adapted for use in, e.g., thermophilic organisms, that can be used to efficiently select modified strains, including modified strains of *C. thermocellum* and *T. saccharolyticum* can be done using methods as described in U.S. Prov. Appl. No. 61/232,648, filed Aug. 10, 2009, the contents of which are herein incorporated by reference. Methods for the expression of foreign genes, knockout and overexpression of native genes, and creation of clean industrial strains that do not contain antibiotic markers or other extraneous DNA can be performed, as described in U.S. Prov. Appl. No. 61/232,648.

Biomass

The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, and sugar-processing residues.

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulent plants, such as but not limited to agave; and forestry wastes, such as but not limited to recycled wood pulp fiber, sawdust, hardwood (e.g., poplar, oak, maple, birch, willow), softwood, or any combination thereof. Lignocellulosic material can comprise one species of fiber; alternatively, lignocellulosic material can comprise a mixture of fibers that originate from different lignocellulosic materials. Particularly advantageous lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and *miscanthus*; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products can be used to produce ethanol or higher value added chemicals, such as organic acids, aromatics, esters, acetone and polymer intermediates. During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate $NAD^+$, an obligate requirement for continued glycolysis and ATP production. The waste products of these $NAD^+$ regeneration systems are commonly referred to as fermentation products.

EXEMPLIFICATION

Example 1

1.1 Production of Mixed Alcohols in Bacterial and Yeast CBP Platforms

Production of mixed alcohols in bacteria and yeast makes use of bacterial and yeast CBP platforms, and their available toolboxes, to produce a combination of propanediol, isopropanol, glycerol and ethanol. Trace amounts of microbially produced propanediol were first detected in 1954 during cultivation of *Clostridium* thermobutyricur. See Enebo, L. 1954, "Studies in cellulose decomposition by an anaerobic thermophilic bacterium and two associated non-cellulolytic species," p. 94-96. Viktor Pettersons Bokindustrie Aktiebolag, Stockholm. Since then, reports have indicated native production of propanediol from common sugars during fermentations of *C. sphenoides* and *T. thermosaccharolyticum*. See Tran-Din, K., & Gottschalk, G., 1985, *Arch. Microbiol.* 142, 87-92; Cameron, D. C., & Clooney, C., 1986, *Bio/Technology* 4, 651-654. Recombinant *E. coli* strains have been developed that produce propanediol from dihydroxyacetone phosphate, an intermediate of sugar metabolism, using multiple recombinant genes. See Altaras, N. E., & Cameron, D. C., 1999, *Appl Environ Microbiol.* 65(3), 1180-5; U.S. Pat. No. 6,303,352.

The objective of this example is to provide new pathways for the production of high yields of mixed alcohols in bacteria and yeast. The bacterial CBP platforms comprise microorganisms that are in the same family as *C. sphenoides* and *T. thermosaccharolyicum*, which contain native genes for propanediol production and, unlike the literature, do not rely on expression of recombinant activities to convert dihydroxyacetone phosphate to propanediol. For example, *T. saccharolyticum* is able to ferment L-Rhamnose to equimolar amounts of propanediol and a mixture of ethanol, acetic acid, lactic acid, $H_2$ and $CO_2$. See Lee et al., *International Journal of Systematic Bacteriology*, 43(1): 41-51 (1993). However, in the past, the exploitation of thermophilic clostridia for production of propanediol was not feasible due to a lack of genetically tractable systems required for stable genetic engineering. The successful genetic engineering of thermophilic clostridia and *thermoanaerobacter* and *thermoanaerobacterium* strains now makes such exploitation for metabolic engineering possible. See U.S. Prov. Appl. No. 61/232,648, filed Aug. 10, 2009. Further, production of propanedial in yeast has been observed by the expression of a single gene, methylglyoxal synthase (mgs), indicating that additional activities necessary to convert methygloxal to propanediol are endogenous to yeast. See Lee, W., & DaSilva, N. A., 2006, *Metabolic Eng.* 8, 58-65.

The 1,2-propandiol produced using these platforms can be used as a valuable intermediate or converted to propionate and propanol using microbes such as *Lactobacillus reuteri* strain isolated from sourdough that is known to do this reaction. See Sriramulu, D. D., et al., 2008, *J Bacteriol.* 190(13):4559-67. Chemical routes might also exist for direct conversion of propanediol to propanol or even propylene.

Isopropanol can be produced by the addition of a pathway to produce acetone and a dehydrogenase capable of utilizing acetone as a substrate. The best known and studied acetone production route is from the metabolism of *Clostridium acetobutylicum*. All enzymes in this pathway have been sequenced and cloned into other hosts such as *E. coli*. See Bermejo, L. L., et al., 1998, *Appl Environ Microbiol.* 64(3), 1079-85. *C. acetobutylicum* has been used in industrial fermentations beginning in the early 1900's and the acetone produced was used as a major source for gunpowder during the First World War. The fermentation was widely used until the 1960's when the process was no longer able to compete with the emergent petrochemical process due to rising costs of fermentable sugars. The bacterial and yeast CBP platforms makes the production of isopropanol readily tractable.

1.2 Pathway Definition and Stoichiometric Calculations for Production of Mixed Alcohols The combined production of propanediol and isopropanol from glucose is outlined in the pathways of FIG. 1 and requires the activity of several distinct enzymes (Table 2).

TABLE 2

List of native and non-native gene candidates pertaining to engineering of mixed alcohols in bacteria and yeast CBP platforms.

| Activity | EC | Cthe | Tsacch | Yeast | Non-native-bacteria | Non-native-yeast |
|---|---|---|---|---|---|---|
| methylglyoxal synthase | 4.2.3.3 | 95 | or2316 | | | *Oryza sativa* mgs |
| aldo-keto reductase (methylglyoxal to acetol) | 1.1.1.- | 152 | or1401 | | | |
| | | 236 | or1402 | | | |
| | | 283 | or785 | | | |
| | | | or414 | | | |
| | | | or2491 | | | |
| aldo-keto reductase (acetol to propanediol) | 1.1.1.- | 101 | or1043 | | | |
| | | 394 | or2289 | | | |
| | | 423 | or411 | | | |
| | | 2445 | or2426 | | | |
| | | 2579 | or0286 | | | |

TABLE 2-continued

List of native and non-native gene candidates pertaining to engineering of mixed alcohols in bacteria and yeast CBP platforms.

| Activity | EC | Cthe | Tsacch | Yeast | Non-native-bacteria | Non-native-yeast |
|---|---|---|---|---|---|---|
| phosphotransacetylase | 2.3.1.8 | 1029 | or1741 | | | Tsacch or1741 |
| acetate kinase | 2.7.2.1 | 1028 | or1742 | | | Tsacch or1742 |
| thiolase | 2.3.1.9 | | | ERG10 | C. acetobutylicum | |
| coA transferase | 2.8.3.8 | | | | C. acetobutylicum | C. acetobutylicum |
| acetoacetate decarboxylase | 4.1.1.4 | | | | C. acetobutylicum | C. acetobutylicum |
| isopropanol dehydrogenase | 1.1.1.80 | 101 | or1411 | ADH1 | | |
| | | 394 | or1043 | ADH2 | | |
| | | 423 | or2426 | ADH3 | | |
| | | 2445 | or2289 | ADH4 | | |
| | | 2579 | or0286 | ADH5 | | |
| | | | | ADH6 | | |
| | | | | ADH7 | | |
| | | | | BDH2 | | |
| | | | | SFA1 | | |
| | | | | YPL088W | | |
| alcohol dehydrogenase | 1.1.1.1 | 423 | or411 | | | |
| PFOR (oxidoreductase) | 1.2.7.1 | 2390-3 | or0047 | | | |
| fructose 1,6-biphosphate aldolase | 4.1.2.13 | 0349 | or0260 | FBA1 | | |
| | | 1019 | or0330 | | | |
| triose-phophate isomerase | 5.3.1.1 | 0139 | or2687 | TPI1 | | |
| glycerol-3-phosphate dehydrogenase | 1.1.1.8 | | | GPD2 | | |
| glycerol-3-phosphatase | 3.1.3.21 | | | GPP1 | | |
| pyruvate formate-lyase | 2.3.1.54 | | | | | E. coli pflA/pflB |
| formate dehydrogenase | 1.2.1.2 | FDH1 | | | | |
| aldehyde reductase | 1.1.1.21 | 101 | or1043 | GRE3 | | |
| | | 394 | or2289 | | | |
| | | 423 | or411 | | | |
| | | 2445 | or2426 | | | |
| | | 2579 | or0286 | | | |
| glyoxylate reductase | 1.1.1.79 | 152 | or1401 | GOR1 | | |
| | | 236 | or1402 | YPL113C | | |
| | | 283 | or785 | | | |
| | | | or414 | | | |
| | | | or2491 | | | |
| methylglyoxal dehydrogenase | 1.2.1.49 | 152 | or1401 | GCY1 | | |
| | | 236 | or1402 | ALD2 | | |
| | | 283 | or785 | ALD3 | | |
| | | | or414 | ALD4 | | |
| | | | or2491 | ALD5 | | |
| | | | | ALD6 | | |
| | | | | HFD1 | | |
| Genes to KO | | | | | | |
| lactate dehydrogenase | 1.1.1.27 | 1053 | or180 | | | |
| pyruvate decarboxylase | 4.1.1.1 | | | PDC1 | | |
| | | | | PDC5 | | |
| | | | | PDC6 | | |

The branched metabolic pathways can be subdivided into distinct production routes as follows:

(i) the conversion of dihydroxyacetone phosphate into propanediol (ii) the conversion of pyruvate into isopropanol (iii) the conversion of pyruvate into ethanol (bacterial CBP platform only)

(iv) the conversion of dihydroxyacetone phosphate into glycerol (yeast CBP platform only).

The combined production of isopropanol, propanediol, and ethanol (routes (i), (ii), and (iii)) from two glucose molecules during bacterial metabolism is governed by the overall stoichiometric equation with a theoretical yield of one propanol, one propanediol, and one ethanol per two glucose, as follows:

$$2C_6H_{12}O_6 \rightarrow C_3H_8O + C_3H_8O_2 + C_2H_6O + 4CO_2 + H_2 + 3ATP$$

The theoretical yield of propanediol, propanol, and ethanol on hexose and pentose sugar for the above pathway is:

| Hexose | Pentose |
|---|---|
| 0.21 g propanediol/g sugar | 0.21 g propanediol/g sugar |
| 0.17 g isopropanol/g sugar | 0.17 g isopropanol/g sugar |
| 0.13 g ethanol/g sugar | 0.13 g ethanol/g sugar |

The combined production of isopropanol, propanediol, and glycerol in yeast, S. cerevisiae, (routes (i), (ii), and (iv)) results in the net gain of one ATP, and is governed by the overall stoichiometric equation:

$$2C_6H_{12}O_6 \rightarrow C_3H_8O + C_3H_8O_2 + C_3H_8O_3 + 3CO_2 + ATP$$

The co-production of isopropanol and propanediol together with the loss of carbon to glycerol and $CO_2$ are necessary to maintain the redox balance. The theoretical yield of propanediol, propanol, and glycerol on hexose and pentose sugar for the above pathway is:

| Hexose | Pentose |
|---|---|
| 0.21 g propanediol/g sugar | 0.21 g propanediol/g sugar |
| 0.17 g isopropanol/g sugar | 0.17 g isopropanol/g sugar |
| 0.26 g glycerol/g sugar | 0.26 g glycerol/g sugar |

The above stoichiometric equations were calculated using a hexose as a carbohydrate source; however, pentose sugars, including but not limited to xylose, can be readily utilized as well. When a pentose sugar is used as the carbohydrate source, six pentose sugars are required as the equivalent for five hexose sugars.

1.3 Production Routes for Mixed Alcohols and Corresponding Enzymology

Bacterial CBP Platforms

The combined production of propanediol, isopropanol, and ethanol from glucose in a bacterial CBP platform can be subdivided into the following distinct production routes: (i) the conversion of dihydroxyacetone phosphate into propanediol; (ii) the conversion of pyruvate into isopropanol; and (iii) the conversion of pyruvate into ethanol (FIG. 1). The microbial hosts utilize carbohydrate sources, shown as glucose in FIG. 1, to produce the mixed alcohols, but as mentioned above, pentose sugars such as xylose can be readily utilized as well, requiring six pentose sugars as equivalent for five hexose sugars. The first step in the pathway uses the microbial host's cellular metabolism to metabolize the carbohydrate source, employing, e.g., the Embden-Meyerhof-Parnas (EMP) pathway to produce dihydroxyacetone phosphate and glyceraldehyde 3-phosphate (FIG. 1). These metabolites can be interchanged using triosephosphate isomerase (E.C. 5.3.1.1).

During route (i), dihydroxyacetone phosphate is converted to methyglyoxal by methylglyoxal synthase (E.C. 4.2.3.3). Methylglyoxal is subsequently converted to either acetol by an oxidoreductase, which is to be identified from EC 1.1.1. (see Table 2), or lactaldehyde by a keto-reductase (E.C. 1.1.1.79, 1.2.1.49). These intermediates are further reduced to propanediol by, oxidoredutases (E.C. 1.1.1) for acetol or (E.C. 1.1.1.2) 1 lactaldehyde.

For route (ii), glyceraldehyde 3-phosphate is further metabolized to pyruvate through standard glycolysis reactions, producing ATP to power the cellular reactions and the required reducing equivalents needed to reduce the carbon end-products. During bacterial metabolism, pyruvate is metabolized to acetyl-CoA, reduced ferredoxin, and $CO_2$ by pyruvate ferredoxin oxidoreductase (E.C. 1.2.7.1) (FIG. 1, light gray box). NADH and $H_2$ are subsequently produced during the oxidation of ferredoxin. Acetyl-CoA is then converted to acetate by phosphate acetytransferse (E.C. 2.3.1.8) and acetate kinase (E.C. 2.7.2.1) in an ATP generating reaction. Two acetyl-CoA molecules are converted to acetoacetyl-CoA by thiolase (E.C. 2.3.1.9). Acetoacetyl-CoA is then converted to acetoacetate by CoA enzyme transferase (E.C. 2.8.3.8), where the CoA species is transferred from acetoacetyl-CoA to acetate, replenishing the acetyl-CoA consumed during the thiolase reaction. Acetoacetate is then converted to acetone by acetoacetate decarboxylase (E.C. 4.1.1.4). The reduction of acetone to isopropanol can be accomplished by an alcohol dehydrogenase (E.C. 1.1.1.80).

In route (iii), acetyl-CoA is converted to ethanol by acetaldehyde dehydrogenase (EC 1.2.1.3) and an alcohol dehydrogenase (E.C. 1.1.1.1), or through a bi-functional enzyme catalyzing both steps.

All the required enzymatic activities have been demonstrated in C. thermosaccharolyticum (see Cameron, D. C., & Clooney, C., 1986, Bio/Technology 4, 651-654) and relevant endogenous enzymes in the bacteria CBP platform production strains that exhibit high levels of homology to the desired enzymatic domains have been identified (see Table 2). The enzymes catalyzing the production of acetone from acetyl-CoA have been identified in the literature, and activities associated with (E.C. 2.3.1.9), (E.C. 2.8.3.8), and (E.C. 4.1.1.4) can be engineered using genes from C. acetobutylicum. See Bermejo, L. L., et al., 1998, Appl Environ Microbiol. 64(3), 1079-85.

The conversion of acetone to isopropanol has been shown by multiple alcohol dehydrogenases and endogenous enzymes from the microbial CBP hosts can be screened for their capability to accept acetone as a substrate. Additional efforts must be made to readily control the flux through the different metabolic branch points through the modulation of enzyme levels and regulation. To this end, the deletion of ldh (E.C. 1.1.1.27) will prevent flow of carbon from pyruvate to lactic acid (see Table 2, "Genes to KO").

Yeast CBP Platforms

The combined production of propanediol, isopropanol, and glycerol from glucose in a yeast CBP platform can be subdivided into the following distinct production routes: (i) the conversion of dihydroxyacetone phosphate into propanediol; (ii) the conversion of pyruvate into isopropanol; and (iv) the conversion of dihydroxyacetone phosphate into glycerol (FIG. 1). As described above, the microbial hosts utilize carbohydrate sources, such as glucose as shown in FIG. 1, or a pentose sugar such as xylose. The first step in the pathway uses the microbial host's cellular metabolism to metabolize the carbohydrate source, employing, e.g., the Embden-Meyerhof-Parnas (EMP) pathway to produce dihydroxyacetone phosphate and glyceraldehyde phosphate (FIG. 1). These metabolites can be interchanged using triosephosphate isomerase (E C. 5.3.1.1).

Route (i) is proposed in the yeast CBP platform in a similar manner as route (i) in the bacteria CBP platform, converting dihydroxyacetone phosphate to methyglyoxal and using the two alternate pathways presented to generate propanediol from methyglyoxal. See FIG. 1. However, based on current yeast literature, only a third route might be available, in part, because all result in the same redox change. All three begin with the production of methylglyoxal from dihydroxyacetone phosphate by methylglyoxal synthase, MGS, (E.C. 4.2.3.3) which can be obtained from one of several potential sources. The introduction of the mgs gene alone in yeast has been shown to result in the production of propanediol, but at relatively low titers; subsequent introduction of a glycerol dehydrogenase (E.C. 1.1.1.6) doubled the amount of propanediol formed. See Hoffman, M. L., 1999, Metabolic engineering of 1,2-propanediol production in *Saccharomyces cerevisiae*. Ph.D. Dissertation, University of Wisconsin-Madison. Alternatively, aldehyde reductase (E.C. 1.1.1.21) may be capable of converting methylglyoxal to lactaldehyde and then subsequently to propanediol. The native yeast aldehyde reductase, GRE3, can be overexpressed to test this possibility. In addition methylglyoxal could potentially be converted to lactaldehyde by glyoxylate reductase (E.C. 1.1.1.79) or by methylglyoxal dehydrogenase (E.C. 1.2.1.49). These enzymatic activities have not been reported in *S. cerevisiae*, but there are a number of endogenous genes which may contain these activities: two potential glyoxylate reductases (GOR1 and YPL113C), a glycerol dehydrogenase (GCY1), six aldehyde dehydrogenases (ALD2-6 and HFD1), and the ten alcohol dehydrogenases mentioned below. See Table 2. It might be desirable to engineer in a combination of the two alternate pathways outlined above for producing propanediol from methylglyoxal to reach a desirable titer for propanediol.

For route (ii), glyceraldehyde 3-phosphate is further metabolized to pyruvate through standard glycolysis reactions, as described above for bacteria CBP platforms. In yeast metabolism, acetyl-CoA and formate is produced from pyruvate by pyruvate formate lyase (E.C. 2.3.1.8) (FIG. 1, dark gray box). Formate is further metabolized to $CO_2$, NADH, and $H_2$ by formate dehydrogenase (E.C. 1.2.1.2) (FIG. 1, dark gray box). Production of isopropanol from acetyl-CoA is performed as described above for the bacteria CBP platform.

Five enzymatic activities can be engineered into yeast for route (ii). The pyruvate formate lyase (PFL) (E.C. 2.3.1.8) is required for the formation of acetyl-CoA in the cytosol, because in a majority of yeast species the endogenously produced acetyl-CoA is sequestered in the mitochondria. Enzymatically active PFL has been expressed in yeast for the production of formate. See Waks, Z., & Silver, P. A., 2009, *Appl. Env. Microbiol.* 75, 1867-1875. *S. cerevisiae* has an endogenous formate dehydrogenase (E.C. 1.2.1.2) to convert the formate generated to $CO_2$ and $H_2$. The cytosolic acetyl-CoA generated is subsequently converted to acetone by the introduction of the *C. acetobutylicum* pathway, as described above for the bacteria CBP platform, working together with the yeast acetyl-CoA acetyltransferase, ERG10, (E.C. 2.3.1.9). An alcohol dehydrogenase executes the final reaction in this section, acetone to isopropanol. The *S. cerevisiae* genome encodes for ten alcohol dehydrogenases (ADH1-7, BDH2, SFA1, and YPL088W), which can be assayed for the capability of converting acetone to isopropanol. See Table 2. If necessary an exogenous alcohol dehydrogenase can be engineered into *S. cerevisiae*. Three pyruvate decarboxylase genes (E.C. 4.1.1.1) can be deleted: PDC1, PDC5, and PDC6. The presence of these three enzymes would result in the loss of significant pyruvate to acetaldehyde.

In route (iv), dihydroxyacetone phosphate is converted to glycerol by glycerol-3-phosphate dehydrogenase (E.C. 1.1.1.8) and glycerol-3-phosphatase (E.C. 3.1.3.21) (FIG. 1, dark gray boxes). The enzymes required for route (iv) are already present in *S. cerevisiae*.

Example 2

2.1 Production of n-Propanol and Isopropanol in Bacterial CBP Platforms

All current native and recombinant propanol producing metabolic pathways have at most a theoretical yield of 0.33 g propanol/g carbohydrate. Yan Y. & Liao J. 2009, *J Indus Microbiol and Biotech* 36(4):471-479. This yield, corresponding to one mole isopropanol per mole glucose, incorporates into isopropanol only 75% of the free energy available from glucose during anaerobic fermentation. The additional 25% of the free energy, also referred to as available electrons, must be incorporated into a co-product during anaerobic fermentation, or consumed by oxygen during aerobic fermentation.

The present example proposes a new pathway for propanol production from lignocellulosic carbohydrates at a yield of 0.44 g/g carbohydrate, and incorporates 100% of the free energy available from carbohydrate conversion. In order to produce propanol at this theoretical maximum yield using biochemical pathways found in nature, production of both n- and iso-forms are required. In the metabolic pathway described here, isopropanol production serves in an ATP generating capacity, while n-propanol production serves as an electron sink to balance the anaerobic fermentation. This pathway allows for a balanced fermentation equation that is thermodynamically feasible.

Both products can be recovered from the fermentation broth via distillation, reducing downstream processing complexity. Isopropanol is a product natively produced by solventogenic Clostridia, and is rapidly produced by *Thermoanaerobacter* species when fed with acetone, indicating the presence of a native alcohol dehydrogenase with high activity for the desired reaction. See Lamed RJ and Zeikus JG. 1981, *The Biochemical J* 195(1):183-190. Acetone production has been extensively studied, and the Clostridial pathway has been heterologously expressed in *E. coli* as described above. See Bermejo, L. L., et al., 1998, *Appl. Environ. Microbiol.* 64(3), 1079-85. n-propanol is a natural product of propanediol degradation, with many microorganisms reported to perform this catalysis under anaerobic conditions. Recently, the genes involved in this conversion have been identified in one species, *Listeria* innocula, which will facilitate the expression of this pathway in the bacterial CBP organisms. See Xue J. et al., 2008, *Applied and Environmental Microbiol.* 74(22):7073-7079. Propanediol, a key intermediate of the n-propanol pathway, is a natural fermentation product of thermophilic bacteria. *T. thermosaccharolyticum* HG-8, the organism reported to produce the highest titer of propanediol, can be engineered for the production of n-propanol.

2.2 Pathway Definition and Stoichiometric Calculations for Production of Propanols The combined production of n-propanol and isopropanol from glucose or xylose is outlined in the pathways of FIG. 2 and requires the activity of several distinct enzymes (Table 3).

TABLE 3

List of native and non-native gene candidates pertaining to engineering of n-propanol and isopropanol in the CBP bacterial platform.

| Activity | EC | C. thermocellum | T. saccharolyticum | Non-native bacteria |
|---|---|---|---|---|
| triose phosphate isomerase | 5.3.1.1 | 139 | or2687 | |
| methylglyoxal synthase | 4.2.3.3 | 95 | or2316 | |
| aldo-keto reductase (methylglyoxal to acetol) | 1.1.1.— | 152<br>236<br>283 | or1401<br>or1402<br>or785<br>or414<br>or2491 | |
| aldo-keto reductase (acetol to propanediol) | 1.1.1.— | 101<br>394<br>423<br>2445<br>2579 | or1043<br>or2289<br>or411<br>or2426<br>or0286 | |
| propanediol dehydratase | 4.2.1.28 | | or0222,<br>or0224-or0226 | T. sacch genes can be expressed in C. therm |
| propanaldehyde dehydrogenase | 1.1.1.202 | 101<br>394<br>423<br>2579 | 0411<br>1043<br>2426<br>2289<br>0286 | |
| phosphotransacetylase | 2.3.1.8 | 1029 | or1741 | |
| acetate kinase | 2.7.2.1 | 1028 | or1742 | |
| thiolase | 2.3.1.9 | | | C. acetobutylicum |
| coA transferase | 2.8.3.8 | | | C. acetobutylicum CtfAB |
| acetoacetate decarboxylase | 4.1.1.4 | | | C. acetobutylicum Adc, Aad |
| PFOR (oxidoreductase) | 1.2.7.1 | 2390-93 | or0047 | |

| Genes to KO | | | | |
|---|---|---|---|---|
| Activity | EC | C. the | T. sacch | Non-native-bacteria |
| alcohol dehydrogenase | 1.1.1.1 | 423 | or411 | |
| lactate dehydrogenase | 1.1.1.27 | 1053 | or180 | |
| hydrogenase | 1.12.7.2 | 425-31 | or1545-48 | |

The combined production of n-propanol and isopropanol from 3 glucose molecules during bacterial metabolism is governed by the overall stoichiometric equation.

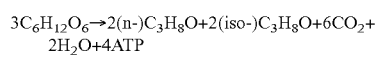

$$3C_6H_{12}O_6 \rightarrow 2(n\text{-})C_3H_8O + 2(iso\text{-})C_3H_8O + 6CO_2 + 2H_2O + 4ATP$$

The theoretical yield of propanols on a hexose sugar for the above pathway is 0.44 g propanols/g hexose.

The combined production of n-propanol and isopropanol from 9 xylose molecules during bacterial metabolism is governed by the overall stoichiometric equation:

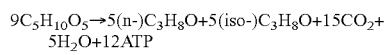

$$9C_5H_{10}O_5 \rightarrow 5(n\text{-})C_3H_8O + 5(iso\text{-})C_3H_8O + 15CO_2 + 5H_2O + 12ATP$$

The theoretical yield of propanols on a pentose sugar for the above pathway is 0.44 g propanols/g hexose.

For this metabolic pathway, product yields are identical for hexose, e.g., glucose, and pentose, e.g., xylose, carbohydrates due to the activity of triosephosphate isomerase (tpi) (E.C. 5.3.1.1). Pentose fermentation produces more of the isomer glyceraldehyde 3-phosphate (GAP) than dihydroxyacetone phosphate (DHAP) compared to hexose fermentation, which produces equimolar ratios of the two compounds. However, qpi allows for the conversion of GAP to DHAP and vice-versa, creating equal product yields for both carbohydrates.

2.3 Production Routes for Propanols and Corresponding Enzymology

The metabolic pathways for the production of n-propanol and isopropanol can be subdivided into two distinct production routes: (i) the conversion of dihydroxyacetone phosphate into n-propanol; and (ii) the conversion of pyruvate into isopropanol.

For the n-propanol route, route (i), dihydroxyacetone phosphate is converted to methyglyoxal by methylglyoxal synthase (E.C. 4.2.3.3). Methylglyoxal is subsequently converted to acetol by an oxidoreductase (E.C. 1.1.1) or to lactaldehyde by a keto-reductase (1.1.1.79 or 1.2.1.49). These intermediates are then further reduced to propanediol by enzymes from (E.C. 1.1.1). Propanediol is then dehydrated to propanal by a diol-hydrolase (E.C. 4.2.1.28) and reduced to n-propanol by a dehydrogenase (E.C. 1.1.1.202). See FIG. 2.

All the required enzymatic activities for the production of propanediol have been demonstrated in C. thermosaccha-

*rolyticum*, a strain that can be genetically engineered. Cameron, D. C., et al., 1998, *Biotechnol. Prog.* 14, 116-125. Relevant endogenous enzymes in the bacterial CBP platform production strains that exhibit high levels of homology to the desired enzymatic domains have also been identified (Table 3). The enzymes leading to propanediol in the bacterial CBP platform production strains can be characterized for implementation in route (i).

For the isopropanol route, route (ii), glyceraldehyde 3-phosphate is further metabolized to pyruvate through standard glycolysis reactions, producing ATP to power cellular reactions and reducing equivalents needed to balance n-propanol production during anaerobic fermentation. Pyruvate is then metabolized to acetyl-CoA, reduced ferredoxin, and $CO_2$ by pyruvate ferredoxin oxidoreductase (E.C. 1.2.7.1). NADH and $H_2$ are subsequently produced during the oxidation of ferredoxin. See FIG. 2.

Acetyl-CoA is then converted to acetate by phosphate acetytransferse (EC 2.3.1.8) and acetate kinase (E.C. 2.7.2.1) in an ATP generating reaction. Two acetyl-CoA molecules are converted to acetoacetyl-CoA by thiolase (E.C. 2.3.1.9). Acetoacetyl-CoA is then converted to acetoacetate by CoA enzyme transferase (E.C. 2.8.3.8), where the CoA species is transferred from acetoacetyl-CoA to acetate, replenishing the acetyl-CoA consumed during the thiolase reaction. Acetoacetate is then converted to acetone by acetoacetate decarboxylase (E.C. 4.1.1.4). The reduction of acetone to isopropanol can be accomplished by alcohol dehydrogenases (E.C. 1.1.1.80).

The enzymes catalyzing the production of acetone from acetyl-CoA have been identified in the literature from *C. acetobutylicum*. See Bermejo, L. L., et al., 1998, *Appl Environ Microbiol.* 64(3), 1079-85. The conversion of acetone to isopropanol has been shown by multiple alcohol dehydrogenases and endogenous bacterial enzymes can be screened for their capability to accept acetone as a substrate.

Gene deletions will also be required to achieve high yields of propanol production. These include deletion of L-lactate dehydrogenase, ldh (E.C. 1.1.1.27); hydrogenase, hyd (E.C. 1.12.7.2); and acetaldehyde dehydrogenase, acdh (E.C. 1.2.1.10).

Example 3

3.1 Production of Isopropanol and Methanol in Bacterial CBP Platforms

Co-production of isopropanol and methanol from lignocellulosic carbohydrates allows for a balanced fermentation equation that is thermodynamically feasible. Isopropanol is theoretically produced at 0.33 g/g carbohydrate and incorporates 75% of the electrons available from carbohydrate conversion. Both isopropanol and methanol can be recovered from the fermentation broth via distillation, reducing downstream processing complexity. Further, methanol is a natural product of pectin degradation, and many characterized methylotropic organisms contain genes for methanol metabolism.

3.2 Pathway Definition and Stoichiometric Calculations for Production of Isopropanol and Methanol The production of isopropanol and methanol from carbohydrates is outlined in the pathways in FIG. 3 and requires the activity of several distinct enzymes (see Table 4).

TABLE 4

List of native and non-native gene candidates pertaining to engineering of isopropanol and methanol in the CBP bacterial platform.

| Activity | EC | C. the | T. sacch | Non-native-bacterial |
|---|---|---|---|---|
| pyruvate formate lyase | 2.3.1.54 | 505 | or0628 | |
| phosphotransacetylase | 2.3.1.8 | 1029 | or1741 | |
| acetate kinase | 2.7.2.1 | 1028 | or1742 | |
| formaldehyde dehydrogenase | 1.2.1.46 | 218 | 2445, 0388 | Pput_0350 *P. putida* |
| methanol dehydrogenase | 1.1.1.244 | 101 | or1411 | |
| | | 394 | or1043 | |
| | | 423 | or2426 | |
| | | 2445 | or2289 | |
| | | 2579 | or286 | |
| formate dehydrogenase | 1.2.1.43 | 342 | or2328 | Moth_2312 *M. thermoacetica* |
| | | 430 | | |
| | | 3004 | | |
| | | 3003 | | |
| thiolase | 2.3.1.9 | | | *C. acetobutylicum* ThlA |
| coA transferase | 2.8.3.8 | | | *C. acetobutylicum* CtfAB |
| acetoacetate decarboxylase | 4.1.1.4 | | | *C. acetobutylicum* Adc, Aad |
| oxidoreductase | 1.1.1.80 | 101 | or1411 | |
| | | 394 | or1043 | |
| | | 423 | or2426 | |
| | | 2445 | or2289 | |
| | | 2579 | or0286 | |

| Genes to KO | EC | C. the | T. sacch |
|---|---|---|---|
| lactate dehydrogenase | 1.1.1.27 | 1053 | or180 |
| alcohol dehydrogenase | 1.1.1.1 | 423 | or411 |

TABLE 4-continued

List of native and non-native gene candidates pertaining to engineering of isopropanol and methanol in the CBP bacterial platform.

| | | | |
|---|---|---|---|
| methylglyoxal synthase | 4.2.2.3 | 95 | or2316 |
| PFOR (oxidoreductase) | 1.2.7.1 | 2390-93 | or0047 |

The combined production of isopropanol and methanol from one glucose molecule during bacterial metabolism is governed by the overall stoichiometric equation, with a theoretical yield of one propanol and one methanol per glucose, as follows:

$$C_6H_{12}O_6 \rightarrow C_3H_8O + CH_4O + 2CO_2 + 3ATP$$

The theoretical yield of isopropanol and methanol on hexose and pentose sugar for the above pathways (see FIG. 3) are:
Hexose Yield:
0.33 g isopropanol/g hexose
0.18 g methanol/g hexose
Pentose Yield:
0.33 g isopropanol/g pentose
0.18 g methanol/g pentose During cellular metabolism, the microbial hosts can utilize hexose or pentose carbohydrate sources, with six pentose sugars equivalent to five hexose sugars, employing, e.g., the Embden-Meyerhof-Parnas (EMP) pathway to produce dihydroxyacetone phosphate and glyceraldehyde 3-phosphate. These metabolites can be interchanged using the triosephosphate isomerase (E.C. 5.3.1.1).

3.3 Production Routes for Isopropanol and Methanol and Corresponding Enzymology The branched metabolic pathways for the combined production of isopropanol and methanol from carbohydrates can be subdivided into the following production routes: (i) the conversion of pyruvate into isopropanol; and (ii) the conversion of formate into $CO_2$ and methanol.

As described above, glyceraldehyde 3-phosphate is metabolized to pyruvate through standard glycolysis reactions, producing ATP to power the cellular reactions and the required reducing equivalents needed to reduce the carbon end-products. From pyruvate, acetyl-CoA and formate are produced by pyruvate formate lyase (E.C. 2.3.1.54). For isopropanol production, route (i), acetyl-CoA is converted to acetate by phosphate acetytransferse (E.C. 2.3.1.8) and acetate kinase (E.C. 2.7.2.1) in an ATP generating reaction. Two acetyl-CoA molecules are converted to acetoacetyl-CoA by thiolase (E.C. 2.3.1.9). Acetoacetyl-CoA is then converted to acetoacetate by CoA enzyme transferase (E.C. 2.8.3.8), where the CoA species is transferred from acetoacetyl-CoA to acetate, replenishing the acetyl-CoA consumed during the thiolase reaction. Acetoacetate is then converted to acetone by acetoacetate decarboxylase (E.C. 4.1.1.4). The reduction of acetone to isopropanol can be accomplished by alcohol dehydrogenases (E.C. 1.1.1.80).

As described above, the enzymes catalyzing the production of acetone from acetyl-CoA have been identified in the literature from *C. acetobutylicum*. See Bermejo, L. L., et al., 1998, *Appl Environ Microbiol.* 64(3), 1079-85. The conversion of acetone to isopropanol has been shown by multiple alcohol dehydrogenases and endogenous bacterial enzymes can be screened for their capability to accept acetone as a substrate.

In route (ii), formate is further metabolized via two pathways in an equimolar ratio first leading to $CO_2$ and NADPH by formate dehydrogenase (E.C. 1.2.1.43), and the second leading to methanol with the incorporation of two NADH and production of water by the combined action of formaldehyde dehydrogenase (E.C. 1.2.1.46) and methanol dehydrogenase (E.C. 1.1.1.244).

The production of $CO_2$ and NADPH via formate is a well characterized pathway with a large body of literature. However, the production of methanol via formate is a less well characterized pathway. The majority of characterized organisms that have methanol metabolism pathways consume methanol, rather than produce it. Methanol production from formate is thermodynamically feasible under anaerobic conditions. The most likely route for engineering a high yielding pathway is to introduce enzymes that natively catalyze the net reaction in the reverse direction and then use evolutionary engineering techniques to select for strains with increased flux towards methanol formation. This strategy for pathway flux improvement has been successfully employed both in the engineering of other metabolic pathways and is anticipated to work for this pathway due to the thermodynamic favorability of the net reaction.

Example 4

4.1 Anaerobic Production of Propanediol and Acetone in Bacterial and Yeast CBP Platforms The native microbial production of propanediol has been well documented in *Clostridium thermosaccharolyticum* by Cameron, D. C., & Clooney, C., 1986 *Bio/Technology* 4, 651-654, although the endogenous enzymes have yet to be identified and cloned. The native enzymes can be identified from the bacterial CBP platform microbes and utilized in the bacterial CBP platform hosts eliminating the need for "recombinant" genes (e.g., *Thermoanaerobacter saccharolyticum* and *Clostridium thermocellum*) and/or readily transferred to the yeast CBP platform hosts.

The theoretical maximum yield for anaerobic propanediol production that includes ATP generation requires the production of a co-fermentation product such as acetate. See U.S. Pat. No. 6,303,352. The pathways presented in this Example achieve the anaerobic maximum theoretical yield and use acetate as an intermediate during the generation of acetone as the co-fermentation product. Acetone was chosen as a co-fermentation product because it is potentially a chemical of value and a less toxic fermentation product to the microorganisms relative to acetate. The simultaneous production of propanediol and acetone represents a novel fermentation process. In addition, relatively little is known about the enzymology converting methygloxal to propanediol, but as described above, can now be ascertained.

4.2 Pathway Definition and Stoichiometric Calculations for Production of Propanediol and Acetone The anaerobic production of propanediol and acetone from carbohydrates is outlined in the pathways in FIG. 4 and requires the activity of several distinct enzymes (wee Table 5).

TABLE 5

List of native and non-native gene candidates pertaining to engineering of propanediol and acetone in the CBP bacterial and CBP yeast platforms.

| Activity | EC | C.the | T.sacch | Yeast | Non-native-bacteria | non-native-yeast |
|---|---|---|---|---|---|---|
| methylglyoxal synthase | 4.2.3.3 | 95 | or2316 | | | *Oryza sativa* mgs |
| aldo-keto reductase (methylglyoxal to acetol) | 1.1.1.- | 152<br>236<br>283 | or1401<br>or1402<br>or785<br>or414<br>or2491 | | | *P. putida* gldA |
| aldo-keto reductase (acetol to propanediol) | 1.1.1.- | 101<br>394<br>423<br>2445<br>2579 | or1043<br>or2289<br>or411<br>or2426<br>or0286 | | | |
| phosphotransacetylase | 2.3.1.8 | 1029 | or1741 | | | Tsacch or1741 |
| acetate kinase | 2.7.2.1 | 1028 | or1742 | | | Tsacch or1742 |
| thiolase | 2.3.1.9 | | | ERG10 | *C. acetobutylicum* ThlA | |
| coA transferase | 2.8.3.8 | | | | *C. acetobutylicum* CtfAB | *C. acetobutylicum* CtfAB |
| acetoacetate decarboxylase | 4.1.1.4 | | | | *C. acetobutylicum* Adc, Aad | *C. acetobutylicum* Adc, Aad |
| alcohol dehydrogenase | 1.1.1.1 | | | ADH1<br>ADH2<br>ADH3<br>ADH4<br>ADH5<br>ADH6<br>ADH7<br>BDH2<br>SFA1<br>YPL088W | | |
| PFOR (oxidoreductase) | 1.2.7.1 | 2390-3 | or0047 | | | |
| fructose 1,6-biphosphate aldolase | 4.1.2.13 | 0349<br>1019 | or0260<br>or0330 | FBA1 | | |
| triose-phophate isomerase | 5.3.1.1 | 0139 | or2687 | TPI1 | | |
| pyruvate formate-lyase | 2.3.1.54 | | | | *E. coli* pflA/pflB | |
| formate dehydrogenase | 1.2.1.2 | | | FDH1 | | |
| aldehyde reductase | 1.1.1.21 | 101<br>394<br>423<br>2445<br>2579 | or1043<br>or2289<br>or411<br>or2426<br>or0286 | GRE3 | | |
| glyoxylate reductase | 1.1.1.79 | 101<br>394<br>423<br>2445<br>2579 | or1043<br>or2289<br>or411<br>or2426<br>or0286 | GOR1<br>YPL113C | | |
| methylglyoxal dehydrogenase | 1.2.1.49 | 152<br>236<br>283 | or1401<br>or1402<br>or785<br>or414<br>or2491 | GCY1<br>ALD2<br>ALD3<br>ALD4<br>ALD5<br>ALD6<br>HFD1 | | |
| glucokinase | 2.7.1.2 | 0390<br>2938 | or0272 | GLK1 | | |
| glucose 6 phophate isomerase | 5.3.1.9 | 0217 | or1389 | PGI1 | | |
| 6-phosphofructokinase | 2.7.1.11 | 1261 | or2875 | PFK1<br>PFK2 | | |

TABLE 5-continued

List of native and non-native gene candidates pertaining to engineering of propanediol and acetone in the CBP bacterial and CBP yeast platforms.

| Activity | EC | C.the | T.sacch | Yeast | Non-native-bacteria | non-native-yeast |
|---|---|---|---|---|---|---|
| Genes to KO | | | | | | |
| lactate dehydrogenase | 1.1.1.27 | 1053 | or180 | | | |
| alcohol dehydrogenase | 1.1.1.1 | 423 | or411 | | | |
| pyruvate decarboxylase | 4.1.1.1 | | | PDC1 | | |
| | | | | PDC5 | | |
| | | | | PDC6 | | |
| glycerol-3-phosphate dehydrogenase | 1.1.1.8 | | | GPD2 | | |
| glycerol-3-phosphatase | 3.1.3.21 | | | GPP1 | | |

The combined production of propanediol and acetone from two glucose molecules during bacterial or yeast anaerobic metabolism is governed by the overall stoichiometric equation, resulting in overall redox balance and the net gain of one ATP, as follows:

$$2C_6H_{12}O_6 \rightarrow 2C_3H_8O_2 + C_3H_6O + 3CO_2 + 1ATP + H_2O$$

The theoretical yield of propanediol and acetone on hexose and pentose sugar for the above pathway are:

| Hexose | Pentose |
|---|---|
| 0.42 g propanediol/g hexose | 0.42 g propanediol/g pentose |
| 0.16 g acetone/g hexose | 0.16 g acetone/g pentose |

During cellular metabolism, the microbial hosts can utilize hexose or pentose carbohydrate sources, with six pentose sugars equivalent to five hexose sugars, employing the Embden-Meyerhof-Parnas (EMP) pathway to produce dihydroxyacetone phosphate and glyceraldehyde 3-phosphate. These metabolites can be interchanged using the triosephosphate isomerase (EC 5.3.1.1).

4.3 Anaerobic Production Routes for Propanediol and Acetone and Corresponding Enzymology The co-production of propanediol and acetone from hexose and pentose sugars in thermophilic clostridia and *S. cerevisiae* can be broken down into three routes: (i) the production of dihydroxyacetone phosphate and glyceraldehyde 3-phosphate from glucose; (ii) the subsequent generation of propanediol from dihydroxyacetone phosphate; and (iii) the generation of acetone from glyceraldehyde 3 phosphate. See FIG. 4.

For the bacterial and yeast CBP platforms, the enzyme activities required for route (i), production of dihydroxyacetone phosphate and glyceraldehyde 3-phosphate from glucose, are part of the native glycolytic pathway, e.g., the EMP pathway, as described above. See Table 5.

For route (ii), the subsequent generation of propanediol from dihydroxyacetone phosphate, two alternative routes are presented, in part because both result in the same redox balance and apriori the best route is not known. Both begin with the production of methylglyoxal from dihydroxyacetone phosphate by methylglyoxal synthase, mgs (E.C. 4.2.3.3). See FIG. 4. This gene is endogenous to the bacterial CBP platform organisms, however for yeast it will have to be obtained from one of several potential sources.

For the bacterial CBP platform, which comprises thermophilic bacteria, acetol is the likely intermediate from methylglyoxal to propanediol, as has been shown in T. thermosaccarolyticum. See Cameron, D. C., & Clooney, C., 1986, *Bio/Technology* 4, 651-654. In *E. coli*, various aldo-keto reductases have been shown to catalyze the conversion of methylglyoxal to acetol (E.C. 1.1.1). See Ko, J., et al., 2005, *J Bacteriol.* 187(16), 5782-9. The list of endogenous aldo-keto reductases for the bacterial platform organisms are shown in Table 5. These genes can be over-expressed and/or deleted to determine their role in propanediol production. It is also possible that lactaldehyde, produced by a glyoxylate reductase (E.C. 1.1.1.79) and a methylglyoxal dehydrogenase (E.C. 1.2.1.49) is an intermediate. To determine if acetol or lactaldehyde is the primary intermediate during conversion of methylglyoxal to propanediol, analytical chemistry procedures such as HPLC can be used to identify these intermediates in fermentation samples. See e.g., Cameron, D. C., & Clooney, C., 1986, *Bio/Technology* 4, 651-654; Altaras, N. E., & Cameron, D. C., 1999, *Appl Environ Microbiol.* 65(3), 1180-5. Alternatively, cells can be fed acetol or lactaldehyde to determine which intermediate is more effectively converted to propanediol. To determine which genes are responsible for the production of propanediol from acetol or lactaldehyde, the native alcohol dehydrogenases and aldo-keto reductases listed in Table 5 can be deleted and/or over-expressed while propanediol production is monitored.

For the yeast CBP platform, multiple routes from methylglyoxal to propanediol also exist. See FIG. 4. One route through lactaldehyde involves introduction of a glycerol dehydrogenase (E.C. 1.1.1), which doubled the amount of propanediol formed. See Hoffman, M. L., 1999, Metabolic engineering of 1,2-propanediol production in *Saccharomyces cerevisiae*. Ph.D. Dissertation, University of Wisconsin-Madison. Alternatively, aldehyde reductase (E.C. 1.1.1.21) may be capable of converting methylglyoxal to lactaldehyde and then subsequently to propanediol—the native yeast aldehyde reductase, GRE3, can be overexpressed to test this possibility. In addition, methylglyoxal could potentially be converted to lactaldehyde by glyoxylate reductase (E.C. 1.1.1.79) or to lactaldehyde by methylglyoxal dehydrogenase (E.C. 1.2.1.49). The presence of these alcohol dehydrogenase activities can be screened among the ten native alcohol dehydrogenases. See Table 5. It might be necessary to engineer in a combination of the two pathways outlined above to reach a desirable titer for propanediol.

The enzymes that convert methylglyoxal to propanediol are oxidoreductases, of which there are examples using either NADH or NADPH as a co-factor. Knowledge of the co-factor is important for producing propanediol in the yeast platform because the compartmentalization of the cell, and the relative difficulty of inter-converting NADH to NADPH, limit the cell's ability to deal with an imbalance in these cofactors. For the anaerobic production of propanediol, an enzyme (or enzymes) that are linked to NADH would be required, since these are the reducing equivalents generated during the production of $CO_2$ and acetone from glyceraldehyde 3-phosphate. Several of the enzymes identified in bacterial systems have this characteristic.

For route (iii), the generation of acetone from glyceraldehydes 3-phosphate, the engineering of non-native enzymatic activities into both the bacterial and yeast platforms is required. The bacterial organisms have a native enzyme activity (E.C. 1.2.7.1) that converts pyruvate to acetyl-CoA (FIG. 4, light gray box), while the yeast platform requires the expression of a non-native activity (E.C. 2.3.1.54) to convert pyruvate to acetyl-CoA (FIG. 9a, dark gray box).

To convert acetyl-CoA to acetone in the bacterial platform, activities associated with (E.C. 2.3.1.9), (E.C. 2.8.3.8), and (E.C. 4.1.1.4) can be engineered using genes from *C. acetobutylicum*, while activities associated with (E.C. 1.2.7.1), (E.C. 2.3.1.8), and (E.C. 2.7.2.1) are in fact endogenous (FIG. 4). See Bermejo, L. L., et al., 1998, *Appl Environ Microbiol.* 64(3), 1079-85. Taken together, these activities will allow the formation of acetone from two molecules of pyruvate. For the yeast platform three enzymatic activities can be engineered into yeast. The pyruvate formate lyase, PFL (E.C. 2.3.1.54), is required for the formation of acetyl-CoA in the cytosol, because the majority of yeast endogenously produced acetyl-CoA is sequestered in the mitochondria. Enzymatically active PFL has been expressed in yeast for the production of formate. Waks, Z., & Silver, P. A., 2009, *Appl. Env. Microbiol.* 75, 1867-1875. *S. cerevisiae* has an endogenous formate dehydrogenase (E.C. 1.2.1.2) to convert the formate generated to $CO_2$ and $H^+$. The cytosolic acetyl-CoA generated can be subsequently converted to acetone by the introduction of the *C. acetobutylicum* pathway (E.C. 2.8.3.8) and (E.C. 4.1.1.4), as described above, working together with the yeast acetyl-CoA acetyltransferase, ERG10 (E.C. 2.3.1.9).

The description of the above pathways describes native and non-native genes required to direct carbon flow from sugars to propanediol and acetone. In addition, to prevent decreases in product yield, i.e., carbon from flowing away from desired end products, various genes can be deleted from each platform. For the bacterial CBP system, these genes are shown in Table 5. The deletion of adh (E.C. 1.1.1.1) will prevent flow from acetyl-CoA to acetaldehyde while the deletion of ldh (E.C. 1.1.1.27) will prevent flow of carbon from pyruvate to lactic acid. Deleting the hydrogenase genes (E.C. 1.12.7.2) will ensure that reducing equivalents generated during glycolysis can be used to make reduced end products such as 1,2-propanediol and not the more oxidized couple of $H_2$ and acetate. For the yeast CBP platform, genes to be deleted are listed in Table 5. Genes encoding activity associated with (E.C. 4.1.1.1) can be deleted to prevent carbon flow from pyruvate to acetaldehyde. In addition, genes associated with (E.C. 1.1.1.8) and (E.C. 3.1.3.21) activity can be deleted to prevent carbon loss from dihydroxyacetone phosphate as glycerol.

Example 5

Aerobic Production of Propanediol in Yeast CBP Platforms

The purpose of the present Example is to provide a novel pathway for the aerobic production of propanediol in yeast CBP platforms. Aerobic production of propanediol provides some benefits in terms of ATP production. For example, the advantages of aerobic production are discussed in Cameron et al., "Metabolic engineering of propanediol pathways," *Biotechnology Progress,* 14(1): 116-125 (1998), where a yield of 0.61 g propanediol/g can be achieved in a non-compartmentalized organism. Indeed, the commercial production of 1,3-propanediol is done via an aerobic process. Although not as high as 0.61 g propanediol/g in a non-compartmentalized organism, the present pathway provides for a high yield of propanediol in a compartmentalized organism as discussed below.

The 1,2-propanediol produced using this platform can be used as a valuable intermediate or converted to propionate and propanol using microbes such as *Lactobacillus reuteri* strain isolated from sourdough that is known to do this reaction. See Sriramulu, D. D., et al., 2008, *J. Bacteriol.* 190(13):4559-67. Chemical routes might also exist for direct conversion of propanediol to propanol or even propylene.

Pathway Definition and Stoichiometric Calculations for Production of Propanediol The aerobic production of propanediol from carbohydrates is outlined in the pathways in FIG. 5 and requires the activity of several distinct enzymes (see Table 5).

The production of propanediol, which is the only soluble product of the reaction, from 6 glucose molecules during yeast aerobic metabolism is governed by the overall stoichiometric equation:

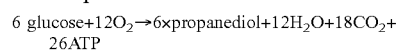
6 glucose+12$O_2$→6×propanediol+12$H_2O$+18$CO_2$+ 26ATP

In order to balance the redox in the cytosol, 1 molecule of glucose 6-phosphate must be completely oxidized by the pentose phosphate pathway (PPP) for every molecule of propanediol produced. In addition, a positive ATP balance is generated via oxidation of the glyceraldehyde 3-phosphate in the TCA cycle and the electron transport chain. See FIG. 4.

The theoretical yield of propanediol on hexose sugar for the above pathway is 0.42 g propanediol/g hexose. 100% xylose could not be converted via this pathway, but a glucose/xylose mixture could convert with a yield similar to glucose alone. Although not as high of a yield as for a non-compartmentalized organism, the proposed pathway provides a high yield for propanediol. Further, the possibility of shuttling NADH to the cytosol from the mitochondrial matrix cannot be ruled out since such a shuttle has been demonstrated. See Bakker, B. M, et al., 2000, *Appl. Env. Micro.* 182, 4730-4737. This would potentially allow higher yields in *S. cerevisiae*. In *Kluyveromyces* type yeasts, yields might also be increased due to shuttling of reducing equivalents to the cytoplasm, and the enhanced activity of the pentose phosphate pathway in these organisms.

5.3 Aerobic Production Routes for Propanediol and Corresponding Enzymology

For the production of dihydroxyacetone phosphate and glyceraldehyde 3-phosphate from glucose, the enzyme activities are part of the native glycolytic pathway, e.g., the EMP pathway, as described above. See Table 5 and FIG. 5.

For the subsequent generation of propanediol from dihydroxyacetone phosphate, two alternative routes are presented as in Example 4 (see FIG. 4), in part because both result in the same redox balance and a priori the best route is not known. Both begin with the production of methylglyoxal from dihydroxyacetone phosphate by methylglyoxal synthase, mgs (E.C. 4.2.3.3). See FIG. 4. For yeast, this gene will have to be obtained from one of several potential sources.

As described above in Example 4, multiple routes from methylglyoxal to propanediol exist in yeast. See FIG. 4. One route through lactaldehyde involves introduction of a glycerol dehydrogenase (E.C. 1.1.1), which doubled the amount of propanediol formed. See Hoffman, M. L., 1999, Metabolic engineering of 1,2-propanediol production in *Saccharomyces cerevisiae*. Ph.D. Dissertation, University of Wisconsin-Madison. Alternatively, aldehyde reductase (E.C. 1.1.1.21) may be capable of converting methylglyoxal to lactaldehyde and then subsequently to propanediol—the native yeast aldehyde reductase, GRE3, can be overexpressed to test this possibility. In addition, methylglyoxal could potentially be converted to lactaldehyde by glyoxylate reductase (E.C. 1.1.1.79) or to lactaldehyde by methylglyoxal dehydrogenase (E.C. 1.2.1.49). The presence of these alcohol dehydrogenase activities can be screened among the ten native alcohol dehydrogenases. See Table 5. It might be necessary to engineer in a combination of the two pathways outlined above to reach a desirable titer for propanediol.

As described above, the enzymes that convert methylglyoxal to propanediol are oxidoreductases, of which there are examples using either NADH or NADPH as a co-factor. Knowledge of the co-factor is important for producing propanediol in the yeast platform because the compartmentalization of the cell, and the relative difficulty of interconverting NADH to NADPH, limit the cell's ability to deal with an imbalance in these cofactors. In the aerobic production of propanediol, the NADPH linked versions of an enzyme (or enzymes) are required, since the production of reducing equivalents in the form of NADPH is accomplished in the pentose phosphate pathway. The *S. cerevisiae* gre3 gene is a good example (and candidate) for use in the aerobic system.

To convert the carbohydrate source to propanediol in yeast using an aerobic process, control of the flux of carbon down particular pathways will be needed. Redox balance is obtained by controlling flux to the PPP and propanediol, while optimal product yield is obtained when the flux to the TCA cycle and electron transport chain is held to a minimal level. Controlling flux to the PPP involves manipulating the expression level of zwf1, which converts glucose 6-phosphate to D-glucono-1,5-lactone 6-phosphate, relative to the activity of pgi, which converts glucose 6-phosphate to fructose 6-phosphate. In order to control the amount of flux to the TCA cycle and the electron transport chain, one of two methods could be used. One would be to down-regulate PDH, and thereby reduce the amount of pyruvate being converted to acetyl-CoA in the mitochondria. The other would be to control the oxygen flux in the fermentation vessel to limit the amount of oxygen available for the electron transport chain. The former genetic approach has an advantage in that it alleviates the necessity of careful process control for aeration at large scale.

Example 6

Identification and Characterization of *T. saccharolyticum* pdu Gene Cluster

Several microorganisms metabolize propanediol to propanol anaerobically. Examples of propanediol utilization can be found among various bacterial species including Thermoanaerobacteria, *Salmonella, Listeria*, and Clostridia. In some microorganisms, e.g., *Listeria* spp. and *Salmonella* spp., the genes required for propanediol utilization (pdu) are clustered on the genome. See generally Scott, K. P., et al., *J. Bacteriol.* 188(12):4340-49 (2006); Bobik, T. A., et al., *J. Bacteriol.* 181(19):5967-75; Xue, J., et al., *Appl. Env. Microbiol.* 74(22):7073-79 (2008).

Two enzyme activities required for conversion of propanediol to propanol include:

1) diol dehydratase (encoded by pduCDE) and
2) dehydrogenase (encoded by pduQ).

See Table 3 above. In several microorganisms, such as *Salmonella* spp. or *Listeria* spp., the first enzyme activity often involves catalysis via a heteromeric diol dehydratase enzyme that is dependent on vitamin B12. The pdu gene clusters are often found to include or be associated with the enzymes required for the synthesis of vitamin B12. Some of the pdu gene clusters include genes for 1) B12 synthesis, 2) AraC type transcription activator, 3) two-component response regulator, 4) an alcohol and aldehyde dehydrogenase, or 5) rnfC homolog. See Scott, K. P., et al., *J. Bacteriol.* 188(12):4340-49 (2006); Bobik, T. A., et al., *J. Bacteriol.* 181(19):5967-75; Xue, J., et al., *Appl. Env. Microbiol.* 74(22):7073-79 (2008).

Thus far, no pdu gene clusters have been identified in thermophilic anaerobic bacteria. This Example provides the identification and characterization of the *T. saccharolyticum* pdu gene cluster for its use in conversion of propanediol to propanol, following, e.g., the scheme described in Example 2.

The pdu gene organization in *T. saccharolyticum* is shown in FIG. 6 and includes several of the genes found in pdu gene clusters from other microorganisms. The *T. saccharolyticum* pdu genes include ABC-sugar transporter components (or201, or202, or203), a two-component response regulator (or206, or207), rhamnose isomerase (or209) rhamulokinase (or208), rhamnulose-1-phosphate lactaldehyde lyase (or227), a putative propanediol:NAD+ oxidoreductase (or211), micro-compartment proteins (pduJ, pduL, etc. or212, or214, or215, or216, or217), an aldehyde dehydrogenase (or219), an alcohol dehydrogenase (or218), a phosphotransacetylase (or213), B12 accessory enzymes (or223, or222, or221, or220), a B-12 dependent diol dehydratase pduCDE (or226, or225, or224), and a transcriptional regulator (or228). The activities of these genes can be characterized, e.g., through various gene deletion studies, growth on rhamnose, and/or expression into heterologous systems such as *T. thermosaccharolyticum* and *C. thermocellum*.

The ability of *T. saccharolyticum*, which harbors the above-identified pdu gene cluster, to produce detectable levels of n-propanol was determined. The wild-type *T. saccharolyticum* YS485 strain was grown in TSC1 medium (Table 6) with 10 g/L CaCO$_3$ and a starting pH of 5.8 at 55° C. and 200 rpm under anaerobic conditions. The medium was supplemented with 0.001 g/L vitamin B12.

TABLE 6

Composition of TSC1 medium.

| Components | Concentration (g/L) |
|---|---|
| (NH$_4$)$_2$SO$_4$ | 1.85 |
| FeSO$_4$*7H$_2$O | 0.05 |
| KH$_2$PO$_4$ | 0.5 |
| MgSO$_4$ | 1 |
| CaCl$_2$*2H$_2$O | 0.05 |
| Trisodium citrate * 2 H$_2$O | 2 |
| Yeast Extract | 8.5 |
| CaCO$_3$ | 10 |
| L-rhamnose | 18 |

Batch fermentation was done and samples were drawn at various time points shown in Table 7. The samples were analyzed by HPLC to detect remaining L-rhamnose and end products, including lactic acid (LA), acetic acid (AA), ethanol (Etoh), 1,2-propanediol (1,2 PD), and n-propanol. The results are depicted in Table 7.

TABLE 7

Production of 1,2-Propanediol and n-Propanol in *T. saccharolyticum* Grown on L-rhamnose

| Time (hr) | L-rhamnose (g/L) | LA (g/L) | AA (g/L) | Etoh (g/L) | 1,2 PD (g/L) | n-propanol (g/L) |
|---|---|---|---|---|---|---|
| 0 | 17.820 | 0.000 | 0.118 | 0.000 | 0.277 | 0.000 |
| 17.5 | 11.440 | 0.242 | 2.054 | 0.315 | 2.248 | 0.363 |
| 24.5 | 2.522 | 0.346 | 4.289 | 0.437 | 4.623 | 1.072 |
| 41.25 | 0.679 | 0.384 | 5.024 | 0.527 | 5.073 | 1.525 |
| 69.5 | 0.427 | 0.407 | 5.135 | 0.567 | 5.134 | 1.638 |

These results demonstrate that *T. saccharolyticum* has the native ability to produce 1,2-propanediol (up to 5.1 g/L) and n-propanol (1.6 g/L) when grown on L-rhamnose. The pdu gene cluster includes some rhamnose utilization and sugar uptake genes indicating that those are likely to be involved in this process. This provides the first example of a thermophilic anaerobic bacterium shown to be capable of producing n-propanol.

Example 7

Production of Propanol Via Propanediol Using a B12-Independent Diol Dehydratase in Yeast As described above, one of the two enzyme activities required for conversion of propanediol to propanol includes a diol dehydratase enzyme, which in several microorganisms is dependent on vitamin B12. Yeast lack the metabolic machinery to synthesize vitamin B12, and thus, it is not possible to engineer a vitamin B12-dependent enzyme in yeast without also providing, e.g., the enzyme activities to synthesize vitamin B12. There have been a few reports of propanediol dehydratase enzymes that do not require vitamin B12. See Raynaud, C., et al., *PNAS (USA)* 100(9):5010-15 (2003); Scott, K. P., el al., *J. Bacteriol.* 188(12):4340-49 (2006); Hartmanis, M. G., and Stadtman, T. C., *Arch. Biochem. Biophys.* 245(1)144-52 (1986).

Because of the requirement for vitamin B12, the anaerobic conversion of propanediol to propanol was thought to be impossible due to the requirement of a vitamin B12-dependent enzyme. Recent reports describing the B12-independent diol dehydratase provide a source and incentive to screen for existing B12-independent diol dehydratases in nature and express them into yeast. See Raynaud, C., et al., *PNAS (USA)* 100(9):5010-15 (2003); Scott, K. P., et al., *J. Bacteriol.* 188(12):4340-49 (2006); Hartmanis, M. G., and Stadtman, T. C., *Arch. Biochem. Biophys.* 245(1)144-52 (1986). If successfully done, this would be the first n-propanol producing yeast engineered so far. The purpose of this Example is to identify and engineer a vitamin B12-independent diol dehydratase, as well as other necessary enzymes, in yeast, e.g., *Saccharomyces cerevisiae*, to anaerobically convert propanediol to propanol.

The metabolic pathway for generating propanol from, e.g., a carbohydrate source, in yeast is similar to the route described above in Example 2 and as shown in FIG. 2. In order to successfully achieve this conversion of glucose, several enzyme activities need to be engineered in yeast. Conversion of glucose to pyruvate and dihydroxyacetone-P are achieved via the endogenous enzyme activities in yeast. Those activities which need to be engineered are highlighted in FIG. 7 and are as follows:

1) The conversion of pyruvate to acetyl-CoA and formate via pyruvate-formate lyase (PFL) (E.C. 2.3.1.8) has been successfully engineered and demonstrated. See Waks, Z. and Silver, P. A., *Appl. Env. Microbiol.* 75(7):1867-75 (2009). This is an important step to generate a pool of acetyl-CoA in the yeast cytosol for its subsequent conversion into isopropanol. Simultaneously, the flux of pyruvate to acetyl-CoA via pyruvate decarboxylase (PDC) needs to be avoided for which the PDC1, PDC5 and PDC6 need to be knocked out. The conversion of formate to carbon dioxide is catalyzed by an endogenous enzyme, formate dehydrogenase (E.C. 1.2.1.2).

2) Acetyl-CoA is further converted to acetate by phosphate acetyltransferse (E.C. 2.3.1.8) and acetate kinase (E.C. 2.7.2.1) in an ATP generating reaction. Two acetyl-CoA molecules are converted to acetoacetyl-CoA by thiolase (E.C. 2.3.1.9). Acetoacetyl-CoA is then converted to acetoacetate by CoA enzyme transferase (E.C. 2.8.3.8), where the CoA species is transferred from acetoacetyl-CoA to acetate, replenishing the acetyl-CoA consumed during the thiolase reaction. Acetoacetate is then converted to acetone by acetoacetate decarboxylase (E.C. 4.1.1.4). The reduction of acetone to isopropanol can be accomplished by alcohol dehydrogenases (E.C. 1.1.1.80).

3) Synthesis of methylglyoxal from dihydroxyacetone-P can be achieved by expression of heterologous methylglyoxal synthase (mgs) and glycerol dehydrogenase (gldA) as has been previously demonstrated. See Lee, W. and DaSilva, N. A., *Metabolic Eng.* 8(1):58-65 (2006).

4) The conversion of propanediol to propanol requires two enzyme activities as described above, involving a diol dehydratase and a dehydrogenase. Although several microorganisms can convert 1,2-propandiol to propanol using a vitamin B12-dependent diol dehydratase, reaction via a vitamin B12-dependent diol dehydratase is not feasible in yeast due to the B12 dependency. The few recently discovered examples of vitamin B12-independent diol dehydratase include those identified from *Clostridium butyricum, Roseburia inulinivorans. Clostridium glycolicum* and *Klebsiella* spp. The *C. butyricum* enzyme is extensively characterized and shown to be functional independent of B12 and in a heterologous system (*E. coli*). See Tang, X., et al., *Appl. Env. Microbiol.* 75(6):1628-34 (2009). The results obtained with the *C. butyricum* B12-independent diol dehydratase activity suggest that the enzyme can be engineered into a heterologous system such as yeast.

In addition to the incorporation of these enzymatic activities, the flux of carbon from pyruvate to ethanol must be disrupted in yeast. This can be accomplished via the deletion of pdc1, pdc5, and pdc6. PDC deletion strains are slow growing and require a small amount of added ethanol or acetate to be viable; however, these issues can be overcome via an evolutionary based approach. See, e.g., van Maris, A. J. A., et al., *Appl. Env. Microbiol.* 70(1):159-66 (2004). The fact that such strains produce pyruvate at high levels indicates that this compound would be available for subsequent conversion to propanol via the proposed pathway above.

In order to identify additional B12-independent diol dehydratases for engineering in part 4 above, other B12-independent diol dehydratase enzymes existing in nature can be identified. Suitable methods for identifying can include, but are not limited to, alignment searches based on homology to known B12-independent diol dehydratases, an enzymatic activity assay combined with protein purification and protein sequencing, and whole-genome transcriptional analysis of 1,2 propanediol utilizing organisms. See, e.g., Scott, K. P. et al., *J. Bact* 188(12):4340-4349 (2006), and Raynaud, C. et al., *PNAS* 100(9):5010-5015 (2003).

Once identified and isolated, the gene responsible for the activity is cloned into yeast along with other enzyme activities as described above. Optimization of expression of the B12-independent diol dehydratase and analytical assays for production of propanol is subsequently followed.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A recombinant microorganism; comprising a plurality of heterologous enzymes, wherein said plurality of heterologous enzymes are expressed; wherein said plurality of heterologous enzymes function in one or more engineered metabolic pathways to convert a carbohydrate source to n-propanol, isopropanol and, optionally, ethanol; and wherein said plurality of heterologous enzymes is activated or upregulated, and comprises:
a heterologous pyruvate formate lyase,
a heterologous methylglyoxal synthase, and
a heterologous vitamin B12-independent diol dehydratase;
wherein said recombinant microorganism is a yeast.

2. The recombinant microorganism of claim 1, wherein said carbohydrate source is lignocellulose.

3. The recombinant microorganism of claim 1, wherein said carbohydrate source is converted to dihydroxyacetone phosphate and glyceraldehyde phosphate.

4. The recombinant microorganism of claim 1, wherein one of said engineered metabolic pathways comprises conversion of pyruvate to isopropanol.

5. The recombinant microorganism of claim 1, wherein one of said engineered metabolic pathway comprises conversion of pyruvate to ethanol.

6. The recombinant microorganism of claim 1, wherein the engineered metabolic pathway that produces isopropanol comprises: (a) conversion of acetyl-CoA to acetate; (b) conversion of acetyl-CoA to acetoacetyl-CoA; (c) conversion of acetoacetyl-CoA to acetoacetate; (d) conversion of acetoacetate to acetone; and (e) reduction of acetone to isopropanol.

7. The recombinant microorganism of claim 1, wherein the engineered metabolic pathway that produces ethanol comprises: (a) conversion of acetyl-CoA to ethanol.

8. The recombinant microorganism of claim 1, wherein said recombinant microorganism is selected from the group consisting of *Saccharomyces cerevisiae*, *Kluyveromyces lactis*, *Kluyveromyces marxianus*, *Pichia pastoris*, *Yarrowia lipolytica*, Hansemila polymorphs, *Phaffia rhodozyma*, *Candida ittliis*, *Arxula adeninivorans*, *Pichia stipitis*, *Debaryomyces hansenii*, *Debaryomyces* polymorphic, *Schizosaccharomyces pombe*, *Candida albicans*, and *Schwanniomyces occidentalis*.

9. The recombinant microorganism of claim 3, wherein one of said engineered metabolic pathways comprises the conversion of dihydroxyacetone phosphate to n-propanol.

10. The recombinant microorganism of claim 9, wherein said dihydroxyacetone phosphate is converted to methylglyoxal with the heterologous methylglyoxal synthase.

11. The recombinant microorganism of claim 10, wherein said methylglyoxal is converted to acetol by an aldo-keto reductase or converted to lactaldehyde by a glyoxylate reductase, the heterologous methylglyoxal dehydrogenase or an aldehyde dehydrogenase.

12. The recombinant microorganism of claim 11, wherein said acetol is converted to propanediol by an aldo-keto reductase or said lactaldehyde is converted to propanediol by an aldehyde reductase.

13. The recombinant microorganism of claim 12, wherein said propanediol is converted to propanal with the heterologous vitamin B12-independent diol dehydratase.

14. The recombinant microorganism of claim 13, wherein said propanal is reduced to n-propanol by a dehydrogenase (E.C.1.1.1.202).

15. The recombinant microorganism of claim 6, wherein acetyl-CoA is converted to acetoacetyl-CoA by a thiolase (E.C.2.3.1.9).

16. The recombinant microorganism of claim 15, wherein said acetoacetyl-CoA is converted to acetoacetate by a CoA transferase.

17. The recombinant microorganism of claim 16, wherein said acetoacetate is converted to acetone by an acetoacetate decarboxylase.

18. The recombinant microorganism of claim 17, wherein said acetone is reduced to isopropanol by an isopropanol dehydrogenase or an alcohol dehydrogenase.

19. The recombinant microorganism of claim 1, wherein the vitamin B12-independent diol dehydratase is from *Clostridium* sp., *Roseburia* sp. or *Klebsiella* sp.

20. The recombinant microorganism of claim 13, wherein the vitamin B12-independent diol dehydratase is from *Clostridium butyricum*, *Clostridium glycolicum* or *Roseburia inulivorans*.

* * * * *

SEQUENCE LISTING

```
<160> NUMBER OF SEQ ID NOS: 167

<210> SEQ ID NO 1
<211> LENGTH: 742
<212> TYPE: PRT
<213> ORGANISM: C. thermocellum

<400> SEQUENCE: 1
```

Met Asp Ala Trp Arg Gly Phe Asn Lys Gly Asn Trp Cys Gln Glu Ile
1               5                   10                  15

Asp Val Arg Asp Phe Ile Ile Arg Asn Tyr Thr Pro Tyr Glu Gly Asp
            20                  25                  30

Glu Ser Phe Leu Val Gly Pro Thr Asp Arg Thr Arg Lys Leu Trp Glu
        35                  40                  45

Lys Val Ser Glu Leu Leu Lys Lys Glu Arg Glu Asn Gly Gly Val Leu
    50                  55                  60

Asp Val Asp Thr His Thr Ile Ser Thr Ile Thr Ser His Lys Pro Gly
65                  70                  75                  80

Tyr Ile Asp Lys Glu Leu Glu Val Ile Val Gly Leu Gln Thr Asp Glu
                85                  90                  95

Pro Leu Lys Arg Ala Ile Met Pro Phe Gly Gly Ile Arg Met Val Ile
            100                 105                 110

Lys Gly Ala Glu Ala Tyr Gly His Ser Val Asp Pro Gln Val Val Glu
        115                 120                 125

Ile Phe Thr Lys Tyr Arg Lys Thr His Asn Gln Gly Val Tyr Asp Val
    130                 135                 140

Tyr Thr Pro Glu Met Arg Lys Ala Lys Lys Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Arg Leu Ile Ala Glu Lys Glu Lys Glu
            180                 185                 190

Met Ala Ser Leu Glu Arg Asp Tyr Ile Asp Tyr Glu Thr Val Arg Asp
        195                 200                 205

Arg Glu Glu Ile Ser Glu Gln Ile Lys Ser Leu Lys Gln Leu Lys Glu
    210                 215                 220

Met Ala Leu Ser Tyr Gly Phe Asp Ile Ser Cys Pro Ala Lys Asp Ala
225                 230                 235                 240

-continued

```
Arg Glu Ala Phe Gln Trp Leu Tyr Phe Ala Tyr Leu Ala Ala Val Lys
                245                 250                 255
Glu Gln Asn Gly Ala Ala Met Ser Ile Gly Arg Ile Ser Thr Phe Leu
            260                 265                 270
Asp Ile Tyr Ile Glu Arg Asp Leu Lys Glu Gly Lys Leu Thr Glu Glu
        275                 280                 285
Leu Ala Gln Glu Leu Val Asp Gln Leu Val Ile Lys Leu Arg Ile Val
    290                 295                 300
Arg Phe Leu Arg Thr Pro Glu Tyr Glu Lys Leu Phe Ser Gly Asp Pro
305                 310                 315                 320
Thr Trp Val Thr Glu Ser Ile Gly Gly Met Ala Leu Asp Gly Arg Thr
                325                 330                 335
Leu Val Thr Lys Ser Ser Phe Arg Phe Leu His Thr Leu Phe Asn Leu
            340                 345                 350
Gly His Ala Pro Glu Pro Asn Leu Thr Val Leu Trp Ser Val Asn Leu
        355                 360                 365
Pro Glu Gly Phe Lys Lys Tyr Cys Ala Lys Val Ser Ile His Ser Ser
    370                 375                 380
Ser Ile Gln Tyr Glu Ser Asp Asp Ile Met Arg Lys His Trp Gly Asp
385                 390                 395                 400
Asp Tyr Gly Ile Ala Cys Cys Val Ser Ala Met Arg Ile Gly Lys Gln
                405                 410                 415
Met Gln Phe Phe Gly Ala Arg Cys Asn Leu Ala Lys Ala Leu Leu Tyr
            420                 425                 430
Ala Ile Asn Gly Gly Lys Asp Glu Met Thr Gly Glu Gln Ile Ala Pro
        435                 440                 445
Met Phe Ala Pro Val Glu Thr Glu Tyr Leu Asp Tyr Glu Asp Val Met
    450                 455                 460
Lys Arg Phe Asp Met Val Leu Asp Trp Val Ala Arg Leu Tyr Met Asn
465                 470                 475                 480
Thr Leu Asn Ile Ile His Tyr Met His Asp Lys Tyr Ala Tyr Glu Ala
                485                 490                 495
Leu Gln Met Ala Leu His Asp Lys Asp Val Phe Arg Thr Met Ala Cys
            500                 505                 510
Gly Ile Ala Gly Leu Ser Val Val Ala Asp Ser Leu Ser Ala Ile Lys
        515                 520                 525
Tyr Ala Lys Val Lys Pro Ile Arg Asn Glu Asn Asn Leu Val Val Asp
    530                 535                 540
Tyr Glu Val Glu Gly Asp Tyr Pro Lys Phe Gly Asn Asn Asp Glu Arg
545                 550                 555                 560
Val Asp Glu Ile Ala Val Gln Val Val Lys Met Phe Met Asn Lys Leu
                565                 570                 575
Arg Lys Gln Arg Ala Tyr Arg Ser Ala Thr Pro Thr Leu Ser Ile Leu
            580                 585                 590
Thr Ile Thr Ser Asn Val Val Tyr Gly Lys Lys Thr Gly Asn Thr Pro
        595                 600                 605
Asp Gly Arg Lys Ala Gly Glu Pro Leu Ala Pro Gly Ala Asn Pro Met
    610                 615                 620
His Gly Arg Asp Ile Asn Gly Ala Leu Ala Val Leu Asn Ser Ile Ala
625                 630                 635                 640
Lys Leu Pro Tyr Glu Tyr Ala Gln Asp Gly Ile Ser Tyr Thr Phe Ser
                645                 650                 655
Ile Ile Pro Lys Ala Leu Gly Arg Asp Glu Glu Thr Arg Ile Asn Asn
```

```
                      660                 665                 670
Leu Lys Ser Met Leu Asp Gly Tyr Phe Lys Gln Gly Gly His His Ile
                675                 680                 685

Asn Val Asn Val Phe Glu Lys Glu Thr Leu Leu Asp Ala Met Glu His
            690                 695                 700

Pro Glu Lys Tyr Pro Gln Leu Thr Ile Arg Val Ser Gly Tyr Ala Val
705                 710                 715                 720

Asn Phe Ile Lys Leu Thr Arg Glu Gln Gln Leu Asp Val Ile Asn Arg
                725                 730                 735

Thr Ile His Gly Lys Ile
            740

<210> SEQ ID NO 2
<211> LENGTH: 358
<212> TYPE: PRT
<213> ORGANISM: C. thermocellum

<400> SEQUENCE: 2

Val Ile Ile Tyr Ser Tyr Lys Tyr Tyr Lys Tyr Ser Phe Tyr Asp Asn
1               5                   10                  15

Ser Phe Gly Ile Met Lys Gly Glu Glu Phe Met Ser Phe Leu Glu Gln
            20                  25                  30

Ile Ile Glu Arg Ala Lys Ser Asp Val Lys Thr Ile Val Leu Pro Glu
        35                  40                  45

Ser Thr Asp Leu Arg Val Ile Lys Ala Ala Ser Met Ile Met Lys Lys
    50                  55                  60

Gly Ile Ala Lys Val Val Leu Ile Gly Asn Glu Lys Glu Ile Lys Ser
65                  70                  75                  80

Leu Ala Gly Asp Ile Asp Leu Glu Gly Val Met Ile Glu Asp Ser Leu
                85                  90                  95

Asn Ser Glu Lys Leu Glu Asp Tyr Ala Asn Thr Leu Tyr Glu Leu Arg
            100                 105                 110

Lys Ser Lys Gly Met Thr Ile Glu Ala Ala Arg Glu Thr Ile Lys Asp
        115                 120                 125

Pro Leu Tyr Tyr Gly Val Met Met Val Lys Lys Gly Glu Ala Asp Gly
    130                 135                 140

Met Val Ala Gly Ala Val Asn Ser Thr Ala Asn Thr Leu Arg Pro Ala
145                 150                 155                 160

Leu Gln Ile Leu Lys Thr Ala Pro Gly Thr Lys Leu Val Ser Ser Phe
                165                 170                 175

Phe Val Met Val Val Pro Asn Cys Glu Tyr Gly His Asn Gly Thr Phe
            180                 185                 190

Val Tyr Ala Asp Cys Gly Leu Val Glu Asn Pro Asp Ala Asp Gln Leu
        195                 200                 205

Ser Glu Ile Ala Ile Ser Ala Ser Lys Ser Phe Glu Met Leu Val Gly
    210                 215                 220

Ala Lys Pro Gln Val Ala Met Leu Ser Tyr Ser Ser Tyr Gly Ser Ala
225                 230                 235                 240

Lys Ser Glu Leu Thr Glu Lys Val Ile Lys Ala Thr Gln Leu Ala Lys
                245                 250                 255

Glu Lys Ala Pro His Leu Ala Ile Asp Gly Glu Leu Gln Val Asp Ala
            260                 265                 270

Ala Ile Val Pro Glu Val Ala Lys Ser Lys Ala Lys Gly Ser Ser Val
        275                 280                 285
```

```
Ala Gly Lys Ala Asn Val Leu Ile Phe Pro Asp Leu Asp Ala Gly Asn
    290                 295                 300

Ile Ala Tyr Lys Leu Thr Gln Arg Leu Ala Lys Ala Glu Ala Tyr Gly
305                 310                 315                 320

Pro Ile Thr Gln Gly Leu Ala Arg Pro Val Asn Asp Leu Ser Arg Gly
                325                 330                 335

Cys Ser Ala Glu Asp Ile Val Gly Val Ala Ala Ile Thr Ala Val Gln
                340                 345                 350

Ala Gln Tyr Val Lys Ala
            355

<210> SEQ ID NO 3
<211> LENGTH: 399
<212> TYPE: PRT
<213> ORGANISM: C. thermocellum

<400> SEQUENCE: 3

Met Asn Ile Leu Val Ile Asn Thr Gly Ser Ser Leu Lys Tyr Gln
1               5                   10                  15

Leu Ile Asp Met Thr Asn Glu Ser Val Leu Ala Lys Gly Val Cys Asp
                20                  25                  30

Arg Ile Gly Leu Glu His Ser Phe Leu Lys His Thr Lys Thr Gly Gly
            35                  40                  45

Glu Thr Val Val Ile Glu Lys Asp Leu Tyr Asn His Lys Leu Ala Ile
50                  55                  60

Gln Glu Val Ile Ser Ala Leu Thr Asp Glu Lys Ile Gly Val Ile Lys
65                  70                  75                  80

Ser Met Ser Glu Ile Ser Ala Val Gly His Arg Ile Val His Gly Gly
                85                  90                  95

Glu Lys Phe Lys Glu Ser Ala Ile Ile Asp Glu Asp Val Met Lys Ala
            100                 105                 110

Ile Arg Asp Cys Val Glu Leu Ala Pro Leu His Asn Pro Ser Asn Ile
        115                 120                 125

Ile Gly Ile Glu Ala Cys Lys Gln Ile Leu Pro Asp Val Pro Met Val
    130                 135                 140

Ala Val Phe Asp Thr Ala Phe His Gln Thr Met Pro Arg His Ala Tyr
145                 150                 155                 160

Ile Tyr Ala Leu Pro Tyr Glu Ile Tyr Glu Lys Tyr Lys Leu Arg Lys
                165                 170                 175

Tyr Gly Phe His Gly Thr Ser His Lys Tyr Val Ala His Arg Ala Ala
            180                 185                 190

Gln Met Leu Gly Lys Pro Ile Glu Ser Leu Lys Leu Ile Thr Cys His
        195                 200                 205

Leu Gly Asn Gly Ala Ser Ile Cys Ala Val Lys Gly Gly Lys Ser Val
    210                 215                 220

Asp Thr Ser Met Gly Phe Thr Pro Leu Gln Gly Leu Cys Met Gly Thr
225                 230                 235                 240

Arg Ser Gly Asn Val Asp Pro Ala Val Ile Thr Tyr Leu Met Glu Lys
                245                 250                 255

Glu Lys Met Asn Ile Asn Asp Ile Asn Asn Phe Leu Asn Lys Lys Ser
            260                 265                 270

Gly Val Leu Gly Ile Ser Gly Val Ser Ser Asp Phe Arg Asp Val Gln
        275                 280                 285

Asp Ala Ala Glu Lys Gly Asp Asp Arg Ala Gln Leu Ala Leu Asp Ile
    290                 295                 300
```

```
Phe Cys Tyr Gly Val Arg Lys Tyr Ile Gly Lys Tyr Ile Ala Val Leu
305                 310                 315                 320

Asn Gly Val Asp Ala Val Phe Thr Ala Gly Ile Gly Glu Asn Asn
            325                 330                 335

Ala Tyr Ile Arg Arg Glu Val Leu Lys Asp Met Asp Phe Phe Gly Ile
            340                 345                 350

Lys Ile Asp Leu Asp Lys Asn Glu Val Lys Gly Lys Glu Ala Asp Ile
            355                 360                 365

Ser Ala Pro Asp Ala Lys Val Lys Thr Leu Val Ile Pro Thr Asn Glu
370                 375                 380

Glu Leu Glu Ile Ala Arg Glu Thr Leu Arg Leu Val Lys Asn Leu
385                 390                 395
```

<210> SEQ ID NO 4
<211> LENGTH: 389
<212> TYPE: PRT
<213> ORGANISM: C. thermocellum

<400> SEQUENCE: 4

```
Met Ile Asn Phe Val Tyr Lys Asn Pro Thr Lys Ile Ile Phe Gly Arg
1               5                   10                  15

Gly Thr Glu Leu Lys Val Gly Glu Glu Val Arg Gln Tyr Ser Gly Lys
            20                  25                  30

Val Leu Leu His Tyr Gly Gly Ser Ile Lys Lys Thr Gly Leu Tyr
            35                  40                  45

Asp Arg Val Val Asn Ser Leu Lys Gln Ala Gly Val Glu Val Val Glu
50                  55                  60

Leu Gly Gly Val Met Pro Asn Pro Arg Leu Gly Leu Val Asn Glu Gly
65                  70                  75                  80

Ile Lys Ile Cys Arg Glu Lys Gly Ile Asp Phe Ile Leu Ala Val Gly
                85                  90                  95

Gly Gly Ser Ala Ile Asp Ser Ala Lys Ala Ile Ala Val Gly Val Pro
            100                 105                 110

Tyr Asp Gly Asp Val Trp Asp Phe Phe Cys Gly Lys Ala Glu Pro Lys
            115                 120                 125

Glu Ala Leu Pro Val Gly Val Val Leu Thr Ile Pro Ala Ala Gly Ser
130                 135                 140

Glu Ala Ser Pro Asn Ser Val Ile Thr Arg Glu Asp Gly Leu Tyr Lys
145                 150                 155                 160

Arg Gly Met Tyr Ser Glu Leu Ile Arg Pro Val Phe Ala Ile Met Asn
                165                 170                 175

Pro Glu Leu Thr Tyr Thr Leu Pro Ala Tyr Gln Thr Ala Cys Gly Thr
            180                 185                 190

Ala Asp Ile Met Ala His Ile Met Glu Arg Tyr Phe Thr Asn Glu Thr
            195                 200                 205

His Thr Asp Leu Thr Asp Arg Leu Cys Glu Ala Thr Leu Lys Thr Met
210                 215                 220

Ile Lys Asn Val Pro Ile Ala Leu Glu Glu Pro Asp Asn Tyr Asn Ala
225                 230                 235                 240

Arg Ala Glu Ile Met Trp Ala Gly Thr Ile Ala His Asn Gly Leu Leu
                245                 250                 255

Gly Thr Gly Arg Ile Glu Asp Trp Ala Ser His Asn Ile Glu His Glu
            260                 265                 270

Ile Ser Ala Ile Tyr Asp Val Ala His Gly Ala Gly Leu Ala Val Val
```

```
               275                 280                 285
Phe Pro Ala Trp Met Lys Tyr Val Tyr Lys Asn Asn Leu Asp Arg Phe
    290                 295                 300
Val Gln Phe Ala Val Arg Val Trp Asn Val Glu Met Asn Phe Asp Glu
305                 310                 315                 320
Pro Glu Arg Thr Ala Leu Glu Gly Ile Glu Arg Leu Lys Lys Phe Phe
                325                 330                 335
Lys Glu Ile Gly Leu Pro Val Ser Leu Lys Glu Met Asn Ile Gly Asp
                340                 345                 350
Asp Arg Leu Glu Glu Met Ala Ser Lys Cys Thr Asn Gly Gly Lys Ala
                355                 360                 365
Thr Ile Gly Asn Phe Val Lys Leu Asn Arg Glu Asp Val Tyr Asn Ile
    370                 375                 380
Leu Lys Leu Ala Val
385

<210> SEQ ID NO 5
<211> LENGTH: 389
<212> TYPE: PRT
<213> ORGANISM: C. thermocellum

<400> SEQUENCE: 5

Met Lys Ala Phe Asn Tyr Tyr Ala Pro Thr Glu Ile Ile Phe Gly Cys
1               5                   10                  15
Gly Arg Val Gln Glu Ile Gly Ser Ile Thr Ala Gln Tyr Gly Lys Lys
                20                  25                  30
Ala Leu Leu Val Thr Val Pro Glu Phe Pro Glu Val Lys Glu Leu Tyr
                35                  40                  45
Glu Lys Val Lys Lys Ser Leu Arg Glu Asn Gly Val Glu Val Val His
                50                  55                  60
Phe Asp Gly Val Ile Pro Asn Pro Thr Thr Asp Val Val Thr Glu Gly
65                  70                  75                  80
Ala Asn Met Ala Lys Ala Ala Gly Val Asp Val Val Ile Gly Leu Gly
                85                  90                  95
Gly Gly Ser Ser Ile Asp Thr Ala Lys Ala Ile Ala Val Glu Ala Thr
                100                 105                 110
His Pro Gly Thr Ala Trp Asp Tyr Asn Cys His Thr Pro Gly Pro Thr
                115                 120                 125
Ser Ala Thr Leu Pro Ile Ile Ala Ile Gly Thr Thr Ala Gly Thr Gly
                130                 135                 140
Ser Gln Cys Thr Gln Cys Ala Val Ile Thr Lys Thr Ser Glu Lys Asp
145                 150                 155                 160
Lys Ser Ala Ile Trp His Lys Asn Ile Phe Pro Lys Val Ala Ile Val
                165                 170                 175
Asp Pro Glu Val Thr Val Thr Met Pro Lys Ser Val Thr Ala Gln Thr
                180                 185                 190
Gly Phe Asp Ala Phe Ala His Asn Phe Glu Ala Tyr Leu Ser Val Lys
                195                 200                 205
Thr Ser Pro Leu Val Glu Met Met Ala Ile Glu Ala Ile Lys Met Ile
                210                 215                 220
Lys Glu Tyr Leu Pro Lys Ala Leu Glu Asn Pro Asn Asp Ile Glu Ala
225                 230                 235                 240
Arg Ser Lys Met Ser Leu Ala Asp Thr Leu Gly Gly Leu Thr Asn Ser
                245                 250                 255
```

```
Asn Ala Gly Val Thr Leu Pro His Gly Leu Met Gln Val Gly
            260                 265                 270
Gly

His Ala Pro His Val Ser His Gly Gln Ala Leu Ala Ile Ile Tyr Pro
            275                 280                 285

Gln Phe Thr Arg Tyr Thr Tyr Ala Trp Ala Ile Glu Lys Phe Ala Lys
            290                 295                 300

Val Gly Arg Ile Phe Asn Pro Ala Leu Asn Glu Leu Ser Asp Glu Glu
305                 310                 315                 320

Ala Ala Lys Glu Ala Cys Val Ala Ile Asp Asp Phe Leu Lys Lys Ile
                325                 330                 335

Gly Leu Trp Ile Gly Phe Lys Asp Val Asn Val Thr Lys Glu Gln Ile
            340                 345                 350

Arg Glu Ile Ala Asp Asp Gly Gln Val Leu Gly Asp Tyr Leu Asn Asn
            355                 360                 365

Pro Arg Val Ala Thr Ile Asp Glu Met Tyr Glu Leu Leu Met Asn Cys
            370                 375                 380

Tyr Glu Arg Lys Glu
385

<210> SEQ ID NO 6
<211> LENGTH: 873
<212> TYPE: PRT
<213> ORGANISM: C. thermocellum

<400> SEQUENCE: 6

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
                20                  25                  30

Thr Tyr Thr Gln Glu Gln Val Asp Lys Ile Phe Phe Glu Ala Ala Met
            35                  40                  45

Ala Ala Asn Lys Met Arg Ile Pro Leu Ala Lys Met Ala Val Glu Glu
        50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
    130                 135                 140

Ser Pro His Pro Arg Ala Lys Asn Ser Thr Ile Glu Ala Ala Lys Ile
145                 150                 155                 160

Val Leu Glu Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220

Ala Ile Ile Asp Asp Ser Ala Asp Ile Val Leu Ala Val Asn Ser Ile
225                 230                 235                 240
```

```
Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Ile Asn Gly Ala Leu Asn Ala Lys Ile Val Gly
    290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
                405                 410                 415

Phe Lys Leu Ala Pro Ser Leu Thr Leu Gly Cys Gly Ser Trp Gly Gly
            420                 425                 430

Asn Ser Val Ser Asp Asn Val Gly Val Lys His Leu Leu Asn Ile Lys
        435                 440                 445

Thr Val Ala Glu Arg Arg Glu Asn Met Leu Trp Phe Arg Thr Pro Glu
    450                 455                 460

Lys Ile Tyr Ile Lys Arg Gly Cys Leu Pro Val Ala Leu Asp Glu Leu
465                 470                 475                 480

Lys Asn Val Met Gly Lys Lys Ala Phe Ile Val Thr Asp Asn Phe
                485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
        515                 520                 525

Leu Ala Ser Ala Lys Ala Gly Ala Ala Glu Met Leu Ala Phe Gln Pro
    530                 535                 540

Asp Thr Ile Ile Ala Val Gly Gly Gly Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
        595                 600                 605

Gly Ser Glu Val Thr Pro Phe Ala Val Ile Thr Asp Glu Lys Thr Gly
    610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655
```

```
Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
        675                 680                 685

Ile Phe Glu Tyr Leu Pro Arg Ala Tyr Glu Asn Gly Ala Ser Asp Pro
    690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
        755                 760                 765

Thr Phe Pro Gln Tyr Asp His Pro Arg Thr Leu Glu Arg Tyr Ala Glu
    770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
        835                 840                 845

Thr Asn Pro Arg Tyr Pro Leu Met Asn Glu Ile Arg Gln Met Tyr Leu
    850                 855                 860

Asn Ala Tyr Tyr Gly Gly Ala Lys Lys
865                 870

<210> SEQ ID NO 7
<211> LENGTH: 347
<212> TYPE: PRT
<213> ORGANISM: C. thermocellum

<400> SEQUENCE: 7

Met Lys Gly Lys Met Lys Val Cys Val Leu Thr Gly Lys Glu Lys Leu
1               5                   10                  15

Glu Trp Val Glu Arg Asp Ile Pro Gln Pro Gly Arg Gly Glu Leu Gln
            20                  25                  30

Ile Lys Leu Lys His Val Gly Val Cys Gly Ser Asp Leu His Phe Tyr
        35                  40                  45

Lys Glu Gly Arg Leu Ala Asn Trp Glu Leu Asp Gly Pro Leu Ala Leu
    50                  55                  60

Gly His Glu Pro Gly Gly Ile Val Ser Ala Ile Gly Glu Gly Val Glu
65                  70                  75                  80

Gly Phe Glu Ile Gly Asp Lys Val Ala Leu Glu Pro Gly Val Pro Cys
                85                  90                  95

Gly Glu Cys Glu Asp Cys Arg Lys Gly His Tyr Asn Leu Cys Lys His
            100                 105                 110

Ile Lys Phe Met Ala Ile Pro His Glu Lys Asp Gly Val Phe Ala Glu
        115                 120                 125

Tyr Cys Val His Ser Ala Ser Met Cys Tyr Lys Leu Pro Glu Asn Val
    130                 135                 140

Asp Thr Met Glu Gly Gly Leu Met Glu Pro Leu Ser Val Ala Leu His
145                 150                 155                 160
```

Ala Thr Glu Leu Ser Asn Ala Lys Ile Gly Glu Thr Ala Ile Val Leu
            165                 170                 175

Gly Ser Gly Cys Ile Gly Leu Cys Thr Val Met Ala Leu Lys Ala Arg
            180                 185                 190

Gly Val Ser Glu Ile Tyr Val Thr Asp Val Val Asp Lys Arg Leu Glu
            195                 200                 205

Lys Ala Leu Glu Val Gly Ala Thr Arg Val Phe Asn Ser Gln Arg Glu
        210                 215                 220

Asp Ile Val Glu Phe Ala Lys Thr Leu Pro Gly Gly Ala Asp Gln
225                 230                 235                 240

Val Tyr Glu Cys Ala Gly Ser Arg Val Thr Thr Leu Gln Thr Cys Lys
            245                 250                 255

Leu Ile Lys Arg Ala Gly Lys Val Thr Leu Val Gly Val Ser Pro Glu
            260                 265                 270

Pro Val Leu Glu Leu Asp Ile Ala Thr Leu Asn Ala Met Glu Gly Thr
        275                 280                 285

Val Tyr Ser Val Tyr Arg Tyr Arg Asn Met Tyr Pro Ile Ala Ile Ala
        290                 295                 300

Ala Val Ser Ser Gly Val Ile Pro Leu Lys Lys Ile Val Ser His Val
305                 310                 315                 320

Phe Asp Phe Lys Asp Cys Ile Glu Ala Ile Glu Tyr Ser Thr Asn His
            325                 330                 335

Lys Asp Glu Val Ile Lys Ser Val Ile Lys Phe
            340                 345

<210> SEQ ID NO 8
<211> LENGTH: 368
<212> TYPE: PRT
<213> ORGANISM: C. thermocellum

<400> SEQUENCE: 8

Met Asn Phe Lys Phe Lys Ile Gly Thr Lys Val Phe Gly Lys Glu
1               5                   10                  15

Cys Val Lys Glu Asn Lys Ala Val Phe Lys Asp Phe Arg Lys Arg Ala
            20                  25                  30

Leu Leu Val Thr Gly Lys Asn Ser Ala Lys Ala Ser Gly Ala Phe Ser
        35                  40                  45

Asp Val Val Glu Val Leu Glu Glu Tyr Gly Ile Asp Tyr Glu Ile Tyr
    50                  55                  60

Asp Arg Val Ala Asn Asn Pro Ser Leu Glu Asn Val Lys Glu Gly Gly
65                  70                  75                  80

Glu Ala Ala Arg Lys Phe Asp Ala Asp Phe Ile Ile Gly Ile Gly Gly
                85                  90                  95

Gly Ser Pro Leu Asp Ala Ser Lys Ala Val Ala Val Leu Ala Thr Asn
            100                 105                 110

Asp Ile Glu Pro Val Asp Leu Tyr Lys Asn Val Phe Glu Asn Lys Pro
        115                 120                 125

Leu Pro Ile Ile Ala Ile Pro Thr Thr Ala Gly Thr Gly Ser Glu Val
    130                 135                 140

Thr Pro Tyr Ser Ile Leu Thr Arg Asp Asp Met Lys Thr Lys Lys Ser
145                 150                 155                 160

Phe Gly Asn Glu Asp Thr Phe Pro Ala Val Ala Phe Ile Asp Ala Arg
                165                 170                 175

Tyr Thr Glu Ser Met Ser Tyr Glu Thr Thr Val Asp Thr Ala Leu Asp

```
                 180                 185                 190
Ala Phe Thr His Ala Leu Glu Gly Tyr Leu Gly Arg Arg Ser Thr Pro
                195                 200                 205

Val Ser Asp Ile Leu Ala Val Glu Ala Ile Arg Ile Phe Gly Glu Cys
    210                 215                 220

Leu Glu Asn Leu Leu Asn Asn Lys Phe Asp Tyr Asp Val Arg Glu Lys
225                 230                 235                 240

Leu Leu Tyr Met Ser Met Leu Gly Gly Met Val Ile Ser His Thr Gly
                245                 250                 255

Thr Thr Ile Ile His Gly Met Gly Tyr Ser Leu Thr Tyr Phe Lys Asp
                260                 265                 270

Ile Pro His Gly Arg Ala Asn Gly Met Leu Val Arg Glu Tyr Leu Lys
            275                 280                 285

Tyr Asn Tyr Glu Ala Ala Lys Glu Lys Thr Asp Asn Val Leu Arg Leu
        290                 295                 300

Leu Lys Val Pro Ser Ile Asp Ala Phe Gly Glu Ile Ile Asp Arg Leu
305                 310                 315                 320

Ile Pro Gln Lys Pro Val Leu Thr Lys Glu Glu Ile Glu Leu Tyr Ala
                325                 330                 335

Ser Leu Ala Met Lys Gln Asn Ser Thr Leu Ser Asn Ala Arg Thr Val
                340                 345                 350

Val Lys Glu Asp Met Glu Ile Phe Lys Asn Thr Phe Gly Lys Gly
            355                 360                 365

<210> SEQ ID NO 9
<211> LENGTH: 131
<212> TYPE: PRT
<213> ORGANISM: C. thermocellum

<400> SEQUENCE: 9

Met Asn Ile Ala Leu Ile Ala His Asp Lys Lys Glu Leu Met Ala
1               5                   10                  15

Ser Phe Cys Ile Ala Tyr Arg Ser Ile Leu Lys Asn His Thr Leu Phe
                20                  25                  30

Ala Thr Gly Thr Thr Gly Ala Ile Ile Val Glu Ala Thr Gly Leu Asn
            35                  40                  45

Val His Arg Phe Leu Pro Gly Val Met Gly Glu Gln Gln Ile Ser Ala
    50                  55                  60

Arg Ala Ala Tyr Asn Glu Leu Asp Leu Val Ile Phe Phe Arg Asp Pro
65                  70                  75                  80

Ile Ser Ala Lys Ser Asp Glu Pro Asp Ile His Ser Leu Leu Arg Glu
                85                  90                  95

Cys Asp Ile Asn Asn Ile Pro Phe Ala Thr Asn Leu Gly Thr Ala Glu
            100                 105                 110

Met Leu Ile Lys Gly Leu Glu Arg Gly Asp Leu Asp Trp Arg Glu Leu
        115                 120                 125

Ile Lys Lys
    130

<210> SEQ ID NO 10
<211> LENGTH: 315
<212> TYPE: PRT
<213> ORGANISM: C. thermocellum

<400> SEQUENCE: 10

Leu Lys Tyr Cys Lys Leu Gly Asn Thr Gly Leu Glu Val Ser Lys Leu
```

-continued

```
 1               5                   10                  15
Cys Phe Gly Gly Leu Ile Ile Gly Pro Leu Gln Ala Asn Leu Pro Pro
                 20                  25                  30
Glu Thr Gly Ala Glu Ile Ile Leu Lys Ser Phe Glu Leu Gly Val Asn
                 35                  40                  45
Phe Ile Asp Thr Ala Glu Leu Tyr Gly Thr Tyr Ser His Ile Gly Lys
 50                  55                  60
Ala Leu Lys Lys Thr Asn Lys Asn Ile Val Val Ala Thr Lys Ser Tyr
 65                  70                  75                  80
Ala Tyr Ser Ala Glu Gly Ala Lys Glu Ser Leu Glu Lys Ala Arg Lys
                 85                  90                  95
Glu Met Asp Ile Asp Val Ile Asp Ile Phe Met Leu His Glu Gln Glu
                 100                 105                 110
Ser Arg Leu Thr Leu Lys Gly His Arg Glu Ala Leu Glu Tyr Tyr Ile
                 115                 120                 125
Ser Met Lys Glu Lys Gly Ile Ile Lys Ala Val Gly Val Ser Thr His
                 130                 135                 140
Asn Val Glu Val Val Glu Ala Cys Cys Glu Met Pro Glu Val Asp Val
 145                 150                 155                 160
Ile His Pro Ile Val Asn Lys Ala Gly Ile Gly Ile Gly Asp Gly Thr
                 165                 170                 175
Ile Asp Asp Met Leu Lys Ala Val Glu Lys Ala Tyr Ser Val Gly Lys
                 180                 185                 190
Gly Ile Tyr Ser Met Lys Pro Leu Gly Gly Asn Leu Ile Lys Ser
                 195                 200                 205
Tyr Lys Glu Ala Met Asp Phe Val Leu Asn Ile Pro Tyr Ile His Ser
 210                 215                 220
Ile Ala Val Gly Met Gln Ser Ile Glu Glu Val Val Met Asn Val Cys
 225                 230                 235                 240
Ile Phe Glu Gly Lys Glu Val Pro Gln Asp Val Gln Lys Ser Leu Glu
                 245                 250                 255
Asn Lys Lys Arg His Leu His Ile Asp Trp Trp Cys Glu Gly Cys Gly
                 260                 265                 270
Lys Cys Val Glu Arg Cys Lys Gln Lys Ala Leu Lys Leu Val Asp Gly
                 275                 280                 285
Lys Ala Lys Val Glu Glu Lys Cys Val Leu Cys Ser Tyr Cys Ala
                 290                 295                 300
Ser Val Cys Pro Val Phe Ala Ile Lys Val Ser
 305                 310                 315
```

<210> SEQ ID NO 11
<211> LENGTH: 376
<212> TYPE: PRT
<213> ORGANISM: C. thermocellum

<400> SEQUENCE: 11

```
Met Gln Tyr Arg Gly Leu Gly Lys Thr Gly Val Lys Val Ser Ala Leu
 1               5                   10                  15
Gly Phe Gly Ala Met Arg Leu Pro Gln Ile Asn Ile Asn Gly Asn Thr
                 20                  25                  30
Arg Val Asp Glu Glu Lys Ser Ile Glu Met Ile His Arg Ala Phe Glu
                 35                  40                  45
Leu Gly Val Asn Tyr Ile Asp Thr Ala Pro Gly Tyr Cys Asn Gly Glu
 50                  55                  60
```

Ser Glu Val Val Val Gly Lys Ala Leu Lys Gly Trp Arg Asp Lys Ile
 65                  70                  75                  80

Tyr Leu Ser Thr Lys Asn Pro Ile Glu Asn Ala Ser Gly Asp Asp Trp
                 85                  90                  95

Arg Lys Arg Leu Glu Asn Ser Leu Lys Lys Leu Asp Thr Asp Tyr Ile
            100                 105                 110

Asp Phe Tyr His Met Trp Gly Ile Asn Trp Glu Thr Tyr Glu Thr Lys
        115                 120                 125

Ile Asp Val Lys Gly Gly Pro Leu Glu Ala Ala Arg Lys Ala Lys Glu
    130                 135                 140

Glu Gly Leu Ile Arg His Ile Ser Phe Ser Phe His Asp Lys Pro Glu
145                 150                 155                 160

Asn Leu Ile Lys Leu Ile Asp Thr Gly Asn Phe Glu Thr Val Leu Cys
                165                 170                 175

Gln Tyr Asn Leu Leu Asp Arg Ser Asn Glu Lys Ala Ile Ala His Ala
            180                 185                 190

Lys Arg Lys Gly Leu Gly Val Ile Ile Met Gly Pro Val Gly Gly Gly
        195                 200                 205

Lys Leu Gly Glu Pro Ser Glu Thr Ile Lys Lys Leu Leu Pro Lys Lys
    210                 215                 220

Thr Val Ser Cys Ala Glu Ile Ala Leu Arg Phe Val Leu Ala Asn Pro
225                 230                 235                 240

Asn Val Asp Cys Ala Leu Ser Gly Met Ser Thr Ile Glu Met Val Glu
                245                 250                 255

Glu Asn Val Arg Val Ala Ser Asn Asp Thr Pro Leu Thr Lys Glu Glu
            260                 265                 270

Leu Glu Met Ile Arg Ala Ser Met Glu Glu Asn Lys Arg Met Glu Asp
        275                 280                 285

Leu Tyr Cys Thr Gly Cys Asn Tyr Cys Met Pro Cys Pro Val Gly Val
    290                 295                 300

Asn Ile Pro Leu Asn Phe Gln Leu Met Asn Tyr His Arg Val Tyr Lys
305                 310                 315                 320

Ile Thr Asp Tyr Ala Arg Gly Gln Tyr Ser Gln Ile Gly Lys Val Glu
                325                 330                 335

Trp Tyr Lys Gly Lys Pro Ala His Glu Cys Ile Glu Cys Gly Val Cys
            340                 345                 350

Glu Thr Lys Cys Pro Gln Lys Leu Glu Ile Arg Lys Gln Leu Lys Glu
        355                 360                 365

Thr Ala Arg Val Leu Ser Val Lys
    370                 375

<210> SEQ ID NO 12
<211> LENGTH: 315
<212> TYPE: PRT
<213> ORGANISM: C. thermocellum

<400> SEQUENCE: 12

Met Lys Tyr Arg Lys Met Gly Arg Thr Gly Leu Tyr Ile Ser Glu Ile
1               5                   10                  15

Ser Leu Gly Ser Trp Leu Thr Tyr Gly Asn Ser Thr Asp Lys Glu Thr
            20                  25                  30

Ala Val Lys Val Ile Asp Thr Ala Tyr Ser Leu Gly Ile Asn Tyr Phe
        35                  40                  45

Asp Thr Ala Asn Val Tyr Ala Asn Gly Arg Ala Glu Val Ile Val Gly
    50                  55                  60

```
Glu Ala Leu Lys Lys Tyr Pro Arg Glu Ser Tyr Ile Leu Ala Thr Lys
 65                  70                  75                  80

Ala Phe Trp Pro Met Gly Thr Gly Pro Asn Asp Lys Gly Leu Ser Arg
                 85                  90                  95

Lys His Val Phe Glu Gln Val His Ala Ser Leu Lys Arg Leu Asn Val
            100                 105                 110

Asp Tyr Ile Asp Ile Phe Tyr Cys His Arg Tyr Asp Pro Glu Thr Pro
        115                 120                 125

Leu Glu Glu Thr Leu Arg Thr Ile Asp Asp Leu Leu Arg Gln Gly Lys
130                 135                 140

Ile Leu Tyr Val Gly Val Ser Glu Trp Thr Ala Ala Gln Met Ala Gln
145                 150                 155                 160

Ala Leu His Ile Ala Asp Arg Tyr Leu Leu Asp Arg Ile Val Val Asn
                165                 170                 175

Gln Pro Gln Tyr Asn Met Phe His Arg Tyr Ile Glu Lys Glu Ile Ile
            180                 185                 190

Pro Phe Gly Glu Lys Asn Gly Ile Ser Gln Ile Val Phe Ser Pro Leu
        195                 200                 205

Ala Gln Gly Val Leu Thr Gly Lys Tyr Lys Pro Gly Gly Asn Ile Pro
210                 215                 220

Arg Asp Ser Arg Ala Ala Asp Pro Asn Ser Asn Met Tyr Ile Gly Gln
225                 230                 235                 240

Phe Leu Lys Glu Asp Lys Leu Leu Lys Val Glu Lys Leu Lys Ala Val
                245                 250                 255

Ala Asp Glu Met Gly Ile Thr Leu Ser Gln Leu Ala Ile Ala Trp Val
            260                 265                 270

Leu Arg Gln Pro Asn Val Thr Ser Ala Leu Ile Gly Ala Ser Lys Pro
        275                 280                 285

Glu Gln Val Glu Glu Asn Val Lys Ala Ser Gly Ile Asn Leu Ser Asp
290                 295                 300

Glu Ile Leu Asn Lys Ile Glu Ala Ile Leu Gln
305                 310                 315

<210> SEQ ID NO 13
<211> LENGTH: 251
<212> TYPE: PRT
<213> ORGANISM: C. thermocellum

<400> SEQUENCE: 13

Met Ser Arg Lys Val Ile Ala Ala Gly Asn Trp Lys Met Asn Lys Thr
 1               5                  10                  15

Pro Lys Glu Ala Val Glu Phe Val Gln Ala Leu Lys Gly Arg Val Ala
             20                  25                  30

Asp Ala Asp Thr Glu Val Val Gly Val Pro Phe Val Cys Leu Pro
         35                  40                  45

Gly Val Val Glu Ala Ala Lys Gly Ser Asn Ile Lys Val Ala Ala Gln
     50                  55                  60

Asn Met His Trp Glu Glu Lys Gly Ala Phe Thr Gly Glu Val Ser Gly
65                  70                  75                  80

Pro Met Leu Ala Glu Leu Gly Val Asp Tyr Val Ile Ile Gly His Ser
                 85                  90                  95

Glu Arg Arg Gln Tyr Phe Gly Glu Thr Asp Glu Thr Val Asn Lys Lys
            100                 105                 110

Val His Ala Ala Phe Lys Tyr Gly Leu Lys Pro Ile Ile Cys Val Gly
```

```
                    115                 120                 125
Glu Ser Leu Thr Gln Arg Glu Gln Gly Val Thr Ala Glu Leu Val Arg
130                 135                 140

Tyr Gln Val Lys Ile Ala Leu Leu Gly Leu Ser Ala Glu Gln Val Lys
145                 150                 155                 160

Glu Ala Val Ile Ala Tyr Glu Pro Ile Trp Ala Ile Gly Thr Gly Lys
                165                 170                 175

Thr Ala Thr Asn Glu Gln Ala Glu Val Cys Gly Ile Ile Arg Glu
                180                 185                 190

Cys Ile Lys Glu Leu Tyr Gly Gln Asp Val Ala Glu Ala Ile Arg Ile
            195                 200                 205

Gln Tyr Gly Gly Ser Val Asn Ala Ala Asn Ala Ala Glu Leu Phe Asn
        210                 215                 220

Met Pro Asn Ile Asp Gly Gly Leu Val Gly Gly Ala Ser Leu Lys Leu
225                 230                 235                 240

Asp Asp Phe Glu Lys Ile Ala Lys Tyr Asn Lys
                245                 250

<210> SEQ ID NO 14
<211> LENGTH: 192
<212> TYPE: PRT
<213> ORGANISM: C. thermocellum

<400> SEQUENCE: 14

Met Gly Lys Val Val Glu Ile Arg Trp His Gly Arg Gly Gln Gly
1               5                   10                  15

Ala Lys Thr Ala Ser Leu Leu Leu Ala Asp Ala Ala Phe Asn Thr Gly
                20                  25                  30

Lys Tyr Ile Gln Gly Phe Pro Glu Tyr Gly Pro Glu Arg Met Gly Ala
            35                  40                  45

Pro Ile Thr Ala Tyr Asn Arg Ile Ser Asp Glu Lys Leu Thr Ile His
        50                  55                  60

Ser Asn Ile Tyr Glu Pro Asp Tyr Val Val Val Asp Asp Thr Leu
65                  70                  75                  80

Leu Thr Ser Val Asp Val Thr Ala Gly Leu Lys Glu Asp Gly Ala Ile
                85                  90                  95

Ile Val Asn Thr Pro Lys Thr Pro Asp Glu Ile Arg Pro Leu Leu Lys
                100                 105                 110

Gly Tyr Lys Gly Lys Val Cys Thr Ile Asp Ala Arg Lys Ile Ser Ile
            115                 120                 125

Glu Thr Leu Gly Lys Tyr Phe Pro Asn Thr Pro Met Leu Gly Ala Val
        130                 135                 140

Val Lys Val Ser Lys Ile Met Asp Glu Glu Phe Leu Lys Asp Met
145                 150                 155                 160

Val Glu Ser Phe Lys His Lys Phe Ala Asn Lys Pro Glu Val Val Glu
                165                 170                 175

Gly Asn Ile Lys Ala Leu Glu Arg Ser Met Gln Glu Val Lys Gly Leu
            180                 185                 190

<210> SEQ ID NO 15
<211> LENGTH: 101
<212> TYPE: PRT
<213> ORGANISM: C. thermocellum

<400> SEQUENCE: 15

Met Ser Lys Glu Leu Arg Asp Val Lys Pro Asp Val Thr Trp Lys Glu
```

```
                1               5                      10                     15
          Ile Thr Ser Gly Gly Val Ile Asp Ser Pro Gly Asn Ala His Leu Phe
                           20                     25                     30

Lys Thr Gly Asp Trp Arg Ser Met Lys Pro Val Trp Asn Glu Glu Lys
                           35                     40                     45

Cys Lys Gln Cys Leu Leu Cys Asn Pro Val Cys Pro Asp Ser Ser Ile
                           50                     55                     60

Met Val Ser Glu Glu Gly Lys Met Thr Gly Ile Asp Tyr Asp His Cys
          65                      70                     75                     80

Lys Gly Cys Gly Ile Cys Ser Lys Val Cys Pro Phe Lys Ala Ile Asp
                           85                     90                     95

Phe Val Glu Glu Val
                          100

<210> SEQ ID NO 16
<211> LENGTH: 394
<212> TYPE: PRT
<213> ORGANISM: C. thermocellum

<400> SEQUENCE: 16

Met Gly Ile Arg Glu Arg Leu Ser Gly Asn Glu Ala Thr Ala Ile Ala
1               5                      10                     15

Met Arg Gln Ile Asn Pro Asp Val Val Ala Ala Phe Pro Ile Thr Pro
                 20                     25                     30

Ser Thr Glu Ile Pro Gln Tyr Phe Ser Ser Tyr Val Ala Asp Gly Leu
                 35                     40                     45

Val Asp Thr Glu Phe Val Ala Val Glu Ser Glu His Ser Ala Met Ser
 50                     55                     60

Ala Cys Ile Gly Ala Gln Ala Ala Gly Ala Arg Ala Met Thr Ala Thr
65                      70                     75                     80

Ser Ala Asn Gly Leu Ala Tyr Met Trp Glu Ala Leu Tyr Ile Ala Ala
                 85                     90                     95

Ser Met Arg Leu Pro Ile Val Leu Ala Ala Val Asn Arg Ala Leu Ser
                100                    105                    110

Gly Pro Ile Asn Ile His Asn Asp His Ser Asp Thr Met Gly Ala Arg
                115                    120                    125

Asp Ser Gly Trp Ile Gln Leu Tyr Ser Glu Asn Asn Gln Glu Ala Tyr
                130                    135                    140

Asp Asn Met Leu Met Ala His Arg Ile Gly Glu His Pro Asp Val Met
145                    150                    155                    160

Leu Pro Val Met Val Cys Gln Asp Gly Phe Ile Thr Ser His Ala Ile
                165                    170                    175

Glu Asn Ile Glu Leu Val Glu Asp Glu Lys Val Lys Ala Phe Val Gly
                180                    185                    190

Glu Tyr Lys Pro Thr His Tyr Leu Leu Asp Arg Glu Asn Pro Ile Ser
                195                    200                    205

Val Gly Pro Leu Asp Leu Gln Met His Tyr Phe Glu His Lys Arg Gln
                210                    215                    220

Gln Ala Gln Ala Met Glu Asn Ala Lys Lys Val Ile Leu Glu Val Ala
225                    230                    235                    240

Glu Glu Phe Tyr Lys Leu Thr Gly Arg Lys Tyr Gly Phe Phe Glu Glu
                245                    250                    255

Tyr Lys Thr Asp Asp Ala Asp Val Ala Ile Val Val Met Asn Ser Thr
                260                    265                    270
```

Ala Gly Thr Val Lys Tyr Val Ile Asp Glu Tyr Arg Ala Lys Gly Lys
            275                 280                 285

Lys Val Gly Leu Ile Lys Pro Arg Val Phe Arg Pro Phe Pro Val Asp
        290                 295                 300

Glu Leu Ala Gln Ala Leu Ser Lys Phe Lys Ala Val Ala Val Met Asp
305                 310                 315                 320

Lys Ala Asp Ser Phe Asn Ala Ala Gly Gly Pro Leu Phe Thr Glu Val
                325                 330                 335

Thr Ser Ala Leu Phe Thr Lys Gly Val Phe Gly Pro Lys Val Ile Asn
            340                 345                 350

Tyr Lys Phe Gly Leu Gly Gly Arg Asp Val Lys Val Asp Asp Ile Glu
        355                 360                 365

Val Val Cys Glu Lys Leu Leu Glu Ile Ala Ser Thr Gly Lys Val Asp
370                 375                 380

Ser Val Tyr Asn Tyr Leu Gly Val Arg Glu
385                 390

<210> SEQ ID NO 17
<211> LENGTH: 311
<212> TYPE: PRT
<213> ORGANISM: C. thermocellum

<400> SEQUENCE: 17

Met Ala Tyr Asn Leu Lys Glu Val Ala Lys Lys Pro Glu Arg Leu Thr
1               5                   10                  15

Gly Gly His Arg Met Cys Ala Gly Cys Gly Ala Pro Ile Val Val Arg
            20                  25                  30

Gln Val Leu Lys Ala Leu Lys Pro Glu Asp His Ala Val Ile Ser Ala
        35                  40                  45

Ala Thr Gly Cys Leu Glu Val Ser Thr Phe Ile Tyr Pro Tyr Thr Ala
    50                  55                  60

Trp Lys Asp Ser Phe Ile His Ser Ala Phe Glu Asn Thr Gly Ala Thr
65                  70                  75                  80

Ile Ser Gly Ala Glu Ala Ala Tyr Lys Val Leu Lys Lys Gly Lys
                85                  90                  95

Ile Glu Gly Glu Thr Lys Phe Ile Ala Phe Gly Asp Gly Gly Thr
            100                 105                 110

Tyr Asp Ile Gly Leu Gln Ala Leu Ser Gly Ala Met Glu Arg Gly His
        115                 120                 125

Asp Met Val Tyr Val Cys Tyr Asp Asn Gly Ala Tyr Met Asn Thr Gly
130                 135                 140

Ile Gln Arg Ser Ser Ala Thr Pro Lys Tyr Ala Asp Thr Thr Thr Ser
145                 150                 155                 160

Pro Val Gly Lys Lys Ile Pro Gly Lys Met Gln Pro Arg Lys Asp Leu
                165                 170                 175

Thr Glu Val Leu Val Asn His Arg Ile Pro Tyr Val Ala Gln Thr Ala
            180                 185                 190

Pro Phe Gly Asn Met Lys Asp Leu Tyr Glu Lys Ala Glu Lys Ala Ile
        195                 200                 205

Tyr Thr Pro Gly Pro Ala Phe Leu Asn Val Leu Ala Pro Cys Pro Arg
    210                 215                 220

Gly Trp Arg Tyr Asn Thr Pro Asp Leu Met Glu Leu Ser Lys Leu Ala
225                 230                 235                 240

Val Glu Thr Cys Phe Trp Pro Leu Tyr Glu Val Ile Asp Gly Lys Tyr
                245                 250                 255

```
Ile Ile Asn Tyr Lys Pro Lys Glu Lys Val Pro Val Lys Glu Phe Leu
                260                 265                 270

Lys Leu Gln Gly Arg Phe Lys His Leu Phe Lys Ala Gly Asn Glu Tyr
            275                 280                 285

Met Leu Glu Glu Ile Gln Lys Glu Val Asp Leu Arg Trp Glu Arg Leu
290                 295                 300

Leu Lys Leu Ala Gly Glu Ala
305             310

<210> SEQ ID NO 18
<211> LENGTH: 317
<212> TYPE: PRT
<213> ORGANISM: C. thermocellum

<400> SEQUENCE: 18

Met Asn Asn Asn Lys Val Ile Lys Lys Val Thr Val Gly Ala Gly
1               5                   10                  15

Phe Val Gly Ser Thr Thr Ala Tyr Thr Leu Met Leu Ser Gly Leu Ile
            20                  25                  30

Ser Glu Ile Val Leu Ile Asp Ile Asn Ala Lys Lys Ala Asp Gly Glu
        35                  40                  45

Val Met Asp Leu Asn His Gly Met Pro Phe Val Arg Pro Val Glu Ile
50                  55                  60

Tyr Arg Gly Asp Tyr Lys Asp Cys Ala Gly Ser Asp Ile Val Ile Ile
65                  70                  75                  80

Thr Ala Gly Ala Asn Gln Lys Glu Gly Glu Thr Arg Ile Asp Leu Val
                85                  90                  95

Lys Arg Asn Thr Glu Val Phe Lys Asn Ile Ile Asn Glu Ile Val Lys
            100                 105                 110

Tyr Asn Asn Asp Cys Ile Leu Leu Val Val Thr Asn Pro Val Asp Ile
        115                 120                 125

Leu Thr Tyr Val Thr Tyr Lys Leu Ser Gly Phe Pro Lys Asn Lys Val
    130                 135                 140

Ile Gly Ser Gly Thr Val Leu Asp Thr Ala Arg Phe Arg Tyr Leu Leu
145                 150                 155                 160

Ser Glu His Val Lys Val Asp Ala Arg Asn Val His Ala Tyr Ile Ile
                165                 170                 175

Gly Glu His Gly Asp Thr Glu Val Ala Ala Trp Ser Leu Ala Asn Ile
            180                 185                 190

Ala Gly Ile Pro Met Asp Arg Tyr Cys Asp Glu Cys His Gln Cys Glu
        195                 200                 205

Glu Gln Ile Ser Arg Asn Lys Ile Tyr Glu Ser Val Lys Asn Ala Ala
    210                 215                 220

Tyr Glu Ile Ile Arg Asn Lys Gly Ala Thr Tyr Tyr Ala Val Ala Leu
225                 230                 235                 240

Ala Val Arg Arg Ile Val Glu Ala Ile Val Arg Asn Glu Asn Ser Ile
                245                 250                 255

Leu Thr Val Ser Ser Leu Leu Glu Gly Gln Tyr Gly Leu Ser Asp Val
            260                 265                 270

Cys Leu Ser Val Pro Thr Ile Val Gly Val Asn Gly Ile Glu Glu Ile
        275                 280                 285

Leu Asn Val Pro Phe Asn Asp Glu Glu Ile Gln Leu Leu Arg Lys Ser
    290                 295                 300

Gly Asn Thr Leu Lys Glu Ile Ile Lys Thr Leu Asp Ile
```

```
305                 310                 315
```

<210> SEQ ID NO 19
<211> LENGTH: 81
<212> TYPE: PRT
<213> ORGANISM: C. thermocellum

<400> SEQUENCE: 19

```
Met Lys Val Ser Ile Cys Ile Gly Ser Ser Cys His Leu Lys Gly Ala
1               5                   10                  15

Lys Gln Ile Val Glu Gln Leu Gln Ser Leu Val Ala Asp Tyr Asn Leu
            20                  25                  30

Lys Glu Lys Val Glu Leu Gly Gly Ala Phe Cys Met Lys Asn Cys Val
        35                  40                  45

Asn Gly Val Ser Val Thr Val Asp Asp Lys Leu Phe Ser Val Thr Pro
    50                  55                  60

Glu Asn Val Lys Ser Phe Phe Glu Thr Glu Ile Leu Lys Lys Leu Glu
65                  70                  75                  80

Asp
```

<210> SEQ ID NO 20
<211> LENGTH: 556
<212> TYPE: PRT
<213> ORGANISM: C. thermocellum

<400> SEQUENCE: 20

```
Met Thr Glu Cys Leu Gln Thr Lys Lys Ser Asn Cys Lys Asn Cys Tyr
1               5                   10                  15

Lys Cys Ile Arg His Cys Pro Val Lys Ser Leu Lys Phe Thr Asp Gly
            20                  25                  30

Gln Ala His Ile Val Arg Asp Glu Cys Val Leu Cys Gly Glu Cys Tyr
        35                  40                  45

Val Val Cys Pro Gln Asn Ala Lys Gln Ile Arg Ser Asp Val Glu Lys
    50                  55                  60

Ala Lys Gln Leu Val Leu Lys Tyr Asp Val Tyr Ala Ser Ile Ala Pro
65                  70                  75                  80

Ser Phe Val Ala Trp Phe His Asn Lys Ser Ile His Asp Met Glu Gln
            85                  90                  95

Ala Leu Ile Lys Leu Gly Phe Lys Gly Ala Asp Glu Thr Ala Lys Gly
            100                 105                 110

Ala Tyr Ile Val Lys Lys Gln Tyr Glu Lys Met Ile Glu Glu Lys Lys
            115                 120                 125

Ser Lys Ile Ile Ile Ser Ser Cys Cys His Thr Val Asn Thr Leu Ile
        130                 135                 140

Gln Arg His Tyr Thr Gly Ala Ile Gln Tyr Leu Ala Asp Val Val Ser
145                 150                 155                 160

Pro Met Leu Ala His Ala Gln Met Leu Lys Lys Glu His Lys Gly Ala
            165                 170                 175

Lys Val Val Phe Ile Gly Pro Cys Ile Ser Lys Lys Asp Glu Ala Glu
            180                 185                 190

Lys Tyr Lys Gly Tyr Val Glu Leu Val Leu Thr Phe Asp Glu Leu Asp
            195                 200                 205

Glu Trp Leu Lys Ser Glu Asn Ile Thr Ile Glu Ser Asn Arg Gly Ser
        210                 215                 220

Ser Lys Glu Gly Arg Thr Arg Ser Phe Pro Val Ser Gly Gly Ile Ile
225                 230                 235                 240
```

```
Ser Ser Met Asp Lys Asp Leu Gly Tyr His Tyr Met Val Val Asp Gly
            245                 250                 255

Met Glu Asn Cys Ile Asn Ala Leu Glu Asn Ile Glu Arg Gly Glu Ile
        260                 265                 270

Asp Asn Cys Phe Ile Glu Met Ser Ala Cys Arg Gly Ser Cys Ile Asn
            275                 280                 285

Gly Pro Pro Ala Arg Arg Lys Ser Asn Asn Ile Val Gly Ala Ile Leu
        290                 295                 300

Ala Val Asn Lys Asn Thr Gly Ala Lys Asp Phe Ser Val Pro Met Pro
305                 310                 315                 320

Glu Pro Glu Lys Leu Lys Lys Glu Phe Arg Phe Glu Gly Val His Lys
                325                 330                 335

Ile Met Pro Gly Gly Thr Ala Ile Glu Glu Ile Leu Lys Lys Met Gly
            340                 345                 350

Lys Thr Ser Ile Glu His Glu Leu Asn Cys Gly Ser Cys Gly Tyr Asp
            355                 360                 365

Thr Cys Arg Asp Lys Ala Val Ala Val Leu Asn Gly Lys Ala Asp Leu
        370                 375                 380

Thr Met Cys Leu Pro Tyr Leu Lys Glu Lys Ala Glu Ser Phe Ser Asp
385                 390                 395                 400

Ala Ile Ile Lys Asn Thr Pro Asn Gly Val Ile Val Leu Asn Glu Asp
                405                 410                 415

Leu Glu Ile Gln Gln Ile Asn Asn Ser Ala Lys Arg Ile Leu Asn Leu
            420                 425                 430

Ser Pro Ser Thr Asp Leu Leu Gly Ser Pro Val Ser Arg Ile Leu Asp
        435                 440                 445

Pro Ile Asp Tyr Ile Leu Ala Leu Arg Glu Gly Lys Asn Cys Tyr Tyr
450                 455                 460

Lys Arg Lys Tyr Phe Ala Glu Tyr Lys Lys Tyr Val Asp Glu Thr Ile
465                 470                 475                 480

Ile Tyr Asp Lys Glu Tyr His Val Ile Ile Ile Met Arg Asp Val
                485                 490                 495

Thr Glu Glu Lys Ile Lys Ala Leu Lys Asn Lys Gln Ser Glu Ala
                500                 505                 510

Ala Ile Glu Ile Ala Asp Lys Val Val Glu Lys Gln Met Arg Val Val
            515                 520                 525

Gln Glu Ile Ala Leu Leu Leu Gly Glu Thr Ala Ala Glu Thr Lys Ile
        530                 535                 540

Ala Leu Thr Lys Leu Lys Glu Thr Met Glu Asp Glu
545                 550                 555

<210> SEQ ID NO 21
<211> LENGTH: 389
<212> TYPE: PRT
<213> ORGANISM: C. thermocellum

<400> SEQUENCE: 21

Met Asn Asp Leu Cys Val Asp Leu Gly Tyr Lys Ser Leu Asn Lys Phe
1               5                   10                  15

Gly Glu Gln Leu Cys Gly Asp Met Ile Gln Val Val Lys Asp Asp Asp
            20                  25                  30

Thr Thr Ile Leu Val Leu Ala Asp Gly Leu Gly Ser Gly Val Lys Ala
        35                  40                  45

Asn Ile Leu Ser Thr Leu Thr Ser Lys Ile Ile Ser Thr Met Ile Ala
```

```
            50                  55                  60
Ala His Met Gly Ile Glu Glu Cys Val Asn Thr Ile Met Ser Thr Leu
 65                  70                  75                  80

Pro Val Cys Lys Val Arg Gly Ile Ala Tyr Ser Thr Phe Thr Ile Ile
                 85                  90                  95

Lys Ile Thr Asn Asn Thr Tyr Ala Glu Ile Ile Gln Tyr Asp Asn Pro
                100                 105                 110

Leu Val Ile Leu Leu Arg Asn Gly Lys Lys Tyr Asp Tyr Pro Thr Gln
            115                 120                 125

Thr Lys Ile Ile Ser Gly Lys Lys Ile Val Glu Ser Lys Ile Arg Leu
        130                 135                 140

Asn Cys Asp Asp Val Phe Val Val Met Ser Asp Gly Ala Ile Tyr Ala
145                 150                 155                 160

Gly Val Gly Gln Thr Leu Asn Tyr Gly Trp Gln Arg Glu Asn Ile Ile
                165                 170                 175

Glu Phe Ile Glu Ser His Tyr Asp Lys Ser Leu Ser Ala Asn Ala Leu
                180                 185                 190

Thr Ser Leu Leu Ile Asp Thr Cys Asn Asn Leu Tyr Ala Asn Met Pro
            195                 200                 205

Gly Asp Asp Thr Thr Ile Ala Ala Ile Lys Ile Arg Lys Arg Gln Val
210                 215                 220

Val Asn Leu Met Phe Gly Pro Pro Gln Asn Pro Glu Asp Val His Asn
225                 230                 235                 240

Met Met Ser Leu Phe Phe Ala Lys Gln Gly Arg His Ile Val Cys Gly
                245                 250                 255

Gly Thr Thr Ser Thr Leu Ala Ala Lys Phe Leu Gly Lys Glu Leu Glu
                260                 265                 270

Thr Thr Ile Asp Tyr Ile Asp Pro Arg Ile Pro Ile Ala Arg Ile
            275                 280                 285

Glu Gly Val Asp Leu Val Thr Glu Gly Val Leu Thr Ile Ser Arg Val
        290                 295                 300

Leu Glu Tyr Ala Lys Asp Tyr Ile Gly Lys Asn Ile Leu Tyr Asn Glu
305                 310                 315                 320

Trp His Ser Lys Asn Asp Gly Ala Ser Ile Ile Ala Arg Met Leu Phe
                325                 330                 335

Glu Glu Ala Thr Asp Ile Asn Phe Tyr Val Gly Lys Ala Ile Asn Pro
                340                 345                 350

Ala His Gln Asn Pro Asn Leu Pro Ile Gly Phe Asn Ile Lys Met Gln
            355                 360                 365

Leu Val Glu Glu Leu Ser Lys Ile Leu Lys Gln Met Gly Lys Thr Ile
        370                 375                 380

Asn Leu Ser Tyr Phe
385

<210> SEQ ID NO 22
<211> LENGTH: 165
<212> TYPE: PRT
<213> ORGANISM: C. thermocellum

<400> SEQUENCE: 22

Met Ser Val Thr Met Ser Glu Ala Phe Asp Tyr Ser Met Ile Asp Asn
 1               5                  10                  15

Ile Leu Ser Glu His Gly Thr Ser Glu Thr Ala Ile Ile Ala Ile Leu
            20                  25                  30
```

```
Gln Ser Ile Gln Glu Glu Tyr His Tyr Ile Pro Lys Glu Val Phe Pro
            35                  40                  45

Tyr Leu Ser Lys Lys Leu Lys Val Ser Glu Ala Arg Ile Phe Ser Val
 50                  55                  60

Ala Thr Phe Tyr Glu Asn Phe Ser Leu Glu Pro Lys Gly Lys Tyr Ile
 65                  70                  75                  80

Ile Lys Val Cys Asp Gly Thr Ala Cys His Val Arg Lys Ser Ile Pro
                 85                  90                  95

Ile Ile Glu Arg Leu Arg Lys Glu Leu Gly Leu Ser Gly Thr Lys Pro
                100                 105                 110

Thr Thr Asp Asp Leu Met Phe Thr Val Glu Thr Val Ser Cys Leu Gly
                115                 120                 125

Ala Cys Gly Leu Ala Pro Val Ile Thr Val Asn Asp Lys Val Tyr Ala
130                 135                 140

Glu Met Thr Pro Asp Lys Ala Ser Glu Leu Ile Lys Gln Leu Arg Glu
145                 150                 155                 160

Gly Asp Ala Asp Ala
                165

<210> SEQ ID NO 23
<211> LENGTH: 624
<212> TYPE: PRT
<213> ORGANISM: C. thermocellum

<400> SEQUENCE: 23

Met Leu Lys Asn Arg Glu Glu Leu Arg Lys Ala Arg Glu Met Tyr Ser
1               5                   10                  15

Arg Tyr Leu Lys Ala Glu Lys Arg Arg Val Leu Val Cys Ala Gly Thr
                20                  25                  30

Gly Cys Val Ser Gly Gly Ser Met Glu Ile Phe Glu Arg Leu Ser Glu
            35                  40                  45

Leu Val Ser Lys Arg Gly Met Asp Cys Gln Val Glu Leu Lys Glu Glu
 50                  55                  60

Pro His Asp Asn Thr Ile Gly Met Lys Lys Ser Gly Cys His Gly Phe
 65                  70                  75                  80

Cys Glu Met Gly Pro Leu Val Arg Ile Glu Pro Glu Gly Tyr Leu Tyr
                 85                  90                  95

Thr Lys Val Lys Leu Glu Asp Cys Glu Glu Ile Val Arg Thr Ile
                100                 105                 110

Val Ala Gly Glu His Ile Glu Arg Leu Ala Tyr Lys Gln Asn Gly Val
                115                 120                 125

Val Tyr Lys Lys Gln Asp Glu Ile Pro Phe Tyr Lys Lys Gln Thr Arg
130                 135                 140

Leu Val Leu Glu His Cys Gly Gln Ile Asp Ser Thr Ser Ile Thr Glu
145                 150                 155                 160

Tyr Leu Ala Thr Gly Gly Tyr Tyr Ala Leu Glu Lys Ala Leu Phe Asp
                165                 170                 175

Met Thr Gly Asp Glu Ile Ile Asn Glu Ile Thr Glu Ala Asn Leu Arg
                180                 185                 190

Gly Arg Gly Gly Gly Phe Pro Ala Gly Arg Lys Trp Ala Gln Val
                195                 200                 205

Lys Arg Gln Asn Ala Lys Gln Lys Tyr Val Val Cys Asn Gly Asp Glu
                210                 215                 220

Gly Asp Pro Gly Ala Phe Met Asp Arg Ser Ile Met Glu Gly Asp Pro
225                 230                 235                 240
```

His Arg Met Ile Glu Gly Met Ile Ile Ala Gly Ile Ala Cys Gly Ala
              245                 250                 255

Ser Glu Gly Tyr Ile Tyr Val Arg Ala Glu Tyr Pro Leu Ala Val Ser
              260                 265                 270

Arg Leu Lys Arg Ala Ile Glu Gln Ala Lys Glu Phe Gly Leu Leu Gly
              275                 280                 285

Glu Asn Ile Leu Gly Ser Asn Phe Ser Phe Asn Ile His Ile Asn Arg
  290                 295                 300

Gly Ala Gly Ala Phe Val Cys Gly Glu Gly Ser Ala Leu Thr Ala Ser
305                 310                 315                 320

Ile Glu Gly Lys Arg Gly Met Pro Arg Val Lys Pro Pro Arg Thr Val
              325                 330                 335

Glu Gln Gly Leu Phe Asp Met Pro Thr Val Leu Asn Asn Val Glu Thr
              340                 345                 350

Phe Ala Asn Val Pro Leu Ile Ile Lys Asn Gly Ala Asp Trp Tyr Lys
              355                 360                 365

Ser Ile Gly Thr Glu Lys Ser Pro Gly Thr Lys Ala Phe Ala Leu Thr
  370                 375                 380

Gly Asn Ile Glu Asn Thr Gly Leu Ile Glu Ile Pro Met Gly Thr Thr
385                 390                 395                 400

Leu Arg Glu Val Ile Phe Asp Ile Gly Gly Met Arg Asn Gly Ala
              405                 410                 415

Asp Phe Lys Ala Val Gln Ile Gly Gly Pro Ser Gly Gly Cys Leu Ser
              420                 425                 430

Glu Lys Asp Leu Asp Leu Pro Leu Asp Phe Asp Ser Leu Lys Lys Ala
              435                 440                 445

Gly Ala Met Ile Gly Ser Gly Gly Leu Val Val Met Asp Ser Asn Thr
  450                 455                 460

Cys Met Val Glu Val Ala Arg Phe Phe Met Asn Phe Thr Gln Asn Glu
465                 470                 475                 480

Ser Cys Gly Lys Cys Val Pro Cys Arg Glu Gly Thr Lys Arg Met Leu
              485                 490                 495

Glu Ile Leu Glu Arg Ile Val Glu Gly Asn Gly Gln Asp Gly Asp Ile
              500                 505                 510

Glu Leu Leu Leu Glu Leu Ala Asp Thr Ile Ser Ala Thr Ala Leu Cys
              515                 520                 525

Gly Leu Gly Lys Ala Ala Ala Phe Pro Val Val Ser Thr Ile Lys Asn
  530                 535                 540

Phe Arg Glu Glu Tyr Glu Ala His Ile Tyr Asp Lys Arg Cys Pro Thr
545                 550                 555                 560

Gly Asn Cys Gln Lys Leu Lys Thr Ile Thr Ile Asp Ala Ser Leu Cys
              565                 570                 575

Lys Gly Cys Ser Lys Cys Ala Arg Ser Cys Pro Val Gly Ala Ile Thr
              580                 585                 590

Gly Lys Val Lys Glu Pro Phe Val Ile Asp Gln Ser Lys Cys Ile Lys
              595                 600                 605

Cys Gly Ala Cys Ile Glu Thr Cys Ala Phe His Ala Ile Leu Glu Gly
              610                 615                 620

<210> SEQ ID NO 24
<211> LENGTH: 566
<212> TYPE: PRT
<213> ORGANISM: C. thermocellum

<400> SEQUENCE: 24

```
Met Asp Asn Arg Glu Tyr Met Leu Ile Asp Gly Ile Pro Val Glu Ile
1               5                   10                  15

Asn Gly Glu Lys Asn Leu Leu Glu Leu Ile Arg Lys Ala Gly Ile Lys
            20                  25                  30

Leu Pro Thr Phe Cys Tyr His Ser Glu Leu Ser Val Tyr Gly Ala Cys
            35                  40                  45

Arg Met Cys Met Val Glu Asn Glu Trp Gly Gly Leu Asp Ala Ala Cys
    50                  55                  60

Ser Thr Pro Pro Arg Ala Gly Met Ser Ile Lys Thr Asn Thr Glu Arg
65                  70                  75                  80

Leu Gln Lys Tyr Arg Lys Met Ile Leu Glu Leu Leu Ala Asn His
                85                  90                  95

Cys Arg Asp Cys Thr Thr Cys Asn Asn Asn Gly Lys Cys Lys Leu Gln
                    100                 105                 110

Asp Leu Ala Met Arg Tyr Asn Ile Ser His Ile Arg Phe Pro Asn Thr
            115                 120                 125

Ala Ser Asn Pro Asp Val Asp Ser Ser Leu Cys Ile Thr Arg Asp
    130                 135                 140

Arg Ser Lys Cys Ile Leu Cys Gly Asp Cys Val Arg Val Cys Asn Glu
145                 150                 155                 160

Val Gln Asn Val Gly Ala Ile Asp Phe Ala Tyr Arg Gly Ser Lys Met
                165                 170                 175

Thr Ile Ser Thr Val Phe Asp Lys Pro Ile Phe Glu Ser Asn Cys Val
            180                 185                 190

Gly Cys Gly Gln Cys Ala Leu Ala Cys Pro Thr Gly Ala Ile Val Val
        195                 200                 205

Lys Asp Asp Thr Gln Lys Val Trp Lys Glu Ile Tyr Asp Lys Asn Thr
210                 215                 220

Arg Val Ser Val Gln Ile Ala Pro Ala Val Arg Val Ala Leu Gly Lys
225                 230                 235                 240

Glu Leu Gly Leu Asn Asp Gly Glu Asn Ala Ile Gly Lys Ile Val Ala
                245                 250                 255

Ala Leu Arg Arg Met Gly Phe Asp Asp Ile Phe Asp Thr Ser Thr Gly
            260                 265                 270

Ala Asp Leu Thr Val Leu Glu Glu Ser Ala Glu Leu Leu Arg Arg Ile
            275                 280                 285

Arg Glu Gly Lys Asn Asp Met Pro Leu Phe Thr Ser Cys Cys Pro Ala
        290                 295                 300

Trp Val Asn Tyr Cys Glu Lys Phe Tyr Pro Glu Leu Leu Pro His Val
305                 310                 315                 320

Ser Thr Cys Arg Ser Pro Met Gln Met Phe Ala Ser Ile Ile Lys Glu
                325                 330                 335

Glu Tyr Ser Thr Ser Ser Lys Arg Leu Val His Val Ala Val Met Pro
            340                 345                 350

Cys Thr Ala Lys Lys Phe Glu Ala Ala Arg Lys Glu Phe Lys Val Asn
        355                 360                 365

Gly Val Pro Asn Val Asp Tyr Val Leu Thr Thr Gln Glu Leu Val Arg
    370                 375                 380

Met Ile Lys Glu Ser Gly Ile Val Phe Ser Glu Leu Glu Pro Glu Ala
385                 390                 395                 400

Ile Asp Met Pro Phe Gly Thr Tyr Thr Gly Ala Gly Val Ile Phe Gly
                405                 410                 415
```

```
Val Ser Gly Gly Val Thr Glu Ala Val Leu Arg Arg Val Val Ser Asp
            420                 425                 430

Lys Ser Pro Thr Ser Phe Arg Ser Leu Ala Tyr Thr Gly Val Arg Gly
        435                 440                 445

Met Asn Gly Val Lys Glu Ala Ser Val Met Tyr Gly Asp Arg Lys Leu
    450                 455                 460

Lys Val Ala Val Ser Gly Leu Lys Asn Ala Gly Asp Leu Ile Glu
465                 470                 475                 480

Arg Ile Lys Ala Gly Glu His Tyr Asp Leu Val Glu Val Met Ala Cys
                485                 490                 495

Pro Gly Gly Cys Ile Asn Gly Gly Gln Pro Phe Val Gln Ser Glu
            500                 505                 510

Glu Arg Glu Lys Arg Gly Lys Gly Leu Tyr Ser Ala Asp Lys Leu Cys
        515                 520                 525

Asn Ile Lys Ser Ser Glu Glu Asn Pro Leu Met Met Thr Leu Tyr Lys
    530                 535                 540

Gly Ile Leu Lys Gly Arg Val His Glu Leu Leu His Val Asp Tyr Ala
545                 550                 555                 560

Ser Lys Lys Glu Ala Lys
                565

<210> SEQ ID NO 25
<211> LENGTH: 81
<212> TYPE: PRT
<213> ORGANISM: C. thermocellum

<400> SEQUENCE: 25

Met Leu Glu Ile Lys Ile Cys Val Gly Ser Ser Cys His Leu Lys Gly
1               5                   10                  15

Ser Tyr Asn Val Ile Asn Glu Phe Gln His Leu Ile Glu Glu Lys Ala
            20                  25                  30

Leu His Asp Lys Ile Asp Ile Lys Ala Thr Phe Cys Met Lys Gln Cys
        35                  40                  45

Gln Lys Asn Gly Val Ala Val Glu Val Asn Asn Glu Ile Phe Gly Val
    50                  55                  60

Leu Pro Glu Ala Ala Glu Glu Phe Phe Lys Asn Val Ile Leu Pro Lys
65                  70                  75                  80

Val

<210> SEQ ID NO 26
<211> LENGTH: 128
<212> TYPE: PRT
<213> ORGANISM: C. thermocellum

<400> SEQUENCE: 26

Met Ser Phe Phe Thr Met Thr Lys Thr Leu Ile Lys Ser Ile Phe His
1               5                   10                  15

Gly Pro Tyr Thr Val Arg Tyr Pro Leu Glu Lys Lys Glu Pro Phe Pro
            20                  25                  30

Ala Ser Arg Gly Arg Ile Glu Ile Asn Ile Gln Asp Cys Ile Phe Cys
        35                  40                  45

Gly Leu Cys Ala Arg Arg Cys Pro Thr Gly Ala Ile Asn Val Glu Lys
    50                  55                  60

Pro Glu Ser Arg Trp Ser Ile Asn Arg Leu Arg Cys Ile Gln Cys Gly
65                  70                  75                  80
```

Tyr Cys Ser Glu Val Cys Pro Lys Lys Cys Leu Lys Met Asn Asn Met
                85                  90                  95

Tyr Pro Ala Pro Ser Phe Glu Asn Ile Glu Asp Val Tyr Gln Asn Ala
            100                 105                 110

Arg Val Pro Asp Asn Lys Glu Asn Asn Arg Asn Ile Ala Gly Ala Cys
        115                 120                 125

<210> SEQ ID NO 27
<211> LENGTH: 359
<212> TYPE: PRT
<213> ORGANISM: C. thermocellum

<400> SEQUENCE: 27

Met Gly Lys Lys Thr Val Ile Pro Phe Gly Pro Gln His Pro Val Leu
1               5                   10                  15

Pro Glu Pro Ile His Leu Asp Leu Val Leu Glu Asp Glu Thr Val Val
            20                  25                  30

Glu Ala Ile Pro Ser Ile Gly Tyr Ile His Arg Gly Leu Glu Lys Leu
        35                  40                  45

Val Glu Lys Lys Asp Tyr Gln Gln Phe Val Tyr Val Ala Glu Arg Ile
    50                  55                  60

Cys Gly Ile Cys Ser Phe Met His Gly Met Gly Tyr Cys Met Ser Ile
65                  70                  75                  80

Glu Asn Ile Met Gly Val Gln Ile Pro Glu Arg Ala Glu Phe Leu Arg
                85                  90                  95

Thr Ile Trp Ala Glu Leu Ser Arg Ile His Ser His Met Leu Trp Leu
            100                 105                 110

Gly Leu Leu Ala Asp Ala Leu Gly Phe Glu Ser Leu Phe Met His Ser
        115                 120                 125

Trp Arg Leu Arg Glu Gln Ile Leu Asp Ile Phe Glu Glu Thr Thr Gly
    130                 135                 140

Gly Arg Val Ile Phe Ser Val Cys Asp Ile Gly Gly Val Arg Arg Asp
145                 150                 155                 160

Ile Asp Ser Glu Met Leu Lys Lys Ile Asn Ser Ile Leu Asp Gly Phe
                165                 170                 175

Glu Lys Glu Phe Ser Glu Ile Thr Lys Val Phe Leu Asn Asp Ser Ser
            180                 185                 190

Val Lys Leu Arg Thr Gln Gly Leu Gly Val Leu Ser Arg Glu Glu Ala
        195                 200                 205

Phe Glu Leu Gly Ala Val Gly Pro Met Ala Arg Ala Ser Gly Ile Asp
    210                 215                 220

Ile Asp Met Arg Lys Ser Gly Tyr Ala Ala Tyr Gly Lys Leu Lys Ile
225                 230                 235                 240

Glu Pro Val Val Glu Thr Ala Gly Asp Cys Tyr Ala Arg Thr Ser Val
                245                 250                 255

Arg Ile Arg Glu Val Phe Gln Ser Ile Asp Leu Ile Arg Gln Cys Ile
            260                 265                 270

Ser Leu Ile Pro Asp Gly Glu Ile Lys Val Lys Ile Val Gly Asn Pro
        275                 280                 285

Ser Gly Glu Tyr Phe Thr Arg Leu Glu Gln Pro Arg Gly Glu Val Leu
    290                 295                 300

Tyr Tyr Val Lys Ala Asn Gly Thr Lys Phe Leu Glu Arg Phe Arg Val
305                 310                 315                 320

Arg Thr Pro Thr Phe Ala Asn Ile Pro Ala Leu Leu His Thr Leu Lys
                325                 330                 335

```
Gly Cys Gln Leu Ala Asp Val Pro Val Leu Ile Leu Thr Ile Asp Pro
                340                 345                 350
Cys Ile Ser Cys Thr Glu Arg
        355
```

<210> SEQ ID NO 28
<211> LENGTH: 119
<212> TYPE: PRT
<213> ORGANISM: C. thermocellum

<400> SEQUENCE: 28

```
Met Ala Gln Gln Thr Ile Asn Thr Ile Ser Pro Asn Glu Leu Leu Ala
1               5                   10                  15
Tyr Ala Leu Arg Leu Lys Asn Ala Asn Tyr Arg Leu Val Ala Ile Ser
                20                  25                  30
Cys Thr Asn Ala Glu Asn Gly Val Glu Met Ser Tyr Ser Phe Asp Ser
            35                  40                  45
Gly Ser Asp Phe Thr Asn Leu Arg Ile Thr Val Ala Pro Gly Asp Glu
        50                  55                  60
Ile Glu Ser Ile Ser Ser Ile Tyr Ser Tyr Ser Phe Leu Tyr Glu Asn
65                  70                  75                  80
Glu Ile Lys Glu Leu Phe Gly Val Asn Ile Thr Gly Ile Ser Pro Asp
                85                  90                  95
Tyr Lys Asp Lys Leu Tyr Arg Ile Ser Val Lys Thr Pro Phe Asn Met
                100                 105                 110
Lys Glu Gly Asp Lys Asn Gly
        115
```

<210> SEQ ID NO 29
<211> LENGTH: 145
<212> TYPE: PRT
<213> ORGANISM: C. thermocellum

<400> SEQUENCE: 29

```
Met Asn Phe Ser Lys Lys Ser Pro Trp Ile Leu His Tyr Asp Gly Ser
1               5                   10                  15
Ser Cys Asn Gly Cys Asp Ile Glu Val Leu Ala Cys Leu Thr Pro Leu
                20                  25                  30
Tyr Asp Ile Glu Arg Phe Gly Val Ile Asn Thr Gly Asn Pro Lys His
            35                  40                  45
Ala Asp Ile Leu Leu Ile Thr Gly Ser Ile Asn Glu Gln Asn Lys Ser
        50                  55                  60
Val Val Lys Gln Leu Tyr Glu Gln Met Ala Asp Pro Lys Val Val Val
65                  70                  75                  80
Ala Val Gly Ile Cys Ala Ala Thr Gly Gly Ile Phe Ser Glu Cys Tyr
                85                  90                  95
Asn Val Ser Gly Gly Val Asp Lys Ile Ile Pro Val Asp Val Tyr Val
                100                 105                 110
Pro Gly Cys Ala Ala Arg Pro Glu Ala Ile Ile Asp Gly Val Val Lys
        115                 120                 125
Ala Leu Gly Ile Leu Glu Glu Arg Gln Lys Tyr Ala Arg Lys Lys Asp
        130                 135                 140
Lys
145
```

<210> SEQ ID NO 30

-continued

```
<211> LENGTH: 291
<212> TYPE: PRT
<213> ORGANISM: C. thermocellum

<400> SEQUENCE: 30

Met Ser Gln Ile Ile Arg Leu Val Leu Tyr Ile Ile Ala Ile Ile
1               5                   10                  15

Val Ala Pro Leu Leu Gly Gly Leu Leu Thr Gly Ile Asp Arg Val Ile
            20                  25                  30

Thr Ala Arg Met Gln Gly Arg Lys Gly Pro Ser Val Leu Gln Pro Phe
        35                  40                  45

Tyr Asp Val Leu Lys Leu Phe Gln Lys Glu Ser Ile Glu Val Asn Thr
    50                  55                  60

Met His Arg Phe Phe Val Tyr Ile Ser Leu Ile Phe Val Ile Phe Thr
65                  70                  75                  80

Thr Val Ile Met Leu Leu Gly Gly Asp Ile Leu Leu Ala Leu Phe Ala
                85                  90                  95

Leu Thr Leu Gly Ser Ile Phe Phe Val Leu Gly Gly Tyr Ala Ser Asn
            100                 105                 110

Ser Pro Tyr Ser Thr Ile Gly Ser Glu Arg Glu Leu Leu Gln Met Met
        115                 120                 125

Ala Phe Glu Pro Met Leu Leu Leu Ala Ala Ile Gly Leu Tyr Tyr Gly
    130                 135                 140

Asp Lys Ser Phe Phe Ile Lys Asp Ile Val Thr Ala Arg Ile Pro Ser
145                 150                 155                 160

Ile Val Tyr Leu Pro Gly Val Phe Leu Gly Leu Leu Tyr Val Leu Thr
                165                 170                 175

Phe Lys Leu Arg Lys Ser Pro Phe Asp Leu Ser Met Ser His His Gly
            180                 185                 190

His Gln Glu Ile Val Gln Gly Ile Thr Thr Glu Tyr Ser Gly Lys Asp
        195                 200                 205

Leu Ala Ile Ile Gln Ile Thr His Trp Tyr Glu Thr Ile Ile Ala Leu
    210                 215                 220

Ala Leu Val Tyr Leu Phe Phe Ala Phe Arg Ser Pro Phe Ser His Val
225                 230                 235                 240

Ile Ala Ile Leu Ala Cys Ile Ile Ala Phe Leu Leu Glu Ile Val Val
                245                 250                 255

Asp Asn Ala Phe Ala Arg Ala Lys Trp Glu Phe Ala Leu Lys Ser Thr
            260                 265                 270

Trp Ile Val Thr Gly Val Leu Ala Ser Val Asn Leu Ile Ile Leu Ser
        275                 280                 285

Phe Phe Arg
    290

<210> SEQ ID NO 31
<211> LENGTH: 636
<212> TYPE: PRT
<213> ORGANISM: C. thermocellum

<400> SEQUENCE: 31

Met Asn Ala Ile Leu Ile Leu Ile Leu Phe Pro Leu Leu Ala Ser Val
1               5                   10                  15

Thr Val Leu Ser Val Arg Lys Asp Ala Ile Arg Asn Ile Ile Val Arg
            20                  25                  30

Ile Phe Ala Phe Ile Thr Gly Ile Leu Thr Leu Phe Val Val Cys Arg
        35                  40                  45
```

-continued

```
Tyr Phe Lys Asp Gly Ile Ser Leu Ser Ile Glu Asn Arg Asn Ile Ile
     50                  55                  60
Asp Met Thr Ile Ser Leu Ala Glu Val Leu Ile Ala Ala Tyr Ile Ile
 65                  70                  75                  80
Phe Thr Gly Ile Lys Asn Lys Lys Phe Ile Val Ser Ile Phe Ala Ala
                     85                  90                  95
Val Gln Thr Ala Leu Ile Leu Trp Phe Glu Phe Thr Gln Lys His Gly
                100                 105                 110
Ile Asn Val His Ser Asp Ile Val Phe Asp Arg Leu Ser Ala Val Met
                115                 120                 125
Val Leu Ile Val Gly Cys Ile Gly Ser Leu Ile Leu Ile Tyr Thr Val
130                 135                 140
Gly Tyr Met Lys Trp Tyr His Ile His His Glu Gly Tyr Lys Glu Arg
145                 150                 155                 160
Lys Ser Phe Phe Phe Ser Val Ile Phe Leu Phe Leu Phe Ala Met Phe
                165                 170                 175
Gly Leu Ile Phe Ser Asn Asn Leu Ile Trp Met Tyr Phe Cys Trp Glu
                180                 185                 190
Leu Thr Thr Leu Cys Ser Tyr Leu Leu Ile Gly Tyr Thr Arg Thr Pro
                195                 200                 205
Glu Ala Val Asn Asn Ser Phe His Ala Leu Ala Ile Asn Leu Gly Gly
    210                 215                 220
Gly Leu Ala Phe Ala Ser Ala Met Val Tyr Ile Gly Thr Asn Phe Lys
225                 230                 235                 240
Thr Leu Glu Leu Ser Ala Leu Thr Ala Met Lys Leu Glu Leu Ala Val
                245                 250                 255
Leu Ile Pro Val Phe Leu Leu Cys Ile Ala Ala Leu Thr Lys Ser Ala
                260                 265                 270
Gln Met Pro Phe Ser Ser Trp Leu Leu Gly Ala Met Val Ala Pro Thr
                275                 280                 285
Pro Ser Ser Ala Leu Leu His Ser Ala Thr Met Val Lys Ala Gly Val
    290                 295                 300
Tyr Leu Leu Ile Arg Leu Ala Pro Leu Leu Ala Gly Thr Thr Ile Gly
305                 310                 315                 320
Lys Val Ile Ala Leu Leu Gly Ala Val Thr Phe Leu Ala Ser Ser Ile
                325                 330                 335
Ile Ala Ile Ser Lys Ser Asp Ala Lys Lys Ile Leu Ala Tyr Ser Thr
                340                 345                 350
Ile Ser Asn Leu Gly Leu Ile Val Thr Cys Ala Ala Ile Gly Thr Gln
                355                 360                 365
Glu Ser Leu Trp Ala Ala Ile Leu Leu Ile Phe His Ser Ile Ser
    370                 375                 380
Lys Ser Leu Leu Phe Leu Thr Gly Gly Ser Val Glu His Gln Ile Gly
385                 390                 395                 400
Ser Arg Asn Val Glu Asp Met Asp Ile Leu Gln Val Ser Arg Arg
                405                 410                 415
Leu Ser Val Tyr Met Ile Val Gly Ile Ala Gly Met Phe Leu Ala Pro
                420                 425                 430
Phe Gly Met Leu Ile Ser Lys Trp Val Ala Met Lys Ala Phe Ile Asp
                435                 440                 445
Ser Lys Asn Ile Leu Thr Val Ile Ile Leu Gly Tyr Gly Ser Ala Thr
    450                 455                 460
```

```
Thr Leu Phe Tyr Trp Thr Lys Trp Met Gly Lys Leu Val Ala Asn Ala
465                 470                 475                 480

Asn Arg Lys Asp His Ile Lys His Thr Phe His Ile Asp Glu Glu Ile
                485                 490                 495

Pro Ile Phe Ile His Ala Val Leu Val Val Leu Ser Cys Phe Thr Phe
            500                 505                 510

Pro Leu Val Ser Arg Tyr Val Leu Val Pro Tyr Leu Ser Gly Leu Phe
            515                 520                 525

Gly Pro Asp Val Pro Ile Pro Ile Gly Thr Ser Asp Val Asn Ile Met
        530                 535                 540

Leu Ile Met Leu Ser Met Leu Leu Ile Leu Pro Ile Ser Phe Ile Pro
545                 550                 555                 560

Ile Tyr Lys Ser Asp Arg Arg Ile Val Pro Ile Tyr Met Ala Gly
                565                 570                 575

Glu Asn Thr Gly Asp Asn Glu Ser Phe Tyr Gly Ala Phe Asp Glu Lys
            580                 585                 590

Arg Lys Val Glu Leu His Asn Trp Tyr Met Lys Asn Phe Phe Ser Val
        595                 600                 605

Lys Lys Leu Thr Phe Trp Ser Asn Leu Leu Cys Ala Val Val Ile Leu
        610                 615                 620

Val Gly Val Val Leu Leu Ile Gly Gly Ile Thr Lys
625                 630                 635

<210> SEQ ID NO 32
<211> LENGTH: 582
<212> TYPE: PRT
<213> ORGANISM: C. thermocellum

<400> SEQUENCE: 32

Met Gln Met Val Asn Val Thr Ile Asp Asn Cys Lys Ile Gln Val Pro
1               5                   10                  15

Ala Asn Tyr Thr Val Leu Glu Ala Ala Lys Gln Ala Asn Ile Asp Ile
            20                  25                  30

Pro Thr Leu Cys Phe Leu Lys Asp Ile Asn Glu Val Gly Ala Cys Arg
        35                  40                  45

Met Cys Val Val Glu Val Lys Gly Ala Arg Ser Leu Gln Ala Ala Cys
    50                  55                  60

Val Tyr Pro Val Ser Glu Gly Leu Glu Val Tyr Thr Gln Thr Pro Ala
65                  70                  75                  80

Val Arg Glu Ala Arg Lys Val Thr Leu Glu Leu Ile Leu Ser Asn His
                85                  90                  95

Glu Lys Lys Cys Leu Thr Cys Val Arg Ser Glu Asn Cys Glu Leu Gln
            100                 105                 110

Arg Leu Ala Lys Asp Leu Asn Val Lys Asp Ile Arg Phe Glu Gly Glu
        115                 120                 125

Met Ser Asn Leu Pro Ile Asp Asp Leu Ser Pro Ser Val Val Arg Asp
130                 135                 140

Pro Asn Lys Cys Val Leu Cys Arg Arg Cys Val Ser Met Cys Lys Asn
145                 150                 155                 160

Val Gln Thr Val Gly Ala Ile Asp Val Thr Glu Arg Gly Phe Arg Thr
                165                 170                 175

Thr Val Ser Thr Ala Phe Asn Lys Pro Leu Ser Glu Val Pro Cys Val
            180                 185                 190

Asn Cys Gly Gln Cys Ile Asn Val Cys Pro Val Gly Ala Leu Arg Glu
        195                 200                 205
```

```
Lys Asp Asp Ile Asp Lys Val Trp Glu Ala Leu Ala Asn Pro Glu Leu
        210                 215                 220

His Val Val Gln Thr Ala Pro Ala Val Arg Val Ala Leu Gly Glu
225                 230                 235                 240

Glu Phe Gly Met Pro Ile Gly Ser Arg Val Thr Gly Lys Met Val Ala
                    245                 250                 255

Ala Leu Ser Arg Leu Gly Phe Lys Lys Val Phe Asp Thr Asp Thr Ala
                260                 265                 270

Ala Asp Leu Thr Ile Met Glu Glu Gly Thr Glu Leu Ile Asn Arg Ile
                275                 280                 285

Lys Asn Gly Gly Lys Leu Pro Leu Ile Thr Ser Cys Ser Pro Gly Trp
290                 295                 300

Ile Lys Phe Cys Glu His Asn Tyr Pro Glu Phe Leu Asp Asn Leu Ser
305                 310                 315                 320

Ser Cys Lys Ser Pro His Glu Met Phe Gly Ala Val Leu Lys Ser Tyr
                    325                 330                 335

Tyr Ala Gln Lys Asn Gly Ile Asp Pro Ser Lys Val Phe Val Val Ser
                340                 345                 350

Ile Met Pro Cys Thr Ala Lys Lys Phe Glu Ala Gln Arg Pro Glu Leu
                355                 360                 365

Ser Ser Thr Gly Tyr Pro Asp Val Asp Val Val Leu Thr Thr Arg Glu
370                 375                 380

Leu Ala Arg Met Ile Lys Glu Thr Gly Ile Asp Phe Asn Ser Leu Pro
385                 390                 395                 400

Asp Lys Gln Phe Asp Asp Pro Met Gly Glu Ala Ser Gly Ala Gly Val
                405                 410                 415

Ile Phe Gly Ala Thr Gly Gly Val Met Glu Ala Ala Ile Arg Thr Val
                420                 425                 430

Gly Glu Leu Leu Ser Gly Lys Pro Ala Asp Lys Ile Glu Tyr Thr Glu
                435                 440                 445

Val Arg Gly Leu Asp Gly Ile Lys Glu Ala Ser Ile Glu Leu Asp Gly
450                 455                 460

Phe Thr Leu Lys Ala Ala Val Ala His Gly Leu Gly Asn Ala Arg Lys
465                 470                 475                 480

Leu Leu Asp Lys Ile Lys Ala Gly Glu Ala Asp Tyr His Phe Ile Glu
                485                 490                 495

Ile Met Ala Cys Pro Gly Gly Cys Ile Asn Gly Gly Gln Pro Ile
                500                 505                 510

Gln Pro Ser Ser Val Arg Asn Trp Lys Asp Ile Arg Cys Glu Arg Ala
                515                 520                 525

Lys Ala Ile Tyr Glu Glu Asp Glu Ser Leu Pro Ile Arg Lys Ser His
530                 535                 540

Glu Asn Pro Lys Ile Lys Met Leu Tyr Glu Glu Phe Phe Gly Glu Pro
545                 550                 555                 560

Gly Ser His Lys Ala His Glu Leu Leu His Thr His Tyr Glu Lys Arg
                565                 570                 575

Glu Asn Tyr Pro Val Lys
            580

<210> SEQ ID NO 33
<211> LENGTH: 566
<212> TYPE: PRT
<213> ORGANISM: C. thermocellum
```

<400> SEQUENCE: 33

```
Met Asp Asn Arg Glu Tyr Met Leu Ile Asp Gly Ile Pro Val Glu Ile
1               5                   10                  15

Asn Gly Glu Lys Asn Leu Leu Glu Leu Ile Arg Lys Ala Gly Ile Lys
            20                  25                  30

Leu Pro Thr Phe Cys Tyr His Ser Glu Leu Ser Val Tyr Gly Ala Cys
                35                  40                  45

Arg Met Cys Met Val Glu Asn Glu Trp Gly Gly Leu Asp Ala Ala Cys
        50                  55                  60

Ser Thr Pro Pro Arg Ala Gly Met Ser Ile Lys Thr Asn Thr Glu Arg
65                  70                  75                  80

Leu Gln Lys Tyr Arg Lys Met Ile Leu Glu Leu Leu Ala Asn His
                85                  90                  95

Cys Arg Asp Cys Thr Thr Cys Asn Asn Asn Gly Lys Cys Lys Leu Gln
                100                 105                 110

Asp Leu Ala Met Arg Tyr Asn Ile Ser His Ile Arg Phe Pro Asn Thr
            115                 120                 125

Ala Ser Asn Pro Asp Val Asp Ser Ser Leu Cys Ile Thr Arg Asp
130                 135                 140

Arg Ser Lys Cys Ile Leu Cys Gly Asp Cys Val Arg Val Cys Asn Glu
145                 150                 155                 160

Val Gln Asn Val Gly Ala Ile Asp Phe Ala Tyr Arg Gly Ser Lys Met
                165                 170                 175

Thr Ile Ser Thr Val Phe Asp Lys Pro Ile Phe Glu Ser Asn Cys Val
            180                 185                 190

Gly Cys Gly Gln Cys Ala Leu Ala Cys Pro Thr Gly Ala Ile Val Val
            195                 200                 205

Lys Asp Asp Thr Gln Lys Val Trp Lys Glu Ile Tyr Asp Lys Asn Thr
210                 215                 220

Arg Val Ser Val Gln Ile Ala Pro Ala Val Arg Val Ala Leu Gly Lys
225                 230                 235                 240

Glu Leu Gly Leu Asn Asp Gly Glu Asn Ala Ile Gly Lys Ile Val Ala
                245                 250                 255

Ala Leu Arg Arg Met Gly Phe Asp Asp Ile Phe Asp Thr Ser Thr Gly
            260                 265                 270

Ala Asp Leu Thr Val Leu Glu Glu Ser Ala Glu Leu Leu Arg Arg Ile
            275                 280                 285

Arg Glu Gly Lys Asn Asp Met Pro Leu Phe Thr Ser Cys Cys Pro Ala
290                 295                 300

Trp Val Asn Tyr Cys Glu Lys Phe Tyr Pro Glu Leu Leu Pro His Val
305                 310                 315                 320

Ser Thr Cys Arg Ser Pro Met Gln Met Phe Ala Ser Ile Ile Lys Glu
            325                 330                 335

Glu Tyr Ser Thr Ser Ser Lys Arg Leu Val His Val Ala Val Met Pro
            340                 345                 350

Cys Thr Ala Lys Lys Phe Glu Ala Ala Arg Lys Glu Phe Lys Val Asn
            355                 360                 365

Gly Val Pro Asn Val Asp Tyr Val Leu Thr Thr Gln Glu Leu Val Arg
            370                 375                 380

Met Ile Lys Glu Ser Gly Ile Val Phe Ser Glu Leu Glu Pro Glu Ala
385                 390                 395                 400

Ile Asp Met Pro Phe Gly Thr Tyr Thr Gly Ala Gly Val Ile Phe Gly
            405                 410                 415
```

```
Val Ser Gly Gly Val Thr Glu Ala Val Leu Arg Arg Val Val Ser Asp
                420                 425                 430

Lys Ser Pro Thr Ser Phe Arg Ser Leu Ala Tyr Thr Gly Val Arg Gly
            435                 440                 445

Met Asn Gly Val Lys Glu Ala Ser Val Met Tyr Gly Asp Arg Lys Leu
        450                 455                 460

Lys Val Ala Val Ser Gly Leu Lys Asn Ala Gly Asp Leu Ile Glu
465                 470                 475                 480

Arg Ile Lys Ala Gly Glu His Tyr Asp Leu Val Glu Val Met Ala Cys
                485                 490                 495

Pro Gly Gly Cys Ile Asn Gly Gly Gln Pro Phe Val Gln Ser Glu
            500                 505                 510

Glu Arg Glu Lys Arg Gly Lys Gly Leu Tyr Ser Ala Asp Lys Leu Cys
        515                 520                 525

Asn Ile Lys Ser Ser Glu Glu Asn Pro Leu Met Met Thr Leu Tyr Lys
        530                 535                 540

Gly Ile Leu Lys Gly Arg Val His Glu Leu Leu His Val Asp Tyr Ala
545                 550                 555                 560

Ser Lys Lys Glu Ala Lys
                565
```

<210> SEQ ID NO 34
<211> LENGTH: 644
<212> TYPE: PRT
<213> ORGANISM: C. thermocellum

<400> SEQUENCE: 34

```
Met Asp Ser Phe Leu Met Lys Gly Tyr Ile Lys Glu Ala Asn Ile Asp
1               5                   10                  15

Tyr Ser Cys Ser Arg Gly Ser Met Glu Asp Leu Pro Lys Trp Glu Phe
                20                  25                  30

Arg Glu Ile Pro Lys Val Pro Arg Ala Val Met Pro Ser Leu Ser Leu
            35                  40                  45

Glu Glu Arg Lys Asn Asn Phe Asn Glu Val Glu Leu Gly Leu Ser Glu
        50                  55                  60

Glu Val Ala Arg Lys Glu Ala Arg Arg Cys Leu Lys Cys Gly Cys Ser
65                  70                  75                  80

Ala Arg Phe Thr Cys Asp Leu Arg Lys Glu Ala Ser Asn His Gly Ile
                85                  90                  95

Val Tyr Glu Glu Pro Ile His Asp Arg Pro Tyr Ile Pro Lys Val Asp
            100                 105                 110

Asp His Pro Phe Ile Val Arg Asp His Asn Lys Cys Ile Ser Cys Gly
        115                 120                 125

Arg Cys Ile Ala Ala Cys Ala Glu Ile Glu Gly Pro Gly Val Leu Thr
130                 135                 140

Phe Tyr Met Lys Asn Gly Arg Gln Leu Val Gly Thr Lys Ser Gly Leu
145                 150                 155                 160

Pro Leu Arg Asp Thr Asp Cys Val Ser Cys Gly Gln Cys Val Thr Ala
                165                 170                 175

Cys Pro Cys Ala Ala Leu Asp Tyr Arg Arg Glu Arg Gly Lys Val Val
            180                 185                 190

Arg Ala Ile Asn Asp Pro Lys Lys Thr Val Val Gly Phe Val Ala Pro
        195                 200                 205

Ala Val Arg Ser Leu Ile Ser Asn Thr Phe Gly Val Ser Tyr Glu Glu
```

```
            210                 215                 220
Ala Ser Pro Phe Met Ala Gly Leu Leu Lys Lys Leu Gly Phe Asp Lys
225                 230                 235                 240

Val Phe Asp Phe Thr Phe Ala Ala Asp Leu Thr Ile Val Glu Glu Thr
                245                 250                 255

Thr Glu Phe Leu Ser Arg Ile Gln Asn Lys Gly Val Met Pro Gln Phe
                260                 265                 270

Thr Ser Cys Cys Pro Gly Trp Ile Asn Phe Val Glu Lys Arg Tyr Pro
                275                 280                 285

Glu Ile Ile Pro His Leu Ser Thr Cys Lys Ser Pro Gln Met Met Met
290                 295                 300

Gly Ala Thr Val Lys Asn His Tyr Ala Lys Leu Met Gly Ile Asn Lys
305                 310                 315                 320

Glu Asp Leu Phe Val Val Ser Ile Val Pro Cys Leu Ala Lys Lys Tyr
                325                 330                 335

Glu Ala Ala Arg Pro Glu Phe Ile His Asp Gly Ile Arg Asp Val Asp
                340                 345                 350

Ala Val Leu Thr Thr Thr Glu Met Leu Glu Met Met Glu Leu Ala Asp
                355                 360                 365

Ile Lys Pro Ser Glu Val Val Pro Gln Glu Phe Asp Glu Pro Tyr Lys
                370                 375                 380

Gln Val Ser Gly Ala Gly Ile Leu Phe Gly Ala Ser Gly Gly Val Ala
385                 390                 395                 400

Glu Ala Ala Leu Arg Met Ala Val Glu Lys Leu Thr Gly Lys Val Leu
                405                 410                 415

Thr Asp His Leu Glu Phe Glu Glu Ile Arg Gly Phe Glu Gly Val Lys
                420                 425                 430

Glu Ser Thr Ile Asp Val Asn Gly Thr Lys Val Arg Val Ala Val Val
                435                 440                 445

Ser Gly Leu Lys Asn Ala Glu Pro Ile Ile Glu Lys Ile Leu Asn Gly
450                 455                 460

Val Asp Val Gly Tyr Asp Leu Ile Glu Val Met Ala Cys Pro Gly Gly
465                 470                 475                 480

Cys Ile Cys Gly Ala Gly His Pro Val Pro Glu Lys Ile Asp Ser Leu
                485                 490                 495

Glu Lys Arg Gln Gln Val Leu Val Asn Ile Asp Lys Val Ser Lys Tyr
                500                 505                 510

Arg Lys Ser Gln Glu Asn Pro Asp Ile Leu Arg Leu Tyr Asn Glu Phe
                515                 520                 525

Tyr Gly Glu Pro Asn Ser Pro Leu Ala His Glu Leu Leu His Thr His
                530                 535                 540

Tyr Thr Pro Lys His Gly Asp Ser Thr Cys Ser Pro Glu Arg Lys Lys
545                 550                 555                 560

Gly Thr Ala Ala Phe Asp Val Gln Glu Phe Thr Ile Cys Met Cys Glu
                565                 570                 575

Ser Cys Met Glu Lys Gly Ala Glu Asn Leu Tyr Asn Asp Leu Ser Ser
                580                 585                 590

Lys Ile Arg Leu Phe Lys Met Asp Pro Phe Val Gln Ile Lys Arg Ile
                595                 600                 605

Arg Leu Lys Glu Thr His Pro Gly Lys Gly Val Tyr Ile Ala Leu Asn
                610                 615                 620

Gly Lys Gln Ile Glu Glu Pro Met Leu Ser Gly Asn Ile Pro Asp Glu
625                 630                 635                 640
```

Ser Glu Ser Glu

<210> SEQ ID NO 35
<211> LENGTH: 493
<212> TYPE: PRT
<213> ORGANISM: C. thermocellum

<400> SEQUENCE: 35

```
Met Lys Thr Leu Glu Asn His Asn Arg Ile Lys Val Thr Val Asn Gly
1               5                   10                  15

Arg Glu Ile Glu Val Tyr Asp Asn Leu Thr Ile Leu Gln Ala Leu Leu
            20                  25                  30

Gln Glu Asp Ile His Ile Pro His Leu Cys Tyr Asp Ile Arg Leu Glu
        35                  40                  45

Arg Ser Asn Gly Asn Cys Gly Leu Cys Val Val Thr Leu Ile Ser Pro
    50                  55                  60

Asp Gly Glu Arg Asp Val Lys Ala Cys Gln Thr Pro Ile Lys Glu Gly
65                  70                  75                  80

Met Val Ile Cys Thr Asn Thr Pro Lys Leu Glu Asn Tyr Arg Lys Ile
                85                  90                  95

Arg Leu Glu Gln Leu Leu Ser Asp His Asn Ala Asp Cys Val Ala Pro
            100                 105                 110

Cys Val Met Thr Cys Pro Ala Asn Ile Asp Ile Gln Ser Tyr Leu Arg
        115                 120                 125

His Val Gly Asn Gly Asp Phe Glu Ala Ala Ile Arg Val Ile Lys Glu
    130                 135                 140

Arg Asn Pro Phe Pro Ile Val Cys Gly Arg Val Cys Pro His Thr Cys
145                 150                 155                 160

Glu Ser Gln Cys Arg Arg Asn Leu Val Asp Ala Pro Val Ala Ile Asn
                165                 170                 175

Tyr Val Lys Arg Phe Ala Ala Asp Trp Asp Met Ala Arg Pro Glu Pro
            180                 185                 190

Trp Thr Pro Glu Lys Lys Pro Pro Thr Gly Lys Lys Ile Ala Ile Val
        195                 200                 205

Gly Ala Gly Pro Ser Gly Leu Ser Ala Ala Tyr Tyr Ser Ala Ile Lys
    210                 215                 220

Gly His Asp Val Thr Val Phe Glu Arg Gln Pro His Pro Gly Gly Met
225                 230                 235                 240

Met Arg Tyr Gly Ile Pro Glu Tyr Arg Leu Pro Lys Ala Ile Leu Asp
                245                 250                 255

Lys Glu Ile Glu Met Ile Lys Lys Leu Gly Val Lys Ile Met Thr Glu
            260                 265                 270

Lys Ala Leu Gly Ile His Ile Arg Leu Glu Asp Leu Ser Lys Asp Phe
        275                 280                 285

Asp Ala Val Tyr Leu Ala Ile Gly Ser Trp Gln Ala Thr Pro Met His
    290                 295                 300

Ile Glu Gly Glu Lys Leu Asp Gly Val Trp Ala Gly Ile Asn Tyr Leu
305                 310                 315                 320

Glu Gln Val Ala Lys Asn Val Asp Ile Pro Leu Gly Asp Asn Val Val
                325                 330                 335

Val Ile Gly Gly Gly Asn Thr Ala Ile Asp Cys Ala Arg Thr Ala Leu
            340                 345                 350

Arg Lys Gly Ala Lys Ser Val Lys Leu Val Tyr Arg Cys Thr Arg Glu
        355                 360                 365
```

```
Glu Met Pro Ala Ala Pro Tyr Glu Val Glu Ala Ile His Glu Gly
    370                 375                 380

Val Glu Met Ile Phe Leu Met Ala Pro Thr Lys Ile Ile Val Lys Asp
385                 390                 395                 400

Gly Lys Lys Leu Val Cys Ile Arg Met Gln Leu Gly Glu Pro Asp
            405                 410                 415

Arg Ser Gly Arg Arg Pro Val Pro Ile Glu Gly Ser Glu Val Glu
        420                 425                 430

Ile Asp Ala Asp Thr Ile Ile Gly Ala Ile Gly Gln Ser Thr Asn Thr
            435                 440                 445

Gln Phe Leu Tyr Asn Asp Leu Pro Val Lys Leu Asn Lys Trp Gly Asp
    450                 455                 460

Ile Glu Val Asn Gly Lys Thr Leu Gln Thr Ser Glu Tyr Asn Ile Phe
465                 470                 475                 480

Ala Gly Gly Asp Cys Val Thr Gly Pro Ala Thr Val Ile
                485                 490

<210> SEQ ID NO 36
<211> LENGTH: 309
<212> TYPE: PRT
<213> ORGANISM: C. thermocellum

<400> SEQUENCE: 36

Met Pro Leu Val Thr Ser Thr Glu Met Phe Lys Lys Ala Tyr Glu Gly
1               5                   10                  15

Lys Tyr Ala Ile Gly Ala Phe Asn Val Asn Asn Met Glu Ile Ile Gln
            20                  25                  30

Gly Ile Thr Glu Ala Ala Lys Glu Val Asn Ala Pro Leu Ile Leu Gln
        35                  40                  45

Val Ser Ala Gly Ala Arg Lys Tyr Ala Asn His Thr Tyr Leu Val Lys
50                  55                  60

Leu Val Glu Ala Ala Val Glu Glu Thr Gly Leu Pro Ile Cys Leu His
65                  70                  75                  80

Leu Asp His Gly Asp Ser Phe Glu Leu Cys Lys Ser Cys Ile Asp Gly
                85                  90                  95

Gly Phe Thr Ser Val Met Ile Asp Gly Ser His Leu Pro Phe Glu Glu
            100                 105                 110

Asn Ile Lys Leu Thr Lys Gln Val Val Asp Tyr Ala His Ser Lys Gly
        115                 120                 125

Val Val Val Glu Gly Glu Leu Gly Arg Leu Ala Gly Ile Glu Asp Asp
    130                 135                 140

Val Asn Val Ser Glu Ala Asp Ala Ala Phe Thr Asp Pro Asp Gln Ala
145                 150                 155                 160

Glu Glu Phe Val Lys Arg Thr Gly Val Asp Ser Leu Ala Ile Ala Ile
                165                 170                 175

Gly Thr Ser His Gly Ala Tyr Lys Phe Lys Gly Glu Ala Lys Leu Arg
            180                 185                 190

Phe Asp Ile Leu Glu Glu Ile Glu Lys Arg Leu Pro Gly Phe Pro Ile
        195                 200                 205

Val Leu His Gly Ala Ser Ser Val Ile Pro Glu Tyr Val Asp Met Ile
    210                 215                 220

Asn Lys Tyr Gly Gly Asp Met Pro Gly Ala Lys Gly Val Pro Glu Asp
225                 230                 235                 240

Met Leu Arg Lys Ala Ala Ser Met Ala Val Cys Lys Ile Asn Ile Asp
```

245                 250                 255
Ser Asp Leu Arg Leu Ala Met Thr Ala Thr Ile Arg Lys Tyr Phe Ala
                260                 265                 270

Glu Asn Pro Ser His Phe Asp Pro Arg Gln Tyr Leu Gly Pro Ala Arg
            275                 280                 285

Asn Ala Ile Lys Glu Leu Val Lys His Lys Ile Val Asn Val Leu Gly
        290                 295                 300

Cys Asp Gly Lys Ala
305

<210> SEQ ID NO 37
<211> LENGTH: 327
<212> TYPE: PRT
<213> ORGANISM: C. thermocellum

<400> SEQUENCE: 37

Met Asp Ile Gln Leu Lys Lys Ser Gly Ile Gly Val Lys Glu Lys Lys
1               5                   10                  15

Ser Lys Asn His Leu Leu Tyr Ser Ile Lys Gln Asn Leu Phe Ala Tyr
            20                  25                  30

Ala Met Leu Ile Pro Thr Phe Val Cys Met Met Cys Ile His Phe Ile
        35                  40                  45

Pro Met Leu Gln Gly Ile Tyr Leu Ser Leu Leu Asp Leu Asn Gln Leu
    50                  55                  60

Thr Met Thr Lys Phe Leu Asn Ala Pro Phe Ile Gly Leu Lys Asn Tyr
65                  70                  75                  80

Tyr Glu Ile Leu Phe Asp Glu Lys Ser Leu Ile Arg Arg Gly Phe Trp
                85                  90                  95

Phe Ala Leu Arg Asn Thr Ala Ile Tyr Thr Val Val Thr Phe Ala
            100                 105                 110

Thr Phe Ala Leu Gly Ile Ile Leu Ala Met Leu Val Asn Arg Glu Phe
        115                 120                 125

Lys Gly Arg Gly Ile Val Arg Thr Ala Leu Leu Met Pro Trp Val Val
    130                 135                 140

Pro Ser Tyr Val Val Gly Met Thr Trp Gly Phe Leu Trp Arg Gln Asp
145                 150                 155                 160

Ser Gly Leu Ile Asn Ile Ile Leu Cys Asp Ile Leu His Ile Leu Pro
                165                 170                 175

Glu Lys Pro Tyr Trp Leu Val Gly Ser Asn Gln Ile Trp Ala Ile Ile
            180                 185                 190

Ile Pro Thr Ile Trp Arg Gly Leu Pro Leu Ser Met Ile Leu Met Leu
        195                 200                 205

Ala Gly Leu Gln Ser Ile Ser Pro Asp Tyr Tyr Glu Ala Ala Asp Ile
    210                 215                 220

Asp Gly Ala Asn Gly Trp Gln Lys Phe Trp His Ile Thr Leu Pro Leu
225                 230                 235                 240

Leu Lys Pro Ile Leu Ala Ile Asn Val Met Phe Ser Leu Ile Ser Asn
                245                 250                 255

Ile Tyr Ser Phe Asn Ile Val Ser Met Met Phe Gly Asn Gly Ala Gly
            260                 265                 270

Ile Pro Gly Glu Trp Gly Asp Leu Leu Met Thr Tyr Ile Gln Arg Asn
        275                 280                 285

Thr Phe Gln Met Trp Arg Phe Gly Pro Ala Ala Ala Leu Met Ile
    290                 295                 300

```
Val Met Phe Phe Val Leu Gly Ile Val Ala Leu Trp Tyr Thr Leu Phe
305                 310                 315                 320

Lys Asp Asp Leu Val Val Lys
                325

<210> SEQ ID NO 38
<211> LENGTH: 404
<212> TYPE: PRT
<213> ORGANISM: C. thermocellum

<400> SEQUENCE: 38

Val Asp Lys Phe Thr Lys Leu Asp Leu Asn Ser Ile Thr Ser Asn Asn
1               5                   10                  15

Arg Met Asn Ile Phe Asn Cys Ile Leu Glu Ala Lys Glu Ile Asn Arg
                20                  25                  30

Ala Val Ile Ala Lys Lys Val Gly Leu Ser Ile Pro Ala Val Met Ser
            35                  40                  45

Ile Thr Asp Asp Leu Ile Gln Lys Gly Ile Ile Tyr Val Ile Gly Lys
50                  55                  60

Gly Lys Ser Ser Gly Gly Lys Arg Pro Glu Leu Leu Ala Val Val Pro
65                  70                  75                  80

Asp Arg Phe Phe Phe Val Gly Val Asp Val Gly Arg Thr Ser Val Arg
                85                  90                  95

Val Val Val Met Asn Asn Cys Arg Asp Val Val Tyr Lys Val Ser Lys
                100                 105                 110

Pro Thr Glu Ser Val Glu Pro Asp Glu Leu Ile Asn Gln Ile Thr Glu
            115                 120                 125

Met Thr Met Glu Ser Ile Asn Glu Ser Lys Phe Pro Leu Asp Arg Val
130                 135                 140

Val Gly Ile Gly Val Ala Met Pro Gly Leu Ile Glu Arg Gly Thr Gly
145                 150                 155                 160

Arg Val Ile Phe Ser Pro Asn Phe Gly Trp Asn Asn Ile Ala Leu Gln
                165                 170                 175

Asp Glu Leu Lys Lys His Leu Pro Phe Asn Val Leu Val Glu Asn Ala
            180                 185                 190

Asn Arg Ala Leu Val Ile Gly Glu Ile Lys Asn Thr Gln Pro Asn Pro
        195                 200                 205

Thr Ser Cys Ile Val Gly Val Asn Leu Gly Tyr Gly Ile Gly Ser Ala
210                 215                 220

Ile Val Leu Pro Asn Gly Leu Tyr Tyr Gly Val Ser Gly Thr Ser Gly
225                 230                 235                 240

Glu Ile Gly His Ile Ile Val Glu Asn His Gly Ser Tyr Cys Ser Cys
                245                 250                 255

Gly Asn Tyr Gly Cys Ile Glu Ser Ile Ala Ser Gly Glu Ala Ile Ala
            260                 265                 270

Arg Glu Ala Arg Ile Ala Ile Ala Asn Lys Ile Gln Ser Ser Val Phe
        275                 280                 285

Glu Lys Cys Glu Gly Asp Leu Lys Lys Ile Asp Ala Lys Met Val Phe
290                 295                 300

Asp Ala Ala Lys Glu Gly Asp His Leu Ala Gln Ser Ile Val Glu Lys
305                 310                 315                 320

Ala Ala Asp Tyr Ile Gly Lys Gly Leu Ala Ile Thr Ile Asn Met Leu
                325                 330                 335

Asp Pro Glu Gln Ile Ile Leu Cys Gly Gly Leu Thr Leu Ser Gly Asp
            340                 345                 350
```

```
Phe Phe Ile Asp Met Ile Lys Lys Ala Val Ser Lys Tyr Gln Met Arg
            355                 360                 365

Tyr Ala Gly Gly Asn Val Lys Ile Val Val Gly Lys Ser Gly Leu Tyr
    370                 375                 380

Ala Thr Ala Ile Gly Gly Ala Trp Ile Val Ala Asn Asn Ile Asp Phe
385                 390                 395                 400

Leu Ser Ser Asn

<210> SEQ ID NO 39
<211> LENGTH: 317
<212> TYPE: PRT
<213> ORGANISM: C. thermocellum

<400> SEQUENCE: 39

Met Tyr Tyr Ile Gly Ile Asp Leu Gly Gly Thr Asn Ile Ala Val Gly
1               5                   10                  15

Leu Val Asn Glu Glu Gly Lys Ile Leu His Lys Asp Ser Val Pro Thr
            20                  25                  30

Leu Arg Glu Arg Pro Tyr Gln Glu Ile Ile Lys Asp Met Ala Met Leu
        35                  40                  45

Thr Leu Lys Val Ile Lys Asp Ala Asp Val Ser Ile Asp Gln Val Lys
50                  55                  60

Ser Ile Gly Val Gly Ser Pro Gly Thr Pro Asn Cys Lys Asp Gly Ile
65                  70                  75                  80

Leu Ile Tyr Asn Asn Asn Leu Asn Phe Arg Asn Val Pro Ile Arg Ser
            85                  90                  95

Glu Ile Gln Lys Tyr Ile Asp Leu Pro Val Tyr Leu Asp Asn Asp Ala
            100                 105                 110

Asn Cys Ala Ala Leu Ala Glu Ser Val Ala Gly Ala Ala Lys Gly Ala
            115                 120                 125

Asn Thr Ser Val Thr Ile Thr Leu Gly Thr Gly Ile Gly Gly Gly Val
            130                 135                 140

Val Ile Asp Gly Lys Ile Tyr Ser Gly Phe Asn Tyr Ala Gly Gly Glu
145                 150                 155                 160

Leu Gly His Thr Val Leu Met Met Asp Gly Glu Pro Cys Thr Cys Gly
                165                 170                 175

Arg Lys Gly Cys Trp Glu Ala Tyr Ala Ser Ala Thr Ala Leu Ile Arg
            180                 185                 190

Gln Ala Arg Lys Ala Ala Glu Ala Asn Pro Asp Ser Leu Ile Asn Lys
        195                 200                 205

Leu Val Gly Gly Asp Leu Ser Lys Ile Asp Ala Lys Ile Pro Phe Asp
    210                 215                 220

Ala Ala Lys Gln Gly Asp Lys Thr Gly Glu Met Val Val Gln Gln Tyr
225                 230                 235                 240

Ile Arg Tyr Ile Ala Glu Gly Leu Ile Asn Met Ile Asn Ile Phe Met
                245                 250                 255

Pro Glu Val Leu Val Ile Gly Gly Gly Val Cys Lys Glu Gly Glu Tyr
            260                 265                 270

Leu Leu Lys Pro Leu Arg Glu Leu Ile Lys Gln Gly Val Tyr Ser Lys
        275                 280                 285

Glu Asp Ile Pro Gln Thr Glu Leu Arg Thr Ala Gln Met Gly Asn Asp
    290                 295                 300

Ala Gly Ile Ile Gly Ala Ala Met Leu Gly Lys Glu Cys
305                 310                 315
```

<210> SEQ ID NO 40
<211> LENGTH: 448
<212> TYPE: PRT
<213> ORGANISM: C. thermocellum

<400> SEQUENCE: 40

Met Glu Arg Ile Lys Phe Asp Tyr Ser Lys Ala Leu Pro Phe Val Ser
1               5                   10                  15

Glu Arg Glu Val Ala Tyr Phe Glu Asn Phe Val Arg Ser Ala His Asp
            20                  25                  30

Met Leu His Asn Lys Thr Gly Ala Gly Asn Asp Phe Val Gly Trp Val
        35                  40                  45

Asp Leu Pro Val Asn Tyr Asp Arg Glu Glu Phe Ala Arg Ile Lys Ala
    50                  55                  60

Ala Ala Glu Lys Ile Lys Ser Asp Ser Asp Ala Leu Val Val Ile Gly
65                  70                  75                  80

Ile Gly Gly Ser Tyr Leu Gly Ala Arg Ala Ala Ile Glu Met Leu Ser
                85                  90                  95

His Ser Phe His Asn Leu Met Pro Lys Ser Lys Arg Asn Ala Pro Glu
            100                 105                 110

Ile Tyr Phe Val Gly Asn Asn Ile Ser Ser Thr Tyr Ile Ala Asp Leu
        115                 120                 125

Leu Glu Val Ile Glu Gly Lys Glu Ile Ser Val Asn Val Ile Ser Lys
    130                 135                 140

Ser Gly Thr Thr Thr Glu Pro Ala Ile Ala Phe Arg Ile Phe Lys Glu
145                 150                 155                 160

Tyr Met Glu Asn Lys Tyr Gly Lys Asp Gly Ala Ser Lys Arg Ile Tyr
                165                 170                 175

Ala Thr Thr Asp Lys Glu Lys Gly Ala Leu Arg Lys Leu Ala Thr Glu
            180                 185                 190

Glu Gly Tyr Glu Thr Phe Val Val Pro Asp Asp Ile Gly Gly Arg Phe
        195                 200                 205

Ser Val Leu Thr Ala Val Gly Leu Leu Pro Ile Ala Val Ala Gly Ile
    210                 215                 220

Asp Ile Asp Ser Met Met Lys Gly Ala Ala Asp Ala Arg Glu Leu Tyr
225                 230                 235                 240

Ser Asn Pro Asn Leu Met Glu Asn Asp Cys Tyr Lys Tyr Ala Ala Val
                245                 250                 255

Arg Asn Ala Leu Tyr Arg Lys Asn Lys Thr Ile Glu Ile Met Val Asn
            260                 265                 270

Tyr Glu Pro Ser Leu His Tyr Phe Thr Glu Trp Trp Lys Gln Leu Tyr
        275                 280                 285

Gly Glu Ser Glu Gly Lys Asp Gln Lys Gly Ile Phe Pro Ala Gly Val
    290                 295                 300

Asp Phe Thr Thr Asp Leu His Ser Met Gly Gln Tyr Ile Gln Asp Gly
305                 310                 315                 320

Leu Arg Asn Ile Phe Glu Thr Val Ile Arg Val Glu Lys Pro Arg Lys
                325                 330                 335

Asn Ile Val Ile Lys Glu Glu Lys Asp Asn Leu Asp Gly Leu Asn Phe
            340                 345                 350

Ile Ala Gly Lys Asp Val Asp Tyr Val Asn Lys Lys Ala Met Glu Gly
        355                 360                 365

Thr Val Leu Ala His Thr Asp Gly Gly Val Pro Asn Leu Val Val Thr

```
                    370                 375                 380
Val Pro Glu Leu Ser Ala Tyr Tyr Phe Gly Asn Met Val Tyr Phe Phe
385                 390                 395                 400

Glu Lys Ala Cys Gly Ile Ser Gly Tyr Leu Leu Gly Val Asn Pro Phe
                    405                 410                 415

Asp Gln Pro Gly Val Glu Ala Tyr Lys Lys Asn Met Phe Ala Leu Leu
                    420                 425                 430

Gly Lys Pro Gly Tyr Glu Glu Gln Arg Lys Lys Leu Glu Glu Arg Leu
                    435                 440                 445
```

<210> SEQ ID NO 41
<211> LENGTH: 324
<212> TYPE: PRT
<213> ORGANISM: C. thermocellum

<400> SEQUENCE: 41

```
Met Ser Ser Val Arg Thr Ile Gly Val Leu Thr Ser Gly Gly Asp Ala
1               5                   10                  15

Pro Gly Met Asn Ala Ala Ile Arg Ser Val Val Arg Thr Gly Leu Tyr
                20                  25                  30

Tyr Gly Phe Lys Val Leu Gly Ile Arg Lys Gly Phe Asn Gly Leu Ile
            35                  40                  45

Asn Gly Asp Ile Glu Glu Leu Thr Ala Arg Ser Val Gly Asp Ile Ile
50                  55                  60

His Arg Gly Gly Thr Ile Leu Gln Thr Ala Arg Ser Pro Gln Phe Lys
65                  70                  75                  80

Thr Glu Glu Gly Leu Lys Lys Ala Met Ser Met Ala Lys Val Phe Gly
                85                  90                  95

Ile Asp Ala Leu Val Val Ile Gly Gly Asp Gly Ser Tyr Arg Gly Ala
            100                 105                 110

Arg Asp Ile Ser Lys Leu Gly Leu Asn Val Ile Gly Ile Pro Gly Thr
        115                 120                 125

Ile Asp Asn Asp Ile Gly Cys Thr Asp Tyr Thr Ile Gly Phe Asp Thr
130                 135                 140

Ala Met Asn Thr Val Gln Asp Ala Ile Asp Lys Ile Arg Asp Thr Ala
145                 150                 155                 160

Tyr Ser His Glu Arg Cys Ser Val Leu Glu Val Met Gly Arg His Ala
                165                 170                 175

Gly Tyr Ile Ala Val Asn Val Ser Ile Ser Gly Gly Ala Glu Ala Val
            180                 185                 190

Val Leu Pro Glu Lys Pro Phe Asp Met Asp Thr Asp Val Ile Lys Pro
        195                 200                 205

Ile Ile Glu Gly Arg Asn Arg Gly Lys Lys His Tyr Leu Val Ile Val
210                 215                 220

Ala Glu Gly Gly Glu Gly Lys Ala Ile Glu Ile Ala Lys Glu Ile Thr
225                 230                 235                 240

Glu Lys Thr Gly Ile Glu Ala Arg Ala Thr Ile Leu Gly His Ile Gln
                245                 250                 255

Arg Gly Gly Ser Pro Thr Val Tyr Asp Arg Val Met Ala Ser Gln Met
            260                 265                 270

Gly Ala Lys Ala Val Glu Val Leu Met Glu Asn Lys Arg Asn Arg Val
        275                 280                 285

Ile Val Phe Lys Asp Asn Gln Ile Gly Asp Met Asp Leu Glu Glu Ala
        290                 295                 300
```

Leu Gln Val Lys Lys Thr Ile Ser Glu Asp Leu Ile Gln Leu Ser Lys
305                 310                 315                 320

Ile Leu Ala Leu

<210> SEQ ID NO 42
<211> LENGTH: 327
<212> TYPE: PRT
<213> ORGANISM: T. saccharolyticum

<400> SEQUENCE: 42

Met Ser Tyr Ile Pro Asn Glu Asn Arg Tyr Glu Lys Met Ile Tyr Arg
1               5                   10                  15

Arg Cys Gly Arg Ser Gly Ile Met Leu Pro Ala Ile Ser Leu Gly Leu
                20                  25                  30

Trp His Asn Phe Gly Gly Tyr Asp Val Phe Glu Asn Met Arg Glu Met
            35                  40                  45

Val Lys Lys Ala Phe Asp Leu Gly Ile Thr His Phe Asp Leu Ala Asn
        50                  55                  60

Asn Tyr Gly Pro Pro Gly Ser Ala Glu Glu Asn Phe Gly Lys Ile
65                  70                  75                  80

Leu Arg Thr Asp Leu Arg Gly Tyr Arg Asp Glu Leu Leu Ile Ser Thr
                85                  90                  95

Lys Ala Gly Tyr Thr Met Trp Pro Gly Pro Tyr Gly Asp Trp Gly Ser
            100                 105                 110

Arg Lys Tyr Leu Leu Ser Ser Leu Asp Gln Ser Leu Lys Arg Met Gly
        115                 120                 125

Ile Asp Tyr Val Asp Ile Phe Tyr Ser His Arg Arg Asp Pro Asn Thr
130                 135                 140

Pro Leu Glu Glu Thr Met Ser Ala Leu Ala Gln Ala Val Arg Gln Gly
145                 150                 155                 160

Lys Ala Leu Tyr Val Gly Ile Ser Asn Tyr Asn Ala Glu Asp Thr Lys
            165                 170                 175

Lys Ala Ala Glu Ile Leu Arg Gln Leu Gly Thr Pro Leu Leu Ile Asn
        180                 185                 190

Gln Pro Ser Tyr Ser Met Phe Asn Arg Trp Ile Glu Asp Gly Leu Thr
    195                 200                 205

Asp Val Leu Glu Glu Glu Gly Val Gly Ser Ile Ala Phe Ser Pro Leu
210                 215                 220

Ala Gln Gly Leu Leu Thr Asp Lys Tyr Leu Asn Gly Val Pro Asp Asp
225                 230                 235                 240

Ser Arg Ala Val Arg Lys Asn Thr Ser Leu Arg Gly Asn Leu Thr Glu
                245                 250                 255

Glu Asn Ile Asn Lys Val Arg Glu Leu Lys Lys Ile Ala Asp Lys Arg
            260                 265                 270

Gly Gln Ser Ile Ala Gln Met Ala Leu Ala Trp Asp Leu Arg Lys Val
        275                 280                 285

Thr Ser Val Ile Ile Gly Ala Ser Arg Val Ser Gln Ile Glu Glu Asn
    290                 295                 300

Val Lys Ala Leu Asp Asn Leu Glu Phe Ser His Glu Glu Leu Lys Gln
305                 310                 315                 320

Ile Asp Glu Ile Leu Ser Lys
                325

<210> SEQ ID NO 43
<211> LENGTH: 131

<212> TYPE: PRT
<213> ORGANISM: T. saccharolyticum

<400> SEQUENCE: 43

```
Leu Asn Ile Ala Leu Ile Ala His Asp Met Lys Lys Ser Ile Met Val
1               5                   10                  15

Asp Phe Ala Ile Ala Tyr Lys Glu Ile Leu Lys Lys Cys Asn Ile Tyr
                20                  25                  30

Ala Thr Gly Ala Thr Gly Gln Leu Val Glu Glu Ala Thr Gly Ile Lys
            35                  40                  45

Val Asn Lys Phe Leu Pro Gly Pro Met Gly Gly Asp Gln Gln Ile Gly
        50                  55                  60

Ala Met Ile Ala Glu Asn Asn Met Asp Leu Val Ile Phe Leu Arg Asp
65                  70                  75                  80

Pro Leu Thr Ala Gln Pro His Glu Pro Asp Ile Leu Ala Leu Leu Arg
                85                  90                  95

Val Cys Asp Val His Ser Ile Pro Leu Ala Thr Asn Leu Ala Thr Ala
                100                 105                 110

Glu Val Leu Ile Lys Gly Leu Asp Ala Gly Phe Leu Glu Trp Arg Asp
            115                 120                 125

Ala Val Lys
        130
```

<210> SEQ ID NO 44
<211> LENGTH: 248
<212> TYPE: PRT
<213> ORGANISM: T. saccharolyticum

<400> SEQUENCE: 44

```
Leu Arg Arg Pro Ile Ile Ala Gly Asn Trp Lys Met Tyr Met Thr Pro
1               5                   10                  15

Ser Glu Ala Val Asn Leu Val Asn Glu Leu Lys Pro Leu Val Ser Gly
                20                  25                  30

Ala Glu Ala Glu Val Val Ile Pro Pro Phe Val Asp Leu Val Asp
            35                  40                  45

Val Lys Lys Ala Ile Asp Ala Ser Asn Ile Lys Leu Gly Ala Gln Asn
        50                  55                  60

Met His Trp Glu Glu Lys Gly Ala Phe Thr Gly Glu Val Ser Pro Ile
65                  70                  75                  80

Met Leu Lys Glu Ile Gly Val Glu Tyr Val Val Ile Gly His Ser Glu
                85                  90                  95

Arg Arg Gln Tyr Phe Ala Glu Thr Asp Glu Thr Val Asn Lys Lys Val
                100                 105                 110

Lys Ser Ala Leu Ser His Gly Leu Lys Pro Ile Val Cys Val Gly Glu
            115                 120                 125

Ser Leu Ser Gln Arg Glu Ala Gly Glu Ala Phe Asn Val Val Arg Glu
        130                 135                 140

Gln Thr Lys Lys Ala Leu Asp Gly Ile Lys Ser Glu Asp Val Leu Asn
145                 150                 155                 160

Val Val Ile Ala Tyr Glu Pro Ile Trp Ala Ile Gly Thr Gly Lys Thr
                165                 170                 175

Ala Thr Ser Lys Asp Ala Asn Asp Val Ile Lys Val Ile Arg Glu Thr
            180                 185                 190

Ile Ala Asp Ile Tyr Ser Ile Asp Ile Ala Asn Glu Val Arg Ile Gln
        195                 200                 205
```

Tyr Gly Gly Ser Val Lys Pro Asp Asn Ala Lys Glu Leu Met Ser Glu
            210                 215                 220

Ser Asp Ile Asp Gly Ala Leu Val Gly Ala Ser Leu Lys Ala Gln
225                 230                 235                 240

Asp Phe Ala Lys Ile Val Asn Tyr
            245

<210> SEQ ID NO 45
<211> LENGTH: 394
<212> TYPE: PRT
<213> ORGANISM: T. saccharolyticum

<400> SEQUENCE: 45

Met Tyr Met Lys Thr Asn Phe Thr Tyr Phe Met Pro Thr Glu Ile Phe
1               5                   10                  15

Gly Pro Gly Thr Leu Gly Lys Leu Ala Thr Val Lys Leu Pro Gly Lys
            20                  25                  30

Lys Ala Leu Leu Val Ile Gly Ser Gly Asn Ser Met Arg Arg His Gly
        35                  40                  45

Tyr Leu Asp Arg Val Val Asn Tyr Leu Lys Gln Asn Gly Val Asp Tyr
    50                  55                  60

Val Val Tyr Asp Lys Ile Leu Pro Asn Pro Ile Ala Glu His Val Ala
65                  70                  75                  80

Glu Gly Ala Lys Val Ala Lys Asp Asn Gly Cys Asp Phe Val Ile Gly
                85                  90                  95

Leu Gly Gly Gly Ser Thr Ile Asp Ser Ser Lys Ala Ile Ala Val Met
            100                 105                 110

Ala Lys Asn Pro Gly Asp Tyr Trp Asp Tyr Val Ser Gly Gly Ser Gly
        115                 120                 125

Lys Gly Met Glu Val Lys Asn Gly Ala Leu Pro Ile Val Ala Ile Pro
    130                 135                 140

Thr Thr Ala Gly Thr Gly Thr Glu Ser Asp Pro Trp Ala Val Val Thr
145                 150                 155                 160

Lys Thr Glu Thr Asn Glu Lys Ile Gly Phe Gly Cys Lys Tyr Thr Tyr
                165                 170                 175

Pro Thr Leu Ser Ile Val Asp Pro Glu Leu Met Val Ser Ile Pro Pro
            180                 185                 190

Lys Phe Thr Ala Tyr Gln Gly Met Asp Ala Phe Phe His Ser Val Glu
        195                 200                 205

Gly Tyr Leu Ala Thr Val Asn Gln Pro Gly Ser Asp Val Leu Ala Leu
    210                 215                 220

Gln Ser Ile Ser Leu Ile Thr Glu Asn Leu Pro Lys Ala Val Ala Asp
225                 230                 235                 240

Gly Asn Asn Met Glu Ala Arg Thr Ala Leu Ala Trp Ala Ser Thr Ala
                245                 250                 255

Ala Gly Ile Val Glu Ser Leu Ser Ser Cys Ile Ser His His Ser Leu
            260                 265                 270

Glu His Ala Leu Ser Ala Tyr His Pro Glu Ile Pro His Gly Ala Gly
        275                 280                 285

Leu Ile Met Leu Ser Val Ser Tyr Phe Ser Phe Met Ala Ser Lys Ala
    290                 295                 300

Pro Glu Arg Phe Val Asp Ile Ala Lys Ala Met Gly Glu Glu Ile Val
305                 310                 315                 320

Gly Asn Thr Val Glu Glu Gln Ala Met Cys Phe Ile Asn Gly Leu Lys
                325                 330                 335

```
Lys Ile Ile Arg Asn Ile Gly Met Glu Asp Leu Ser Leu Ser Ser Phe
            340                 345                 350

Gly Val Thr Glu Asp Glu Ala Thr Lys Leu Ala Lys Asn Ala Met Asp
            355                 360                 365

Thr Met Gly Gly Leu Phe Asn Val Asp Pro Tyr Lys Leu Ser Leu Asp
370                 375                 380

Glu Val Val Ser Ile Tyr Lys Asn Cys Phe
385                 390
```

<210> SEQ ID NO 46
<211> LENGTH: 343
<212> TYPE: PRT
<213> ORGANISM: T. saccharolyticum

<400> SEQUENCE: 46

```
Val Asp Asp Lys Lys Val Phe Asp His Leu Phe Ile Leu Thr Asp Asp
1               5                   10                  15

Thr Gly Met Met Gln His Ser Val Gly Ser Val Pro Asp Pro Lys Tyr
            20                  25                  30

Gly Tyr Thr Thr Asp Asp Asn Gly Arg Ala Leu Ile Ala Cys Ala Met
            35                  40                  45

Met Tyr Glu Lys Tyr Lys Asp Asp Ala Tyr Ile Asn Leu Ile Lys Lys
50                  55                  60

Tyr Leu Ser Phe Leu Met Tyr Ala Gln Glu Asp Asp Gly Arg Phe Arg
65                  70                  75                  80

Asn Phe Met Ser Phe Asp Arg Lys Phe Ile Asp Glu Asp Phe Ser Glu
            85                  90                  95

Asp Cys Phe Gly Arg Cys Met Trp Ala Leu Gly Tyr Leu Ile Asn Ser
            100                 105                 110

Asn Ile Asp Glu Arg Val Lys Leu Pro Ala Tyr Lys Met Ile Glu Lys
            115                 120                 125

Ser Leu Leu Leu Val Asp Thr Leu Asn Tyr Ile Arg Gly Lys Ala Tyr
            130                 135                 140

Thr Leu Ile Gly Leu Tyr Tyr Ile Tyr Asn Ser Phe Lys Asn Leu Asp
145                 150                 155                 160

Lys Asp Phe Val Arg Lys Lys Met Asp Lys Leu Ala His Asp Ile Val
            165                 170                 175

Glu Glu Tyr Glu Lys Asn Ser Ser Glu Asp Trp Gln Trp Phe Glu Asp
            180                 185                 190

Val Val Ser Tyr Asp Asn Gly Val Ile Pro Leu Ser Leu Leu Lys Tyr
            195                 200                 205

Phe Ser Ile Ala Lys Asp Glu Glu Val Leu Asp Ile Ala Leu Lys Thr
210                 215                 220

Ile Asp Phe Leu Asp Ser Val Cys Phe Lys Asn Gly Tyr Phe Lys Ala
225                 230                 235                 240

Val Gly Cys Lys Gly Trp Tyr Arg Lys Gly Lys Asp Ile Ala Glu Tyr
            245                 250                 255

Asp Glu Gln Pro Val Glu Ala Tyr Thr Met Ala Leu Met Tyr Ile Glu
            260                 265                 270

Ala Tyr Lys Leu Thr Gly Asp Glu Lys Tyr Lys Lys Arg Ala Ile Asp
            275                 280                 285

Cys Asp Lys Trp Phe Tyr Gly Lys Asn Ser Lys Gly Leu Ser Leu Tyr
            290                 295                 300

Asp Glu Asp Ser Gly Gly Cys Ser Asp Gly Ile Thr Glu Asp Gly Val
```

Asn Ser Asn Glu Gly Ala Glu Ser Leu Ile Ser Ile Met Ile Ser His
        305                 310                 315                 320

Cys Ala Ile Asp Gln Leu Lys
            340

<210> SEQ ID NO 47
<211> LENGTH: 350
<212> TYPE: PRT
<213> ORGANISM: T. saccharolyticum

<400> SEQUENCE: 47

Met Lys Thr Ser Glu Leu Leu Ala Met Val Val Glu Lys Gly Ala Ser
1               5                   10                  15

Asp Leu His Ile Thr Val Gly Val Pro Val Leu Arg Ile Asn Gly
            20                  25                  30

Gln Leu Ile Lys Leu Asn Leu Pro Gln Leu Thr Pro Gln Asp Thr Glu
            35                  40                  45

Glu Ile Thr Lys Asp Leu Leu Ser Ser Asp Glu Leu Lys Lys Leu Glu
        50                  55                  60

Asp Met Gly Asp Ile Asp Leu Ser Tyr Ser Val Lys Gly Leu Gly Arg
65                  70                  75                  80

Phe Arg Ile Asn Ala Tyr Lys Gln Arg Gly Thr Tyr Ser Leu Ala Ile
                85                  90                  95

Arg Ser Val Ala Leu Arg Ile Pro Thr Ile Asp Glu Leu Gly Leu Pro
            100                 105                 110

Glu Val Ile Lys Glu Leu Ala Leu Lys Thr Arg Gly Leu Ile Ile Val
            115                 120                 125

Thr Gly Pro Thr Gly Ser Gly Lys Ser Thr Thr Leu Ala Ser Met Ile
        130                 135                 140

Asp Leu Ile Asn Glu Glu Arg Asn Cys His Ile Leu Thr Leu Glu Asp
145                 150                 155                 160

Pro Ile Glu Tyr Leu His Lys His Lys Lys Ser Ile Val Asn Gln Arg
                165                 170                 175

Glu Ile Gly His Asp Ala Ala Ser Tyr Ala Ser Ala Leu Arg Ala Ala
            180                 185                 190

Leu Arg Glu Asp Pro Asp Val Ile Leu Val Gly Glu Met Arg Asp Leu
        195                 200                 205

Glu Thr Ile Gln Ile Ala Ile Thr Ala Ala Glu Thr Gly His Leu Val
    210                 215                 220

Leu Ser Thr Leu His Thr Ile Gly Ser Ala Lys Thr Ile Asp Arg Ile
225                 230                 235                 240

Ile Asp Val Phe Pro Pro His Gln Gln Gln Ile Lys Val Gln Leu
                245                 250                 255

Ser Asn Val Leu Glu Gly Ile Val Ser Gln Gln Leu Leu Pro Lys Ile
            260                 265                 270

Asp Asn Ser Gly Arg Val Val Ala Val Glu Val Met Ile Ala Thr Pro
        275                 280                 285

Ala Ile Arg Asn Leu Ile Arg Glu Gly Lys Ser Phe Gln Ile Gln Ser
    290                 295                 300

Met Val Gln Thr Gly Asn Lys Phe Gly Met Val Thr Met Asp Met Trp
305                 310                 315                 320

Ile Ser Gln Leu Leu Lys Arg Asn Leu Ile Ser Met Asp Asp Ala Leu
                325                 330                 335

Thr Tyr Cys Val Asp Arg Glu Asn Phe Ser Arg Leu Val Val
            340                 345                 350

<210> SEQ ID NO 48
<211> LENGTH: 564
<212> TYPE: PRT
<213> ORGANISM: T. saccharolyticum

<400> SEQUENCE: 48

Met Ile Lys Lys Lys Leu Gly Asp Leu Leu Val Glu Val Gly Leu Leu
1               5                   10                  15

Asp Glu Ser Gln Leu Asn Asn Ala Ile Lys Ile Gln Lys Lys Thr Gly
            20                  25                  30

Glu Lys Leu Gly Lys Ile Leu Val Lys Glu Gly Tyr Leu Thr Glu Glu
        35                  40                  45

Gln Ile Ile Glu Ala Leu Glu Phe Gln Leu Gly Ile Pro His Ile Asp
    50                  55                  60

Met Lys Lys Val Phe Ile Asp Ala Asn Val Ala Lys Leu Ile Pro Glu
65                  70                  75                  80

Ser Met Ala Lys Arg His Val Ala Ile Pro Ile Lys Lys Glu Asn Asn
                85                  90                  95

Ser Ile Phe Val Ala Met Ala Asp Pro Leu Asn Ile Phe Ala Ile Asp
            100                 105                 110

Asp Ile Lys Leu Val Thr Lys Leu Asp Val Lys Pro Leu Ile Ala Ser
        115                 120                 125

Glu Asp Gly Ile Leu Lys Ala Ile Asp Arg Val Phe Gly Lys Glu Glu
    130                 135                 140

Ala Glu Arg Ala Val Gln Asp Phe Lys Lys Glu Leu Ser His Asp Ser
145                 150                 155                 160

Ala Glu Asp Asp Gly Asn Leu Leu Arg Asp Ile Ser Glu Asp Glu Ile
                165                 170                 175

Asn Asn Ala Pro Ala Val Arg Leu Val Asn Ser Ile Ile Glu Gln Ala
            180                 185                 190

Val Lys Asn Arg Ala Ser Asp Val His Ile Glu Pro Thr Glu Asn Asp
        195                 200                 205

Leu Arg Ile Arg Phe Arg Ile Asp Gly Glu Leu His Glu Ala Met Arg
    210                 215                 220

Val Phe Lys Ser Thr Gln Gly Pro Val Ile Thr Arg Ile Lys Ile Met
225                 230                 235                 240

Ala Asn Met Asn Ile Ala Glu Arg Arg Ile Pro Gln Asp Gly Lys Ile
                245                 250                 255

Glu Met Asn Ala Gly Gly Lys Asn Ile Asp Ile Arg Val Ser Ser Leu
            260                 265                 270

Pro Thr Ile Tyr Gly Glu Lys Leu Val Leu Arg Ile Leu Asp Lys Ser
        275                 280                 285

Gly Tyr Ile Ile Thr Lys Asp Lys Leu Gly Leu Gly Asn Asp Asp Leu
    290                 295                 300

Lys Leu Phe Asp Asn Leu Leu Lys His Pro Asn Gly Ile Ile Leu Leu
305                 310                 315                 320

Thr Gly Pro Thr Gly Ser Gly Lys Thr Thr Thr Leu Tyr Ala Met Leu
                325                 330                 335

Asn Glu Leu Asn Lys Pro Asp Lys Asn Ile Ile Thr Val Glu Asp Pro
            340                 345                 350

Val Glu Tyr Thr Leu Glu Gly Leu Asn Gln Val Gln Val Asn Glu Lys
        355                 360                 365

```
Ala Gly Leu Thr Phe Ala Ser Ala Leu Arg Ser Ile Leu Arg Gln Asp
    370                 375                 380

Pro Asp Ile Ile Met Ile Gly Glu Ile Arg Asp Arg Glu Thr Ala Glu
385                 390                 395                 400

Ile Ala Ile Arg Ser Ser Ile Thr Gly His Leu Val Leu Ser Thr Leu
                405                 410                 415

His Thr Asn Asp Ser Ala Gly Ala Ile Thr Arg Leu Ile Asp Met Gly
            420                 425                 430

Ile Glu Pro Tyr Leu Val Ser Ser Val Val Gly Val Ile Ala Gln
            435                 440                 445

Arg Leu Ala Arg Lys Ile Cys Asp Asn Cys Lys Ile Glu Tyr Asp Ala
    450                 455                 460

Ser Lys Arg Glu Lys Ile Ile Leu Gly Ile Asp Ala Asp Glu Ser Leu
465                 470                 475                 480

Lys Leu Tyr Arg Ser Lys Gly Cys Ala Val Cys Asn Lys Thr Gly Tyr
                485                 490                 495

Arg Gly Arg Val Pro Ile Tyr Glu Ile Met Met Thr Pro Lys Ile
            500                 505                 510

Lys Glu Leu Thr Asn Glu Lys Ala Pro Ala Asp Val Ile Leu Asn Glu
    515                 520                 525

Ala Val Ser Asn Gly Met Ser Thr Leu Lys Glu Ser Ala Lys Lys Leu
    530                 535                 540

Val Leu Ser Gly Val Thr Thr Val Asp Glu Met Leu Arg Leu Thr Tyr
545                 550                 555                 560

Asp Asp Ala Tyr

<210> SEQ ID NO 49
<211> LENGTH: 1175
<212> TYPE: PRT
<213> ORGANISM: T. saccharolyticum

<400> SEQUENCE: 49

Met Ser Lys Val Met Lys Thr Met Asp Gly Asn Thr Ala Ala His
1               5                   10                  15

Val Ala Tyr Ala Phe Thr Glu Val Ala Ala Ile Tyr Pro Ile Thr Pro
                20                  25                  30

Ser Ser Pro Met Ala Glu His Val Asp Glu Trp Ser Ala His Gly Arg
            35                  40                  45

Lys Asn Leu Phe Gly Gln Glu Val Lys Val Ile Glu Met Gln Ser Glu
    50                  55                  60

Ala Gly Ala Ala Gly Ala Val His Gly Ser Leu Ala Ala Gly Ala Leu
65                  70                  75                  80

Thr Thr Thr Phe Thr Ala Ser Gln Gly Leu Leu Leu Met Ile Pro Asn
                85                  90                  95

Met Tyr Lys Ile Ala Gly Glu Leu Leu Pro Gly Val Phe His Val Ser
                100                 105                 110

Ala Arg Ala Leu Ala Ser His Ala Leu Ser Ile Phe Gly Asp His Gln
            115                 120                 125

Asp Val Met Ala Cys Arg Gln Thr Gly Phe Ala Leu Leu Ala Ser Gly
    130                 135                 140

Ser Val Gln Glu Val Met Asp Leu Gly Ser Val Ala His Leu Ala Ala
145                 150                 155                 160

Ile Lys Gly Arg Val Pro Phe Leu His Phe Phe Asp Gly Phe Arg Thr
                165                 170                 175
```

```
Ser His Glu Tyr Gln Lys Ile Glu Val Met Asp Tyr Glu Asp Leu Arg
            180                 185                 190

Lys Leu Leu Asp Met Asp Ala Val Arg Glu Phe Lys Lys Arg Ala Leu
        195                 200                 205

Asn Pro Glu His Pro Val Thr Arg Gly Thr Ala Gln Asn Pro Asp Ile
    210                 215                 220

Tyr Phe Gln Glu Arg Glu Ala Ser Asn Arg Tyr Tyr Asn Ala Val Pro
225                 230                 235                 240

Glu Ile Val Glu Glu Tyr Met Lys Glu Ile Ser Lys Ile Thr Gly Arg
                245                 250                 255

Glu Tyr Lys Leu Phe Asn Tyr Tyr Gly Ala Pro Asp Ala Glu Arg Ile
            260                 265                 270

Val Ile Ala Met Gly Ser Val Thr Glu Thr Ile Glu Glu Thr Ile Asp
        275                 280                 285

Tyr Leu Leu Lys Lys Gly Glu Lys Val Gly Val Val Lys Val His Leu
    290                 295                 300

Tyr Arg Pro Phe Ser Phe Lys His Phe Met Asp Ala Ile Pro Lys Thr
305                 310                 315                 320

Val Lys Lys Ile Ala Val Leu Asp Arg Thr Lys Glu Ala Gly Ala Phe
                325                 330                 335

Gly Glu Pro Leu Tyr Glu Asp Val Arg Ala Ala Phe Tyr Asp Ser Glu
            340                 345                 350

Met Lys Pro Ile Ile Val Gly Gly Arg Tyr Gly Leu Gly Ser Lys Asp
        355                 360                 365

Thr Thr Pro Ala Gln Ile Val Ala Val Phe Asp Asn Leu Lys Ser Asp
    370                 375                 380

Thr Pro Lys Asn Asn Phe Thr Ile Gly Ile Val Asp Asp Val Thr Tyr
385                 390                 395                 400

Thr Ser Leu Pro Val Gly Glu Glu Ile Glu Thr Thr Ala Glu Gly Thr
                405                 410                 415

Ile Ser Cys Lys Phe Trp Gly Phe Gly Ser Asp Gly Thr Val Gly Ala
            420                 425                 430

Asn Lys Ser Ala Ile Gln Ile Ile Gly Asp Asn Thr Asp Met Tyr Ala
        435                 440                 445

Gln Ala Tyr Phe Ser Tyr Asp Ser Lys Lys Ser Gly Gly Val Thr Ile
    450                 455                 460

Ser His Leu Arg Phe Gly Lys Lys Pro Ile Arg Ser Thr Tyr Leu Ile
465                 470                 475                 480

Asn Asn Ala Asp Phe Val Ala Cys His Lys Gln Ala Tyr Val Tyr Asn
                485                 490                 495

Tyr Asp Val Leu Ala Gly Leu Lys Gly Gly Thr Phe Leu Leu Asn
            500                 505                 510

Cys Thr Trp Lys Pro Glu Glu Leu Asp Glu Lys Leu Pro Ala Ser Met
        515                 520                 525

Lys Arg Tyr Ile Ala Lys Asn Ile Asn Phe Tyr Ile Ile Asn Ala
    530                 535                 540

Val Asp Ile Ala Lys Glu Leu Gly Leu Gly Ala Arg Ile Asn Met Ile
545                 550                 555                 560

Met Gln Ser Ala Phe Phe Lys Leu Ala Asn Ile Ile Pro Ile Asp Glu
                565                 570                 575

Ala Val Lys His Leu Lys Asp Ala Ile Val Lys Ser Tyr Gly His Lys
            580                 585                 590
```

Gly Glu Lys Ile Val Asn Met Asn Tyr Ala Ala Val Asp Arg Gly Ile
            595                 600                 605

Asp Ala Leu Val Lys Val Asp Val Pro Ala Ser Trp Ala Asn Ala Glu
        610                 615                 620

Asp Glu Ala Lys Val Glu Arg Asn Val Pro Asp Phe Ile Lys Asn Ile
625                 630                 635                 640

Ala Asp Val Met Asn Arg Gln Glu Gly Asp Lys Leu Pro Val Ser Ala
                645                 650                 655

Phe Val Gly Met Glu Asp Gly Thr Phe Pro Met Gly Thr Ala Ala Tyr
            660                 665                 670

Glu Lys Arg Gly Ile Ala Val Asp Val Pro Glu Trp Gln Ile Asp Asn
        675                 680                 685

Cys Ile Gln Cys Asn Gln Cys Ala Tyr Val Cys Pro His Ala Ala Ile
    690                 695                 700

Arg Pro Phe Leu Leu Asn Glu Glu Val Lys Asn Ala Pro Glu Gly
705                 710                 715                 720

Phe Thr Ser Lys Lys Ala Ile Gly Lys Gly Leu Glu Gly Leu Asn Phe
                725                 730                 735

Arg Ile Gln Val Ser Val Leu Asp Cys Thr Gly Cys Gly Val Cys Ala
            740                 745                 750

Asn Thr Cys Pro Ser Lys Glu Lys Ser Leu Ile Met Lys Pro Leu Glu
        755                 760                 765

Thr Gln Leu Asp Gln Ala Lys Asn Trp Glu Tyr Ala Met Ser Leu Ser
770                 775                 780

Tyr Lys Glu Asn Pro Leu Gly Thr Asp Thr Val Lys Gly Ser Gln Phe
785                 790                 795                 800

Glu Lys Pro Leu Leu Glu Phe Ser Gly Ala Cys Ala Gly Cys Gly Glu
            805                 810                 815

Thr Pro Tyr Ala Arg Leu Val Thr Gln Leu Phe Gly Asp Arg Met Leu
        820                 825                 830

Ile Ala Asn Ala Thr Gly Cys Ser Ser Ile Trp Gly Gly Ser Ala Pro
    835                 840                 845

Ser Thr Pro Tyr Thr Val Asn Lys Asp Gly His Gly Pro Ala Trp Ala
850                 855                 860

Asn Ser Leu Phe Glu Asp Asn Ala Glu Phe Gly Phe Gly Met Ala Leu
865                 870                 875                 880

Ala Val Lys Gln Gln Arg Glu Lys Leu Ala Asp Ile Val Lys Glu Ala
                885                 890                 895

Leu Glu Leu Asp Leu Thr Gln Asp Leu Lys Asn Ala Leu Lys Leu Trp
            900                 905                 910

Leu Asp Asn Phe Asn Ser Ser Glu Ile Thr Lys Lys Thr Ala Asn Ile
        915                 920                 925

Ile Val Ser Leu Ile Gln Asp Tyr Lys Thr Asp Ser Lys Val Lys
    930                 935                 940

Glu Leu Leu Asn Glu Ile Leu Asp Arg Lys Glu Tyr Leu Val Lys Lys
945                 950                 955                 960

Ser Gln Trp Ile Phe Gly Gly Asp Gly Trp Ala Tyr Asp Ile Gly Phe
                965                 970                 975

Gly Gly Leu Asp His Val Leu Ala Ser Gly Glu Asp Val Asn Val Leu
            980                 985                 990

Val Phe Asp Thr Glu Val Tyr Ser Asn Thr Gly Gly Gln Ser Ser Lys
        995                 1000                1005

Ala Thr  Pro Val Gly Ala Ile  Ala Gln Phe Ala Ala  Ala Gly Lys

```
            1010                1015                1020

Gly Ile Gly Lys Lys Asp Leu Gly Arg Ile Ala Met Ser Tyr Gly
    1025                1030                1035

Tyr Val Tyr Val Ala Gln Ile Ala Met Gly Ala Asn Gln Ala Gln
    1040                1045                1050

Thr Ile Lys Ala Leu Lys Glu Ala Glu Ser Tyr Pro Gly Pro Ser
    1055                1060                1065

Leu Ile Ile Ala Tyr Ala Pro Cys Ile Asn His Gly Ile Lys Leu
    1070                1075                1080

Gly Met Gly Cys Ser Gln Ile Glu Glu Lys Lys Ala Val Glu Ala
    1085                1090                1095

Gly Tyr Trp His Leu Tyr Arg Tyr Asn Pro Met Leu Lys Ala Glu
    1100                1105                1110

Gly Lys Asn Pro Phe Ile Leu Asp Ser Lys Ala Pro Thr Ala Ser
    1115                1120                1125

Tyr Lys Glu Phe Ile Met Gly Glu Val Arg Tyr Ser Ser Leu Ala
    1130                1135                1140

Lys Thr Phe Pro Glu Arg Ala Glu Ala Leu Phe Glu Lys Ala Glu
    1145                1150                1155

Glu Leu Ala Lys Glu Lys Tyr Glu Thr Tyr Lys Lys Leu Ala Glu
    1160                1165                1170

Gln Asn
    1175

<210> SEQ ID NO 50
<211> LENGTH: 311
<212> TYPE: PRT
<213> ORGANISM: T. saccharolyticum

<400> SEQUENCE: 50

Met Ser Lys Val Ala Ile Ile Gly Ser Gly Phe Val Gly Ala Thr Ser
1               5                   10                  15

Ala Phe Thr Leu Ala Leu Ser Gly Thr Val Thr Asp Ile Val Leu Val
            20                  25                  30

Asp Leu Asn Lys Asp Lys Ala Ile Gly Asp Ala Leu Asp Ile Ser His
        35                  40                  45

Gly Ile Pro Leu Ile Gln Pro Val Asn Val Tyr Ala Gly Asp Tyr Lys
    50                  55                  60

Asp Val Lys Gly Ala Asp Val Ile Val Val Thr Ala Gly Ala Ala Gln
65                  70                  75                  80

Lys Pro Gly Glu Thr Arg Leu Asp Leu Val Lys Lys Asn Thr Ala Ile
                85                  90                  95

Phe Lys Ser Met Ile Pro Glu Leu Leu Lys Tyr Asn Asp Lys Ala Ile
            100                 105                 110

Tyr Leu Ile Val Thr Asn Pro Val Asp Ile Leu Thr Tyr Val Thr Tyr
        115                 120                 125

Lys Ile Ser Gly Leu Pro Trp Gly Arg Val Phe Gly Ser Gly Thr Val
    130                 135                 140

Leu Asp Ser Ser Arg Phe Arg Tyr Leu Leu Ser Lys His Cys Asn Ile
145                 150                 155                 160

Asp Pro Arg Asn Val His Gly Arg Ile Ile Gly Glu His Gly Asp Thr
                165                 170                 175

Glu Phe Ala Ala Trp Ser Ile Thr Asn Ile Ser Gly Ile Ser Phe Asn
            180                 185                 190
```

Glu Tyr Cys Ser Ile Cys Gly Arg Val Cys Asn Thr Asn Phe Arg Lys
            195                 200                 205

Glu Val Glu Glu Glu Val Val Asn Ala Ala Tyr Lys Ile Ile Asp Lys
    210                 215                 220

Lys Gly Ala Thr Tyr Tyr Ala Val Ala Val Ala Val Arg Arg Ile Val
225                 230                 235                 240

Glu Cys Ile Leu Arg Asp Glu Asn Ser Ile Leu Thr Val Ser Ser Pro
                245                 250                 255

Leu Asn Gly Gln Tyr Gly Val Lys Asp Val Ser Leu Ser Leu Pro Ser
            260                 265                 270

Ile Val Gly Arg Asn Gly Val Ala Arg Ile Leu Asp Leu Pro Leu Ser
        275                 280                 285

Asp Glu Glu Val Glu Lys Phe Arg His Ser Ala Ser Val Met Ala Asp
    290                 295                 300

Val Ile Lys Gln Leu Asp Ile
305                 310

<210> SEQ ID NO 51
<211> LENGTH: 741
<212> TYPE: PRT
<213> ORGANISM: T. saccharolyticum

<400> SEQUENCE: 51

Met Ile Asn Glu Trp Arg Gly Phe Gln Glu Gly Lys Trp Gln Lys Thr
1               5                   10                  15

Ile Asp Val Gln Asp Phe Ile Gln Lys Asn Tyr Thr Leu Tyr Glu Gly
            20                  25                  30

Asp Asp Ser Phe Leu Glu Gly Pro Thr Glu Lys Thr Ile Lys Leu Trp
        35                  40                  45

Asn Lys Val Leu Glu Leu Met Lys Glu Glu Leu Lys Lys Gly Val Leu
    50                  55                  60

Asp Ile Asp Thr Lys Thr Val Ser Ser Ile Thr Ser His Asp Ala Gly
65                  70                  75                  80

Tyr Ile Asp Lys Asp Leu Glu Glu Ile Val Gly Leu Gln Thr Asp Lys
                85                  90                  95

Pro Leu Lys Arg Ala Ile Met Pro Tyr Gly Gly Ile Arg Met Val Lys
            100                 105                 110

Lys Ala Cys Glu Ala Tyr Gly Tyr Lys Val Asp Pro Lys Val Glu Glu
        115                 120                 125

Ile Phe Thr Lys Tyr Arg Lys Thr His Asn Asp Gly Val Phe Asp Ala
    130                 135                 140

Tyr Thr Pro Glu Ile Arg Ala Ala Arg His Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Ile Asp Arg Leu Ile Glu Glu Lys Glu Lys Glu
            180                 185                 190

Lys Leu Glu Leu Asp Tyr Asp Glu Phe Asp Glu Ala Thr Ile Arg Leu
        195                 200                 205

Arg Glu Glu Leu Thr Glu Gln Ile Lys Ala Leu Asn Glu Met Lys Glu
    210                 215                 220

Met Ala Leu Lys Tyr Gly Tyr Asp Ile Ser Lys Pro Ala Lys Asn Ala
225                 230                 235                 240

Lys Glu Ala Val Gln Trp Thr Tyr Phe Ala Phe Leu Ala Ala Ile Lys
                245                 250                 255

Glu Gln Asn Gly Ala Ala Met Ser Leu Gly Arg Val Ser Thr Phe Leu
            260                 265                 270

Asp Ile Tyr Ile Glu Arg Asp Leu Lys Glu Gly Thr Leu Thr Glu Lys
            275                 280                 285

Gln Ala Gln Glu Leu Met Asp His Phe Val Met Lys Leu Arg Met Val
290                 295                 300

Arg Phe Leu Arg Thr Pro Asp Tyr Asn Glu Leu Phe Ser Gly Asp Pro
305                 310                 315                 320

Val Trp Val Thr Glu Ser Ile Gly Val Gly Val Asp Gly Arg Pro
            325                 330                 335

Leu Val Thr Lys Asn Ser Phe Arg Ile Leu Asn Thr Leu Tyr Asn Leu
            340                 345                 350

Gly Pro Ala Pro Glu Pro Asn Leu Thr Val Leu Trp Ser Lys Asn Leu
            355                 360                 365

Pro Glu Asn Phe Lys Arg Phe Cys Ala Lys Val Ser Ile Asp Thr Ser
            370                 375                 380

Ser Ile Gln Tyr Glu Asn Asp Asp Leu Met Arg Pro Ile Tyr Asn Asp
385                 390                 395                 400

Asp Tyr Ser Ile Ala Cys Cys Val Ser Ala Met Lys Thr Gly Glu Gln
            405                 410                 415

Met Gln Phe Phe Gly Ala Arg Ala Asn Leu Ala Lys Ala Leu Leu Tyr
            420                 425                 430

Ala Ile Asn Gly Gly Ile Asp Glu Arg Tyr Lys Thr Gln Val Ala Pro
            435                 440                 445

Lys Phe Asn Pro Ile Thr Ser Glu Tyr Leu Asp Tyr Asp Glu Val Met
            450                 455                 460

Ala Ala Tyr Asp Asn Met Leu Glu Trp Leu Ala Lys Val Tyr Val Lys
465                 470                 475                 480

Ala Met Asn Ile Ile His Tyr Met His Asp Lys Tyr Ala Tyr Glu Arg
            485                 490                 495

Ser Leu Met Ala Leu His Asp Arg Asp Ile Val Arg Thr Met Ala Phe
            500                 505                 510

Gly Ile Ala Gly Leu Ser Val Ala Ala Asp Ser Leu Ser Ala Ile Lys
            515                 520                 525

Tyr Ala Lys Val Lys Ala Ile Arg Asp Glu Asn Gly Ile Ala Ile Asp
            530                 535                 540

Tyr Glu Val Glu Gly Asp Phe Pro Lys Phe Gly Asn Asp Asp Arg
545                 550                 555                 560

Val Asp Ser Ile Ala Val Asp Ile Val Glu Arg Phe Met Asn Lys Leu
            565                 570                 575

Lys Lys His Lys Thr Tyr Arg Asn Ser Ile Pro Thr Leu Ser Val Leu
            580                 585                 590

Thr Ile Thr Ser Asn Val Val Tyr Gly Lys Lys Thr Gly Ala Thr Pro
            595                 600                 605

Asp Gly Arg Lys Ala Gly Glu Pro Phe Ala Pro Gly Ala Asn Pro Met
610                 615                 620

His Gly Arg Asp Thr Lys Gly Ala Ile Ala Ser Met Asn Ser Ser Lys
625                 630                 635                 640

Ile Pro Tyr Asp Ser Ser Leu Asp Gly Ile Ser Tyr Thr Phe Thr Ile
            645                 650                 655

Val Pro Asn Ala Leu Gly Lys Asp Asp Glu Asp Lys Ile Asn Asn Leu
            660                 665                 670

```
Val Gly Leu Asp Gly Tyr Ala Phe Asn Ala Gly His His Ile Asn
            675                 680                 685

Ile Asn Val Leu Asn Arg Asp Met Leu Asp Ala Met Glu His Pro
    690                 695                 700

Glu Lys Tyr Pro Gln Leu Thr Ile Arg Val Ser Gly Tyr Ala Val Asn
705                 710                 715                 720

Phe Asn Lys Leu Thr Arg Glu Gln Gln Leu Glu Val Ile Ser Arg Thr
                725                 730                 735

Phe His Glu Ser Met
            740
```

<210> SEQ ID NO 52
<211> LENGTH: 81
<212> TYPE: PRT
<213> ORGANISM: T. saccharolyticum

<400> SEQUENCE: 52

```
Met Val Ile Thr Val Cys Val Gly Ser Ser Cys His Leu Lys Gly Ser
1               5                   10                  15

Tyr Asp Val Ile Asn Lys Leu Lys Glu Met Ile Lys Asn Tyr Gly Ile
                20                  25                  30

Glu Asp Lys Val Glu Leu Lys Ala Asp Phe Cys Met Gly Asn Cys Leu
            35                  40                  45

Arg Ala Val Ser Val Lys Ile Asp Gly Ala Cys Leu Ser Ile Lys
        50                  55                  60

Pro Asn Ser Val Glu Arg Phe Phe Lys Glu His Val Leu Gly Glu Leu
65                  70                  75                  80

Lys
```

<210> SEQ ID NO 53
<211> LENGTH: 572
<212> TYPE: PRT
<213> ORGANISM: T. saccharolyticum

<400> SEQUENCE: 53

```
Met Ser Val Ile Asn Phe Lys Glu Ala Asn Cys Arg Asn Cys Tyr Lys
1               5                   10                  15

Cys Ile Arg Tyr Cys Pro Val Lys Ala Ile Lys Val Asn Asp Glu Gln
                20                  25                  30

Ala Glu Ile Ile Glu Tyr Arg Cys Ile Ala Cys Gly Arg Cys Leu Asn
            35                  40                  45

Ile Cys Pro Gln Asn Ala Lys Thr Val Arg Ser Asp Val Glu Arg Val
        50                  55                  60

Gln Ser Phe Leu Asn Lys Gly Glu Lys Val Ala Phe Thr Val Ala Pro
65                  70                  75                  80

Ser Tyr Pro Ala Leu Val Gly His Asp Gly Ala Leu Asn Phe Leu Lys
                85                  90                  95

Ala Leu Lys Ser Leu Gly Ala Glu Met Ile Val Glu Thr Ser Val Gly
            100                 105                 110

Ala Met Leu Ile Ser Lys Glu Tyr Glu Arg Tyr Tyr Asn Asp Leu Lys
        115                 120                 125

Tyr Asp Asn Leu Ile Thr Thr Ser Cys Pro Ser Val Asn Tyr Leu Val
    130                 135                 140

Glu Lys Tyr Tyr Pro Asp Leu Ile Lys Cys Leu Val Pro Val Val Ser
145                 150                 155                 160

Pro Met Val Ala Val Gly Arg Ala Ile Lys Asn Ile His Gly Glu Gly
```

```
            165                 170                 175
Val Lys Val Val Phe Ile Gly Pro Cys Leu Ala Lys Lys Ala Glu Met
            180                 185                 190

Ser Asp Phe Ser Cys Glu Gly Ala Ile Asp Ala Val Leu Thr Phe Glu
            195                 200                 205

Glu Val Met Asn Leu Phe Asn Thr Asn Lys Ile Gly Val Glu Cys Thr
            210                 215                 220

Lys Glu Asn Leu Glu Asp Val Asp Ser Glu Ser Arg Phe Lys Leu Tyr
225                 230                 235                 240

Pro Ile Glu Gly Lys Thr Met Asp Cys Met Asp Val Asp Leu Asn Leu
            245                 250                 255

Arg Lys Phe Ile Ser Val Ser Ile Glu Asn Val Lys Asp Ile Leu
            260                 265                 270

Asn Asp Leu Arg Ala Gly Asn Leu His Gly Tyr Trp Ile Glu Ala Asn
            275                 280                 285

Ala Cys Asp Gly Gly Cys Ile Asn Gly Pro Ala Phe Gly Lys Leu Glu
            290                 295                 300

Ser Gly Ile Ala Lys Arg Lys Glu Val Ile Ser Tyr Ser Arg Met
305                 310                 315                 320

Lys Glu Arg Phe Ser Gly Asp Phe Ser Gly Ile Thr Asp Phe Ser Leu
            325                 330                 335

Asp Leu Ser Arg Lys Phe Ile Asp Leu Ser Asp Arg Trp Lys Met Pro
            340                 345                 350

Ser Glu Met Glu Ile Lys Glu Ile Leu Ser Lys Ile Gly Lys Phe Ser
            355                 360                 365

Val Glu Asp Glu Leu Asn Cys Gly Ala Cys Gly Tyr Asp Thr Cys Arg
            370                 375                 380

Glu Lys Ala Ile Ala Val Phe Asn Gly Met Ala Glu Pro Tyr Met Cys
385                 390                 395                 400

Leu Pro Tyr Met Arg Gly Arg Ala Glu Thr Leu Ser Asn Ile Ile Ile
            405                 410                 415

Ser Ser Thr Pro Asn Ala Ile Ile Ala Val Asn Asn Glu Tyr Glu Ile
            420                 425                 430

Gln Asp Met Asn Arg Ala Phe Glu Lys Met Phe Leu Val Asn Ser Ala
            435                 440                 445

Met Val Lys Gly Glu Asp Leu Ser Leu Ile Phe Asp Ile Ser Asp Phe
            450                 455                 460

Val Glu Val Ile Glu Asn Lys Lys Ser Ile Phe Asn Lys Lys Val Ser
465                 470                 475                 480

Phe Lys Asn Tyr Gly Ile Ile Ala Leu Glu Ser Ile Tyr Tyr Leu Glu
            485                 490                 495

Glu Tyr Lys Ile Ala Ile Gly Ile Phe Thr Asp Ile Thr Lys Met Glu
            500                 505                 510

Lys Gln Lys Glu Ser Phe Ser Lys Leu Lys Arg Glu Asn Tyr Gln Leu
            515                 520                 525

Ala Gln Gln Val Ile Asp Arg Gln Met Lys Val Ala Gln Glu Ile Ala
            530                 535                 540

Ser Leu Leu Gly Glu Thr Thr Ala Glu Thr Lys Val Ile Leu Thr Lys
545                 550                 555                 560

Met Lys Asp Met Leu Leu Asn Gln Gly Asp Asp Glu
            565                 570
```

<210> SEQ ID NO 54

```
<211> LENGTH: 386
<212> TYPE: PRT
<213> ORGANISM: T. saccharolyticum

<400> SEQUENCE: 54

Met Ser His Tyr Ile Asp Ile Ala His Ala Ser Leu Asn Lys Tyr Asp
1               5                   10                  15

Glu Glu Leu Cys Gly Asp Ser Val Gln Ile Arg Lys Lys Asp Tyr
                20                  25                  30

Ala Met Ala Val Met Ala Asp Gly Leu Gly Ser Gly Val Lys Ala Asn
                35                  40                  45

Ile Leu Ser Thr Leu Thr Thr Arg Ile Val Ser Lys Met Leu Asp Met
    50                  55                  60

Gly Ser Glu Leu Arg Asp Val Val Glu Thr Val Ala Glu Thr Leu Pro
65                  70                  75                  80

Ile Cys Lys Glu Arg Asn Ile Ala Tyr Ser Thr Phe Thr Val Val Ser
                85                  90                  95

Ile Tyr Gly Asp Asn Ala His Leu Val Glu Tyr Asp Asn Pro Ser Val
                100                 105                 110

Phe Tyr Phe Lys Asn Gly Val His Lys Lys Val Asp Arg Lys Cys Val
            115                 120                 125

Glu Ile Gly Asp Lys Lys Ile Phe Glu Ser Ser Phe Lys Leu Asp Leu
130                 135                 140

Asn Asp Ala Leu Ile Val Ser Asp Gly Val Ile His Ala Gly Val
145                 150                 155                 160

Gly Gly Ile Leu Asn Leu Gly Trp Gln Trp Asp Asn Val Lys Gln Tyr
                165                 170                 175

Leu Ser Lys Val Leu Glu Val Tyr Ser Asp Ala Ser Asp Ile Cys Ser
                180                 185                 190

Gln Leu Ile Thr Thr Cys Asn Asn Leu Tyr Lys Asn Arg Pro Gly Asp
            195                 200                 205

Asp Thr Thr Ala Ile Val Ile Lys Val Asn Glu Ser Lys Val Thr
                210                 215                 220

Val Met Val Gly Pro Pro Ile Leu Lys Asn Met Asp Glu Trp Val Val
225                 230                 235                 240

Lys Lys Leu Met Lys Ser Glu Gly Leu Lys Val Val Cys Gly Gly Thr
                245                 250                 255

Ala Ala Lys Ile Val Ser Arg Ile Leu Asn Lys Asp Val Ile Thr Ser
            260                 265                 270

Thr Glu Tyr Ile Asp Pro Asp Ile Pro Pro Tyr Ala His Ile Asp Gly
            275                 280                 285

Ile Asp Leu Val Thr Glu Gly Val Leu Thr Leu Arg Lys Thr Val Glu
    290                 295                 300

Ile Phe Lys Glu Tyr Met Asn Asp Lys Asp Ser Asn Leu Leu Arg Phe
305                 310                 315                 320

Ser Lys Lys Asp Ala Ala Thr Arg Leu Phe Lys Ile Leu Asn Tyr Ala
                325                 330                 335

Thr Asp Val Asn Phe Leu Val Gly Gln Ala Val Asn Ser Ala His Gln
                340                 345                 350

Asn Pro Asp Phe Pro Ser Asp Leu Arg Ile Lys Val Arg Ile Val Glu
                355                 360                 365

Glu Leu Ile Ser Leu Leu Glu Arg Leu Asn Lys Asn Val Glu Val Asn
    370                 375                 380

Tyr Phe
```

385

<210> SEQ ID NO 55
<211> LENGTH: 504
<212> TYPE: PRT
<213> ORGANISM: T. saccharolyticum

<400> SEQUENCE: 55

```
Leu Phe Lys Phe Asn Thr Asp Val Gln Met Leu Lys Tyr Glu Val Leu
1               5                   10                  15

Tyr Asn Val Ala Lys Leu Thr Leu Glu Asp Arg Leu Glu Asp Glu Tyr
                20                  25                  30

Asp Glu Ile Pro Tyr Glu Ile Pro Gly Thr Lys Pro Arg Phe Arg
            35                  40                  45

Cys Cys Val Tyr Lys Glu Arg Ala Ile Ile Glu Gln Arg Thr Lys Val
        50                  55                  60

Ala Met Gly Lys Asn Leu Lys Arg Thr Met Lys His Ala Val Asp Gly
65                  70                  75                  80

Glu Glu Pro Ile Ile Gln Val Leu Asp Ile Ala Cys Glu Glu Cys Pro
                85                  90                  95

Ile Lys Arg Tyr Arg Val Thr Glu Ala Cys Arg Gly Cys Ile Thr His
            100                 105                 110

Arg Cys Thr Glu Val Cys Pro Lys Gly Ala Ile Thr Ile Ile Asn Lys
        115                 120                 125

Lys Ala Asn Ile Asp Tyr Asp Lys Cys Ile Glu Cys Gly Arg Cys Lys
130                 135                 140

Asp Ala Cys Pro Tyr Asn Ala Ile Ser Asp Asn Leu Arg Pro Cys Ile
145                 150                 155                 160

Arg Ser Cys Ser Ala Lys Ala Ile Thr Met Asp Glu Glu Leu Lys Ala
                165                 170                 175

Ala Ile Asn Tyr Glu Lys Cys Thr Ser Cys Gly Ala Cys Thr Leu Ala
            180                 185                 190

Cys Pro Phe Gly Ala Ile Thr Asp Lys Ser Tyr Ile Val Asp Ile Ile
        195                 200                 205

Arg Ala Ile Lys Ser Gly Lys Lys Val Tyr Ala Leu Val Ala Pro Ala
    210                 215                 220

Ile Ala Ser Gln Phe Lys Asp Val Thr Val Gly Gln Ile Lys Ser Ala
225                 230                 235                 240

Leu Lys Glu Phe Gly Phe Val Asp Val Ile Glu Val Ala Leu Gly Ala
                245                 250                 255

Asp Phe Val Ala Met Glu Glu Ala Lys Glu Phe Ser His Lys Ile Lys
            260                 265                 270

Asp Ile Lys Val Met Thr Ser Ser Cys Cys Pro Ala Phe Val Ala His
        275                 280                 285

Ile Lys Lys Ser Tyr Pro Glu Leu Ser Gln Asn Ile Ser Thr Thr Val
    290                 295                 300

Ser Pro Met Thr Ala Ile Ser Lys Tyr Ile Lys Lys His Asp Pro Met
305                 310                 315                 320

Ala Val Thr Val Phe Ile Gly Pro Cys Thr Ala Lys Lys Ser Glu Val
                325                 330                 335

Met Arg Asp Asp Val Lys Gly Ile Thr Asp Phe Ala Met Thr Phe Glu
            340                 345                 350

Glu Met Val Ala Val Leu Asp Ala Ala Lys Ile Asp Met Lys Glu Gln
        355                 360                 365
```

```
Gln Asp Val Glu Val Asp Asp Ala Thr Leu Phe Gly Arg Lys Phe Ala
    370                 375                 380

Arg Ser Gly Gly Val Leu Glu Ala Val Val Glu Ala Val Lys Glu Ile
385                 390                 395                 400

Gly Ala Asp Val Glu Val Asn Pro Val Val Cys Asn Gly Leu Asp Glu
                405                 410                 415

Cys Asn Lys Thr Leu Lys Ile Met Lys Ala Gly Lys Leu Pro Asn Asn
            420                 425                 430

Phe Ile Glu Gly Met Ala Cys Ile Gly Gly Cys Ile Gly Gly Ala Gly
        435                 440                 445

Val Ile Asn Asn Val Asn Gln Ala Lys Leu Ala Val Asn Lys Phe
450                 455                 460

Gly Asp Ser Ser Tyr His Lys Ser Ile Lys Asp Arg Ile Ser Gln Phe
465                 470                 475                 480

Asp Thr Asp Asp Val Asp Phe His Val Asp Ser Gly Glu Asp Glu Ser
                485                 490                 495

Ser Glu Thr Ser Phe Lys Glu Ala
            500

<210> SEQ ID NO 56
<211> LENGTH: 581
<212> TYPE: PRT
<213> ORGANISM: T. saccharolyticum

<400> SEQUENCE: 56

Met Asp Lys Val Arg Ile Thr Ile Asp Gly Ile Pro Ala Glu Val Pro
1               5                   10                  15

Ala Asn Tyr Thr Val Leu Gln Ala Ala Lys Tyr Ala Lys Ile Glu Ile
                20                  25                  30

Pro Thr Leu Cys Tyr Leu Glu Ile Asn Glu Ile Gly Ala Cys Arg
            35                  40                  45

Leu Cys Val Val Glu Ile Lys Gly Val Arg Asn Leu Gln Ala Ser Cys
 50                  55                  60

Val Tyr Pro Val Ser Asp Gly Met Glu Ile Tyr Thr Asn Thr Pro Arg
65                  70                  75                  80

Val Arg Glu Ala Arg Arg Ser Asn Leu Glu Leu Ile Leu Ser Ala His
                85                  90                  95

Asp Arg Ser Cys Leu Thr Cys Val Arg Ser Gly Asn Cys Glu Leu Gln
            100                 105                 110

Asp Leu Ser Arg Lys Ser Gly Ile Asp Glu Ile Arg Phe Met Gly Glu
        115                 120                 125

Asn Ile Lys Tyr Gln Lys Asp Glu Ser Ser Pro Ser Ile Val Arg Asp
130                 135                 140

Pro Asn Lys Cys Val Leu Cys Arg Arg Cys Val Ala Thr Cys Asn Asn
145                 150                 155                 160

Val Gln Asn Val Phe Ala Ile Gly Met Val Asn Arg Gly Phe Lys Thr
                165                 170                 175

Ile Val Ala Pro Ser Phe Gly Arg Gly Leu Asn Glu Ser Pro Cys Ile
            180                 185                 190

Ser Cys Gly Gln Cys Ile Glu Ala Cys Pro Val Gly Ala Ile Tyr Glu
        195                 200                 205

Lys Asp His Thr Lys Ile Val Tyr Asp Ala Leu Leu Asp Glu Lys Lys
    210                 215                 220

Tyr Val Val Val Gln Thr Ala Pro Ala Val Arg Val Ala Leu Gly Glu
225                 230                 235                 240
```

-continued

```
Glu Phe Gly Met Pro Tyr Gly Ser Ile Val Thr Gly Lys Met Val Ser
                245                 250                 255

Ala Leu Lys Arg Leu Gly Phe Asp Lys Val Phe Asp Thr Asp Phe Ala
            260                 265                 270

Ala Asp Leu Thr Ile Ile Glu Glu Gly Asn Glu Leu Leu Lys Arg Leu
        275                 280                 285

Asn Glu Gly Gly Lys Leu Pro Met Ile Thr Ser Cys Ser Pro Gly Trp
    290                 295                 300

Ile Asn Tyr Cys Glu Arg Tyr Tyr Pro Glu Phe Ile Asp Asn Leu Ser
305                 310                 315                 320

Thr Cys Lys Ser Pro His Met Met Met Gly Ala Ile Ile Lys Ser Tyr
                325                 330                 335

Phe Ala Glu Lys Glu Gly Ile Asp Pro Lys Asp Ile Phe Val Val Ser
            340                 345                 350

Ile Met Pro Cys Thr Ala Lys Lys Tyr Glu Ile Asp Arg Pro Gln Met
        355                 360                 365

Ile Val Asp Gly Met Lys Asp Val Asp Ala Val Leu Thr Thr Arg Glu
    370                 375                 380

Leu Ala Arg Met Ile Lys Gln Ser Gly Ile Asp Phe Val Asn Leu Pro
385                 390                 395                 400

Asp Ser Glu Tyr Asp Asn Pro Leu Gly Glu Ser Ser Gly Ala Gly Val
                405                 410                 415

Ile Phe Gly Ala Thr Gly Gly Val Met Glu Ala Ala Leu Arg Thr Val
            420                 425                 430

Ala Asp Ile Val Glu Gly Lys Asp Ile Glu Asn Phe Glu Tyr Glu Glu
        435                 440                 445

Val Arg Gly Leu Glu Gly Ile Lys Glu Ala Lys Ile Asp Ile Gly Gly
    450                 455                 460

Lys Glu Ile Lys Ile Ala Val Ala Asn Gly Thr Gly Asn Ala Lys Lys
465                 470                 475                 480

Leu Leu Asp Lys Ile Lys Asn Gly Glu Ala Glu Tyr His Phe Ile Glu
                485                 490                 495

Val Met Gly Cys Pro Gly Gly Cys Ile Met Gly Gly Gly Gln Pro Ile
            500                 505                 510

His Asn Pro Asn Glu Lys Asp Leu Val Arg Lys Ser Arg Leu Lys Ala
        515                 520                 525

Ile Tyr Glu Ala Asp Lys Asp Leu Pro Ile Arg Lys Ser His Lys Asn
    530                 535                 540

Pro Met Ile Thr Lys Leu Tyr Glu Glu Phe Leu Ile Ser Pro Leu Gly
545                 550                 555                 560

Glu Lys Ser His His Leu Leu His Thr Thr Tyr Ser Lys Asp Leu
                565                 570                 575

Tyr Pro Met Asn Asp
            580

<210> SEQ ID NO 57
<211> LENGTH: 282
<212> TYPE: PRT
<213> ORGANISM: T. saccharolyticum

<400> SEQUENCE: 57

Leu Asn Asp Ile Leu Val Lys Ala Arg Asn Asn Lys Tyr Ala Ile Gly
1               5                   10                  15

Gly Phe Asn Phe Asn Phe Tyr Asp Asp Ala Leu Gly Ile Ile Ser Ala
```

```
            20                  25                  30
Ala Tyr Glu Leu Lys Ser Pro Ile Ile Leu Met Ala Ser Glu Gly Cys
        35                  40                  45

Val Lys Phe Leu Gly Val Lys His Ile Val Asn Phe Val Asn Gln Leu
    50                  55                  60

Lys Asp Glu Tyr Asn Ile Pro Ile Ile Leu His Leu Asp His Gly Lys
65                  70                  75                  80

Asp Ile Glu Ile Ile Lys Asn Cys Ile Asp Asn Lys Phe Asp Ser Ile
                85                  90                  95

Met Tyr Asp Gly Ser Leu Leu Asn Phe Glu Glu Asn Ile Lys Asn Thr
            100                 105                 110

Lys Phe Ile Ala Asp Leu Cys His Asp Lys Gly Met Thr Ile Glu Gly
        115                 120                 125

Glu Leu Gly Arg Ile Ser Gly Ala Glu Glu Asn Ile Glu Asn Ser Glu
    130                 135                 140

Asp Val Phe Thr Asp Pro Asp Ser Val Ala Glu Phe Thr Glu Arg Ser
145                 150                 155                 160

Asp Val Asp Ser Leu Ala Val Ala Ile Gly Asn Ala His Gly Leu Tyr
                165                 170                 175

Lys Gly Arg Pro Arg Leu Asp Phe Glu Arg Leu Ser Lys Ile Asn Lys
            180                 185                 190

Ile Ser Lys Val Pro Leu Val Leu His Gly Gly Thr Gly Ile Pro Tyr
        195                 200                 205

Glu Asp Ile Gln Lys Ala Ile Gln Leu Gly Ile Ser Lys Val Asn Val
    210                 215                 220

Gly Thr Glu Ile Lys Ile Ala Tyr Ile Lys Ser Ile Lys Lys His Leu
225                 230                 235                 240

Glu Thr Ile Asn Asp Asn Asp Ile Arg His Leu Val Ser Met Val Gln
                245                 250                 255

Asn Asp Ile Lys Glu Leu Val Lys Gln Tyr Leu Asp Ile Phe Gly Thr
            260                 265                 270

Ala Asn Lys Tyr Ser Gln Leu Gln Ser Met
        275                 280

<210> SEQ ID NO 58
<211> LENGTH: 283
<212> TYPE: PRT
<213> ORGANISM: T. saccharolyticum

<400> SEQUENCE: 58

Met Leu Val Thr Gly Ile Glu Leu Leu Lys Ala Asn Glu Glu Gly
1               5                   10                  15

Tyr Ala Val Gly Ala Phe Asn Thr Ser Asn Leu Glu Ile Thr Gln Ala
            20                  25                  30

Ile Val Glu Ala Ala Glu Glu Met Arg Ser Pro Ala Ile Ile Gln Val
        35                  40                  45

Ser Glu Gly Gly Leu Lys Tyr Ala Gly Ile Glu Thr Ile Ser Ala Ile
    50                  55                  60

Val Arg Thr Leu Ala Thr Lys Ala Ser Val Pro Ile Ala Leu His Leu
65                  70                  75                  80

Asp His Gly Thr Asp Phe Asn Asn Val Met Lys Cys Leu Arg Asn Gly
                85                  90                  95

Trp Thr Ser Val Met Met Asp Ala Ser Lys Leu Pro Leu Glu Lys Asn
            100                 105                 110
```

```
Ile Glu Val Thr Lys Asn Val Val Thr Ile Ala His Gly Met Gly Val
            115                 120                 125

Ser Val Glu Ala Glu Ile Gly Lys Ile Gly Thr Glu Asp Asn Val
    130                 135                 140

Thr Val Asp Glu Arg Glu Ala Ser Met Thr Asp Pro Asp Glu Ala Phe
145                 150                 155                 160

Lys Phe Ala Lys Glu Thr Gly Val Asp Tyr Leu Ala Ile Ser Ile Gly
                165                 170                 175

Thr Ala His Gly Pro Tyr Lys Gly Glu Pro Lys Leu Asp Phe Asp Arg
            180                 185                 190

Leu Val Lys Ile Lys Glu Met Leu Lys Met Pro Ile Val Leu His Gly
                195                 200                 205

Ala Ser Gly Val Pro Glu Ala Asp Ile Arg Lys Ala Val Ser Leu Gly
    210                 215                 220

Val Asn Lys Ile Asn Ile Asp Thr Asp Ile Arg Gln Ala Phe Ala Ala
225                 230                 235                 240

Arg Leu Arg Glu Leu Leu Lys Asn Asp Glu Glu Val Tyr Asp Pro Arg
                245                 250                 255

Lys Ile Leu Gly Pro Cys Lys Glu Ala Met Lys Glu Val Ile Lys Asn
            260                 265                 270

Lys Met Arg Met Phe Gly Ser Glu Gly Arg Ala
        275                 280

<210> SEQ ID NO 59
<211> LENGTH: 400
<212> TYPE: PRT
<213> ORGANISM: T. saccharolyticum

<400> SEQUENCE: 59

Met Ile Thr Gly Asp Gln Leu Leu Ile Lys Gln Ile Asn Lys Ser Ile
1               5                   10                  15

Val Leu Asn Thr Ile Arg Lys Lys Gly Leu Ile Ser Arg Ala Asp Leu
            20                  25                  30

Ala Asn Ile Thr Gly Leu Asn Lys Ser Thr Val Ser Ser Leu Val Asp
        35                  40                  45

Glu Leu Ile Lys Glu Gly Phe Val Glu Glu Gly Pro Gly Glu Ser
    50                  55                  60

Lys Gly Gly Arg Lys Pro Ile Met Leu Met Ile Asn Ser Leu Ala Gly
65                  70                  75                  80

Cys Val Ile Gly Val Asp Leu Asp Val Asn Tyr Ile Leu Val Ile Leu
                85                  90                  95

Thr Asp Ile Leu Ala Asn Ile Leu Trp Gln Lys Arg Ile Asn Leu Lys
            100                 105                 110

Leu Gly Glu Ser Lys Glu Asp Ile Ile Ser Lys Met Leu Glu Leu Ile
        115                 120                 125

Asp Glu Ala Ile Lys Asn Ser Pro Asn Thr Val Lys Gly Ile Leu Gly
    130                 135                 140

Ile Gly Ile Gly Val Pro Gly Ile Thr Asp Tyr Lys Arg Gly Val Val
145                 150                 155                 160

Leu Lys Ala Pro Asn Leu Asn Trp Glu Asn Val Glu Leu Lys Lys Met
                165                 170                 175

Val Glu Glu Arg Phe Asn Leu Lys Val Tyr Ile Asp Asn Glu Ala Asn
            180                 185                 190

Thr Gly Ala Ile Gly Glu Lys Trp Phe Gly Gly Gly Arg Asn Ala Lys
        195                 200                 205
```

-continued

```
Asn Phe Val Tyr Val Ser Ala Gly Ile Gly Ile Gly Thr Gly Ile Ile
            210                 215                 220

Ile Asn Asn Glu Leu Tyr Arg Gly Ser Asn Gly Leu Ala Gly Glu Met
225                 230                 235                 240

Gly His Met Thr Ile Asp Ile Asn Asp His Met Cys Ser Cys Gly Asn
                245                 250                 255

Arg Gly Cys Trp Glu Asn Tyr Ala Ser Glu Lys Ser Leu Phe Arg Tyr
            260                 265                 270

Ile Lys Glu Arg Leu Glu Ala Gly Gln Glu Asp Asp Phe Ile Asp Ser
            275                 280                 285

Glu Asn Ile Asp Ser Leu Asp Ile Asn Asp Ile Ala Gly Tyr Ala Glu
            290                 295                 300

Leu Gly Ser Lys Leu Ala Ile Asp Ala Ile Asn Glu Ile Ser Lys Asn
305                 310                 315                 320

Leu Ser Val Gly Ile Val Asn Ile Val Asn Thr Phe Asn Pro Asp Leu
                325                 330                 335

Val Leu Ile Gly Asn Thr Leu Ser Ala Ile Gly Asp Met Leu Ile Asp
                340                 345                 350

Ala Val Lys Glu Tyr Val Arg Glu Lys Cys Leu Val Ser Arg Tyr Asn
            355                 360                 365

Asp Ile Ala Ile Glu Ile Ser Lys Leu Gly Met Leu Glu Arg Ala Ile
            370                 375                 380

Gly Ala Val Thr Leu Val Ile Ser Glu Val Phe Ser Tyr Pro Gly Leu
385                 390                 395                 400

<210> SEQ ID NO 60
<211> LENGTH: 451
<212> TYPE: PRT
<213> ORGANISM: T. saccharolyticum

<400> SEQUENCE: 60

Met Thr Asn Val Leu Asn Phe Asp Tyr Ser Asn Ala Leu Asn Phe Val
1               5                   10                  15

Asn Glu His Glu Ile Ser Tyr Leu Glu Lys Gln Ala Leu Leu Ser Leu
            20                  25                  30

Asp Met Val Leu Asn Lys Thr Ala Gln Gly Ser Asp Phe Leu Gly Trp
        35                  40                  45

Val Asp Leu Pro Lys Asp Tyr Asp Lys Glu Glu Phe Ala Arg Ile Lys
    50                  55                  60

Lys Ala Ala Glu Lys Ile Lys Ser Asp Ser Asp Ala Leu Val Val Ile
65                  70                  75                  80

Gly Ile Gly Gly Ser Tyr Leu Gly Ala Arg Ala Ala Ile Glu Met Leu
                85                  90                  95

Thr His Ser Phe Tyr Asn Val Leu Pro Gln Ser Val Arg Lys Ala Pro
            100                 105                 110

Glu Ile Tyr Phe Ala Gly Asn Ser Ile Ser Ser Thr Tyr Leu Gln Asp
        115                 120                 125

Leu Leu Glu Ile Leu Glu Gly Lys Asp Val Ser Ile Asn Val Ile Ser
130                 135                 140

Lys Ser Gly Thr Thr Thr Glu Pro Ala Ile Ala Phe Arg Val Phe Arg
145                 150                 155                 160

Asp Phe Leu Glu Lys Lys Tyr Gly Lys Glu Ala Lys Ser Arg Ile
            165                 170                 175

Tyr Val Thr Thr Asp Arg Gln Lys Gly Ala Leu Lys Lys Leu Ala Asp
```

```
            180                 185                 190
Glu Glu Gly Tyr Glu Thr Phe Val Ile Pro Asp Asp Val Gly Gly Arg
        195                 200                 205

Tyr Ser Val Leu Thr Ala Val Gly Leu Leu Pro Ile Ala Ala Ala Gly
        210                 215                 220

Ile Asp Ile Asp Glu Met Met Lys Gly Ala Tyr Asp Ala Ser Ile Val
225                 230                 235                 240

Phe Lys Lys Pro Asp Ile Lys Glu Asn Leu Ser Met Gln Tyr Ala Val
                245                 250                 255

Leu Arg Asn Ala Leu Tyr Arg Lys Gly Lys Ser Val Glu Ile Leu Val
            260                 265                 270

Asn Tyr Glu Pro Arg Leu His Tyr Phe Ser Glu Trp Trp Lys Gln Leu
        275                 280                 285

Tyr Gly Glu Ser Glu Gly Lys Asp His Lys Gly Ile Tyr Pro Ala Ser
        290                 295                 300

Val Asp Phe Ser Thr Asp Leu His Ser Met Gly Gln Phe Ile Gln Asp
305                 310                 315                 320

Gly Ser Arg Ile Met Phe Glu Thr Val Ile Asn Val Glu Lys Pro Leu
                325                 330                 335

Lys Glu Ile Thr Ile Asn Glu Asp Lys Asp Asn Val Asp Gly Leu Asn
            340                 345                 350

Phe Leu Thr Gly Lys Thr Val Asp Leu Val Asn Lys Lys Ala Phe Glu
        355                 360                 365

Gly Thr Val Leu Ala His Asn Asp Gly Gly Val Pro Asn Leu Ile Val
        370                 375                 380

Asn Val Pro Glu Ile Ser Ala Tyr Asn Phe Gly Tyr Leu Val Tyr Phe
385                 390                 395                 400

Phe Glu Met Ala Cys Gly Ile Ser Gly Tyr Leu Asn Gly Val Asn Pro
                405                 410                 415

Phe Asp Gln Pro Gly Val Glu Ala Tyr Lys Lys Asn Met Phe Ala Leu
            420                 425                 430

Leu Gly Lys Pro Gly Tyr Glu Lys Glu Lys Glu Glu Leu Glu Lys Arg
        435                 440                 445

Leu Lys Arg
        450

<210> SEQ ID NO 61
<211> LENGTH: 372
<212> TYPE: PRT
<213> ORGANISM: T. saccharolyticum

<400> SEQUENCE: 61

Met Tyr Asn Ile Gln Leu Asp Ser Pro Asn Leu Gly Asp Lys Glu Lys
1               5                   10                  15

Asp Tyr Leu Val Lys Cys Ile Glu Ser Gly Tyr Val Ser Thr Val Gly
            20                  25                  30

Pro Phe Val Pro Glu Phe Glu Arg Arg Phe Ala Glu Phe Leu Asn Val
        35                  40                  45

Asn His Cys Val Ser Val Gln Ser Gly Thr Ala Ala Leu Tyr Met Ala
    50                  55                  60

Leu Tyr Glu Leu Gly Ile Lys Asp Gly Asp Glu Val Ile Val Pro Ala
65                  70                  75                  80

Ile Thr Phe Val Ala Thr Val Asn Pro Ile Val Tyr Cys Gly Ala Thr
                85                  90                  95
```

```
Pro Val Phe Val Asp Val Asp Lys Asp Thr Trp Asn Ile Asp Pro Lys
                100                 105                 110

Glu Ile Glu Lys Ala Ile Thr Pro Lys Thr Lys Ala Ile Ile Pro Val
            115                 120                 125

His Leu Tyr Gly Asn Pro Cys Asp Met Asp Lys Ile Met Glu Ile Ala
        130                 135                 140

Lys Glu Asn Asn Ile Tyr Val Ile Glu Asp Ala Thr Glu Ser Leu Gly
145                 150                 155                 160

Ala Leu Tyr Lys Gly Arg Met Thr Gly Thr Ile Gly His Ile Gly Cys
                165                 170                 175

Phe Ser Phe Asn Gly Asn Lys Val Ile Thr Gly Gly Gly Met
            180                 185                 190

Val Ala Ser Asn Asn Glu Asp Trp Val Ser His Ile Arg Phe Leu Val
        195                 200                 205

Asn Gln Ala Arg Asp Met Thr Gln Gly Tyr Phe His Thr Glu Ile Gly
        210                 215                 220

Phe Asn Tyr Arg Met Thr Asn Leu Glu Ala Ser Leu Gly Ile Ala Gln
225                 230                 235                 240

Leu Glu Arg Leu Ala Gly Phe Leu Glu Lys Lys Arg Met Tyr Phe Glu
                245                 250                 255

Ile Tyr Lys Lys Ile Phe Asn Gly Ile Glu Glu Ile Ser Leu Gln Thr
                260                 265                 270

Glu Tyr Glu Gly Ala Lys Ser Ser Asp Trp Leu Ser Ser Val Lys Ile
            275                 280                 285

Asp Cys Lys Lys Val Gly Met Thr Ile His Gln Ile Gln Asp Glu Leu
        290                 295                 300

Lys Arg Arg Gly Ile Pro Thr Arg Arg Ile Phe Asn Pro Ile Val Asp
305                 310                 315                 320

Leu Pro Pro Tyr Lys Lys Tyr Lys Lys Gly Ser Tyr Ser Asn Ser Tyr
                325                 330                 335

Glu Ile Tyr Glu Asn Gly Leu Asn Leu Pro Ser Ser Thr Leu Asn Thr
            340                 345                 350

Tyr Glu Asp Val Lys Tyr Val Ala Lys Thr Leu Leu Asp Ile Leu Ser
        355                 360                 365

Ile Lys Lys Arg
    370

<210> SEQ ID NO 62
<211> LENGTH: 253
<212> TYPE: PRT
<213> ORGANISM: T. saccharolyticum

<400> SEQUENCE: 62

Met Leu Ala Ile Glu Arg Arg Lys Arg Ile Met Arg Leu Ile Gln Glu
1               5                   10                  15

Asn Gln Ser Val Leu Val Pro Glu Leu Ser Lys Leu Phe Asn Val Thr
            20                  25                  30

Glu Glu Thr Ile Arg Arg Asp Leu Glu Lys Leu Glu Ala Glu Gly Leu
        35                  40                  45

Leu Lys Arg Thr Tyr Gly Gly Ala Val Ile Asn Glu Asn Ser Ser Ala
    50                  55                  60

Asp Ile Pro Leu Asn Ile Arg Glu Ile Thr Asn Ile Glu Ser Lys Gln
65                  70                  75                  80

Ala Ile Ser Met Lys Val Ala Glu Tyr Ile Glu Asp Gly Asp Thr Leu
                85                  90                  95
```

```
Leu Leu Asp Ser Ser Thr Val Leu Gln Val Ala Lys Gln Leu Lys
                100                 105                 110

Phe Lys Lys Lys Leu Thr Val Ile Thr Asn Ser Glu Lys Ile Ile Leu
            115                 120                 125

Glu Leu Ala Asn Ala Lys Asp Cys Lys Val Ile Ser Thr Gly Gly Val
130                 135                 140

Leu Lys Gln Asn Ser Met Ser Leu Ile Gly Asn Phe Ala Glu Asp Met
145                 150                 155                 160

Ile Lys Asn Phe Cys Val Asp Lys Ala Ile Ile Ser Ser Lys Gly Phe
                165                 170                 175

Asp Met Thr Asn Gly Ile Thr Glu Ser Asn Glu Met Glu Ala Glu Ile
            180                 185                 190

Lys Lys Ala Met Ala Asn Ser Ala Glu Lys Val Phe Leu Leu Leu Asp
        195                 200                 205

His Asn Lys Phe Asp Lys Ser Ser Phe Val Lys Met Phe Asp Leu Asp
    210                 215                 220

Lys Ile Asp Tyr Leu Phe Thr Asp Arg Lys Leu Ser Leu Glu Trp Glu
225                 230                 235                 240

Glu Phe Leu Lys Lys His Asn Ile Asp Leu Ile Tyr Cys
                245                 250
```

<210> SEQ ID NO 63
<211> LENGTH: 761
<212> TYPE: DNA
<213> ORGANISM: T. saccharolyticum

<400> SEQUENCE: 63

```
atgcttgcga tagaacgaag gaagaggata atgaggctta tacaggaaaa tcaaagcgtt      60
tggtgcctga gttaagtaaa ttgtttaatg tgacagagga aactataagg agagatttag     120
agaaacttga agcagaaggg cttttaaaga ggacttatgg tggtgctgtt ataaatgaaa     180
attcaagtgc tgatatcccc ttaaatataa gggaaataac gaatatagaa agcaaacagg     240
ccataagtat gaaggttgcc gaatacattg aagatggtga tacacttttg cttgattcaa     300
gctctacagt tcttcaagta gcaaagcaat taaaattcaa aaagaagctt acagtcataa     360
caaattcgga aaagataata ttagaattag caaatgcgaa agattgcaaa gtcatttcta     420
caggaggagt attgaagcaa aattctatgt cgctaattgg aaatttcgcg gaagatatga     480
taaaaaattt ctgtgtagat aaagccataa tatcatcaaa aggttttgac atgacaaatg     540
gcattacaga gtcaaacgaa atggaagctg aaataaaaaa agccatggcc aactcggcag     600
aaaaagtgtt tttacttctt gatcacaaca aatttgacaa gtcatcgttc gtcaagatgt     660
ttgacttaga taaatcgat tatctatttta ccgataaaa gctgtcttta gaatgggaag     720
aattcttgaa aaacacaat attgatttaa tctattgtta g                        761
```

<210> SEQ ID NO 64
<211> LENGTH: 259
<212> TYPE: PRT
<213> ORGANISM: T. saccharolyticum

<400> SEQUENCE: 64

```
Val Tyr Ser Glu Tyr Glu Val Lys Lys Gln Ile Cys Glu Ile Gly Lys
1               5                   10                  15

Arg Ile Tyr Met Asn Gly Phe Val Ala Ala Asn Asp Gly Asn Ile Thr
            20                  25                  30
```

Val Arg Ile Gly Glu Asn Glu Ile Thr Thr Pro Thr Gly Val Ser
        35                  40                  45

Lys Gly Phe Met Thr Pro Asp Met Leu Leu Asn Ile Asn Leu Asn Gly
 50                  55                  60

Glu Val Leu Lys Ser Ser Gly Asp Tyr Lys Pro Ser Thr Glu Ile Lys
 65                  70                  75                  80

Met His Leu Arg Val Tyr Arg Glu Arg Pro Asp Val Lys Ser Val Ile
                 85                  90                  95

His Ala His Pro Pro Phe Gly Thr Gly Phe Ala Ile Val Gly Ile Pro
                100                 105                 110

Leu Thr Lys Pro Ile Met Pro Glu Ala Val Ile Ser Leu Gly Cys Val
                115                 120                 125

Pro Ile Ala Glu Tyr Gly Thr Pro Ser Thr Glu Glu Leu Pro Asp Ala
                130                 135                 140

Val Ser Lys Tyr Leu Gln Asn Tyr Asp Ala Leu Leu Leu Glu Asn His
145                 150                 155                 160

Gly Ala Leu Thr Tyr Gly Pro Asp Leu Ile Ser Ala Tyr Tyr Lys Met
                165                 170                 175

Glu Ser Leu Glu Phe Tyr Ala Lys Leu Thr Phe Ile Ser Thr Leu Leu
                180                 185                 190

Gly Gly Pro Lys Glu Leu Ser Asp Ser Gln Val Glu Lys Leu Tyr Glu
                195                 200                 205

Ile Arg Arg Lys Phe Gly Leu Lys Gly Arg His Pro Gly Asp Leu Cys
                210                 215                 220

Ser Thr Leu Gly Cys Ser Thr Asn Ser Ala Lys Ser Asn Asp Asp Asp
225                 230                 235                 240

Ile Ser Glu Leu Val Asn Val Ile Thr Lys Lys Val Leu Glu Gln Leu
                245                 250                 255

Lys Tyr Asn

<210> SEQ ID NO 65
<211> LENGTH: 780
<212> TYPE: DNA
<213> ORGANISM: T. saccharolyticum

<400> SEQUENCE: 65
gtgtattctg aatatgaggt aaaaaaacag atctgcgaaa taggaaagag aatctacatg      60
aatgggtttg tggcagcgaa tgacggcaat atcaccgtta ggattggtga aaatgaaata     120
ataacgacgc ctaccggtgt cagcaaaggt ttcatgactc agacatgct attaaatatt      180 aatttaaacg gtgaagtatt aaaatcttca ggcgactaca aaccgtccac agaaataaag     240
atgcatctta gagtctatag agaaaggcca gatgtcaaat cagtcataca tgcacatcca     300
ccatttggca caggttttgc tattgtaggg atcccgctta caaagccaat aatgccagaa     360
gcagttatat ctttaggctg tgtgccgata gccgaatacg ggacgccttc tacagaagag     420
ctgccagatg ccgtctctaa atatttgcaa aattacgatg cgcttttatt agaaaatcat     480
ggtgcgttga catacggtcc tgatttaatt agcgcatact acaagatgga atcacttgaa     540
ttttacgcaa aattgacatt tatttctaca cttctcggag gtccaaaaga attatcagat     600
agccaagtag aaaagcttta tgaaattagg agaaaattcg gtttaaaagg aagacatcca     660
ggcgatttgt gcagtacatt aggatgcagc acaaattctg caaaatcgaa tgatgatgac     720
atttctgaac ttgtgaatgt tatcactaag aaagtattag aacaattgaa atacaattaa     780

```
<210> SEQ ID NO 66
<211> LENGTH: 554
<212> TYPE: PRT
<213> ORGANISM: T. saccharolyticum

<400> SEQUENCE: 66

Met Lys His Ser Lys Arg Phe Glu Val Leu Gly Lys Arg Pro Val Asn
1               5                   10                  15

Gln Asp Gly Phe Ile Asn Glu Trp Pro Glu Lys Gly Phe Ile Ala Met
            20                  25                  30

Cys Ser Pro Asn Asp Pro Lys Pro Ser Ile Lys Ile Glu Asn Asp Lys
        35                  40                  45

Ile Val Glu Met Asp Gly Lys Arg Arg Glu Asp Phe Asp Phe Ile Asp
50                  55                  60

Leu Phe Ile Ala Asp His Ala Ile Asn Ile Tyr Gln Ala Glu Lys Ser
65                  70                  75                  80

Met Lys Met Asn Ser Leu Asp Ile Ala Lys Met Leu Val Asp Ile Asn
                85                  90                  95

Val Glu Arg Lys Thr Ile Ile Lys Val Val Ser Gly Leu Thr Pro Ala
            100                 105                 110

Lys Ile Met Glu Val Val Asn His Leu Asn Val Glu Met Met Met
        115                 120                 125

Ala Met Gln Lys Met Arg Ala Arg Lys Ile Pro Ala Asn Gln Ser His
130                 135                 140

Ile Thr Asn Leu Lys Asp Asn Pro Val Gln Ile Ala Ala Asp Ala Ala
145                 150                 155                 160

Glu Cys Ala Leu Arg Gly Phe Arg Glu Glu Thr Thr Val Gly Val
                165                 170                 175

Thr Lys Tyr Ala Pro Phe Asn Ala Ile Ala Leu Leu Ile Gly Ser Gln
            180                 185                 190

Ala Leu Lys Arg Gly Val Leu Thr Gln Cys Ala Val Glu Glu Ala Thr
        195                 200                 205

Glu Leu Glu Leu Gly Met Arg Gly Phe Thr Thr Tyr Ala Glu Thr Ile
210                 215                 220

Ser Val Tyr Gly Thr Glu Ser Val Phe Ile Asp Gly Asp Asp Thr Pro
225                 230                 235                 240

Tyr Ser Lys Ala Phe Leu Ala Ser Ala Tyr Ala Ser Arg Gly Leu Lys
                245                 250                 255

Met Arg Phe Thr Ser Gly Thr Gly Ser Glu Val Leu Met Gly Asn Ala
            260                 265                 270

Glu Gly Lys Ser Met Leu Tyr Leu Glu Ile Arg Cys Ile Met Val Thr
        275                 280                 285

Lys Gly Ala Gly Val Gln Gly Leu Gln Asn Gly Ala Ile Ser Cys Ile
290                 295                 300

Gly Ile Thr Ser Ser Val Pro Ser Gly Ile Arg Ala Val Leu Ala Glu
305                 310                 315                 320

Asn Leu Ile Ala Ser Met Leu Asp Leu Glu Val Ala Ser Gly Asn Asp
                325                 330                 335

Gln Thr Phe Thr His Ser Asp Ile Arg Arg Thr Ala Arg Thr Met Met
            340                 345                 350

Gln Phe Leu Pro Gly Thr Asp Phe Ile Phe Ser Gly Tyr Ser Gly Thr
        355                 360                 365

Pro Asn Tyr Asp Asn Met Phe Ala Gly Ser Asn Phe Asp Ala Glu Asp
370                 375                 380
```

```
Phe Asp Asp Tyr Asn Val Leu Gln Arg Asp Leu Met Val Asp Gly Gly
385                 390                 395                 400

Leu Arg Pro Val Lys Glu Glu Asp Val Val Glu Val Arg Arg Lys Ala
            405                 410                 415

Ala Lys Ala Leu Gln Asp Val Phe Arg Glu Leu Asn Leu Gly Val Val
        420                 425                 430

Thr Asp Glu Glu Val Glu Ala Ala Tyr Ala His Gly Ser Lys Asp
    435                 440                 445

Met Pro Glu Arg Asp Val Leu Ser Asp Leu Glu Ser Ile Asp Glu Met
    450                 455                 460

Met Lys Arg Gly Ile Thr Gly Ile Asp Ile Val Lys Ala Leu Tyr Arg
465                 470                 475                 480

Ser Gly His Glu Asp Ile Ala Glu Asn Ile Leu Asn Met Leu Lys Gln
            485                 490                 495

Arg Ile Ser Gly Asp Tyr Leu Gln Thr Ser Ala Ile Leu Asp Glu Asp
            500                 505                 510

Phe Asn Val Ile Ser Ala Ile Asn Cys Pro Asn Asp Tyr Leu Gly Pro
        515                 520                 525

Gly Thr Gly Tyr Arg Ile Asp Lys Asp Arg Trp Glu Glu Ile Lys Asn
    530                 535                 540

Ile Pro Tyr Thr Ile Asn Pro Asp Asn Leu
545                 550

<210> SEQ ID NO 67
<211> LENGTH: 1665
<212> TYPE: DNA
<213> ORGANISM: T. saccharolyticum

<400> SEQUENCE: 67
atgaaacatt ctaagcgatt tgaggttctc ggcaaaagac ctgtaaatca ggatggattt     60
ataaatgaat ggccagaaaa aggcttcata gcaatgtgta gtcccaatga tcctaagcca    120
tcaataaaga ttgaaaacga caagatcgtt gagatggatg ggaagagaag agaagacttt    180
gattttatag atttattcat agctgatcac gctataaata tttatcaggc tgagaaatcc    240
atgaaaatga actcgcttga tatagccaaa atgcttgtag atataaatgt agagagaaag    300
actataataa aagtagtttc gggacttaca cctgccaaaa taatggaagt tgtaaatcat    360
cttaatgtcg ttgaaatgat gatggctatg cagaaaatgc gagcaagaaa gattccggct    420
aatcaatcac atattacaaa tcttaaagat aatcctgtgc agattgcagc ggatgctgcc    480
gaatgtgctt taagaggttt tagggaagaa gagaccaccg taggagtgac aaaatatgct    540
ccgtttaatg caatagcgtt attgataggg tctcaggcat taaaaagagg cgtgcttact    600
caatgtgctt tgaggaggc gacggaactt gaattaggca tgagggggatt taccacatac    660 gctgagacta tatctgtttta tggaactgaa agtgttttta tagatggtga cgatacacct    720
tactccaaag cattccttgc ttctgcttat gcgtcaagag gattgaaaat gaggtttacg    780
tcaggtacag gttcagaagt tcttatggga aatgcagagg gtaaatcgat gttgtacctg    840
gaaatcaggt gcatcatggt tacaaaaggt gcaggagtgc aggggcttca aaatggtgca    900
ataagctgta taggcataac tagctcagtt ccttcaggta aagggcggt gctggctgaa    960 aaccttatag catctatgct tgatttagag gtagcatcag gcaatgatca gactttaca   1020 cattcagaca taagaaggac agcaaggact atgatgcagt ttttacccgg tactgatttc   1080
atattttcag gttacagtgg aacgcctaat tatgacaata tgtttgcagg ttccaatttt   1140
```

-continued

```
gatgcagaag attttgatga ctacaatgta ctgcaaaggg atttaatggt agatggaggg      1200
ttaaggcctg taaaagaaga agatgtggta gaagtgaggc gaaaggcagc taaagctttg      1260
caggatgtat ttagagagtt aaatcttgga gtagttacag atgaagaagt agaagcagca      1320
gcatatgcac acggcagcaa agatatgcct gaaagagatg ttttgtctga ccttgaatca      1380
atcgatgaga tgatgaaaag agggattaca ggcattgaca tcgtaaaggc tttatataga      1440
tctggacatg aggatatagc ggaaaacatt ttaaacatgt taaaacagcg catatctgga      1500
gactatttgc agacatcagc tattcttgat gaagatttta atgttataag cgccataaat      1560
tgtccaaatg attacttagg acctggaaca ggatatagga ttgataaaga tagatgggaa      1620
gagataaaga atattcctta caccattaat cctgacaatt tgtaa                     1665
```

<210> SEQ ID NO 68
<211> LENGTH: 208
<212> TYPE: PRT
<213> ORGANISM: T. saccharolyticum

<400> SEQUENCE: 68

```
Met Tyr Val Asp Glu Glu Leu Leu Lys Glu Ile Thr Lys Arg Val Ile
1               5                   10                  15

Glu Glu Leu Asn Asn Lys His Lys Thr Asp Asn Val Pro Ser Tyr Phe
            20                  25                  30

Ile Glu Asn Gly Val Ala Tyr Lys Gly Lys Asn Ile Glu Glu Val Val
        35                  40                  45

Ile Gly Val Gly Pro Ala Phe Gly Lys His Ile Lys Lys Thr Ile Asn
    50                  55                  60

Gly Leu Asp His Arg Asp Val Ile Lys Glu Ile Ile Ala Gly Ile Glu
65                  70                  75                  80

Glu Glu Gly Met Val His Arg Ile Val Arg Val Leu Lys Thr Ser Asp
                85                  90                  95

Val Ala Phe Ile Gly Lys Glu Ala Ala Leu Leu Ser Gly Ser Gly Ile
            100                 105                 110

Gly Ile Gly Ile Gln Ser Lys Gly Thr Thr Val Ile His Gln Lys Asp
        115                 120                 125

Leu Tyr Pro Leu Ser Asn Leu Glu Leu Phe Pro Gln Ala Pro Leu Leu
    130                 135                 140

Asn Leu Glu Leu Tyr Arg Glu Ile Gly Lys Asn Ala Ala Arg Tyr Ala
145                 150                 155                 160

Lys Gly Met Met Val Lys Pro Ile Leu Ile Gln Asn Asp Tyr Met Val
                165                 170                 175

Arg Pro Lys Tyr Gln Val Lys Ala Ala Ile Met His Ile Lys Glu Thr
            180                 185                 190

Glu Lys Ile Leu Lys Asn Ala Gln Ser Ile Gln Leu Thr Ile Asp Leu
        195                 200                 205
```

<210> SEQ ID NO 69
<211> LENGTH: 627
<212> TYPE: DNA
<213> ORGANISM: T. saccharolyticum

<400> SEQUENCE: 69

```
atgtacgtag atgaagaact gttaaaagaa attactaaac gtgttataga agaattaaat        60
aataagcata aaactgataa tgtgccttcg tattttattg aaaatggagt tgcctataag       120
ggtaaaaata tagaggaagt cgtcattggt gttgggcctg catttggaaa gcatataaaa       180
```

```
aagactataa atggccttga ccatagagat gtcataaaag aaataattgc aggcatcgaa    240
gaagaaggta tggttcatag aattgtaaga gttctaaaga cttctgatgt ggcgttcata    300
ggcaaagaag ctgcttttatt aagcggatcg ggaataggca taggcataca atcaaaaggt   360
actacagtga ttcatcaaaa agatttatat cctttaagca atttagaact gtttccacaa    420
gctccactgc taaatttaga attatacagg gaaataggca aaaatgcggc gagatatgct    480
aaaggcatga tggtaaagcc tattttgatt caaaatgatt acatggtgag acctaaatac    540
caagtgaaag ctgctataat gcatataaaa gagacggaaa agatattgaa aaatgctcaa    600
tcaatccaat tgacgataga cttgtaa                                       627
```

<210> SEQ ID NO 70
<211> LENGTH: 132
<212> TYPE: PRT
<213> ORGANISM: T. saccharolyticum

<400> SEQUENCE: 70

```
Met Glu Glu Tyr Pro Leu Ser Lys Ser Ala Phe Asp Lys Leu Val Thr
 1               5                  10                  15

Lys Thr Gly Lys His Leu Asn Glu Ile Asn Ile Glu Asn Val Met Lys
            20                  25                  30

Gly Asn Val Lys Pro Asp Asp Ile Lys Ile Ser Lys Glu Val Leu Leu
        35                  40                  45

Met Gln Gly Gln Ile Ala Glu Arg Tyr Gly Arg His Gln Met Lys Glu
    50                  55                  60

Asn Phe Thr Arg Ala Ser Glu Leu Thr Asp Val Pro Asp Glu Lys Ile
65                  70                  75                  80

Leu Glu Ile Tyr Glu Ser Leu Arg Pro Phe Arg Ser Thr Lys Glu Glu
                85                  90                  95

Leu Ile Asn Leu Ala Tyr Glu Leu Arg Asp Lys Tyr Asn Ala Ile Asn
            100                 105                 110

Cys Ala Asn Leu Ile Leu Glu Ala Ala Glu Val Tyr Glu Lys Arg Asn
        115                 120                 125

Ile Leu Lys Thr
    130
```

<210> SEQ ID NO 71
<211> LENGTH: 399
<212> TYPE: DNA
<213> ORGANISM: T. saccharolyticum

<400> SEQUENCE: 71

```
atggaagaat atccgctatc aaaaagtgct tttgataaat tggtgacaaa aacaggcaaa    60
catttgaatg aaataaatat tgaaaatgta atgaagggaa acgtaaaacc cgatgatatc    120
aagatatcca agaagtgctc tttaatgcaa gggcaaattg cagaaagata cggcaggcat    180
cagatgaagg agaatttcac aagagcatcg gagcttacag atgttccaga tgaaaagatt    240
ttggaaatat atgagagctt aaggccgttt agatctacaa aggaagagct tataaatctt    300
gcctatgaat taagagataa gtacaatgcc attaactgtg caaacttgat acttgaggct    360
gctgaagtat atgaaaaaag aaatatttttg aaaacttaa                         399
```

<210> SEQ ID NO 72
<211> LENGTH: 605
<212> TYPE: PRT
<213> ORGANISM: T. saccharolyticum

<400> SEQUENCE: 72

```
Met Lys Leu Ile Ala Gly Val Asp Ile Gly Asn Ser Thr Thr Glu Val
1               5                   10                  15

Cys Ile Ala Ala Ile Lys Asp Asp Asn Thr Leu Glu Phe Leu Ser Ser
            20                  25                  30

Ser Leu Thr Ala Thr Thr Gly Val Lys Gly Thr Val Asp Asn Val Thr
        35                  40                  45

Gly Val Ile Asn Gly Leu Thr Glu Ala Leu Lys Lys Ile Gly Lys Asn
    50                  55                  60

Ile Arg Asp Leu Ser Leu Ile Arg Ile Asn Glu Ala Ala Pro Val Val
65                  70                  75                  80

Cys Gly Ala Ala Met Glu Thr Ile Thr Glu Thr Val Ile Thr Gly Ser
                85                  90                  95

Thr Met Ile Gly His Asn Pro Ser Thr Pro Gly Gly Val Gly Leu Gly
            100                 105                 110

Val Gly Glu Ile Ile His Ile Asn Asp Leu Ala Asp Ala Thr Lys Gly
        115                 120                 125

Lys Asn Tyr Ile Val Val Ile Pro Lys Glu Ile Gly Tyr Glu Glu Ala
    130                 135                 140

Ser Ile Met Ile Asn Lys Ser Phe Glu Asn Asp Ile Asp Val Lys Ala
145                 150                 155                 160

Ala Ile Val Gln Ser Asp Glu Ala Val Leu Ile Asn Asn Arg Leu Lys
                165                 170                 175

Lys Ile Ile Pro Ile Val Asp Glu Val Arg Gln Ile Glu Lys Ile Pro
            180                 185                 190

Ser Gly Val Val Ala Ala Val Glu Val Ala Pro Glu Gly Lys Ser Ile
        195                 200                 205

Ser Thr Leu Ser Asn Pro Tyr Gly Ile Ala Thr Ile Phe Asp Leu Thr
210                 215                 220

Pro Glu Glu Thr Lys Tyr Val Ile Pro Ile Ser Lys Ser Leu Met Gly
225                 230                 235                 240

Lys Lys Ser Ala Val Val Ile Lys Thr Pro Arg Gly Gln Val Lys Glu
                245                 250                 255

Arg Ile Ile Pro Ala Gly Asn Leu Leu Ile Met Gly Pro Thr Met Ser
            260                 265                 270

Ser Lys Val Ser Val Asp Ser Gly Ala Glu Ala Ile Met Glu Ser Val
        275                 280                 285

Glu Glu Val Gly Thr Ile Asp Asp Val Glu Gly Glu Glu Asn Thr Asn
    290                 295                 300

Val Gly Asn Met Ile Lys Asn Leu Lys Asn Lys Met Ala Asn Ile Thr
305                 310                 315                 320

Gly Gln Lys Val Asp Lys Ile Lys Ile Lys Asp Ile Phe Ala Val Asp
                325                 330                 335

Thr Thr Val Pro Val Lys Val Glu Gly Gly Leu Ala Gly Glu Thr Ser
            340                 345                 350

Met Glu Lys Ala Val Val Leu Ala Ala Met Val Lys Thr Asp Thr Leu
        355                 360                 365

Pro Met Ile Glu Ile Ala Glu Lys Leu Gln Arg Lys Leu Gly Val Phe
370                 375                 380

Val Lys Ile Ala Gly Val Glu Ala Val Met Ala Thr Leu Gly Ala Leu
385                 390                 395                 400

Thr Thr Pro Gly Thr Lys Leu Pro Leu Ala Ile Leu Asp Ile Gly Gly
            405                 410                 415
```

```
Gly Ser Thr Asp Ala Ala Leu Ile Asp Glu Lys Gly Ile Val Lys Ser
            420                 425                 430

Ile His Met Ala Gly Ala Gly Glu Leu Val Thr Met Leu Ile Asp Ser
        435                 440                 445

Glu Leu Gly Leu Asn Asp Arg Tyr Leu Ser Glu Ile Lys Arg Asn
    450                 455                 460

Pro Ile Gly Lys Val Glu Ser Leu Phe His Ile Arg Met Glu Asn Arg
465                 470                 475                 480

Glu Ile Lys Phe Phe Asp Lys Pro Leu Asn Pro Arg Tyr Tyr Gly Arg
                485                 490                 495

Ile Val Ile Leu Lys Glu Asn Asp Met Ile Pro Val Phe Lys Glu Asp
            500                 505                 510

Leu Thr Met Glu Lys Ile Ile Tyr Val Arg Arg Gln Ala Lys Asp Lys
        515                 520                 525

Val Phe Val Lys Asn Ala Ile Arg Ala Leu Lys Lys Ile Ala Pro Glu
    530                 535                 540

Asn Asn Leu Arg Arg Ile Pro Asn Val Val Leu Val Gly Gly Ser Ala
545                 550                 555                 560

Leu Asp Phe Glu Ile Pro Glu Met Ile Leu Ser Glu Leu Ser Lys Tyr
                565                 570                 575

Lys Ile Ile Ala Gly Arg Gly Asn Ile Arg Lys Ile Glu Gly Pro Arg
            580                 585                 590

Asn Ala Val Ala Thr Gly Leu Val Met Ser Tyr Leu Gly
        595                 600                 605

<210> SEQ ID NO 73
<211> LENGTH: 1817
<212> TYPE: DNA
<213> ORGANISM: T. saccharolyticum

<400> SEQUENCE: 73
atgaaactca tagcaggtgt tgatattggc aattctacaa cagaagtgtg tatagccgct      60
attaaagatg acaatacatt agaattttta agcagttcct tgacagctac gacaggtgta    120
aaaggcactg tggataatgt gacaggggtt attaatggat tgactgaggc actaaaaaaa    180
attggcaaga atattaggga tttaagcctc attagaatca atgaagccgc cccagttgtc    240
tgtggtgctg ctatggagac aataacggaa actgttatca ctggttcgac tatgataggt    300
cataatccat ccacgccggg tggtgtcgga cttggagtag cgagataat acatataaat     360 gatttagctg atgctactaa aggcaaaaat tacattgtgg ttatacctaa ggagattggc    420
tatgaagaag cttcaataat gataaacaaa tcttttgaaa acgatattga tgtaaaagct    480
gctatagttc aaagcgatga agcagtttta atcaacaaca ggcttaaaaa gattatacca    540
attgttgacg aagtaaggca gatagaaaag attccatcgg tgttgtagc ggctgtagag     600 gtggcaccag aaggcaagtc cataagcacg ttatcaaatc cttatggtat cgcaacaata    660
tttgacttaa ctccagaaga gacaaagtat gtcataccga tttcgaaaag tttgatgggg    720
aaaaagtcag cagttgtcat aaaaacaccg aggggacaag tgaaagaaag aataattccg    780
gctggtaatc tcttaatcat ggggcctact atgtcatcaa agtaagtgt tgattctggt     840 gctgaagcta taatggaatc agttgaagaa gtcggcacaa ttgatgacgt agaaggtgaa    900
gaaaatacaa atgttgggaa tatgataaaa aatctaaaaa acaagatggc aaatataact    960
gggcaaaaag tagataagat aaagattaaa gatatcttcg ctgttgatac gacagtccct   1020
```

```
gttaaagtag agggcggact tgctggtgag acttcaatgg aaaaagcagt cgtgttggcg    1080
gctatggtaa agacagatac gcttcgatga tagaaattgc agaaaagctt caaagaaagt    1140
tgggtgtatt tgtaaaaata gctggagtag aagctgtgat ggctacatta ggtgcgctta    1200
caactccagg cacaaagttg ccacttgcaa tactggatat cggtggggt tctacagatg     1260 cagctttgat tgatgaaaaa ggcattgtaa aatctataca catggcaggt gctggagaat    1320
tagtcacaat gcttattgat tcagaattag ggttaaatga tagatatttg tctgaagaaa    1380
taaagagaaa tccgattgga aaagttgaaa gcctatttca cataagaatg gaaaataggg    1440
agataaagtt ttttgacaaa cctttaaatc ctcgatatta cggtaggatc gtaattttaa    1500
aagaaaatga catgatccct gtatttaaag aagatttgac aatggaaaag attatttacg    1560
tgcgaagaca agcgaaggat aaagttttcg ttaaaaatgc tattagagct ttgaaaaaaa    1620
ttgctccgga aaataattta aggcgaatac caaatgtagt cttggttggc ggttctgctt    1680
tggactttga aattccagag atgattttat cagagctatc aaaatacaaa atcatagcag    1740
gcagagggaa tataagaaaa atcgaagggc caagaaatgc tgtagcgaca ggtcttgtga    1800
tgtcttattt agggtga                                                  1817
```

<210> SEQ ID NO 74
<211> LENGTH: 112
<212> TYPE: PRT
<213> ORGANISM: T. saccharolyticum

<400> SEQUENCE: 74

```
Met Glu Phe Ile Lys Pro Gln Ile Val Ile Phe Ala Asn Thr Glu Asn
1               5                   10                  15

Lys Tyr Ile Ile Asn Glu Val Ile Ala Gly Ile Glu Glu Glu Gly Ala
            20                  25                  30

Leu Tyr Arg Leu Ser Tyr Asn Glu Cys Ala Asp Val Met Lys Met Ala
        35                  40                  45

Tyr Asp Ala Ala Lys Ala Ser Val Leu Gly Ile Gly Ile Gly Ile Ser
    50                  55                  60

Gly Asp Leu Val Cys Leu His Ser Lys Asn Leu Glu Ile Asn Thr Pro
65                  70                  75                  80

Leu Ile Leu Ser Lys Thr Ser Glu Asn Phe Asp Pro Arg Leu Val Gly
                85                  90                  95

Cys Asn Ala Ala Lys Tyr Val Lys Gly Leu Pro Leu Lys Tyr Leu Asp
            100                 105                 110
```

<210> SEQ ID NO 75
<211> LENGTH: 339
<212> TYPE: DNA
<213> ORGANISM: T. saccharolyticum

<400> SEQUENCE: 75

```
atggaattta taaagcctca aatagtgatt tttgcaaata cagaaaacaa atatataata      60
aacgaggtta tagctggcat tgaagaagaa ggtgcattat atagattatc ttacaatgaa    120
tgtgctgatg ttatgaaaat ggcttatgat gcagcaaaag catctgtatt aggtatcgga    180
ataggcatat ctggagattt agtgtgtttg cactctaaaa acttggaaat caatacacct    240
ttgattcttt caaagacaag tgaaaacttt gatccacgac tcgttggatg caatgctgca    300
aaatatgtaa agggtttgcc acttaaatac ttagattag                           339
```

<210> SEQ ID NO 76

```
<211> LENGTH: 56
<212> TYPE: PRT
<213> ORGANISM: T. saccharolyticum

<400> SEQUENCE: 76
```

| | | | | | | | | | | | | | | |
|---|---|---|---|---|---|---|---|---|---|---|---|---|---|---|
|Met|Ser|Val|Tyr|Thr|Lys|Thr|Gly|Asp|Asp|Gly|Tyr|Thr|Leu|Leu|Leu|
|1| | | |5| | | | |10| | | | |15|

| | | | | | | | | | | | |
|---|---|---|---|---|---|---|---|---|---|---|---|
|Asn|Gly|Glu|Arg|Ile|Pro|Lys|Asp|Asp|Leu|Arg|Ile|Glu|Thr|Leu|Gly|
| | |20| | | |25| | | |30| | | | |

|Asn|Leu|Asp|Glu|Leu|Thr|Ser|Tyr|Leu|Gly|Phe|Ala|Lys|Ala|Gln|Ile|
| | |35| | | |40| | | |45| | | | |

|Asn|Asp|Asp|Ser|Ile|Lys|Lys|Arg|
| |50| | | |55| | |

```
<210> SEQ ID NO 77
<211> LENGTH: 171
<212> TYPE: DNA
<213> ORGANISM: T. saccharolyticum

<400> SEQUENCE: 77
atgagtgttt atactaaaac tggtgatgat ggttacacgt tgctattaaa tggagaaaga      60
attccaaagg acgatttgag aatagagaca ttgggaaatt tggatgaatt gacaagctat    120
ttaggatttg caaaagctca aataaatgat gattccataa aaagagata g              171

<210> SEQ ID NO 78
<211> LENGTH: 225
<212> TYPE: PRT
<213> ORGANISM: T. saccharolyticum

<400> SEQUENCE: 78
```

|Met|Val|Lys|Ile|Lys|Asn|Gly|Phe|Val|Ile|Pro|Gly|Lys|Asn|Gln|Ile|
|---|---|---|---|---|---|---|---|---|---|---|---|---|---|---|---|
|1| | | |5| | | | |10| | | | |15| |

|Ser|Ala|Leu|Leu|Asp|Ile|Val|Arg|Thr|Ile|Thr|Arg|Lys|Thr|Glu|Arg|
| | | |20| | | |25| | | |30| | | | |

|Ser|Leu|Ile|Lys|Val|Asp|Lys|Lys|Tyr|Pro|Val|Asn|Ile|Asn|Ser|Lys|
| | |35| | | |40| | | |45| | | | | |

|Val|Tyr|Ile|Asn|Arg|Leu|Ser|Asp|Tyr|Leu|Phe|Val|Leu|Ala|Arg|Tyr|
| |50| | | |55| | | |60| | | | | | |

|Met|Glu|Ile|Arg|Thr|Glu|Ile|Glu|Gly|Lys|Val|Lys|Asp|Val|Ile|Arg|
|65| | | |70| | | |75| | | | |80| | |

|Lys|His|Tyr|Gly|Lys|Asn|Lys|Gly|Glu|Ile|Lys|Leu|Asn|Leu|Asp|Ile|
| | | |85| | | |90| | | |95| | | | |

|Ala|Lys|Asn|Leu|Met|Ala|Lys|Val|Glu|Lys|Lys|Ala|Glu|Ser|Ile|Asn|
| | |100| | | |105| | | |110| | | | | |

|Leu|Pro|Val|Ala|Ile|Ala|Ile|Val|Asp|Met|His|Gly|Asn|Leu|Ile|Ala|
| | |115| | | |120| | | |125| | | | | |

|Ala|His|Phe|Met|Asp|Gly|Thr|Leu|Leu|Glu|Ser|Met|Asn|Leu|Ala|Ile|
| |130| | | |135| | | |140| | | | | | |

|Asn|Lys|Ala|Tyr|Thr|Ser|Val|Val|Leu|Lys|Met|Ser|Thr|Gln|Glu|Leu|
|145| | | |150| | | |155| | | | |160| | |

|Ser|Lys|Leu|Ala|Gln|Pro|Gly|Gln|Pro|Leu|Tyr|Gly|Ile|Asn|Thr|Thr|
| | | |165| | | |170| | | |175| | | | |

|Asp|Asn|Arg|Ile|Val|Val|Phe|Gly|Gly|Gly|Cys|Pro|Ile|Lys|His|Gln|
| | |180| | | |185| | | |190| | | | | |

|Gly|Glu|Ile|Val|Gly|Gly|Ile|Gly|Val|Ser|Gly|Gly|Thr|Val|Glu|Gln|
| | |195| | | |200| | | |205| | | | | |

Asp Ile Glu Leu Ser Ile Tyr Gly Ala Asp Val Phe Glu Glu Val Ile
    210                 215                 220

Ser
225

<210> SEQ ID NO 79
<211> LENGTH: 678
<212> TYPE: DNA
<213> ORGANISM: T. saccharolyticum

<400> SEQUENCE: 79
atggtaaaga ttaaaaatgg ttttgtaata cctggtaaaa accaaatctc agcattatta      60
gatattgtaa ggactataac gagaaaaact gagagaagct taatcaaagt tgacaagaaa     120
tatcctgtaa atattaattc gaaagtttac atcaatagat tgtctgatta tttgtttgtt     180
ttagcaaggt atatggaaat aagaacggaa atagaagaaa agtaaaagat cgtgataaga     240
aagcattatg aaagaacaa aggcgaaata aagctaaatt tagatatagc aaaaaattta     300
atggctaagg tagaaaagaa ggcagaaagc attaatctac cggttgctat tgcaatagtt     360
gacatgcatg gcaatttgat agcggctcat tttatggatg gtacacttct tgaaagcatg     420
aatctagcta taaataaagc ttatacatca gtggtgctta aaatgtcgac gcaagagtta     480
tcaaaacttg cacaaccagg gcagcctctt tacgggataa atacaactga taatagaatc     540
gtagtgtttg gaggtgggtg ccctataaaa catcaaggtg aaatagttgg tggaattgga     600
gttagcggtg gtacagtaga acaagatata gaactttcta tttatggtgc agatgtattt     660
gaggaggtta tatcatga                                                    678

<210> SEQ ID NO 80
<211> LENGTH: 467
<212> TYPE: PRT
<213> ORGANISM: T. saccharolyticum

<400> SEQUENCE: 80

Met Lys Val Lys Glu Glu Asp Ile Glu Ala Ile Val Lys Lys Val Leu
1               5                   10                  15

Ser Glu Phe Asn Phe Glu Lys Asn Thr Lys Ser Phe Arg Asp Phe Gly
            20                  25                  30

Val Phe Gln Asp Met Asn Asp Ala Ile Arg Ala Ala Lys Asp Ala Gln
        35                  40                  45

Lys Lys Leu Arg Asn Met Ser Met Glu Ser Arg Glu Lys Ile Ile Gln
    50                  55                  60

Asn Ile Arg Lys Lys Ile Met Glu Asn Lys Lys Ile Leu Ala Glu Met
65                  70                  75                  80

Gly Val Ser Glu Thr Gly Met Gly Lys Val Glu His Lys Ile Ile Lys
                85                  90                  95

His Glu Leu Val Ala Leu Lys Thr Pro Gly Thr Glu Asp Ile Val Thr
            100                 105                 110

Thr Ala Trp Ser Gly Asp Lys Gly Leu Thr Leu Val Glu Met Gly Pro
        115                 120                 125

Phe Gly Val Ile Gly Thr Ile Thr Pro Ser Thr Asn Pro Ser Glu Thr
    130                 135                 140

Val Leu Cys Asn Ser Ile Gly Met Ile Ala Ala Gly Asn Ser Val Val
145                 150                 155                 160

Phe Asn Pro His Pro Gly Ala Val Asn Val Ser Asn Tyr Ala Val Lys
                165                 170                 175

| | | | | | | | | | | | |
|---|---|---|---|---|---|---|---|---|---|---|---|
|Leu|Val|Asn|Glu|Ala|Val|Met|Glu|Ala|Gly|Gly|Pro|Glu|Asn|Leu|Val|
| | | |180| | | |185| | | |190|

Leu Val Asn Glu Ala Val Met Glu Ala Gly Gly Pro Glu Asn Leu Val
                180                 185                 190

Ala Ser Val Glu Lys Pro Thr Leu Glu Thr Gly Asn Ile Met Phe Lys
            195                 200                 205

Ser Pro Asp Val Ser Leu Leu Val Ala Thr Gly Pro Gly Val Val
210                 215                 220

Thr Ser Val Leu Ser Ser Gly Lys Arg Ala Ile Gly Ala Gly Ala Gly
225                 230                 235                 240

Asn Pro Pro Val Val Asp Glu Thr Ala Asp Ile Lys Lys Ala Ala
                245                 250                 255

Lys Asp Ile Val Asp Gly Ala Thr Phe Asp Asn Asn Leu Pro Cys Ile
            260                 265                 270

Ala Glu Lys Glu Val Val Ser Val Asp Lys Ile Thr Asp Glu Leu Ile
            275                 280                 285

Tyr Tyr Met Gln Gln Asn Gly Cys Tyr Lys Ile Glu Gly Arg Glu Ile
            290                 295                 300

Glu Lys Leu Ile Glu Leu Val Leu Asp His Lys Gly Gly Lys Ile Thr
305                 310                 315                 320

Leu Asn Arg Lys Trp Val Gly Lys Asp Ala His Leu Ile Leu Lys Ala
                325                 330                 335

Ile Gly Ile Asp Ala Asp Glu Ser Val Arg Cys Ile Ile Phe Glu Ala
                340                 345                 350

Glu Lys Asp Asn Pro Leu Val Val Glu Glu Leu Met Met Pro Ile Leu
            355                 360                 365

Gly Ile Val Arg Ala Lys Asn Val Asp Glu Ala Ile Met Ile Ala Thr
370                 375                 380

Glu Leu Glu His Gly Asn Arg His Ser Ala His Met His Ser Lys Asn
385                 390                 395                 400

Val Asp Asn Leu Thr Lys Phe Gly Lys Ile Ile Asp Thr Ala Ile Phe
                405                 410                 415

Val Lys Asn Ala Pro Ser Tyr Ala Ala Leu Gly Tyr Gly Gly Glu Gly
            420                 425                 430

Tyr Cys Thr Phe Thr Ile Ala Ser Arg Thr Gly Glu Gly Leu Thr Ser
            435                 440                 445

Ala Arg Thr Phe Thr Lys Ser Arg Arg Cys Val Leu Ala Asp Gly Leu
    450                 455                 460

Ser Ile Arg
465

<210> SEQ ID NO 81
<211> LENGTH: 1404
<212> TYPE: DNA
<213> ORGANISM: T. saccharolyticum

<400> SEQUENCE: 81

```
atgaaagtta aagaggaaga tattgaagcg atcgtcaaaa aagtcttatc ggaatttaat      60
tttgaaaaaa atactaaaag tttcagagat tttggcgtat tcaagatat gaatgatgct      120 attcgtgctg caaaagatgc ccagaaaaaa ttgagaaata tgtccatgga gtcgagagaa      180
aagattatac agaatataag aaaaaagatt atggagaata aaaaaatact tgcagagatg      240
ggcgtcagtg aaactggcat ggggaaagta gagcacaaaa taataaaaca tgagcttgta      300
gcacttaaga cacctggtac cgaagatata gtgacaacag catggtctgg cgataaggga      360
ctgacattgg ttgaaatggg gccatttggt gtaataggta cgattactcc ttcgacaaat      420
```

-continued

```
ccaagtgaaa ccgtcctttg caatagcata ggtatgatag ccgcaggtaa ttcagtcgta    480
tttaatccac atccaggtgc ggtaaatgta tctaattacg ctgtcaagtt agtaaatgaa    540
gcggtgatgg aagctggcgg ccctgagaat ttagtcgcat ctgttgaaaa acctacactt    600
gaaactggaa atattatgtt caagagtcct gatgtttcgc tattagtagc gacaggcgga    660
cctggtgtag taacatcggt tctctcatct ggcaaaaggg caataggagc aggagcagga    720
aatccaccag ttgtagttga tgaaacggca gatataaaaa aagctgcgaa agatatagtc    780
gatggtgcta catttgacaa caatttgcct tgtattgctg aaaaggaagt agtttctgta    840
gataaaataa cagatgaact gatttactac atgcaacaga atggctgcta caagattgag    900
gggcgagaaa ttgaaaagct cattgaactt gtattggatc acaaaggtgg caagataaca    960
ttaaacagga aatgggttgg caaagatgct catttaatac taaaagctat aggcatagat   1020
gctgatgaaa gcgtaaggtg cataattttt gaggcggaaa agacaatcc gttagtggta   1080
gaagagctga tgatgcctat tttaggaata gtaagagcca aaaatgtaga tgaagcgata   1140
atgattgcga cagagttaga acatggcaat aggcattcag cacatatgca ttctaaaaac   1200
gttgataatt taacaaagtt tggaaaaata attgacactg ctatatttgt aaaaaatgct   1260
ccatcgtatg ccgcgttagg atatggtggt gaaggttatt gcacatttac gattgcaagc   1320
agaacaggtg aaggattgac atctgcaagg acttttacta aaagtcgtag atgtgtcttg   1380
gcagatggat tatcaataag atag                                          1404
```

<210> SEQ ID NO 82
<211> LENGTH: 403
<212> TYPE: PRT
<213> ORGANISM: T. saccharolyticum

<400> SEQUENCE: 82

```
Met Glu Val Asn Gln Ile Asp Ile Glu Glu Ile Val Lys Lys Ile Leu
1               5                   10                  15

Asn Asp Leu Arg Asn Glu Pro Lys Glu Asn Ile Lys Glu Ser Asn Ser
            20                  25                  30

Lys Ile Pro Ser Ile Cys Arg Ala Ala Val Leu Thr Asp Val Lys Lys
        35                  40                  45

Ile Glu Val Lys Glu Phe Asn Ile Pro Glu Ile Asn Asp Asp Glu Met
    50                  55                  60

Leu Val Lys Val Glu Gly Cys Gly Val Cys Gly Thr Asp Val His Glu
65                  70                  75                  80

Tyr Lys Gly Asp Pro Phe Gly Leu Ile Pro Leu Val Leu Gly His Glu
                85                  90                  95

Gly Thr Gly Glu Ile Val Lys Leu Gly Lys Asn Val Arg Arg Asp Ser
            100                 105                 110

Ala Gly Lys Glu Ile Lys Glu Gly Asp Lys Ile Val Thr Ser Val Val
        115                 120                 125

Pro Cys Gly Glu Cys Asp Ile Cys Leu Asn His Pro Asp Lys Thr Asn
    130                 135                 140

Leu Cys Glu Asn Ser Lys Ile Tyr Gly Leu Ile Ser Asp Asp Asn Tyr
145                 150                 155                 160

His Leu Asn Gly Trp Phe Ser Glu Tyr Ile Val Ile Arg Lys Gly Ser
                165                 170                 175

Thr Phe Tyr Lys Val Asn Asp Ile Asn Leu Asn Leu Arg Leu Leu Val
            180                 185                 190

Glu Pro Ala Ala Val Val Val His Ala Val Glu Arg Ala Lys Ser Thr
```

```
            195                 200                 205
Gly Leu Met Lys Phe Asn Ser Lys Val Leu Val Gln Gly Cys Gly Pro
    210                 215                 220

Ile Gly Leu Leu Leu Leu Ser Val Val Lys Thr Leu Gly Val Glu Asn
225                 230                 235                 240

Ile Ile Ala Val Asp Gly Asp Glu Asn Arg Leu Asn Met Ala Lys Arg
                245                 250                 255

Leu Gly Ala Thr Ala Leu Ile Asn Phe Thr Lys Tyr Ser Asn Ile Asp
                260                 265                 270

Glu Leu Val Asp Ala Val Lys Lys Ala Ser Asp Gly Ile Gly Ala Asp
                275                 280                 285

Phe Ala Phe Gln Cys Thr Gly Val Pro Ser Ala Ala Ser Asn Ile Trp
290                 295                 300

Lys Phe Val Arg Arg Gly Gly Gly Leu Cys Glu Val Gly Phe Phe Val
305                 310                 315                 320

Asn Asn Gly Asp Cys Lys Ile Asn Pro His Tyr Asp Ile Cys Asn Lys
                325                 330                 335

Glu Ile Thr Ala Val Gly Ser Trp Thr Tyr Thr Pro Gln Asp Tyr Leu
                340                 345                 350

Thr Thr Phe Asp Phe Leu Lys Arg Ala Lys Glu Ile Gly Leu Pro Ile
                355                 360                 365

Glu Glu Leu Ile Thr His Arg Phe Ser Leu Asp Lys Met Asn Glu Ala
                370                 375                 380

Met Glu Val Asn Met Lys Gln Glu Gly Ile Lys Val Val Tyr Ile Asn
385                 390                 395                 400

Asp Arg Phe

<210> SEQ ID NO 83
<211> LENGTH: 1212
<212> TYPE: DNA
<213> ORGANISM: T. saccharolyticum

<400> SEQUENCE: 83
atggaagtca atcagataga cattgaggag atagttaaga aaatattaaa tgatttaaga      60
aatgagccta agaaaacat  taaagagagc aattcaaaaa taccatctat ctgcagagct     120
gctgtactta cagatgttaa aaaaatagaa gtaaaagaat ttaatattcc agaaataaat     180
gatgatgaaa tgcttgtcaa ggtggaaggc tgtggcgttt gcggtactga tgttcatgaa     240
tacaaaggag atccttttgg acttatacca ttggttttag acacgaagg  tacaggtgag     300 atagtcaagc tggggaaaaa cgtgagacga gattctgctg gtaaagaaat caaagaaggc     360
gataagattg ttacatctgt cgttccgtgc ggtgaatgcg atatatgttt gaatcatcca     420
gacaagacaa atttgtgtga aaactcaaag atttacggct taatatccga tgataattac     480
catttaaatg gttggttctc agagtacatc gtcataagga aaggctcaac attttataag     540
gtcaatgata taaaccttaa tttgaggctt ttggtagaac cggctgcagt agtcgtacat     600
gcagtagagc gcgcaaaatc cacaggtctt atgaaattca acagtaaagt tctcgtacaa     660
ggctgtggcc ctataggatt actgctattg tcggttgtaa agacgcttgg agtagaaaat     720
atcatagccg tcgacggcga tgagaataga ctcaacatgg ctaaaagatt aggtgctaca     780
gcactcatta ttttactaa  atacagcaat attgatgagc ttgttgatgc tgttaaaaaa     840
gcaagcgatg gaattggcgc agattttgca tttcaatgta caggcgttcc ttctgcagcg     900
tctaatattt ggaagtttgt aaggcgggga ggtggtttat gcgaagttgg attttttgta     960
```

```
aataatggtg attgtaagat aaaccccat tatgatattt gcaataagga gataacagca    1020
gttggctcat ggacttacac tcctcaagac tatttgacaa cttttgattt tctcaaaaga    1080
gctaaagaaa taggacttcc aattgaagag ctgataacac atagattttc acttgataaa    1140
atgaatgaag ctatggaagt taatatgaag caggaaggga taaagtagt gtatataaat    1200 gacagatttt ag                                                       1212
```

<210> SEQ ID NO 84
<211> LENGTH: 101
<212> TYPE: PRT
<213> ORGANISM: T. saccharolyticum

<400> SEQUENCE: 84

```
Met Gln Ala Val Gly Leu Ile Glu Val Tyr Gly Leu Val Ala Ala Phe
1               5                   10                  15

Val Ala Ala Asp Ala Ala Cys Lys Lys Ala Asn Val Val Ile Glu Ser
            20                  25                  30

Phe Asp Asn Asn Lys Pro Leu Asn Ala Glu Ala Leu Pro Val Pro Leu
        35                  40                  45

Ile Ile Val Val Lys Leu Arg Gly Asp Leu Glu Asp Val Lys Ile Ala
    50                  55                  60

Val Asp Ala Ala Val Asp Ala Ala Asn Lys Ile Ser Gly Val Val Ala
65                  70                  75                  80

Thr Asn Ile Ile Ala Lys Pro Glu Glu Asp Thr Glu Lys Leu Leu Lys
                85                  90                  95

Leu Asn Cys Leu Lys
            100
```

<210> SEQ ID NO 85
<211> LENGTH: 306
<212> TYPE: DNA
<213> ORGANISM: T. saccharolyticum

<400> SEQUENCE: 85

```
atgcaggctg ttggattgat tgaagtttat ggattagtag cggcatttgt ggcagcagat      60
gctgcatgca aaaagcgaa tgtcgtaata gagtcttttg acaacaataa gccattaaat     120
gctgaagcat tgccagttcc attgataata gtcgttaagc tcagaggaga tcttgaggat     180
gtaaaaatag cggtagatgc tgcagttgat gcagctaata aaatatctgg tgtagttgct     240
acaaatataa tagcaaaacc agaagaagat actgaaaagc tattaaagct aaattgtctt     300
aaataa                                                               306
```

<210> SEQ ID NO 86
<211> LENGTH: 92
<212> TYPE: PRT
<213> ORGANISM: T. saccharolyticum

<400> SEQUENCE: 86

```
Met Val Gln Glu Ala Leu Gly Met Val Glu Thr Arg Gly Leu Val Ala
1               5                   10                  15

Ala Ile Glu Ala Ala Asp Ala Met Val Lys Ala Ala Asp Val Thr Leu
            20                  25                  30

Ile Gly Thr Glu Lys Ile Gly Ser Gly Leu Val Thr Val Met Val Arg
        35                  40                  45

Gly Asp Val Gly Ala Val Lys Ala Ala Thr Glu Val Gly Ala Ser Ala
    50                  55                  60
```

Ala Ser Lys Leu Gly Glu Leu Val Ala Val His Val Ile Pro Arg Pro
65                  70                  75                  80

His Thr Asp Val Glu Lys Ile Leu Pro Thr Ile Lys
                85                  90

<210> SEQ ID NO 87
<211> LENGTH: 279
<212> TYPE: DNA
<213> ORGANISM: T. saccharolyticum

<400> SEQUENCE: 87
atggtacaag aagcattggg aatggtagaa acgagaggat tggtagcagc aatagaagca    60
gcagatgcta tggtaaaggc tgcggatgtc actttgatag aactgaaaaa aataggttca   120
ggacttgtaa cagtcatggt aagaggagat gtcggtgcag taaaagcagc gacagaagtt   180
ggcgcaagtg cagcttcaaa attgggagag ttagtggctg ttcacgtaat accaaggcct   240
catactgatg ttgaaaagat actgccgaca attaaataa                          279

<210> SEQ ID NO 88
<211> LENGTH: 105
<212> TYPE: PRT
<213> ORGANISM: T. saccharolyticum

<400> SEQUENCE: 88

Met Tyr Ala Ile Gly Leu Ile Glu Val Asn Gly Phe Val Thr Ala Val
1               5                   10                  15

Glu Thr Leu Asp Ala Met Leu Lys Thr Ala Asn Val Glu Phe Val Thr
                20                  25                  30

Trp Glu Lys Lys Leu Gly Gly Arg Leu Val Thr Ile Ile Lys Gly
        35                  40                  45

Asp Val Ser Ala Val Glu Ala Ile Leu Thr Gly Lys Ile Glu Ala
        50                  55                  60

Asp Lys Ile Thr Arg Thr Val Ala Tyr Ala Val Ile Pro Asn Pro His
65                  70                  75                  80

Pro Glu Thr Ile Lys Met Val Asn Ile Ser Ala Gly Lys Leu Phe Lys
                85                  90                  95

Ala Asp Gly Gly Glu Ile Asn Glu Phe
            100                 105

<210> SEQ ID NO 89
<211> LENGTH: 318
<212> TYPE: DNA
<213> ORGANISM: T. saccharolyticum

<400> SEQUENCE: 89
atgtatgcaa ttggacttat tgaagtaaat gggtttgtca cagcggttga acactggat     60 gcaatgttga aaacagccaa tgtagagttt gtaacatggg agaaaaaact tggaggcaga   120
cttgtgacaa tcattattaa aggagatgtt tcagcagttg aagaagcaat tttaactgga   180
aagattgaag ctgacaagat tacacggaca gtagcatacg cagttattcc aaatccacat   240
ccagaaacta aaagatggt aaatattagt gcaggaaagc tatttaaagc agatggtggt    300
gaaataaatg agttctga                                                 318

<210> SEQ ID NO 90
<211> LENGTH: 127
<212> TYPE: PRT
<213> ORGANISM: T. saccharolyticum

<400> SEQUENCE: 90

Met Ser Ser Glu Glu Lys Asp Thr Asn Ala Lys Asp Val Lys Val Glu
1               5                   10                  15

Lys Gln Lys Asn Asn Leu Thr Lys Thr Ser Asn Lys Glu Phe Lys Glu
            20                  25                  30

Glu Leu Ile Met Glu Gln Gln Ala Leu Gly Met Val Glu Thr Arg Gly
        35                  40                  45

Leu Val Ala Ala Ile Glu Ala Asp Ala Met Val Lys Ala Ala Asn
    50                  55                  60

Val Thr Leu Ile Gly Thr Glu Lys Ile Gly Ser Gly Leu Val Thr Val
65                  70                  75                  80

Met Val Arg Gly Asp Val Gly Ala Val Lys Ala Ala Thr Glu Thr Gly
                85                  90                  95

Ala Asn Ala Ala Lys Lys Leu Gly Glu Leu Val Ala Val His Val Ile
            100                 105                 110

Pro Arg Pro His Ala Asp Val Glu Lys Ile Leu Pro Thr Ile Lys
        115                 120                 125

<210> SEQ ID NO 91
<211> LENGTH: 384
<212> TYPE: DNA
<213> ORGANISM: T. saccharolyticum

<400> SEQUENCE: 91
atgagttctg aagaaaagga tacgaatgca aaagatgtta agtcgaaaa gcagaaaaat      60 aatttaacga aacatcaaa taaagaattt aaggaggaat tgattatgga caacaagca     120 ttaggaatgg tagagacgag aggattggta gcagcgatag aagctgctga tgcaatggta   180
aaggctgcta atgtcacgtt aataggaact gaaaaaatag gttcaggact tgtaacagtc   240
atggtaagag gagatgttgg tgcagtaaaa gcagcgacag agactggagc aaatgcagct   300
aaaaagttag gggagttagt agctgttcac gtaataccaa gacctcatgc agatgtagag   360
aaaatactgc ctacgataaa gtag                                          384

<210> SEQ ID NO 92
<211> LENGTH: 217
<212> TYPE: PRT
<213> ORGANISM: T. saccharolyticum

<400> SEQUENCE: 92

Val Ile Thr Val Asn Glu Lys Leu Ile Glu Ile Ser Lys Thr Ile
1               5                   10                  15

Ala Asp Thr Ile Ser Glu Arg Asn Ser Leu Lys Ile Pro Val Gly Val
            20                  25                  30

Ser Ala Arg His Val His Leu Thr Lys Glu His Leu Asp Ile Leu Phe
        35                  40                  45

Gly Lys Asp Tyr Ile Leu Lys Lys Lys Glu Leu Met Gly Gly Gln
    50                  55                  60

Phe Ala Ala Glu Glu Cys Val Thr Ile Ile Gly Phe Lys Leu Asn Ala
65                  70                  75                  80

Ile Glu Lys Val Arg Val Leu Gly Pro Leu Arg Asp Lys Thr Gln Val
                85                  90                  95

Glu Ile Ser Lys Thr Asp Ala Ile Ser Leu Gly Leu Asn Pro Pro Ile
            100                 105                 110

Arg Glu Ser Gly Asp Ile Lys Gly Ser Ser Pro Ile Thr Ile Val Gly

```
              115                 120                 125
Pro Arg Gly Ala Ile Ser Leu Lys Glu Gly Cys Ile Ile Ala Lys Arg
    130                 135                 140

His Ile His Met Ser Pro Glu Asp Ser Lys Arg Phe Asn Val Lys Asp
145                 150                 155                 160

Asp Asp Ile Ile Ser Val Lys Ile Asn Gly Gln Arg Gly Gly Ile Leu
                165                 170                 175

Glu Asn Val Gln Ile Arg Val Asp Glu Lys Tyr Thr Leu Glu Met His
            180                 185                 190

Ile Asp Thr Asp Glu Ala Asn Cys Met Gly Leu Lys Ser Gly Asp Phe
        195                 200                 205

Val Glu Ile Val Arg Asp Asn Arg Ser
210                 215

<210> SEQ ID NO 93
<211> LENGTH: 654
<212> TYPE: DNA
<213> ORGANISM: T. saccharolyticum

<400> SEQUENCE: 93
gtgataacag tgaacgaaaa attgatagag attatatcaa aaactatagc ggatacgatt      60
agtgaaagga attcgcttaa gataccagta ggcgtatcag cccgacatgt acatctgact     120
aaagaacatt tggatatatt atttggaaaa gattatatcc ttaaaaagaa aaaggaattg     180
atgggtggac agttcgcagc agaggaatgt gtgacaatta tcggatttaa attaaatgct     240
attgagaaag tgagagtttt gggtccttta agagataaaa cgcaggtaga aatatcgaag     300
accgatgcaa taagtttagg gttaaaccct cctatacggg aatcaggtga tataaaaggt     360
tcatcgccaa ttacaattgt agggccgaga ggagcaatat cattaaaaga aggatgtata     420
atagcaaaac gacatattca catgtcaccg gaagattcca aaagattcaa tgttaaagac     480
gacgatataa tatcagtaaa aataaatggt cagcgaggcg gaatttttaga aaatgtacag     540 attagagttg acgaaaagta tacacttgag atgcatattg acacagatga agctaattgc     600
atgggactaa aaagcggcga ttttgttgaa atagtaagag ataataggag ttga           654

<210> SEQ ID NO 94
<211> LENGTH: 92
<212> TYPE: PRT
<213> ORGANISM: T. saccharolyticum

<400> SEQUENCE: 94

Leu Ile Ile Ala Lys Val Val Gly Thr Val Ile Ser Thr Arg Lys Asn
1               5                   10                  15

Gln Asn Leu Ile Gly Asn Lys Phe Leu Ile Val Glu Pro Val Ser Glu
            20                  25                  30

Met Asn Tyr Asp Ser Lys Asn Arg Val Val Ala Ile Asp Asn Val Gly
        35                  40                  45

Ala Gly Val Gly Glu Ile Val Leu Val Thr Phe Gly Ser Ser Ala Arg
    50                  55                  60

Ile Gly Cys Gly Met Pro Asp Ser Pro Val Asp Ala Ala Ile Val Gly
65                  70                  75                  80

Ile Val Asp Ser Ile Lys Asp Ile Ile Ile Asp Asp
                85                  90

<210> SEQ ID NO 95
<211> LENGTH: 279
```

-continued

<212> TYPE: DNA
<213> ORGANISM: T. saccharolyticum

<400> SEQUENCE: 95

```
ttgataatag ctaaagttgt tggtactgtt atttctaccc gcaagaatca aaatttaata      60
ggcaataaat ttttaatagt agaaccagta agtgaaatga attatgacag taaaaatagg     120
gttgttgcaa tagataatgt aggtgcaggt gtaggagaga tagtattagt tacctttgga     180
agttcagcaa gaatcggttg tggtatgcca gattcgcctg tagatgcggc aattgtcgga     240
attgttgata gcataaaaga tattatcatt gatgattag                             279
```

<210> SEQ ID NO 96
<211> LENGTH: 456
<212> TYPE: PRT
<213> ORGANISM: T. saccharolyticum

<400> SEQUENCE: 96

```
Met Met Asn Ile Asp Glu Leu Lys Asn Ile Val Phe Glu Asn Gly Ile
 1               5                  10                  15

Val Gly Ala Gly Gly Ala Gly Phe Pro Thr His Ala Lys Leu Thr Thr
            20                  25                  30

Gly Ile Asp Thr Ile Ile Leu Asn Gly Ala Glu Cys Glu Pro Leu Leu
        35                  40                  45

Arg Val Asp Arg Gln Leu Leu Ala Ile Tyr Thr Asp Glu Ile Leu Met
    50                  55                  60

Thr Leu Ser Phe Ile Val Asp Thr Leu Gly Ala Lys Arg Gly Ile Val
65                  70                  75                  80

Ala Ile Lys Ser Ala Tyr Lys Thr Ala Ile Ser Ser Val Lys Asn Leu
                85                  90                  95

Ile Gly Asn Tyr Lys Asn Leu Glu Leu Lys Val Leu Pro Asp Val Tyr
            100                 105                 110

Pro Ala Gly Asp Glu Val Val Leu Ile Tyr Glu Thr Thr Gly Arg Ile
        115                 120                 125

Val Pro Glu Gly Ser Ile Pro Ile Ser Val Gly Thr Leu Val Met Asn
    130                 135                 140

Val Glu Thr Val Leu Asn Val Tyr Asn Ala Ile Tyr Leu Lys His Pro
145                 150                 155                 160

Val Thr Glu Lys Tyr Val Thr Val Thr Gly Asp Val Lys Tyr Pro Ser
                165                 170                 175

Thr Phe Lys Ala Lys Val Gly Thr Ser Val Ala Arg Leu Ile Glu Lys
            180                 185                 190

Ala Gly Gly Cys Leu Glu Lys Asp Cys Glu Val Ile Met Gly Gly Pro
        195                 200                 205

Met Thr Gly Lys Ile Val Asp Val Lys Thr Pro Ile Thr Lys Thr Thr
    210                 215                 220

Lys Ala Ile Ile Val Leu Pro Lys Asp His Pro Val Ile Thr Lys Arg
225                 230                 235                 240

Lys Thr Asn Ile Arg Ile Gly Leu Lys Arg Ala Met Ser Val Cys Ser
                245                 250                 255

Gln Cys Gln Met Cys Thr Asp Leu Cys Pro Arg Asn Leu Leu Gly His
            260                 265                 270

Ser Ile Lys Pro His Lys Val Met Asn Ala Val Ala Asn Ser Ile Ile
        275                 280                 285

Asp Asp Thr Ala Ala Tyr Thr Met Thr Met Leu Cys Ser Glu Cys Gly
    290                 295                 300
```

Leu Cys Glu Met Tyr Ser Cys His Gln Ser Leu Ser Pro Arg Lys Ile
305                 310                 315                 320

Ile Ser Gln Ile Lys Ile Lys Leu Arg Gln Asn Gly Val Lys Asn Pro
            325                 330                 335

His Asn Lys Arg Pro Glu Thr Ala Asn Val Met Arg Asp Glu Arg Leu
        340                 345                 350

Val Pro Met Glu Arg Leu Ile Ser Arg Leu Ser Leu Lys Lys Tyr Asp
    355                 360                 365

Val Asp Ala Pro Met Asn Phe Asp Thr Val Ile Pro Ser His His Val
370                 375                 380

Val Met Gln Leu Ser Gln His Val Gly Ala Lys Ala Ile Pro Val Val
385                 390                 395                 400

Lys Val Gly Asp Ile Val Lys Glu Gly Asp Leu Ile Gly Asp Val Pro
                405                 410                 415

Asn Asn Lys Leu Gly Ala Lys Leu His Ala Ser Ile Asp Gly Ile Ile
            420                 425                 430

Ile Asp Val Thr Asp Asp Ser Ile Val Ile Lys Pro Arg Gly Asp Phe
        435                 440                 445

Asp Gly Gln Ser Asp Arg Ile Gly
    450                 455

<210> SEQ ID NO 97
<211> LENGTH: 1371
<212> TYPE: DNA
<213> ORGANISM: T. saccharolyticum

<400> SEQUENCE: 97
atgatgaata ttgatgaact taaaaatatc gtatttgaaa atggaatagt cggtgcaggc        60
ggagctggat ttcctacaca tgcaaaactt actacaggta tagatacaat catattaaat       120
ggcgctgaat gtgaaccgct tttaagagta gataggcagc tacttgcaat atatactgat       180
gaaatattga tgactttatc attcatagtt gatactttag gagccaaacg tggcattgta       240
gcaataaaat cagcatacaa aactgccatc agctcagtta agaatttgat tggtaattat       300
aaaaacttgg agttaaaggt attgccagac gtttatcctg ctggtgatga agttgtatta       360
atatatgaaa cgactggaag aattgtgcca gaaggttcta tacctatttc tgttggcacg       420
ttggtaatga atgtggaaac tgtgcttaat gtttataatg ctatttattt aaaacatcca       480
gtcacagaaa gtatgtaac agtaacggga gatgtcaaat atcccagcac atttaaagca       540
aaagtaggaa catctgtagc tcgtcttatt gaaaaagcag gaggatgctt agaaaaagat       600
tgtgaagtga taatgggtgg tcctatgact gggaaaatag ttgatgtaaa gactccaata       660
acaaaaacta caaagctat tatcgttctc ccaaaagacc accctgtgat aacaaagaga       720
aagacaaaca taaggatagg gttaaaacga gcaatgtctg tttgctctca atgccaaatg       780
tgcacagatc tatgtcctag aaatttatta ggtcattcca tcaaacctca taagtcatg       840 aatgcagttg caaatagtat tatttgatgat accgctgcat atacgatgac aatgttatgt       900
tctgaatgtg gattgtgcga gatgtattca tgtcatcaaa gtttgtcgcc gagaaagata       960
ataagccaga taagataaa attaaggcaa atggtgtaa aaaatccaca caacaaaga      1020 ccagaaacag caaatgtcat gcgagatgag agattagtgc cgatggaaag gcttatttca      1080
agactttcgc tcaaaaaata cgatgtagat gctccgatga ttttgatac tgttattcct      1140 tcacatcacg ttgtcatgca actaagtcag catgttggtg ccaaagcgat acctgtagta      1200
aaggtaggag atattgtgaa agaaggagat ctgataggcg atgtgcctaa taataagctg    1260
ggtgctaaat tgcatgccag tattgacggc attataatag atgtaactga tgacagtatt    1320
gttatcaaac caagaggtga ttttgatgga caaagcgata ggattggttg a             1371

<210> SEQ ID NO 98
<211> LENGTH: 182
<212> TYPE: PRT
<213> ORGANISM: T. saccharolyticum

<400> SEQUENCE: 98

Met Asp Lys Ala Ile Gly Leu Val Glu Tyr Lys Ser Val Ala Thr Gly
1               5                   10                  15

Ile Thr Ala Ala Asp Asp Met Ala Lys Thr Ala Asp Val Glu Ile Ile
            20                  25                  30

Glu Ala Tyr Thr Val Cys Pro Gly Lys Tyr Ile Val Leu Leu Ala Gly
        35                  40                  45

Lys Leu Ser Ala Val Asn Ser Ala Ile Glu Lys Gly Ile Asn Gln Tyr
    50                  55                  60

Ser Glu Asn Val Ile Asp Ser Phe Ile Leu Gly Asn Pro His Glu Thr
65                  70                  75                  80

Ile Tyr Lys Ala Met Ser Gly Thr Ser Val Ile Glu Asp Val Glu Ala
                85                  90                  95

Leu Gly Ile Ile Glu Thr Phe Ser Ala Ala Ser Ile Ile Leu Ala Ala
            100                 105                 110

Asp Thr Ala Ala Lys Ala Ala Lys Val Asn Leu Val Glu Ile Arg Ile
        115                 120                 125

Ala Arg Gly Met Cys Gly Lys Ser Tyr Leu Leu Leu Thr Gly Glu Leu
    130                 135                 140

Ala Ala Val Glu Ala Ser Ile Asn Ala Gly Cys Lys Ala Leu Glu Arg
145                 150                 155                 160

Thr Gly Met Leu Leu Asn Lys Ser Ile Ile Pro Asn Pro Asp Arg Ala
                165                 170                 175

Ile Trp Asp Lys Ile Ile
            180

<210> SEQ ID NO 99
<211> LENGTH: 549
<212> TYPE: DNA
<213> ORGANISM: T. saccharolyticum

<400> SEQUENCE: 99
atggacaaag cgataggatt ggttgaatac aaatcagttg ctacaggtat aactgctgct      60
gatgacatgg ctaaaactgc tgatgtggaa ataatagaag catatacagt atgtccgggg     120
aaatacattg ttctgttagc tgggaaatta agtgcagtta attcggcgat agaaaagggc     180
ataaatcagt attcggaaaa tgtcattgat agctttatat tgggaaatcc gcatgaaaca     240
atatataaag ctatgagtgg cacgtctgta attgaagata gaagcact tggtatcata      300 gagacatttt ctgcagcatc aataatactt gcagcagata cggctgcaaa agctgcaaaa     360
gtgaatctgg tagagataag aatagccaga ggtatgtgcg gcaagtcata tctactgctt     420
acaggagaac ttgctgctgt tgaagcatct ataaatgcag gatgcaaagc tttggagaga     480
acgggtatgc ttttaaataa gtctataata cccaatccag atagagctat ttgggataag     540
ataatttaa                                                            549

```
<210> SEQ ID NO 100
<211> LENGTH: 425
<212> TYPE: PRT
<213> ORGANISM: T. saccharolyticum

<400> SEQUENCE: 100
```

| Met | Tyr | Glu | Ala | Glu | Lys | Asp | Lys | Ile | Leu | Asn | Asp | Tyr | Tyr | Asn | Ala |
|---|---|---|---|---|---|---|---|---|---|---|---|---|---|---|---|
| 1 | | | | 5 | | | | | 10 | | | | | 15 | |

Lys Glu Ile Tyr Ala Lys Phe Asp Ile Asp Ile Asp Lys Val Leu Asp
            20                  25                  30

Lys Met Lys Lys Ile Arg Ile Ser Leu His Cys Trp Gln Gly Asp Asp
         35                  40                  45

Val Thr Gly Phe Glu Lys Ser Ala Asn Gly Leu Ser Gly Gly Gly Ile
     50                  55                  60

Leu Ala Thr Gly Asn Trp Pro Gly Arg Ala Arg Asn Gly Glu Glu Leu
 65              70                  75                  80

Arg Gln Asp Ile Glu Lys Ala Leu Ser Leu Ile Pro Gly Lys His Lys
                 85                  90                  95

Ile Asn Leu His Ala Ile Tyr Ala Glu Thr Asp Gly Glu Phe Val Asp
            100                 105                 110

Arg Asp Glu Ile Asn Val Glu His Phe Arg Lys Trp Ile Tyr Trp Ala
            115                 120                 125

Lys Glu Asn Gly Leu Gly Leu Asp Phe Asn Pro Thr Phe Phe Ser His
130                 135                 140

Pro Lys Ala Asn Asp Gly Tyr Thr Leu Ser Ser Lys Asp Glu Asn Ile
145                 150                 155                 160

Arg Lys Phe Trp Ile Gln His Gly Lys Arg Cys Arg Glu Ile Ala Asn
                165                 170                 175

Glu Ile Gly Arg Glu Leu Lys Thr Gln Cys Val Asn Asn Val Trp Ile
            180                 185                 190

Pro Asp Gly Ser Lys Asp Leu Pro Ala Asn Arg Ile Glu His Arg Lys
        195                 200                 205

Ile Leu Lys Glu Ser Leu Asp Glu Ile Phe Ser Val Lys Tyr Asp Lys
210                 215                 220

Ser Asn Ile Val Asp Ser Val Glu Ser Lys Leu Phe Gly Ile Gly Ser
225                 230                 235                 240

Glu Ser Tyr Val Val Gly Ser His Glu Phe Tyr Met Asn Tyr Ala Ser
                245                 250                 255

Arg Asn Asp Val Met Leu Cys Leu Asp Met Gly His Phe His Pro Thr
            260                 265                 270

Glu Asn Ile Ala Asp Lys Ile Ser Ser Ile Leu Thr Phe Asn Asp Asn
        275                 280                 285

Leu Leu Ile His Val Ser Arg Gly Val Arg Trp Asp Ser Asp His Val
290                 295                 300

Val Ile Leu Asn Glu Asp Leu Leu Ser Leu Ala Lys Glu Ile Arg Arg
305                 310                 315                 320

Cys Asp Ala Tyr Asp Lys Val Tyr Ile Ala Leu Asp Phe Phe Asp Ala
                325                 330                 335

Ser Ile Asn Arg Ile Met Ala Trp Val Ile Gly Ala Arg Ala Thr Leu
            340                 345                 350

Lys Ala Ile Leu Ile Ser Leu Leu Glu Pro Val His Leu Leu Met Glu
        355                 360                 365

Glu Glu Asn Lys Gly Asn Phe Gly Ala Arg Leu Ala Leu Met Glu Glu
370                 375                 380

Phe Lys Thr Leu Pro Phe Tyr Ser Val Trp Asn Lys Tyr Cys Met Asp
385                 390                 395                 400

Glu Asn Val Pro Ile Gly Thr Ser Trp Ile Asp Asp Val Lys Glu Tyr
                405                 410                 415

Glu Lys Glu Ile Val Lys Asn Arg Ala
            420                 425

<210> SEQ ID NO 101
<211> LENGTH: 1278
<212> TYPE: DNA
<213> ORGANISM: T. saccharolyticum

<400> SEQUENCE: 101

```
atgtatgaag cagaaaaaga taaaatttta aatgattatt ataatgcaaa agagatttat    60
gcaaagtttg acatagatat tgataaagta ttagataaaa tgaagaagat tcgtatttca   120
cttcactgct ggcaaggcga tgatgtaact ggattcgaaa aaagtgccaa tggattaagc   180
ggtggaggta ttttggcgac aggaaactgg cctggtagag caagaaatgg tgaagaatta   240
aggcaagaca ttgaaaaagc cttaagcctt ataccaggca acacaaaaat caatttacat   300
gccatttacg cagaaacgga tggtgaattt gtagacagag atgaaataaa cgtggagcat   360
ttcaggaaat ggatttactg ggcaaaagaa atggccttg gccttgactt caatcctacg   420
ttttttttcgc atcctaaagc aaatgatggc tatacgcttt caagcaaaga tgaaaacata   480
agaaaatttt ggatccaaca tggtaaaaga tgccgtgaaa tcgcaaatga ataggaaga   540
gagctaaaaa ctcaatgtgt gaataatgtt tggattcctg atggttcaaa agatttgcct   600
gctaatagga ttgaacacag aaaaatactt aaagaatctt tagatgagat attttcagta   660
aaatatgaca aatcaaatat cgttgattct gttgaaagca aattatttgg cattggatct   720
gaaagctatg tggttggttc acatgagttt tatatgaact atgcgtcgag aaatgatgta   780
atgctgtgcc ttgatatggg acattttcat cctactgaga atattgctga taagatatca   840
tcaatactta cattcaatga caatttgttg attcatgtaa gccgtggtgt ccggtgggat   900
agcgaccatg tagtcatttt aaatgaagat ttgctttcat tagcaaaaga ataagaaga   960
tgtgatgctt atgacaaagt gtatattgca ttagatttct ttgatgcaag cataaatagg  1020
ataatggcat gggtaatagg tgcaagagcg acgctaaaag ccatattaat atcactatta  1080
gagcctgtgc atctacttat ggaagaggag aataaaggaa attttggtgc aagacttgct  1140
ttgatggagg aattcaaaac attgccattt tactctgttt ggaacaaata ctgcatggac  1200
gaaaatgtgc ctattggtac atcgtggatt gatgatgtta agaatatga aaagaaatt  1260
gtaaaaata gggcttaa                                                  1278
```

<210> SEQ ID NO 102
<211> LENGTH: 475
<212> TYPE: PRT
<213> ORGANISM: T. saccharolyticum

<400> SEQUENCE: 102

Met Lys Asp Ile Val Tyr Asn Leu Ala Phe Asp Phe Gly Ala Ser Ser
1               5                   10                  15

Gly Arg Leu Met Leu Ser Ala Phe Asp Gly Glu Lys Ile Thr Ile Glu
            20                  25                  30

Glu Ile Tyr Arg Phe Pro Asn Glu Pro Val Lys Leu Gly Gln Ser Phe
        35                  40                  45

Tyr Trp Asp Phe Leu Arg Leu Phe His Glu Leu Lys Asn Gly Leu Lys

```
              50                  55                  60
Ile Ala Ser Lys Arg Lys Ile Lys Ile Ser Gly Ile Gly Ile Asp Thr
65                  70                  75                  80

Trp Gly Val Asp Tyr Gly Leu Leu Asp Lys Asn Asp Gln Leu Ile Ser
                    85                  90                  95

Asn Pro Phe His Tyr Arg Asp Lys Arg Thr Asp Gly Ile Ile Lys Asp
                100                 105                 110

Phe Glu Asn Met Ala Leu Leu Glu Glu Ile Tyr Asn Val Thr Gly Ile
                115                 120                 125

Gln Phe Met Glu Phe Asn Thr Ile Phe Gln Leu Tyr Cys Asp Tyr Lys
            130                 135                 140

Lys Arg Pro Glu Leu Leu Asp Asn Ala Lys Thr Leu Leu Phe Ile Pro
145                 150                 155                 160

Asp Leu Phe Asn Phe Tyr Leu Thr Asn Glu Lys Tyr Asn Glu Tyr Thr
                165                 170                 175

Val Ala Ser Thr Ser Gln Met Leu Asp Ala Asn Lys Lys Asp Trp Ala
                180                 185                 190

Asn Asp Leu Ile Glu Lys Leu Asn Leu Pro Glu Gly Ile Phe Gln Lys
            195                 200                 205

Ile Leu Met Pro Gly Asn Thr Ile Gly Tyr Leu Thr Lys Glu Ile Gln
            210                 215                 220

Glu Glu Thr Gly Leu Ser Glu Val Pro Val Ile Ser Val Gly Ser His
225                 230                 235                 240

Asp Thr Ala Ser Ala Val Ala Gly Thr Pro Ile Glu Asn Gly Ser Ser
                245                 250                 255

Ala Tyr Leu Ile Cys Gly Thr Trp Ser Leu Leu Gly Val Glu Ser Glu
                260                 265                 270

Lys Pro Ile Ile Asn Glu Asn Thr Lys Lys Tyr Asn Phe Thr Asn Glu
                275                 280                 285

Gly Gly Val Glu Gly Leu Ile Arg Leu Leu Lys Asn Ile Asn Gly Leu
            290                 295                 300

Trp Ile Ile Gln Gln Leu Lys Gln Ser Trp Asn Ser Asn Gly Ile Lys
305                 310                 315                 320

Ile Gly Phe Pro Glu Ile Ser Gln Met Ala Ser Lys Ala Glu His Glu
                325                 330                 335

Glu Phe Ile Ile Asn Pro Asp Lys Leu Phe Ile Ala Pro Asp Asp
                340                 345                 350

Met Ala Glu Ala Ile Arg Gln Tyr Cys Thr Lys Thr Gly Gln Gly Leu
            355                 360                 365

Pro Gln Asn Ile Gly Asp Ile Ala Arg Ala Ala Tyr Asn Gly Ile Val
            370                 375                 380

Glu Gln Tyr Lys Asn Cys Leu Asn Asn Leu Glu Asp Ile Val Gly Gln
385                 390                 395                 400

Glu Ile Asp Asn Ile His Met Val Gly Gly Ile Gln Asp Lys Phe
                405                 410                 415

Leu Cys Lys Leu Thr Ala Asp Val Thr Gly Lys Val Ile Thr Gly
                420                 425                 430

Pro Val Glu Ala Ser Ile Tyr Gly Asn Val Ile Val Gln Leu Met Ala
                435                 440                 445

Leu Gly Tyr Ile Lys Asp Leu Arg Glu Gly Arg Lys Ile Ile Lys Asn
            450                 455                 460

Ser Ile Glu Asn Asp Glu Glu Met Phe Ala Lys
465                 470                 475
```

<210> SEQ ID NO 103
<211> LENGTH: 1428
<212> TYPE: DNA
<213> ORGANISM: T. saccharolyticum

<400> SEQUENCE: 103

```
atgaaagata ttgtgtataa tctggctttt gattttggag cttcaagtgg ccgtcttatg      60
ctatccgcgt ttgatggcga aaaaatcaca attgaagaga tttatagatt tccaaatgag     120
ccagtcaagc tgggacaatc attttattgg gattttttaa ggcttttttca cgaattaaaa     180
aacggattaa aaatagcatc aaagaggaaa atcaaaatat ccggcattgg tatagacact     240
tggggtgtcg attatggatt gcttgataaa aatgatcaat tgatttcaaa tccttttcat     300
tacagagata aagaacggga tggcataata aaagattttg aaaatatggc gttactggag     360
gaaatctaca acgtaactgg tatacagttt atggaattta atacaatatt ccaattgtat     420
tgcgattata aaaagcgtcc agaattattg gataatgcaa agacattgtt gtttattcca     480
gatttatta  acttttattt gacaaatgag aaatacaatg aatatactgt tgcatccaca     540
tcgcaaatgt tggatgctaa caagaaagat tgggcaaatg atcttataga aaagttaaat     600
ttgccagaag gtattttttca aaagatactg atgccaggaa atacaattgg ttatctaaca     660
aaagaaattc aagaagaaac aggattgtct gaagttcccg tgatttctgt tggcagccat     720
gatacggcat cagcagttgc aggtacacct attgaaaacg gttcaagtgc ttatttgatt     780
tgtggtactt ggtcattatt aggtgttgaa agtgaaaaac ctataataaa tgaaaataca     840
aagaagtaca atttttacaaa tgaaggcggt gtcgaaggcc ttataaggct acttaaaaat     900
attaatggtc tgtggataat tcagcaatta aaacaaagtt ggaattcaaa tggcattaaa     960
ataggatttc cagaaatcag ccagatggca tctaaagcag agcacgaaga atttatcata    1020
aatcctgatg acaaattgtt tatagctcca gatgatatgg ctgaggcgat aaggcaatat    1080
tgtacaaaaa caggacaggg tttgccgcag aatattggcg acatagcaag agccgcttac    1140
aatggtatag ttgaacaata caaaaattgc ttaaacaatt tagaagatat tgtagggcaa    1200
gaaatagata atattcacat ggttggtggt gggatacagg ataagttcct gtgcaagctg    1260
actgcagatg ttacagggaa aaagtcata  acaggccctg tagaagcttc aatctatggc    1320
aatgtgatag tccagcttat ggcattggga tatataaaag acttgagaga aggaagaaag    1380
ataataaaga attctataga gaatgatgaa gagatgtttg ctaaatag                 1428
```

<210> SEQ ID NO 104
<211> LENGTH: 254
<212> TYPE: PRT
<213> ORGANISM: T. saccharolyticum

<400> SEQUENCE: 104

```
Val Ser Asn Ile Tyr Thr Leu Val Val Glu Asp Glu Tyr Glu Ile
 1               5                  10                  15

Arg Thr Gly Leu Val Asn Cys Phe Pro Trp Asn Lys Met Gly Phe Val
                20                  25                  30

Val Ala Glu Glu Phe Glu Asn Gly Gly Glu Cys Phe Gly Tyr Leu Cys
            35                  40                  45

Lys Asn Lys Val Asp Thr Ile Leu Cys Asp Ile Lys Met Pro Val Met
        50                  55                  60

Ser Gly Ile Glu Leu Ala Lys Lys Ile Phe Glu Ser Asn Ile Ser Thr
65                  70                  75                  80
```

```
Lys Ile Val Ile Ser Gly Tyr Thr Asp Phe Glu Tyr Ala Arg Gln
                85                  90                  95

Ala Leu Arg Tyr Gly Val Lys Asp Tyr Ile Val Lys Pro Thr Lys Tyr
            100                 105                 110

Asn Glu Ile Ile Asp Val Phe Ser Arg Ile Lys Glu Leu Asp Asn
                115                 120                 125

Glu Asn Thr Lys Glu Ile Leu Asn Asn Ser Cys Asn Asn Glu Ile Asp
        130                 135                 140

Gln Tyr Ser Ser Ile Ile Ser Ile Ile Glu Lys Tyr Val Asp Glu His
145                 150                 155                 160

Tyr Arg Asp Val Thr Leu Glu Asp Val Ala Lys Val Val Tyr Met Asn
                165                 170                 175

Pro Tyr Tyr Leu Ser Lys Tyr Phe Lys Gln Lys Thr Gly Met Asn Phe
                180                 185                 190

Ser Asp Tyr Ile Thr Glu Val Arg Met Lys Lys Ala Val Glu Phe Leu
            195                 200                 205

Lys Asn Pro Leu Tyr Lys Thr Tyr Glu Ile Ser Tyr Met Ile Gly Tyr
        210                 215                 220

Lys Asn Pro Lys Asn Phe Thr Arg Ala Phe Lys Lys Tyr Tyr Lys Lys
225                 230                 235                 240

Ser Pro Arg Glu Phe Val Asn Ser Ala Ile Asn Phe Lys Glu
                245                 250

<210> SEQ ID NO 105
<211> LENGTH: 765
<212> TYPE: DNA
<213> ORGANISM: T. saccharolyticum

<400> SEQUENCE: 105
gtgtctaata tttatacgct tgtagtagta gaagatgaat atgagataag aacaggatta      60
gttaactgct ttccatggaa caaaatgggt tttgttgttg cagaagaatt tgaaaatgga     120
ggagaatgtt ttgagtattt tgtgtaaaaat aaggttgata caattttatg tgatataaaa    180
atgccagtta tgtctggtat agagttggca agaaaaattt ttgaaagtaa tataagcact     240
aaaatagtta taatcagtgg ttatactgat tttgaatatg ccagacaggc gttaagatat     300
ggtgttaaag attatatagt aaaacctact aaatataatg aaataattga tgttttcagc     360
agaataaaaa aagaattaga caatgaaaat acaaaggaaa tattgaataa ctcatgtaac     420
aatgaaattg atcagtacag cagcataatt tcaatcatag aaaaatatgt tgatgaacat     480
tacagagatg tgacattgga agatgtagct aaagtagttt atatgaatcc gtattattta     540
agcaaatatt ttaaacaaaa aaccggtatg aattttctg attatataac tgaggtcaga     600
atgaaaaaag ctgtagagtt tctaaaaaat cctttgtata aaacttatga aataagttat     660
atgattggat ataaaaatcc aaaaaatttt actagagcat ttaaaaaata ttataaaaaa     720
tccccaagag aatttgtaaa ttcagcaata aattttaagg aatga                     765

<210> SEQ ID NO 106
<211> LENGTH: 588
<212> TYPE: PRT
<213> ORGANISM: T. saccharolyticum

<400> SEQUENCE: 106

Met Arg Glu Leu Asn Asn Lys Phe Phe Tyr Lys Asn Leu Phe Val Leu
1               5                   10                  15
```

```
Ala Leu Pro Leu Ile Leu Ile Val Ile Val Leu Gly Ser Phe Ser Ile
             20                  25                  30

Leu Ile Thr Glu Arg Tyr Val Arg Asp Glu Ile Tyr Lys Asn Ser Arg
         35                  40                  45

Glu Ile Leu Lys Gln Ser Ser Asn Asp Leu Ser Ile Leu Phe Asn Asp
     50                  55                  60

Ile Asn Lys Ile Tyr Leu Thr Phe Gly Thr Asn Lys Asp Val Thr Leu
 65                  70                  75                  80

Tyr Leu Glu Arg Ile Leu Asn Thr Asn Lys Tyr Ser Leu Asp Asp Met
                 85                  90                  95

Trp His Leu Ser Met Ile Glu Ser Leu Phe Asp Ser Thr Ser Phe Ser
                100                 105                 110

Glu Pro Tyr Ile Gln Ser Ile Tyr Leu Tyr Phe Asn Asn Pro Asn Lys
            115                 120                 125

Asn Phe Leu Val Thr Gly Asn Gly Ile Asn Ser Val Thr Asn Tyr Ile
        130                 135                 140

Asp Asn Lys Trp Tyr Asp Ser Phe Leu Asn Ala Pro Lys Asp Glu Ile
145                 150                 155                 160

Ser Trp Ile Glu Val Arg Asn Leu Lys Met Tyr Ser Phe Asp Lys Lys
                165                 170                 175

Gly Ile Lys Val Leu Ser Ile Tyr Lys Lys Ile Ala Asn Phe Asn Gly
            180                 185                 190

Asp Lys Ile Asp Gly Val Leu Val Leu Asn Ile Tyr Leu Asp Tyr Ile
        195                 200                 205

Glu Asn Leu Leu Asn Thr Ser Thr Ile Phe Pro Asp Gln Lys Ile Leu
210                 215                 220

Ile Leu Asp Ala His Asp Asn Leu Ile Cys Gln Asn Ile Asn Gly Asn
225                 230                 235                 240

Phe Thr Gly Lys Ile Asp Leu Asp Asn Tyr Ser Lys Ala Asn Ile Ile
                245                 250                 255

Thr Lys Leu Glu Ser Pro Asn Tyr Asn Ile Lys Tyr Val Ser Ile Val
            260                 265                 270

Pro Lys Lys Tyr Leu Tyr Glu Val Pro Ile Lys Leu Leu Lys Met Thr
        275                 280                 285

Leu Val Leu Leu Leu Thr Ser Ile Phe Phe Val Ile Leu Ile Thr Phe
290                 295                 300

Arg Ile Thr Lys Arg Asn Tyr Glu Asn Val Asn Lys Ile Leu Lys Ile
305                 310                 315                 320

Ile Glu Ala Glu Lys Thr Asn Glu Ile Phe Pro Glu Ile Pro Val Glu
                325                 330                 335

Ser Arg Asp Glu Tyr Ser Tyr Ile Ile Tyr Asn Ile Ile Asn Ser Tyr
            340                 345                 350

Ile Glu Lys Ser Gln Leu Lys Met Glu Leu Ala Glu Lys Lys Tyr Lys
        355                 360                 365

Met Lys Ala Met Glu Leu Leu Ala Leu Gln Ser Gln Ile Ser Pro His
370                 375                 380

Phe Leu Ser Asn Ala Leu Glu Ile Ile Tyr Leu Arg Ala Leu Ser Tyr
385                 390                 395                 400

Thr Asn Gly Pro Asn Asp Val Thr Lys Met Ile Glu Asn Leu Ser Gln
                405                 410                 415

Ile Leu Lys Tyr Leu Leu Ser Asn Pro Asn Glu Thr Val Thr Val Lys
            420                 425                 430

Glu Glu Ile Glu Asn Thr Lys Ala Tyr Ile Gln Ile Leu Lys Val Arg
```

```
                435                 440                 445
Tyr Arg Asp Lys Phe Lys Val Asn Leu Ile Tyr Asp Glu Ser Ile Leu
    450                 455                 460

Ser Cys Leu Met Met Lys Leu Met Leu Gln His Leu Ile Glu Asn Ser
465                 470                 475                 480

Ile Lys His Gly Leu Lys Lys Asn Tyr Glu Gly Ser Ile Lys Ile
                485                 490                 495

Lys Ile Lys Ala Val Asp Lys Lys Ile Lys Ile Ser Val Ile Asp
            500                 505                 510

Asn Gly Ile Gly Met Ser Lys Glu Arg Leu Asn Tyr Val Lys Arg Ile
        515                 520                 525

Leu Asp Ser Asp Phe Asp Phe Tyr Glu His Ile Gly Leu Met Asn Thr
    530                 535                 540

Asn Glu Arg Leu Lys Leu Leu Tyr Gly Lys Asp Cys Glu Ile Leu Ile
545                 550                 555                 560

Arg Ser Lys Leu Asn Ile Gly Thr Ala Val Tyr Ile Ile Phe Pro Tyr
                565                 570                 575

Gln Leu Lys Asn Gln Asn Asn Asp Asp Tyr Asn Lys
            580                 585

<210> SEQ ID NO 107
<211> LENGTH: 1767
<212> TYPE: DNA
<213> ORGANISM: T. saccharolyticum

<400> SEQUENCE: 107
atgagagaat taaacaataa attttttat aaaaatcttt ttgttttggc attgccatta      60
attttaattg ttattgtatt aggttcattt tcaatattaa taacagaaag atatgttaga    120
gatgaaatat acaaaaatag tagagaaata ttaaagcaaa gcagtaatga tttgtcaatt    180
ttatttaatg atataaataa aatttattta acatttggaa caaacaaaga tgtgacattg    240
tatttggaaa ggatcttaaa tacaaataaa tattctttag atgatatgtg gcatcttagc    300
atgatagaaa gtttatttga ttctacgtcg ttttcagaac cttatataca atcaatttat    360
ttgtatttta acaatcctaa taaaaatttt ttagtgacag gaaatggtat taattctgta    420
acaaattata ttgataataa atggtatgac agcttttta atgcaccaaa agatgagatt    480
tcttggatag aggttagaaa tttaaaaatg tatagtttcg ataaaagggg ataaaagtc     540 ctaagtatat acaaaaaaat tgcaaacttt aacggggata aaattgatgg tgtgcttgta    600
ctaaatatat atttggacta tattgaaaat ttgctaaata cttcaacaat atttcctgac    660
caaaaaattc ttatattaga tgcccacgac aatttaatat gtcaaaatat taatgggaat    720
ttcactggga agatagactt agataattat agcaaagcaa acatcataac aaaattagaa    780
tctccaaatt ataatataaa atatgtatct attgttccta aaaaatacct ttatgaagtt    840
cctataaagc ttttaaagat gactttagtt ttacttttga cgtcaatttt ttttgtgata    900
ttgataacat ttagaatcac taaacgaaat tacgaaaatg taaataaaat attaaagatt    960
atagaggcag aaaagacaaa tgagatattt ccagaaattc cagtagaaag tagagatgag   1020
tacagctata taatttacaa cattattaat agttatattg aaaaaagtca attgaaaatg   1080
gaattagcag aaaagaagta taaatgaaa gcaatggagt tattagcact gcaatcgcaa    1140
attagtcctc atttttgtc taatgcgttg gagattattt atcttagggc attgtcatac    1200
acaaacggtc ctaatgatgt cacaaaaatg attgaaaatt tgtcacagat tttaaagtat   1260
```

-continued

```
ttgttaagta atccaaatga aacagtaact gtaaagaag aaattgaaaa tacaaaggca    1320
tatatacaaa tattgaaggt caggtataga gataaattta agtaaatct aatttatgat    1380 gaaagtattt tatcatgtct catgatgaaa ctgatgctgc aacatttaat agaaaattct   1440
ataaaacatg ggcttaagaa gaaaaattat gaaggatcaa taaaaatcaa aataaaagca   1500
gttgataaaa agaaaataaa aatttcagta atcgataatg gcataggaat gtccaaagag   1560
aggctaaatt atgtaaaaag aattcttgac tctgacttcg atttttatga acatattgga   1620
ctaatgaata caaatgaacg gttaaaactt ctctatggga aagattgtga aatattaata   1680
agaagtaaat tgaatattgg tactgccgta tatataattt ttccatatca attaaaaaat   1740
cagaataatg atgattataa taagtga                                      1767
```

<210> SEQ ID NO 108
<211> LENGTH: 687
<212> TYPE: PRT
<213> ORGANISM: T. saccharolyticum

<400> SEQUENCE: 108

```
Met Gly Ile Asn Arg Tyr Asp Leu Val Lys Arg His Asn Val Ile Leu
1               5                   10                  15

Glu Lys Ala Asp Ile Glu Asn Pro Leu Ser Val Gly Asn Gly Glu Ile
                20                  25                  30

Ala Phe Thr Ala Asp Ile Thr Gly Met Gln Thr Phe Ile Asp Asp Tyr
            35                  40                  45

Lys Ser Ile Pro Leu Cys Thr Met Ser Gln Trp Gly Phe His Thr Thr
        50                  55                  60

Pro Ala Gln Asn Asp Lys Gly Tyr Tyr Thr Leu Glu Asp Leu Asn Leu
65                  70                  75                  80

Lys Tyr Tyr Asp Ala Phe Asp Arg Lys Val Gly Tyr Val Thr Ser Ala
                85                  90                  95

Glu Asn Gln Glu Asn Val Phe Asn Trp Leu Arg Ser Asn Pro His Arg
            100                 105                 110

Ile Asn Leu Gly Asn Ile Gly Leu Asn Ile Ile Leu Asp Asp Gly Thr
        115                 120                 125

Lys Ala Glu Leu Lys Asp Ile Phe Glu Ile His Gln Val Leu Asp Leu
130                 135                 140

Trp Asn Gly Ile Leu Ile Ser Asp Phe Lys Val Glu Lys Val Pro Val
145                 150                 155                 160

His Val Glu Thr Phe Cys His Pro Tyr Glu Asp Met Ile Asn Phe Ser
                165                 170                 175

Val Glu Ser Glu Leu Leu Lys Gln Asn Lys Ile Tyr Ile Glu Val Lys
            180                 185                 190

Phe Pro Tyr Gly Ala Ala Asn Ile Ser Gly Ser Asp Trp Asp Arg Asn
        195                 200                 205

Asp Arg His Asp Thr Asn Val Val Asp Tyr Gly Arg Asp Phe Val Glu
    210                 215                 220

Leu Leu Arg Thr Val Asp Glu Asp Val Tyr Phe Val Lys Ile Glu Tyr
225                 230                 235                 240

Ser Lys Gly Val Tyr Leu Asn Arg Ile Gly Glu Asn His Phe Ala Leu
                245                 250                 255

Lys Gln Lys Glu Tyr Asn Gly Arg Ile Glu Phe Ser Cys Leu Phe Ser
            260                 265                 270

Lys Gln Lys Pro Leu Lys Cys Leu His Ser Phe Ser Glu Ser Lys Arg
        275                 280                 285
```

```
Met Cys Lys Glu Tyr Trp Asn Ser Phe Trp Arg Gly Gly Ala Ile
        290                 295                 300

Asp Phe Ser Lys Cys Glu Asp Lys Arg Ala Phe Glu Leu Glu Arg Arg
305                 310                 315                 320

Val Ile Leu Ser Gln Tyr Leu Thr Ala Ile Gln Cys Ser Gly Ser Met
                325                 330                 335

Pro Pro Gln Glu Thr Gly Leu Thr Cys Asn Ser Trp Tyr Gly Lys Phe
                340                 345                 350

His Leu Glu Met His Trp Trp His Ala Val His Phe Ala Leu Trp Gly
                355                 360                 365

Arg Met Pro Leu Leu Ser Arg Ser Ile Trp Trp Tyr Arg Ser Ile Phe
370                 375                 380

Asn Val Ser Arg Asp Ile Ala Arg Lys Gln Gly Tyr Lys Gly Val Arg
385                 390                 395                 400

Trp Pro Lys Met Val Gly Pro Asp Gly Arg Asp Ser Pro Ser Pro Ile
                405                 410                 415

Gly Pro Leu Leu Val Trp Gln Gln Pro His Leu Ile Tyr Tyr Ser Glu
                420                 425                 430

Leu Phe Phe Arg Glu Asn Pro Thr Glu Thr Leu Asp Met Phe Lys
                435                 440                 445

Asp Ile Val Ile Asn Thr Ala Asp Phe Ile Ala Ser Phe Val Ala Tyr
450                 455                 460

Asp Arg Lys Asn Asp Arg Tyr Ile Leu Ala Pro Pro Leu Ile Pro Ala
465                 470                 475                 480

Gln Glu Asn His Asp Pro Asn Val Thr Leu Asn Pro Val Phe Glu Leu
                485                 490                 495

Glu Tyr Phe Ser Phe Ala Leu Glu Ile Ala Val Lys Trp Ile Glu Arg
                500                 505                 510

Leu Gly Leu Asn Val Asn Gln Glu Trp Asn Glu Ile Arg Phe Lys Leu
                515                 520                 525

Ala Asn Leu Pro Ser Lys Asp Gly Val Tyr Ile Ser His Glu Lys Cys
530                 535                 540

Ile Asn Thr Tyr Glu Lys Phe Asn Phe Asp His Pro Ser Met Leu Ala
545                 550                 555                 560

Ala Leu Gly Met Leu Pro Gly Arg Lys Val Asp Lys Glu Thr Met Arg
                565                 570                 575

Arg Thr Leu His Arg Val Leu Lys Glu Trp Lys Phe Glu Glu Met Trp
                580                 585                 590

Gly Trp Asp Phe Pro Met Met Ala Met Thr Ala Thr Arg Leu Gly Glu
                595                 600                 605

Pro Glu Thr Ala Ile Asn Ile Leu Leu Met Asp Ser Pro Lys Asn Thr
610                 615                 620

Tyr Met Val Asn Gly His Asn Asn Gln Ile Pro Asn Lys Glu Leu Pro
625                 630                 635                 640

Val Tyr Leu Pro Gly Asn Gly Leu Leu Ala Ala Met Ala Leu Met
                645                 650                 655

Thr Ala Gly Trp Asp Gly Asn Ser Gln Ser Thr Pro Gly Phe Pro Lys
                660                 665                 670

Asn Gly Met Trp Asn Val Glu Trp Glu Gly Leu Lys Ala Met Ile
                675                 680                 685

<210> SEQ ID NO 109
<211> LENGTH: 2064
```

<212> TYPE: DNA
<213> ORGANISM: T. saccharolyticum

<400> SEQUENCE: 109

```
atgggaatta acagatatga tcttgtaaaa aggcataatg taattttgga aaaagcagat      60
atcgaaaatc cattgtcagt aggtaatgga gaaattgctt ttacagctga tataacggga     120
atgcaaactt ttattgatga ctataagagc attcctttat gtaccatgtc acagtggggg     180
tttcatacta cgccggcaca gaatgataag ggctattata ctttggaaga tttgaacctc     240
aagtattacg atgcatttga ccgaaaggtt ggatatgtaa catcagcaga aaatcaagag     300
aatgtattta attggttgag gagtaatcct catagaatta atttaggtaa tataggatta     360
aatataattc ttgatgatgg cacaaaagca gaattgaaag atattttcga atacaccaa      420
gtattagatt tgtggaacgg aatattgata agtgacttta aagtcgaaaa agtccctgtt     480
cacgttgaga cttttgcca tccatatgaa gatatgataa attttctgt tgaatcagaa       540
ctgctaaaac aaaataaaat ttatattgaa gtaaaatttc catatggtgc ggccaatata     600
tcaggctccg attgggatag aaatgataga catgatacaa atgtggttga ttatggcaga     660
gattttgtcg aattattgag aactgtcgat gaagatgttt attttgtaaa atagagtac     720
tcaaaaggcg tttatttaaa tagaatcggg gaaaatcatt ttgcattaaa gcaaaaagag     780
tataatggga gaatagaatt ttcgtgcttg ttttcgaagc aaaaacctct taagtgcttg     840
cattcattta gtgaaagcaa aaggatgtgt aaagaatatt ggaatagctt ttggagagga     900
ggtggtgcaa tagatttttc aaagtgtgag gataaaagag cttttgaatt ggagagaagg     960
gtaatacttt cgcaatatct tacagctatt caatgttcgg gttctatgcc gccgcaagaa    1020
acagggctca cctgtaatag ctggtatggt aaatttcatt tggaaatgca ttggtggcat    1080
gctgtacatt ttgctttatg gggtagaatg cctttgctga gtagaagtat atggtggtac    1140
aggagcattt tcaatgtatc acgtgacatt gcgagaaagc aaggatacaa aggtgtacgc    1200
tggcctaaaa tggttggacc agatggaagg gatagcccct ctccgatagg accattgctt    1260
gtttggcagc agcctcatct tatatattac agtgaactgt ttttagaga aaatcctacg     1320
gaagaaacat tagatatgtt taaagacata gtaattaata ctgctgattt tattgcatca    1380
tttgttgcat atgatagaaa aaatgataga tatatacttg cgccacctt gattccagca     1440
caagaaaatc atgatcctaa cgttacatta aatccggtat ttgaattgga gtattttcg     1500
tttgcgctgg aaatagcagt taaatggatt gaaaggttag gactaaatgt gaaccaagag    1560
tggaatgaaa tacgttttaa attagctaat ttaccttcaa aagacggtgt atatatatcg    1620
catgaaaaat gtattaacac ttatgagaaa tttaattttg accatccatc tatgcttgca    1680
gcattgggga tgctaccagg ccgcaaggtt gataaagaaa ctatgagaag gactttacat    1740
agagtattaa aagagtggaa atttgaggaa atgtggggtt gggattttcc gatgatggct    1800
atgactgcaa caagattagg cgaaccggag acagcaataa atattccttt gatggattca    1860
ccaaaaaata cttatatggt aaatggccat aataaccaaa taccgaataa agaactacca    1920
gtatatttgc ctggaaatgg tggactattg gcggcaatgg ccctcatgac agctggttgg    1980
gatgggaata gccaaagcac acctggatttt cctaaaaatg ggatgtggaa tgttgaatgg    2040
gaagggttaa aagcgatgat atga                                           2064
```

<210> SEQ ID NO 110
<211> LENGTH: 293
<212> TYPE: PRT

<213> ORGANISM: T. saccharolyticum

<400> SEQUENCE: 110

| | | | | | | | | | | | | | | | |
|---|---|---|---|---|---|---|---|---|---|---|---|---|---|---|---|
| Met | Ile | Lys | Arg | Lys | Asp | Leu | Tyr | Ile | Arg | Asp | Pro | Phe | Val | Pro |
| 1 | | | | 5 | | | | | 10 | | | | | 15 |
| Val | Pro | Asn | Glu | Lys | Ile | Tyr | Tyr | Met | Phe | Gly | Thr | Thr | Asp | Ile | Asn |
| | | | 20 | | | | | 25 | | | | | 30 | | |
| Cys | Trp | Asn | Asp | Glu | Lys | Ala | Thr | Gly | Phe | Tyr | Tyr | Lys | Ser | Ser |
| | | 35 | | | | | 40 | | | | | 45 | | |
| Asp | Leu | Glu | Asn | Phe | Glu | Gly | Pro | Phe | Ile | Ala | Phe | Arg | Pro | Asp | Lys |
| | 50 | | | | | 55 | | | | | 60 | | | | |
| Asn | Phe | Ile | Trp | Asp | Lys | Asn | Phe | Trp | Ala | Pro | Glu | Val | His | Lys | Tyr |
| 65 | | | | | 70 | | | | | 75 | | | | | 80 |
| Asn | Asp | Met | Tyr | Tyr | Met | Phe | Ala | Thr | Phe | Phe | Ala | Asp | Gly | Arg | Asn |
| | | | | 85 | | | | | 90 | | | | | 95 | |
| Arg | Gly | Thr | Gln | Ile | Leu | Val | Ser | Glu | Lys | Ile | Ser | Gly | Pro | Tyr | Arg |
| | | | 100 | | | | | 105 | | | | | 110 | | |
| Pro | Trp | Ser | Ile | Glu | Pro | Val | Thr | Pro | Lys | Asp | Trp | Met | Cys | Leu | Asp |
| | | | 115 | | | | | 120 | | | | | 125 | | |
| Gly | Thr | Phe | Tyr | Val | Asp | Glu | Asn | Gly | Glu | Pro | Trp | Met | Ile | Phe | Cys |
| | 130 | | | | | 135 | | | | | 140 | | | | |
| His | Glu | Trp | Val | Gln | Ile | Tyr | Asp | Gly | Glu | Ile | Cys | Ala | Val | Arg | Leu |
| 145 | | | | | 150 | | | | | 155 | | | | | 160 |
| Ser | Lys | Asp | Leu | Lys | Thr | Thr | Ile | Gly | Asn | Pro | Ile | Thr | Leu | Phe | Lys |
| | | | | 165 | | | | | 170 | | | | | 175 | |
| Ala | Ser | Ser | Ala | Asn | Trp | Thr | Arg | Ser | Ile | Lys | Lys | Ile | Lys | Asp | His |
| | | | 180 | | | | | 185 | | | | | 190 | | |
| Glu | Cys | Tyr | Val | Thr | Asp | Gly | Pro | Phe | Ile | Tyr | Arg | Ser | Glu | Glu | Gly |
| | | | 195 | | | | | 200 | | | | | 205 | | |
| Lys | Leu | Tyr | Met | Leu | Trp | Ser | Ser | Phe | Ile | Glu | Asn | Asn | Ile | Tyr | Ala |
| | 210 | | | | | 215 | | | | | 220 | | | | |
| Val | Gly | Ile | Ser | Leu | Ser | Arg | Thr | Gly | Lys | Ile | Thr | Gly | Pro | Trp | Val |
| 225 | | | | | 230 | | | | | 235 | | | | | 240 |
| His | Ser | Glu | Asn | Pro | Ile | Phe | Ala | Gly | Asp | Gly | Gly | His | Gly | Met | Ile |
| | | | | 245 | | | | | 250 | | | | | 255 | |
| Phe | Lys | Thr | Phe | Glu | Gly | Asn | Leu | Thr | Leu | Ala | Val | His | Thr | Pro | Asn |
| | | | 260 | | | | | 265 | | | | | 270 | | |
| Lys | Arg | Lys | Glu | Glu | Arg | Pro | Leu | Phe | Ile | Thr | Leu | Glu | Lys | Ser | Val |
| | | 275 | | | | | 280 | | | | | 285 | | | |
| Leu | Asn | Asp | Thr | Leu | | | | | | | | | | | |
| | | | 290 | | | | | | | | | | | | |

<210> SEQ ID NO 111
<211> LENGTH: 882
<212> TYPE: DNA
<213> ORGANISM: T. saccharolyticum

<400> SEQUENCE: 111

```
atgataaaac gaaaggatct ttatatacgt gatccatttg tagttccagt accgaatgaa      60
aaaatatatt atatgtttgg aactactgat ataaattgct ggaatgatga aaaagcaact     120
ggatttgatt actataaatc atctgattta gaaaattttg aaggaccttt tattgcattt     180
agaccagata aaaactttat ttgggataaa aattttggg ctccagaagt gcacaaatac     240
aatgacatgt attatatgtt tgctacattt ttcgctgatg gcagaaatag aggaacgcaa     300
```

```
atttagtat ctgaaaaaat aagtgggcca tatagaccat ggagtattga accggtgacg    360
ccgaaggatt ggatgtgttt agatgggact ttttatgtag atgagaatgg ggaaccctgg    420
atgatatttt gccatgaatg ggtacaaata tatgatgggg aaatttgtgc tgtaagattg    480
tcgaaagatt taaaaacaac gataggaaat cctattacac ttttaaagc ttccagtgct    540
aattggacaa gaagtattaa aaagattaaa gatcatgaat gctacgttac ggatggccct    600
tttattata ggtctgaaga gggaaagctt tatatgttgt ggtccagttt tattgaaaac    660
aatatatacg ctgttggtat atcattatcg agaacaggca aaataaccgg cccgtgggta    720
cacagtgaaa atccaatttt cgcaggtgat ggtgggcatg gtatgatatt taagaccttt    780
gaagggaatc taacattggc agtacacaca cctaataaaa ggaaagaaga acggccccttt    840
tttataactt tagaaaaatc tgtgcttaat gataccttat aa    882
```

<210> SEQ ID NO 112
<211> LENGTH: 442
<212> TYPE: PRT
<213> ORGANISM: T. saccharolyticum

<400> SEQUENCE: 112

```
Met Phe Lys Lys Ile Thr Ser Leu Leu Ile Ser Leu Leu Leu Ile Ile
1               5                   10                  15

Ser Leu Val Thr Gly Cys Ser Ser Ser Asn Ser Ser Ser Ser
            20                  25                  30

Lys Asn Ser Ser Glu Asn Asn Thr Ser Pro Lys Thr Val Thr Leu Arg
        35                  40                  45

Phe Met Trp Trp Gly Gly Asp Ala Arg His Lys Ala Thr Leu Asp Ala
    50                  55                  60

Ile Ser Leu Tyr Glu Lys Glu His Pro Asn Val Lys Ile Asn Ala Glu
65                  70                  75                  80

Tyr Gly Gly Val Thr Asp Tyr Leu Gln Lys Leu Ile Thr Gln Leu Ser
                85                  90                  95

Ser Gly Thr Ala Pro Asp Leu Ile Gln Ile Asp Val Thr Trp Leu Gln
            100                 105                 110

Gln Leu Phe Ser Gln Gly Asp Phe Phe Ala Asp Leu Ser Lys Leu Lys
        115                 120                 125

Asp Ile Asn Val Asn Ala Phe Asp Gln Asn Phe Leu Lys Asn Tyr Cys
130                 135                 140

Tyr Val Asn Asn Lys Leu Ile Gly Leu Pro Thr Gly Ile Asn Asn Ser
145                 150                 155                 160

Ala Met Tyr Ile Asn Lys Asp Phe Phe Asn Lys Phe Gly Ile Asp Asp
                165                 170                 175

Lys Thr Val Trp Thr Trp Asp Asn Leu Leu Gln Thr Ala Lys Met Val
            180                 185                 190

His Glu Lys Asp Lys Asn Ala Tyr Leu Leu Asp Ala Asp Ser Thr Ile
        195                 200                 205

Cys Asp Tyr Ile Leu Val Thr Tyr Val Gly Gln Lys Thr Gly Asn Gln
210                 215                 220

Trp Val Lys Asp Asp Tyr Thr Leu Gly Phe Asp Lys Gln Thr Leu Thr
225                 230                 235                 240

Glu Ala Phe Lys Tyr Leu Asn Asp Leu Phe Glu Val Gly Ala Ile Glu
                245                 250                 255

Pro Phe Ser Gln Ser Ala Pro Tyr Glu Gly Lys Pro Asp Gln Asn Pro
            260                 265                 270
```

```
Met Trp Leu Asn Gly Gln Thr Gly Met Leu Trp Asn Trp Ser Ser Ile
            275                 280                 285

Tyr Ala Gly Val Lys Ala Asn Ile Lys Asn Leu Ser Leu Ala Leu Pro
            290                 295                 300

Pro Ile Asp Pro Asn Ala Lys Gln Thr Gly Ile Val Val Arg Pro Ser
305                 310                 315                 320

Gln Leu Ile Ala Ile Asn Lys Asp Ser Lys Asn Ile Asp Glu Ala Ala
            325                 330                 335

Lys Phe Leu Asn Trp Phe Phe Thr Asn Thr Asp Ala Ile Lys Thr Leu
            340                 345                 350

Lys Asp Val Arg Gly Val Pro Ala Thr Ala Asp Ala Arg Lys Ile Leu
            355                 360                 365

Ser Glu Asn Asn Leu Leu Asp Ser Thr Leu Thr Asp Asn Ala Asn Gln
            370                 375                 380

Ala Met Glu Lys Met Ala Pro Pro Glu Asn Gly Ile Ser Gly Asn Gln
385                 390                 395                 400

Glu Leu Glu Lys Ile Asn Thr Asp Ile Ile Gln Glu Leu Ala Tyr Lys
            405                 410                 415

Lys Ile Thr Pro Glu Gln Ala Ala Asp Glu Leu Ile Asn Thr Tyr Lys
            420                 425                 430

Gln Lys Leu Pro Glu Leu Lys Ser Gln Gln
            435                 440

<210> SEQ ID NO 113
<211> LENGTH: 1329
<212> TYPE: DNA
<213> ORGANISM: T. saccharolyticum

<400> SEQUENCE: 113
atgtttaaaa aaattacatc tctgttaata tcgcttcttt tgataatttc attagttaca      60
ggatgtagca gttcttcgaa ttcttcgagt tcatcgaaaa atagttctga aaataatacc     120
agcccaaaaa ccgtaacatt aagatttatg tggtggggtg gagatgccag acataaagca     180
acacttgatg ccataagtct ttatgaaaaa gaacatccca atgtaaagat taatgctgaa     240
tatggcggcg ttactgacta tctccaaaag ctgataactc aattaagcag tggtacagca     300
cctgatctta tacaaataga tgtaacatgg ttgcagcaac ttttttagcca aggtgatttt     360 tttgcagatt taagtaagtt aaaagatatc aatgtgaatg catttgatca aaattttctt     420
aaaaattatt gctatgtcaa caataagttg ataggtttgc ctacaggaat aaacaattcg     480
gcaatgtata ttaacaaaga cttttttaat aaatttggca tagacgataa gacggtttgg     540
acatgggata tctcttgca aaccgctaag atggtgcatg aaaaggataa aaatgcttat     600
cttttagatg ctgattctac tatttgtgat tatatattgg tcacatacgt ggggcaaaaa     660
actggaaatc agtgggtgaa agatgattac actttaggtt ttgataaaca acattgaca      720 gaggcattca atatttaaa cgatttgttc gaagtaggcg ctatagagcc attttctcaa     780
agtgctccat acgaaggaaa acctgatcaa atcctatgt ggcttaatgg tcaaacgggt      840
atgctttgga actggtcatc tatatatgct ggtgtaaaag caaacataaa gaacctgtca     900
ttggcattgc cacctattga ccctaatgca aaacagacag gcatagttgt aagaccatca     960
cagcttattg ctattaacaa ggattctaaa aatatcgatg aagcagcaaa atttttaaat    1020 tggttctttta cgaatacaga tgctataaaa acacttaaag atgtcagagg agttccagct    1080
accgcagatg cacgcaaaat ttatcagaa aataatttgt tggattcgac tttaactgat     1140
```

```
aatgcaaatc aagctatgga aaagatggca cctcctgaaa acggtataag tggtaatcaa    1200
gagttagaaa agataaatac tgatatcata caagaactgg cttataaaaa gataacgcca    1260
gagcaggctg ctgatgaatt gataaatact tataaacaga aacttccaga attaaaaagc    1320
cagcaataa                                                            1329
```

<210> SEQ ID NO 114
<211> LENGTH: 295
<212> TYPE: PRT
<213> ORGANISM: T. saccharolyticum

<400> SEQUENCE: 114

```
Met Ser Tyr Asn Lys Lys Arg Asn Leu Met Gly Tyr Leu Tyr Ile Ser
1               5                   10                  15

Pro Trp Ile Ile Gly Phe Leu Ile Phe Thr Leu Tyr Pro Phe Ala Met
            20                  25                  30

Thr Phe Ile Tyr Ser Phe Cys Asn Tyr Ser Ile Thr Lys Ser Pro Val
        35                  40                  45

Phe Ile Gly Leu Gly Asn Tyr Ile Thr Met Phe Thr Lys Asp Met Tyr
    50                  55                  60

Phe Trp Pro Ser Leu Ile Asn Thr Ile Lys Tyr Val Leu Met Thr Val
65                  70                  75                  80

Pro Leu Lys Leu Cys Phe Ala Leu Phe Val Ala Met Ile Leu Asn Ile
                85                  90                  95

Asp Ile Lys Gly Val Asn Val Phe Arg Thr Thr Tyr Tyr Leu Pro Ser
            100                 105                 110

Ile Phe Gly Gly Ser Val Ala Leu Ser Val Ile Trp Lys Phe Leu Phe
        115                 120                 125

Met Asp Asn Gly Ile Met Asn Lys Phe Leu Ser Tyr Phe His Ile His
    130                 135                 140

Gly Pro Ser Trp Leu Gly Asn Pro His Ile Ser Leu Phe Thr Ile Ser
145                 150                 155                 160

Leu Leu Ser Val Trp Glu Phe Gly Ser Ser Met Val Ile Phe Leu Ala
                165                 170                 175

Ala Leu Lys Gln Val Pro Asn Glu Leu Tyr Glu Ala Ser Met Leu Asp
            180                 185                 190

Gly Ala Ser Lys Ile Arg Arg Phe Phe Ser Ile Thr Leu Pro Met Ile
        195                 200                 205

Ser Pro Val Leu Leu Phe Asn Leu Val Met Gln Thr Ile Asn Ala Phe
    210                 215                 220

Gln Glu Phe Thr Gly Pro Tyr Val Ile Thr Gly Gly Pro Met Asn
225                 230                 235                 240

Ser Thr Tyr Val Tyr Ser Met Leu Ile Tyr Asp Asn Ala Phe Arg Tyr
                245                 250                 255

Phe Arg Met Gly Tyr Ser Ser Ala Leu Ser Trp Ile Leu Phe Leu Leu
            260                 265                 270

Ile Leu Ile Val Thr Val Ile Phe Lys Ser Ser Asn Thr Trp Val
        275                 280                 285

Tyr Tyr Glu Asn Gly Gly Arg
    290                 295
```

<210> SEQ ID NO 115
<211> LENGTH: 888
<212> TYPE: DNA
<213> ORGANISM: T. saccharolyticum

```
<400> SEQUENCE: 115
atgagttata ataaaaagag aaatttgatg gggtatttat atattagtcc atggattata    60
ggcttttaa tatttactct gtatccattt gctatgactt ttatctattc attttgtaac    120
tacagtatta caaaatcacc tgtatttatt ggattaggca attatataac tatgtttact    180
aaagatatgt attttggcc atctttaatt aatactataa aatatgtatt aatgacagtt    240
cctttaaaat tatgttttgc acttttgtt gcaatgatct taaatattga tattaaagga    300
gttaatgtgt ttagaacaac ttattatctg ccttctattt ttggaggaag tgttgcttta    360
tctgttatat ggaaatttt attcatggat aatggtatta tgaataaatt tctttcatac    420
tttcatatac acgggccaag ttggcttgga aacccacaca tatcattatt tactataagt    480
ttattgtcag tgtgggaatt tgggtcttct atggtaatat ttttggcagc cctaaaacag    540
gtcccgaatg agttgtatga agcatctatg ttagatggtg caagcaaaat aagaaggttt    600
ttctcaataa ctttacctat gatatcgcct gtgctattat ttaatttggt tatgcagact    660
ataaatgctt tcaggaatt tacaggtcca tacgtgataa ctggtggagg accgatgaac    720
tctacttatg tgtacagtat gttgatttat gataatgcgt ttaggtattt taggatgggt    780
tattcatctg ccttgtcttg gattttattt ttgttaatat tgattgttac agttataata    840
tttaaatctt caaatacatg ggtgtattac gaaaatggag gtagatga              888

<210> SEQ ID NO 116
<211> LENGTH: 285
<212> TYPE: PRT
<213> ORGANISM: T. saccharolyticum

<400> SEQUENCE: 116

Met Lys Ala Lys Asn Ser Gln Asn Asn Asp Ile Ile Arg Lys Val Phe
1               5                   10                  15
Ile Tyr Val Phe Leu Val Ala Phe Gly Ile Phe Met Ile Tyr Pro Leu
            20                  25                  30
Leu Trp Val Phe Ala Ser Ser Phe Lys Ser Asn Asp Glu Ile Phe Lys
        35                  40                  45
Ser Ile Ser Leu Ile Pro Lys His Ile Val Thr Asn Ser Tyr Phe Glu
    50                  55                  60
Gly Trp Lys Gly Thr Gly Gln Tyr Ser Phe Gly Thr Phe Ile Leu Asn
65                  70                  75                  80
Ser Ile Thr Leu Val Val Pro Val Val Phe Thr Ala Ile Ser Ser
            85                  90                  95
Thr Ile Val Ala Tyr Gly Phe Ala Arg Phe Glu Phe Pro Leu Lys Thr
            100                 105                 110
Ile Leu Phe Thr Leu Met Ile Ser Thr Met Met Leu Pro Gly Thr Ala
        115                 120                 125
Val Leu Ile Pro Arg Tyr Ile Leu Phe Asn Trp Leu Gly Trp Ile Asn
    130                 135                 140
Thr Tyr Lys Pro Phe Ile Val Pro Ala Leu Phe Gly Thr Thr Pro Phe
145                 150                 155                 160
Phe Ile Phe Met Met Val Gln Phe Leu Arg Gly Leu Pro Lys Glu Leu
            165                 170                 175
Glu Glu Ser Ala Thr Ile Asp Gly Cys Asn Ser Phe Gln Ile Leu Met
        180                 185                 190
Lys Ile Leu Ile Pro Leu Cys Lys Pro Ala Ile Ile Ser Met Cys Ile
    195                 200                 205
```

```
Phe Gln Phe Ile Trp Thr Trp Asn Asp Phe Phe Asn Pro Leu Ile Tyr
        210                 215                 220
Ile Asn Ser Val Glu Lys Tyr Thr Val Ser Leu Gly Leu Asn Met Thr
225                 230                 235                 240
Ile Asp Gly Thr Ser Val Val Asn Trp Asn Gln Ile Met Ala Met Thr
                    245                 250                 255
Ile Ile Ser Met Ile Pro Ser Ile Ile Phe Ser Ala Gln Lys
            260                 265                 270
Tyr Phe Val Glu Gly Ile Ala Thr Thr Gly Leu Lys Asn
            275                 280                 285

<210> SEQ ID NO 117
<211> LENGTH: 858
<212> TYPE: DNA
<213> ORGANISM: T. saccharolyticum

<400> SEQUENCE: 117
atgaaagcaa agaatagtca aataacgat ataatcagaa aagtatttat atatgttttc      60
ttggtggctt ttggtatttt catgatatat cctttacttt gggttttgc atcatcattt     120
aaatcaaatg atgaaatctt taaatcgata agccttatac aaaacacat tgtgacaaat     180
tcatattttg aaggatggaa aggtacggga caatactctt ttggtacatt tattttaaac    240
agcattacgc ttgttgtacc tgttgttgta tttactgcta tatcatcaac aattgtagcc    300
tatggatttg caagatttga gtttccgctt aaaactattt tgtttacttt gatgatatct    360
actatgatgt tgccgggcac tgcagttttg taccaagat atatattgtt taattggtta    420
ggctggataa acacttataa accatttatt gttcccgctt tgttcggaac aacgcctttt    480
ttcatttta tgatggttca attttttgaga ggtcttccta aagaattaga agaatcggct    540
acaattgatg gttgcaattc atttcaaata cttatgaaga ttttaatacc attgtgtaaa    600
cctgcaatta tttctatgtg tatatttcag ttcatttgga cttggaatga ctttttttaat   660
ccattgatat atatcaacag tgtagaaaaa tatacagttt ctctcgggct taatatgaca    720
attgatggga cttcagttgt aaattggaac caaataatgg caatgacaat tatttcaatg    780
ataccgagca tcataatatt ttttttcagcg caaaaatact tcgttgaagg tattgcaaca    840
actggattaa agaactaa                                                   858

<210> SEQ ID NO 118
<211> LENGTH: 465
<212> TYPE: PRT
<213> ORGANISM: T. saccharolyticum

<400> SEQUENCE: 118

Met Arg Tyr Thr Asp Gly Lys Val His Asp Ile Thr Ile Ala Tyr Ile
1               5                   10                  15
Gly Gly Gly Ser Arg Gly Trp Ala Trp Asn Leu Met Thr Asp Leu Ala
                20                  25                  30
Lys Glu Glu Ser Ile Ser Gly Thr Val Lys Leu Tyr Asp Ile Asp Tyr
            35                  40                  45
Asp Ala Ala His Asp Asn Glu Ile Ile Gly Asn Ala Leu Ser Met Arg
        50                  55                  60
Gln Asp Val Lys Gly Lys Trp Leu Tyr Lys Ala Cys Glu Thr Leu Glu
65                  70                  75                  80
Glu Ser Leu Lys Gly Ala Asp Phe Val Ile Ile Ser Ile Leu Pro Gly
                85                  90                  95
```

Thr Phe Asp Glu Met Glu Ser Asp Val His Ala Pro Glu Lys Tyr Gly
            100                 105                 110

Ile Tyr Gln Ser Val Gly Asp Thr Val Gly Pro Gly Ile Val Arg
        115                 120                 125

Ala Leu Arg Thr Ile Pro Met Phe Val Asp Ile Ala Asn Ala Ile Lys
    130                 135                 140

Glu His Cys Pro Asp Ala Trp Val Ile Asn Tyr Thr Asn Pro Met Thr
145                 150                 155                 160

Leu Cys Val Arg Thr Leu Tyr Glu Ile Phe Pro Gln Ile Lys Ala Phe
                165                 170                 175

Gly Cys Cys His Glu Val Phe Gly Thr Gln Lys Leu Leu Ser Arg Ala
                180                 185                 190

Leu Gln Asp Ile Glu Gly Ile Glu Asn Val Pro Arg Glu Glu Ile Lys
                195                 200                 205

Ile Asn Val Leu Gly Ile Asn His Phe Thr Trp Ile Asp Asn Ala Arg
                210                 215                 220

Tyr Lys Asp Ile Asp Leu Met Tyr Val Tyr Lys Gln Phe Val Asn Lys
225                 230                 235                 240

Tyr Tyr Glu Ser Gly Phe Val Ser Asp Ala Asn Asn Asn Trp Met Asn
                245                 250                 255

Asn Ser Phe Val Ser Ala Glu Arg Val Lys Phe Asp Leu Phe Leu Arg
                260                 265                 270

Tyr Gly Val Ile Ala Ala Ala Gly Asp Arg His Leu Ala Glu Phe Val
                275                 280                 285

Pro Gly Tyr Trp Tyr Leu Lys Asp Pro Glu Thr Val Arg Glu Trp Met
    290                 295                 300

Phe Gly Leu Thr Thr Val Ser Trp Arg Lys Glu Asp Leu Lys Arg Arg
305                 310                 315                 320

Leu Glu Arg Ser Lys Arg Leu Lys Thr Gly Glu Lys Phe Glu Leu
                325                 330                 335

Lys Glu Thr Gly Glu Glu Gly Val Arg Gln Ile Lys Ala Leu Leu Gly
                340                 345                 350

Leu Gly Asp Leu Val Thr Asn Val Asn Met Pro Asn His Gly Gln Ile
                355                 360                 365

Glu Gly Ile Pro Tyr Gly Ala Val Val Glu Thr Asn Ala Leu Phe Ser
    370                 375                 380

Gly Asn Lys Leu Lys Pro Val Leu Ser Gly Lys Leu Pro Asp Asn Val
385                 390                 395                 400

Asn Ser Leu Val Leu Arg Gln Val Tyr Asn Gln Glu Thr Thr Leu Lys
                405                 410                 415

Ala Ala Leu Lys Arg Asp Phe Asp Leu Ala Phe Ser Ala Phe Val Asn
                420                 425                 430

Asp Pro Leu Val Thr Ile Ser Leu Lys Asp Ala Lys Lys Leu Phe Lys
            435                 440                 445

Glu Met Leu Glu Asn Thr Lys Lys Tyr Leu Asp Gly Trp Lys Ile Lys
    450                 455                 460

Ala
465

<210> SEQ ID NO 119
<211> LENGTH: 1398
<212> TYPE: DNA
<213> ORGANISM: T. saccharolyticum

<400> SEQUENCE: 119

-continued
atgagatata cagatggaaa ggttcatgac attactattg cttatatcgg tggtggttca 60
agaggatggg cgtggaattt aatgactgac ttagcaaaag aggaaagtat ttctggtaca 120
gtaaagttat acgacataga ttacgatgcg gcacatgaca atgagataat aggcaatgct 180
ttatcaatga gacaggatgt taaaggcaaa tggctttata aagcttgtga gacgttagaa 240
gagtcactaa aaggtgctga ttttgtcata atatctattt tgccaggtac gttcgacgag 300

atggaatctg atgttcatgc accagaaaag tatggcattt atcagtcagt aggtgataca 360
gtaggacctg gtggaatagt cagagcttta aggacgattc cgatgtttgt ggacattgcc 420
aatgcgatta aagagcattg tccagatgca tgggtcataa attatacaaa tcctatgaca 480
ctttgtgtaa ggacattgta tgaaattttc cctcaaatta aagcatttgg atgctgccat 540
gaagtttttg gcacacagaa gctattatct cgtgctctgc aggatataga aggcattgaa 600
aatgttccga gggaagagat aaagataaat gttttaggta taaatcattt tacgtggatc 660
gacaatgcaa ggtacaaaga catagattta atgtatgttt ataaacaatt tgtgaataag 720
tactatgaaa gcggatttgt cagcgatgct aacaataatt ggatgaacaa ttcatttgta 780
tctgcagaga gagtaaagtt tgatctgttt ttgaggtatg gagtaatagc tgcagcggga 840
gatagacatc tggcggaatt tgtgccggga tattggtatt taaaagatcc agagacagtc 900
agagaatgga tgtttggctt aacgactgta agttggagaa aagaagactt aaaacgcagg 960
cttgaaagaa gtaaaaggct taagacaggt gaggaaaaat ttgagttaaa ggaaacaggc 1020
gaagaaggtg ttaggcaaat taaagcacta ttaggcttag gcgatttagt gactaatgtc 1080
aacatgccga accatggaca gattgaagga ataccatacg gtgcggtagt tgaaacaaac 1140
gctttatttt caggtaataa actaaagcct gtattatcag gaaaattgcc tgacaatgta 1200
aacagcctcg tgttaaggca agtatacaac caagaaacga cgttgaaagc tgctttaaag 1260
agagattttg atttggcttt tagtgctttt gtaaatgatc cacttgttac aatatcttta 1320
aaagatgcaa aaaaattatt taaggaaatg cttgaaaata cgaagaaata tctagatgga 1380
tggaaaataa aagcttga 1398

<210> SEQ ID NO 120
<211> LENGTH: 392
<212> TYPE: PRT
<213> ORGANISM: C. acetobutylicum

<400> SEQUENCE: 120

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala

```
                115                 120                 125
Arg Trp Gly Tyr Arg Met Gly Asn Ala Lys Phe Val Asp Glu Met Ile
            130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Ile Lys Gly Arg Lys
            195                 200                 205

Gly Glu Thr Val Val Asp Thr Asp Glu His Pro Arg Phe Gly Ser Thr
            210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
            290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
            370                 375                 380

Thr Ala Ile Leu Leu Glu Lys Cys
385                 390

<210> SEQ ID NO 121
<211> LENGTH: 218
<212> TYPE: PRT
<213> ORGANISM: C. acetobutylicum

<400> SEQUENCE: 121

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
                20                  25                  30

Thr Lys Leu Ile Asp Phe Leu Val Asn Leu Asn Ile Lys Asn Leu Thr
            35                  40                  45

Ile Ile Ser Asn Asp Thr Cys Tyr Pro Asn Thr Gly Ile Gly Lys Leu
50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95
```

Leu Ser Pro Gln Gly Thr Leu Val Glu Arg Ile Arg Ala Gly Gly Ser
             100                 105                 110

Gly Leu Gly Gly Val Leu Thr Lys Thr Gly Leu Gly Thr Leu Ile Glu
        115                 120                 125

Lys Gly Lys Lys Ile Ser Ile Asn Gly Thr Glu Tyr Leu Leu Glu
130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
                180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
        210                 215

<210> SEQ ID NO 122
<211> LENGTH: 221
<212> TYPE: PRT
<213> ORGANISM: C. acetobutylicum

<400> SEQUENCE: 122

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
        210                 215                 220

<210> SEQ ID NO 123
<211> LENGTH: 244
<212> TYPE: PRT
<213> ORGANISM: C. acetobutylicum

<400> SEQUENCE: 123

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
            35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
            115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
    195                 200                 205

Ala Met Ala Pro Leu Asn Asp Leu Pro Val Lys Glu Ile Val Ser Ser
210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 124
<211> LENGTH: 244
<212> TYPE: PRT
<213> ORGANISM: C. acetobutylicum

<400> SEQUENCE: 124

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
            35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

```
Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 125
<211> LENGTH: 899
<212> TYPE: PRT
<213> ORGANISM: M. thermoacetica

<400> SEQUENCE: 125

Met Val Asn Leu Thr Ile Asp Gly Gln Arg Val Thr Ala Pro Glu Gly
1               5                   10                  15

Met Thr Ile Leu Glu Val Ala Arg Glu Asn Gly Ile His Ile Pro Thr
            20                  25                  30

Leu Cys His His Pro Lys Leu Arg Pro Leu Gly Tyr Cys Arg Leu Cys
        35                  40                  45

Leu Val Asp Ile Glu Gly Ala Ala Lys Pro Met Thr Ala Cys Asn Thr
    50                  55                  60

Pro Val Ala Glu Gly Met Val Ile Arg Thr Ser Thr Pro Val Ile Glu
65                  70                  75                  80

Glu Met Arg Lys Gly Ile Ile Glu Met Leu Leu Ser Leu His Pro Glu
                85                  90                  95

Asp Cys Leu Thr Cys Glu Lys Ala Gly Asn Cys Gln Leu Gln Asp Cys
            100                 105                 110

Ala Tyr Thr Tyr Gly Val Lys His Gly Glu Leu Pro Val Lys Arg Glu
        115                 120                 125

Glu Leu Pro Val Leu Lys Glu Asn Pro Phe Ile Val Arg Asp Tyr Asn
    130                 135                 140

Lys Cys Ile Val Cys Gly Arg Cys Val Arg Ala Cys Gln Glu Val Gln
145                 150                 155                 160

Val Gln Arg Val Val Asp Leu Val Gly Lys Gly Ser Ala Ala Arg Val
                165                 170                 175

Gly Ala Thr Lys Ala Gly Ala Glu Val Ser Leu Glu Glu Gly Gly Cys
            180                 185                 190

Val Phe Cys Gly Asn Cys Val Gln Val Cys Pro Val Gly Ala Leu Thr
        195                 200                 205

Glu Lys Ala Gly Leu Gly Gln Gly Arg Glu Trp Glu Phe Lys Lys Val
    210                 215                 220

Arg Ser Ile Cys Ser Tyr Cys Gly Val Gly Cys Asn Leu Thr Leu Tyr
225                 230                 235                 240
```

```
Val Lys Asp Gly Lys Val Lys Val Arg Gly Tyr Glu Asn Pro Glu
            245                 250                 255

Val Asn Asn Gly Trp Leu Cys Val Lys Gly Arg Phe Gly Phe Asp Tyr
            260                 265                 270

Ile His Asn Pro Asp Arg Ile Thr Arg Pro Leu Ile Arg Glu Gly Asp
            275                 280                 285

Arg Glu Lys Gly Tyr Phe Arg Glu Ala Ser Trp Glu Glu Ala Leu Ala
            290                 295                 300

Leu Val Ser Gln Lys Leu Thr Gln Ile Lys Gly Ser Tyr Gly Ser Glu
305                 310                 315                 320

Ala Leu Gly Phe Leu Cys Ser Ala Lys Cys Thr Asn Glu Glu Asn Tyr
                325                 330                 335

Leu Leu Gln Lys Leu Ala Arg Gly Val Leu Gly Thr Asn Asn Val Asp
            340                 345                 350

His Cys Ala Arg Leu His Ser Ser Thr Val Ala Gly Leu Ala Thr Thr
            355                 360                 365

Phe Gly Ser Gly Ala Met Thr Asn Ser Ile Ala Asp Ile Ala Ser Ala
    370                 375                 380

Asp Cys Ile Phe Val Ile Gly Ser Asn Thr Thr Glu Asn His Pro Val
385                 390                 395                 400

Ile Ala Leu Lys Val Lys Glu Ala Val Arg Arg Gly Ala Arg Leu Ile
                405                 410                 415

Val Ala Asp Pro Arg Arg Ile Glu Leu Val Asn Phe Ser Tyr Leu Trp
            420                 425                 430

Leu Arg Gln Lys Pro Gly Thr Asp Leu Ala Leu Leu Asn Gly Leu Leu
            435                 440                 445

His Val Ile Ile Lys Glu Glu Leu Tyr Asp Lys Glu Phe Ile Ala Gln
    450                 455                 460

Arg Thr Glu Gly Phe Glu Ala Leu Lys Leu Ala Val Glu Glu Tyr Thr
465                 470                 475                 480

Pro Ala Lys Val Ser Glu Val Thr Gly Val Pro Ala Gly Asp Ile Ile
                485                 490                 495

Glu Ala Ala Arg Thr Tyr Ala Arg Gly Pro Ser Ser Thr Ile Leu Tyr
            500                 505                 510

Ala Met Gly Ile Thr Gln His Ile Thr Gly Thr Ala Asn Val Met Ala
            515                 520                 525

Leu Ala Asn Leu Ala Met Ala Cys Gly Gln Val Gly Lys Glu Gly Ser
            530                 535                 540

Gly Val Asn Pro Leu Arg Gly Gln Ser Asn Val Gln Gly Ala Cys Asp
545                 550                 555                 560

Met Gly Gly Leu Pro Asn Val Leu Pro Gly Tyr Gln Pro Val Thr Asp
                565                 570                 575

Pro Gly Val Arg His Lys Phe Ser Glu Ala Trp Gly Val Pro Asp Leu
            580                 585                 590

Pro Gly Glu Pro Gly Leu Thr Leu Met Glu Met Ala Ala Ala Gln
            595                 600                 605

Glu Gly Lys Leu Lys Gly Met Tyr Ile Leu Gly Glu Asn Pro Val Leu
    610                 615                 620

Thr Asp Pro Asp Val Ser His Val Lys Glu Ala Leu Lys Asn Leu Glu
625                 630                 635                 640

Phe Leu Val Val Gln Asp Ile Phe Leu Thr Glu Thr Ala Arg Met Ala
                645                 650                 655

Asp Val Val Leu Pro Gly Ala Ser Phe Ala Glu Lys Glu Gly Thr Phe
```

```
                    660                 665                 670
Thr Ser Thr Glu Arg Arg Val Gln Leu Leu His Lys Ala Ile Glu Pro
            675                 680                 685

Pro Gly Glu Ala Arg Pro Asp Trp Leu Ile Leu Asn Asp Leu Leu Leu
        690                 695                 700

Leu Met Gly Tyr Pro Arg Lys Tyr Ser Ser Pro Gly Glu Ile Met Gln
705                 710                 715                 720

Glu Ile Ala Gly Leu Thr Pro Ser Tyr Ala Gly Ile Thr Tyr Glu Arg
                725                 730                 735

Leu Glu Asp Lys Gly Leu Gln Trp Pro Val Leu Ser Leu Glu His Pro
            740                 745                 750

Gly Thr Pro Val Leu His Arg Glu Lys Phe Ser Arg Gly Tyr Gly Gln
        755                 760                 765

Phe Gln Val Val His Tyr Arg Pro Pro Ala Glu Glu Pro Asp Glu Glu
770                 775                 780

Tyr Pro Phe Leu Phe Thr Thr Gly Arg Asn Leu Tyr His Tyr His Thr
785                 790                 795                 800

Val Ile Ser Arg Lys Ser Arg Gly Leu Glu Glu Met Cys Pro Ala Pro
                805                 810                 815

Val Val Glu Ile Asn Asp Asn Asp Ala Ala Arg Leu Gly Ile Arg Glu
            820                 825                 830

Gly Glu Met Ile Glu Ile Val Ser Arg Arg Gly Lys Val Arg Val Lys
        835                 840                 845

Ala Leu Val Thr Asp Arg Ile Pro Arg Gly Gln Val Phe Met Asn Phe
850                 855                 860

His Phe His Glu Ala Ala Ala Asn Leu Leu Thr Ile Ala Ala Leu Asp
865                 870                 875                 880

Pro Val Ala Lys Ile Pro Glu Tyr Lys Thr Cys Ala Val Ala Ile Lys
                885                 890                 895

Val Lys Lys

<210> SEQ ID NO 126
<211> LENGTH: 152
<212> TYPE: PRT
<213> ORGANISM: Oryza sativa

<400> SEQUENCE: 126

Met Glu Leu Thr Thr Arg Thr Ile Ala Glu Arg Lys His Ile Ala Leu
1               5                   10                  15

Val Ala His Asp His Arg Lys Gln Ala Leu Leu Glu Trp Val Glu Ser
                20                  25                  30

His Lys Thr Ile Leu Ala Gln His Gln Leu Tyr Ala Thr Gly Thr Thr
            35                  40                  45

Gly Asn Leu Ile Gln Arg Ala Ser Gly Ile Pro Val Thr Ser Met Leu
        50                  55                  60

Ser Gly Pro Met Gly Gly Asp Gln Gln Val Gly Ala Leu Ile Ala Glu
65                  70                  75                  80

Gly Lys Ile Asp Met Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Arg Ser Thr Ala Asp Phe Leu Ile Asp
        115                 120                 125

Ser Pro Leu Phe Lys Ser Glu Val Ala Ile Ala Ile Pro Asp Tyr Gln
```

```
                130                 135                 140
Arg Tyr Leu Gln Asp Arg Leu Lys
145                 150
```

<210> SEQ ID NO 127
<211> LENGTH: 350
<212> TYPE: PRT
<213> ORGANISM: T. saccharolyticum

<400> SEQUENCE: 127

```
Met Lys Thr Ser Glu Leu Leu Ala Met Val Val Glu Lys Gly Ala Ser
1               5                   10                  15

Asp Leu His Ile Thr Val Gly Val Pro Val Leu Arg Ile Asn Gly
            20                  25                  30

Gln Leu Ile Lys Leu Asn Leu Pro Gln Leu Thr Pro Gln Asp Thr Glu
            35                  40                  45

Glu Ile Thr Lys Asp Leu Leu Ser Ser Asp Glu Leu Lys Lys Leu Glu
        50                  55                  60

Asp Met Gly Asp Ile Asp Leu Ser Tyr Ser Val Lys Gly Leu Gly Arg
65                  70                  75                  80

Phe Arg Ile Asn Ala Tyr Lys Gln Arg Gly Thr Tyr Ser Leu Ala Ile
                85                  90                  95

Arg Ser Val Ala Leu Arg Ile Pro Thr Ile Asp Glu Leu Gly Leu Pro
            100                 105                 110

Glu Val Ile Lys Glu Leu Ala Leu Lys Thr Arg Gly Leu Ile Ile Val
            115                 120                 125

Thr Gly Pro Thr Gly Ser Gly Lys Ser Thr Thr Leu Ala Ser Met Ile
        130                 135                 140

Asp Leu Ile Asn Glu Glu Arg Asn Cys His Ile Leu Thr Leu Glu Asp
145                 150                 155                 160

Pro Ile Glu Tyr Leu His Lys His Lys Lys Ser Ile Val Asn Gln Arg
                165                 170                 175

Glu Ile Gly His Asp Ala Ala Ser Tyr Ala Ser Ala Leu Arg Ala Ala
            180                 185                 190

Leu Arg Glu Asp Pro Asp Val Ile Leu Val Gly Glu Met Arg Asp Leu
            195                 200                 205

Glu Thr Ile Gln Ile Ala Ile Thr Ala Ala Glu Thr Gly His Leu Val
        210                 215                 220

Leu Ser Thr Leu His Thr Ile Gly Ser Ala Lys Thr Ile Asp Arg Ile
225                 230                 235                 240

Ile Asp Val Phe Pro Pro His Gln Gln Gln Ile Lys Val Gln Leu
                245                 250                 255

Ser Asn Val Leu Glu Gly Ile Val Ser Gln Gln Leu Leu Pro Lys Ile
            260                 265                 270

Asp Asn Ser Gly Arg Val Val Ala Val Glu Val Met Ile Ala Thr Pro
        275                 280                 285

Ala Ile Arg Asn Leu Ile Arg Glu Gly Lys Ser Phe Gln Ile Gln Ser
        290                 295                 300

Met Val Gln Thr Gly Asn Lys Phe Gly Met Val Thr Met Asp Met Trp
305                 310                 315                 320

Ile Ser Gln Leu Leu Lys Arg Asn Leu Ile Ser Met Asp Asp Ala Leu
                325                 330                 335

Thr Tyr Cys Val Asp Arg Glu Asn Phe Ser Arg Leu Val Val
            340                 345                 350
```

<210> SEQ ID NO 128
<211> LENGTH: 365
<212> TYPE: PRT
<213> ORGANISM: Pseudomonas putida

<400> SEQUENCE: 128

```
Met Asp Arg Ala Ile Gln Ser Pro Gly Lys Tyr Val Gln Gly Ala Asp
1               5                   10                  15

Ala Leu Gln Arg Leu Gly Asp Tyr Leu Lys Pro Leu Ala Asp Ser Trp
            20                  25                  30

Leu Val Ile Ala Asp Lys Phe Val Leu Gly Phe Ala Glu Asp Thr Ile
        35                  40                  45

Arg Gln Ser Leu Ser Lys Ala Gly Leu Ala Met Asp Ile Val Ala Phe
    50                  55                  60

Asn Gly Glu Cys Ser Gln Gly Glu Val Asp Arg Leu Cys Gln Leu Ala
65                  70                  75                  80

Thr Gln Asn Gly Arg Ser Ala Ile Val Gly Ile Gly Gly Lys Thr
            85                  90                  95

Leu Asp Thr Ala Lys Ala Val Ala Phe Phe Gln Lys Val Pro Val Ala
            100                 105                 110

Val Ala Pro Thr Ile Ala Ser Thr Asp Ala Pro Cys Ser Ala Leu Ser
        115                 120                 125

Val Leu Tyr Thr Asp Glu Gly Glu Phe Asp Arg Tyr Leu Met Leu Pro
    130                 135                 140

Thr Asn Pro Ala Leu Val Val Asp Thr Ala Ile Val Ala Arg Ala
145                 150                 155                 160

Pro Ala Arg Leu Leu Ala Ala Gly Ile Gly Asp Ala Leu Ala Thr Trp
                165                 170                 175

Phe Glu Ala Arg Ala Ala Ser Arg Ser Ala Ala Thr Met Ala Gly
            180                 185                 190

Gly Pro Ala Thr Gln Thr Ala Leu Asn Leu Ala Arg Phe Cys Tyr Asp
        195                 200                 205

Thr Leu Leu Glu Glu Gly Glu Lys Ala Met Leu Ala Val Gln Ala Gln
    210                 215                 220

Val Val Thr Pro Ala Leu Glu Arg Ile Val Glu Ala Asn Thr Tyr Leu
225                 230                 235                 240

Ser Gly Val Gly Phe Glu Ser Gly Gly Val Ala Ala His Ala Val
                245                 250                 255

His Asn Gly Leu Thr Ala Val Ala Glu Thr His His Phe Tyr His Gly
            260                 265                 270

Glu Lys Val Ala Phe Gly Val Leu Val Gln Leu Ala Leu Glu Asn Ala
        275                 280                 285

Ser Asn Ala Glu Met Gln Glu Val Met Ser Leu Cys His Ala Val Gly
    290                 295                 300

Leu Pro Ile Thr Leu Ala Gln Leu Asp Ile Thr Glu Asp Ile Pro Thr
305                 310                 315                 320

Lys Met Arg Ala Val Ala Glu Leu Ala Cys Ala Pro Gly Glu Thr Ile
                325                 330                 335

His Asn Met Pro Gly Gly Val Thr Val Glu Gln Val Tyr Gly Ala Leu
            340                 345                 350

Leu Val Ala Asp Gln Leu Gly Gln His Phe Leu Glu Phe
        355                 360                 365
```

<210> SEQ ID NO 129

```
<211> LENGTH: 564
<212> TYPE: PRT
<213> ORGANISM: T. saccharolyticum

<400> SEQUENCE: 129
```

| | | | | | | | | | | | | | | |
|---|---|---|---|---|---|---|---|---|---|---|---|---|---|---|
| Met | Ile | Lys | Lys | Leu | Gly | Asp | Leu | Leu | Val | Glu | Val | Gly | Leu | Leu |
| 1 | | | 5 | | | | | 10 | | | | | 15 | |
| Asp | Glu | Ser | Gln | Leu | Asn | Asn | Ala | Ile | Lys | Ile | Gln | Lys | Lys | Thr | Gly |
| | | | 20 | | | | | 25 | | | | | 30 | | |
| Glu | Lys | Leu | Gly | Lys | Ile | Leu | Val | Lys | Glu | Gly | Tyr | Leu | Thr | Glu | Glu |
| | | 35 | | | | | 40 | | | | | 45 | | | |
| Gln | Ile | Ile | Glu | Ala | Leu | Glu | Phe | Gln | Leu | Gly | Ile | Pro | His | Ile | Asp |
| | 50 | | | | | 55 | | | | | 60 | | | | |
| Met | Lys | Lys | Val | Phe | Ile | Asp | Ala | Asn | Val | Ala | Lys | Leu | Ile | Pro | Glu |
| 65 | | | | | 70 | | | | | 75 | | | | | 80 |
| Ser | Met | Ala | Lys | Arg | His | Val | Ala | Ile | Pro | Ile | Lys | Lys | Glu | Asn | Asn |
| | | | | 85 | | | | | 90 | | | | | 95 | |
| Ser | Ile | Phe | Val | Ala | Met | Ala | Asp | Pro | Leu | Asn | Ile | Phe | Ala | Ile | Asp |
| | | | 100 | | | | | 105 | | | | | 110 | | |
| Asp | Ile | Lys | Leu | Val | Thr | Lys | Leu | Asp | Val | Lys | Pro | Leu | Ile | Ala | Ser |
| | | 115 | | | | | 120 | | | | | 125 | | | |
| Glu | Asp | Gly | Ile | Leu | Lys | Ala | Ile | Asp | Arg | Val | Phe | Gly | Lys | Glu | Glu |
| | 130 | | | | | 135 | | | | | 140 | | | | |
| Ala | Glu | Arg | Ala | Val | Gln | Asp | Phe | Lys | Lys | Glu | Leu | Ser | His | Asp | Ser |
| 145 | | | | | 150 | | | | | 155 | | | | | 160 |
| Ala | Glu | Asp | Asp | Gly | Asn | Leu | Leu | Arg | Asp | Ile | Ser | Glu | Asp | Glu | Ile |
| | | | | 165 | | | | | 170 | | | | | 175 | |
| Asn | Asn | Ala | Pro | Ala | Val | Arg | Leu | Val | Asn | Ser | Ile | Ile | Glu | Gln | Ala |
| | | | 180 | | | | | 185 | | | | | 190 | | |
| Val | Lys | Asn | Arg | Ala | Ser | Asp | Val | His | Ile | Glu | Pro | Thr | Glu | Asn | Asp |
| | | 195 | | | | | 200 | | | | | 205 | | | |
| Leu | Arg | Ile | Arg | Phe | Arg | Ile | Asp | Gly | Glu | Leu | His | Glu | Ala | Met | Arg |
| | 210 | | | | | 215 | | | | | 220 | | | | |
| Val | Phe | Lys | Ser | Thr | Gln | Gly | Pro | Val | Ile | Thr | Arg | Ile | Lys | Ile | Met |
| 225 | | | | | 230 | | | | | 235 | | | | | 240 |
| Ala | Asn | Met | Asn | Ile | Ala | Glu | Arg | Arg | Ile | Pro | Gln | Asp | Gly | Lys | Ile |
| | | | | 245 | | | | | 250 | | | | | 255 | |
| Glu | Met | Asn | Ala | Gly | Gly | Lys | Asn | Ile | Asp | Ile | Arg | Val | Ser | Ser | Leu |
| | | | 260 | | | | | 265 | | | | | 270 | | |
| Pro | Thr | Ile | Tyr | Gly | Glu | Lys | Leu | Val | Leu | Arg | Ile | Leu | Asp | Lys | Ser |
| | | 275 | | | | | 280 | | | | | 285 | | | |
| Gly | Tyr | Ile | Ile | Thr | Lys | Asp | Lys | Leu | Gly | Leu | Gly | Asn | Asp | Leu |
| | 290 | | | | | 295 | | | | | 300 | | | | |
| Lys | Leu | Phe | Asp | Asn | Leu | Leu | Lys | His | Pro | Asn | Gly | Ile | Ile | Leu | Leu |
| 305 | | | | | 310 | | | | | 315 | | | | | 320 |
| Thr | Gly | Pro | Thr | Gly | Ser | Gly | Lys | Thr | Thr | Leu | Tyr | Ala | Met | Leu |
| | | | | 325 | | | | | 330 | | | | | 335 | |
| Asn | Glu | Leu | Asn | Lys | Pro | Asp | Lys | Asn | Ile | Ile | Thr | Val | Glu | Asp | Pro |
| | | | 340 | | | | | 345 | | | | | 350 | | |
| Val | Glu | Tyr | Thr | Leu | Glu | Gly | Leu | Asn | Gln | Val | Gln | Val | Asn | Glu | Lys |
| | | 355 | | | | | 360 | | | | | 365 | | | |
| Ala | Gly | Leu | Thr | Phe | Ala | Ser | Ala | Leu | Arg | Ser | Ile | Leu | Arg | Gln | Asp |
| | 370 | | | | | 375 | | | | | 380 | | | | |
| Pro | Asp | Ile | Ile | Met | Ile | Gly | Glu | Ile | Arg | Asp | Arg | Glu | Thr | Ala | Glu |

```
                385                 390                 395                 400
Ile Ala Ile Arg Ser Ser Ile Thr Gly His Leu Val Leu Ser Thr Leu
                405                 410                 415
His Thr Asn Asp Ser Ala Gly Ala Ile Thr Arg Leu Ile Asp Met Gly
                420                 425                 430
Ile Glu Pro Tyr Leu Val Ser Ser Val Val Gly Val Ile Ala Gln
                435                 440                 445
Arg Leu Ala Arg Lys Ile Cys Asp Asn Cys Lys Ile Glu Tyr Asp Ala
450                 455                 460
Ser Lys Arg Glu Lys Ile Ile Leu Gly Ile Asp Ala Asp Glu Ser Leu
465                 470                 475                 480
Lys Leu Tyr Arg Ser Lys Gly Cys Ala Val Cys Asn Lys Thr Gly Tyr
                485                 490                 495
Arg Gly Arg Val Pro Ile Tyr Glu Ile Met Met Thr Pro Lys Ile
                500                 505                 510
Lys Glu Leu Thr Asn Glu Lys Ala Pro Ala Asp Val Ile Leu Asn Glu
                515                 520                 525
Ala Val Ser Asn Gly Met Ser Thr Leu Lys Glu Ser Ala Lys Lys Leu
                530                 535                 540
Val Leu Ser Gly Val Thr Thr Val Asp Glu Met Leu Arg Leu Thr Tyr
545                 550                 555                 560
Asp Asp Ala Tyr

<210> SEQ ID NO 130
<211> LENGTH: 218
<212> TYPE: PRT
<213> ORGANISM: C. acetobutylicum

<400> SEQUENCE: 130

Met Asn Ser Lys Ile Ile Arg Phe Glu Asn Leu Arg Ser Phe Phe Lys
1               5                   10                  15
Asp Gly Met Thr Ile Met Ile Gly Gly Phe Leu Asn Cys Gly Thr Pro
                20                  25                  30
Thr Lys Leu Ile Asp Phe Leu Val Asn Leu Asn Ile Lys Asn Leu Thr
            35                  40                  45
Ile Ile Ser Asn Asp Thr Cys Tyr Pro Asn Thr Gly Ile Gly Lys Leu
    50                  55                  60
Ile Ser Asn Asn Gln Val Lys Lys Leu Ile Ala Ser Tyr Ile Gly Ser
65              70                  75                  80
Asn Pro Asp Thr Gly Lys Lys Leu Phe Asn Asn Glu Leu Glu Val Glu
                85                  90                  95
Leu Ser Pro Gln Gly Thr Leu Val Glu Arg Ile Arg Ala Gly Gly Ser
                100                 105                 110
Gly Leu Gly Gly Val Leu Thr Lys Thr Gly Leu Gly Thr Leu Ile Glu
            115                 120                 125
Lys Gly Lys Lys Lys Ile Ser Ile Asn Gly Thr Glu Tyr Leu Leu Glu
    130                 135                 140
Leu Pro Leu Thr Ala Asp Val Ala Leu Ile Lys Gly Ser Ile Val Asp
145                 150                 155                 160
Glu Ala Gly Asn Thr Phe Tyr Lys Gly Thr Thr Lys Asn Phe Asn Pro
                165                 170                 175
Tyr Met Ala Met Ala Ala Lys Thr Val Ile Val Glu Ala Glu Asn Leu
                180                 185                 190
Val Ser Cys Glu Lys Leu Glu Lys Glu Lys Ala Met Thr Pro Gly Val
```

```
                195                 200                 205
Leu Ile Asn Tyr Ile Val Lys Glu Pro Ala
    210                 215

<210> SEQ ID NO 131
<211> LENGTH: 221
<212> TYPE: PRT
<213> ORGANISM: C. acetobutylicum

<400> SEQUENCE: 131

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220

<210> SEQ ID NO 132
<211> LENGTH: 244
<212> TYPE: PRT
<213> ORGANISM: C. acetobutylicum

<400> SEQUENCE: 132

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
```

```
                   85                  90                  95
Tyr Leu Asp Asn Glu Pro Ala Ile Ala Val Gly Arg Glu Leu Ser Ala
                100                 105                 110

Tyr Pro Lys Lys Leu Gly Tyr Pro Lys Leu Phe Val Asp Ser Asp Thr
            115                 120                 125

Leu Val Gly Thr Leu Asp Tyr Gly Lys Leu Arg Val Ala Thr Ala Thr
        130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 133
<211> LENGTH: 246
<212> TYPE: PRT
<213> ORGANISM: Escherichia coli

<400> SEQUENCE: 133

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
                20                  25                  30

Arg Cys Leu Tyr Cys His Asn Arg Asp Thr Trp Asp Thr His Gly Gly
            35                  40                  45

Lys Glu Val Thr Val Glu Asp Leu Met Lys Glu Val Val Thr Tyr Arg
        50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
```

```
              210                 215                 220
Pro Lys Lys Glu Thr Met Glu Arg Val Lys Gly Ile Leu Glu Gln Tyr
225                 230                 235                 240

Gly His Lys Val Met Phe
                245

<210> SEQ ID NO 134
<211> LENGTH: 760
<212> TYPE: PRT
<213> ORGANISM: Escherichia coli

<400> SEQUENCE: 134

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
        50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335
```

```
Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
            450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
            515                 520                 525

Gly Leu Ser Val Ala Ala Asp Ser Leu Ser Ala Ile Lys Tyr Ala Lys
            530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
            595                 600                 605

Ser Asn Val Val Tyr Gly Lys Lys Thr Gly Asn Thr Pro Asp Gly Arg
            610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
            690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
```

-continued

```
                    755                 760

<210> SEQ ID NO 135
<211> LENGTH: 398
<212> TYPE: PRT
<213> ORGANISM: Saccharomyces cerevisiae

<400> SEQUENCE: 135

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
                20                  25                  30

Val Ala Leu Lys Gly Ala Leu Ala Lys Val Pro Glu Leu Asp Ala Ser
            35                  40                  45

Lys Asp Phe Asp Glu Ile Ile Phe Gly Asn Val Leu Ser Ala Asn Leu
        50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
                100                 105                 110

Val Val Ala Gly Gly Cys Glu Ser Met Thr Asn Ala Pro Tyr Tyr Met
            115                 120                 125

Pro Ala Ala Arg Ala Gly Ala Lys Phe Gly Gln Thr Val Leu Val Asp
        130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
                180                 185                 190

Gln Lys Glu Gly Lys Phe Asp Asn Glu Ile Val Pro Val Thr Ile Lys
            195                 200                 205

Gly Phe Arg Gly Lys Pro Asp Thr Gln Val Thr Lys Asp Glu Glu Pro
        210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
                260                 265                 270

Asn Leu Lys Pro Leu Ala Ile Ile Lys Gly Trp Gly Glu Ala Ala His
            275                 280                 285

Gln Pro Ala Asp Phe Thr Trp Ala Pro Ser Leu Ala Val Pro Lys Ala
        290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
                340                 345                 350

Gly His Pro Leu Gly Cys Ser Gly Ala Arg Val Val Val Thr Leu Leu
            355                 360                 365
```

Ser Ile Leu Gln Gln Glu Gly Gly Lys Ile Gly Val Ala Ala Ile Cys
370                 375                 380

Asn Gly Gly Gly Ala Ser Ser Ile Val Ile Glu Lys Ile
385                 390                 395

<210> SEQ ID NO 136
<211> LENGTH: 348
<212> TYPE: PRT
<213> ORGANISM: Saccharomyces cerevisiae

<400> SEQUENCE: 136

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Val Lys Leu Pro Leu Val
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 137
<211> LENGTH: 348
<212> TYPE: PRT
<213> ORGANISM: Saccharomyces cerevisiae

<400> SEQUENCE: 137

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345
```

<210> SEQ ID NO 138
<211> LENGTH: 375
<212> TYPE: PRT

<213> ORGANISM: Saccharomyces cerevisiae

<400> SEQUENCE: 138

```
Met Leu Arg Thr Ser Thr Leu Phe Thr Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335

Ser Arg Gly Leu Ile Lys Ser Pro Ile Lys Ile Val Gly Leu Ser Glu
            340                 345                 350

Leu Pro Lys Val Tyr Asp Leu Met Glu Lys Gly Lys Ile Leu Gly Arg
        355                 360                 365

Tyr Val Val Asp Thr Ser Lys
    370                 375
```

<210> SEQ ID NO 139
<211> LENGTH: 382

```
<212> TYPE: PRT
<213> ORGANISM: Saccharomyces cerevisiae

<400> SEQUENCE: 139

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
            35                  40                  45

Ser Gly Arg Val Gln Lys Met Leu Glu Glu Arg Asp Leu Asn Val Ala
        50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
        195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
370                 375                 380

<210> SEQ ID NO 140
```

-continued

```
<211> LENGTH: 351
<212> TYPE: PRT
<213> ORGANISM: Saccharomyces cerevisiae

<400> SEQUENCE: 140

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 141
<211> LENGTH: 360
<212> TYPE: PRT
<213> ORGANISM: Saccharomyces cerevisiae

<400> SEQUENCE: 141
```

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65              70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
    355                 360

<210> SEQ ID NO 142
<211> LENGTH: 361
<212> TYPE: PRT
<213> ORGANISM: Saccharomyces cerevisiae

<400> SEQUENCE: 142

Met Leu Tyr Pro Glu Lys Phe Gln Gly Ile Gly Ile Ser Asn Ala Lys

-continued

```
1               5                   10                  15
Asp Trp Lys His Pro Lys Leu Val Ser Phe Asp Pro Lys Pro Phe Gly
                20                  25                  30

Asp His Asp Val Asp Val Glu Ile Glu Ala Cys Gly Ile Cys Gly Ser
                35                  40                  45

Asp Phe His Ile Ala Val Gly Asn Trp Gly Pro Val Pro Glu Asn Gln
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
                100                 105                 110

Tyr Cys Thr Asn Asp His Val Leu Thr Met Trp Thr Pro Tyr Lys Asp
                115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
                180                 185                 190

Gly His Met Gly Ile Leu Leu Ala Lys Ala Met Gly Ala Glu Val Tyr
                195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Leu Val Val Cys Ser Ser Ser Leu Ser
                245                 250                 255

Lys Val Asn Phe Asp Ser Ile Val Lys Ile Met Lys Ile Gly Gly Ser
                260                 265                 270

Ile Val Ser Ile Ala Ala Pro Glu Val Asn Glu Lys Leu Val Leu Lys
    275                 280                 285

Pro Leu Gly Leu Met Gly Val Ser Ile Ser Ser Ala Ile Gly Ser
                290                 295                 300

Arg Lys Glu Ile Glu Gln Leu Leu Lys Leu Val Ser Glu Lys Asn Val
305                 310                 315                 320

Lys Ile Trp Val Glu Lys Leu Pro Ile Ser Glu Gly Val Ser His
                325                 330                 335

Ala Phe Thr Arg Met Glu Ser Gly Asp Val Lys Tyr Arg Phe Thr Leu
                340                 345                 350

Val Asp Tyr Asp Lys Lys Phe His Lys
        355                 360
```

<210> SEQ ID NO 143
<211> LENGTH: 417
<212> TYPE: PRT
<213> ORGANISM: Saccharomyces cerevisiae

<400> SEQUENCE: 143

```
Met Arg Ala Leu Ala Tyr Phe Gly Lys Gly Asn Ile Arg Phe Thr Asn
1               5                   10                  15
```

His Leu Lys Glu Pro His Ile Val Ala Pro Asp Glu Leu Val Ile Asp
            20                  25                  30

Ile Glu Trp Cys Gly Ile Cys Gly Thr Asp Leu His Glu Tyr Thr Asp
        35                  40                  45

Gly Pro Ile Phe Phe Pro Glu Asp Gly His Thr His Glu Ile Ser His
    50                  55                  60

Asn Pro Leu Pro Gln Ala Met Gly His Glu Met Ala Gly Thr Val Leu
65                  70                  75                  80

Glu Val Gly Pro Gly Val Lys Asn Leu Lys Val Gly Asp Lys Val Val
                85                  90                  95

Val Glu Pro Thr Gly Thr Cys Arg Asp Arg Tyr Arg Trp Pro Leu Ser
            100                 105                 110

Pro Asn Val Asp Lys Glu Trp Cys Ala Ala Cys Lys Lys Gly Tyr Tyr
        115                 120                 125

Asn Ile Cys Ser Tyr Leu Gly Leu Cys Gly Ala Gly Val Gln Ser Gly
    130                 135                 140

Gly Phe Ala Glu Arg Val Val Met Asn Glu Ser His Cys Tyr Lys Val
145                 150                 155                 160

Pro Asp Phe Val Pro Leu Asp Val Ala Ala Leu Ile Gln Pro Leu Ala
                165                 170                 175

Val Cys Trp His Ala Ile Arg Val Cys Glu Phe Lys Ala Gly Ser Thr
            180                 185                 190

Ala Leu Ile Ile Gly Ala Gly Pro Ile Gly Leu Gly Thr Ile Leu Ala
        195                 200                 205

Leu Asn Ala Ala Gly Cys Lys Asp Ile Val Val Ser Glu Pro Ala Lys
210                 215                 220

Val Arg Arg Glu Leu Ala Glu Lys Met Gly Ala Arg Val Tyr Asp Pro
225                 230                 235                 240

Thr Ala His Ala Ala Lys Glu Ser Ile Asp Tyr Leu Arg Ser Ile Ala
                245                 250                 255

Asp Gly Gly Asp Gly Phe Asp Tyr Thr Phe Asp Cys Ser Gly Leu Glu
            260                 265                 270

Val Thr Leu Asn Ala Ala Ile Gln Cys Leu Thr Phe Arg Gly Thr Ala
        275                 280                 285

Val Asn Leu Ala Met Trp Gly His His Lys Ile Gln Phe Ser Pro Met
    290                 295                 300

Asp Ile Thr Leu His Glu Arg Lys Tyr Thr Gly Ser Met Cys Tyr Thr
305                 310                 315                 320

His His Asp Phe Glu Ala Val Ile Glu Ala Leu Glu Glu Gly Arg Ile
                325                 330                 335

Asp Ile Asp Arg Ala Arg His Met Ile Thr Gly Arg Val Asn Ile Glu
            340                 345                 350

Asp Gly Leu Asp Gly Ala Ile Met Lys Leu Ile Asn Glu Lys Glu Ser
        355                 360                 365

Thr Ile Lys Ile Ile Leu Thr Pro Asn Asn His Gly Glu Leu Asn Arg
    370                 375                 380

Glu Ala Asp Asn Glu Lys Lys Glu Ile Ser Glu Leu Ser Ser Arg Lys
385                 390                 395                 400

Asp Gln Glu Arg Leu Arg Glu Ser Ile Asn Glu Ala Lys Leu Arg His
                405                 410                 415

Thr

<210> SEQ ID NO 144

<211> LENGTH: 386
<212> TYPE: PRT
<213> ORGANISM: Saccharomyces cerevisiae

<400> SEQUENCE: 144

```
Met Ser Ala Ala Thr Val Gly Lys Pro Ile Lys Cys Ile Ala Ala Val
1               5                   10                  15

Ala Tyr Asp Ala Lys Lys Pro Leu Ser Val Glu Glu Ile Thr Val Asp
            20                  25                  30

Ala Pro Lys Ala His Glu Val Arg Ile Lys Ile Glu Tyr Thr Ala Val
        35                  40                  45

Cys His Thr Asp Ala Tyr Thr Leu Ser Gly Ser Asp Pro Glu Gly Leu
    50                  55                  60

Phe Pro Cys Val Leu Gly His Glu Gly Ala Gly Ile Val Glu Ser Val
65                  70                  75                  80

Gly Asp Asp Val Ile Thr Val Lys Pro Gly Asp His Val Ile Ala Leu
                85                  90                  95

Tyr Thr Ala Glu Cys Gly Lys Cys Lys Phe Cys Thr Ser Gly Lys Thr
            100                 105                 110

Asn Leu Cys Gly Ala Val Arg Ala Thr Gln Gly Lys Gly Val Met Pro
        115                 120                 125

Asp Gly Thr Thr Arg Phe His Asn Ala Lys Gly Glu Asp Ile Tyr His
    130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
            180                 185                 190

Asn Val Gln Lys Gly Asp Thr Val Ala Val Phe Gly Cys Gly Thr Val
        195                 200                 205

Gly Leu Ser Val Ile Gln Gly Ala Lys Leu Arg Gly Ala Ser Lys Ile
    210                 215                 220

Ile Ala Ile Asp Ile Asn Asn Lys Lys Lys Gln Tyr Cys Ser Gln Phe
225                 230                 235                 240

Gly Ala Thr Asp Phe Val Asn Pro Lys Glu Asp Leu Ala Lys Asp Gln
                245                 250                 255

Thr Ile Val Glu Lys Leu Ile Glu Met Thr Asp Gly Gly Leu Asp Phe
            260                 265                 270

Thr Phe Asp Cys Thr Gly Asn Thr Lys Ile Met Arg Asp Ala Leu Glu
        275                 280                 285

Ala Cys His Lys Gly Trp Gly Gln Ser Ile Ile Ile Gly Val Ala Ala
    290                 295                 300

Ala Gly Glu Glu Ile Ser Thr Arg Pro Phe Gln Leu Val Thr Gly Arg
305                 310                 315                 320

Val Trp Lys Gly Ser Ala Phe Gly Gly Ile Lys Gly Arg Ser Glu Met
                325                 330                 335

Gly Gly Leu Ile Lys Asp Tyr Gln Lys Gly Ala Leu Lys Val Glu Glu
            340                 345                 350

Phe Ile Thr His Arg Arg Pro Phe Lys Glu Ile Asn Gln Ala Phe Glu
        355                 360                 365

Asp Leu His Asn Gly Asp Cys Leu Arg Thr Val Leu Lys Ser Asp Glu
    370                 375                 380

Ile Lys
```

<210> SEQ ID NO 145
<211> LENGTH: 342
<212> TYPE: PRT
<213> ORGANISM: Saccharomyces cerevisiae

<400> SEQUENCE: 145

Met Val Leu Val Lys Gln Val Arg Leu Gly Asn Ser Gly Leu Lys Ile
1               5                   10                  15

Ser Pro Ile Val Ile Gly Cys Met Ser Tyr Gly Ser Lys Lys Trp Ala
            20                  25                  30

Asp Trp Val Ile Glu Asp Lys Thr Gln Ile Phe Lys Ile Met Lys His
        35                  40                  45

Cys Tyr Asp Lys Gly Leu Arg Thr Phe Asp Thr Ala Asp Phe Tyr Ser
    50                  55                  60

Asn Gly Leu Ser Glu Arg Ile Ile Lys Glu Phe Leu Glu Tyr Tyr Ser
65                  70                  75                  80

Ile Lys Arg Glu Thr Val Val Ile Met Thr Lys Ile Tyr Phe Pro Val
                85                  90                  95

Asp Glu Thr Leu Asp Leu His His Asn Phe Thr Leu Asn Glu Phe Glu
            100                 105                 110

Glu Leu Asp Leu Ser Asn Gln Arg Gly Leu Ser Arg Lys His Ile Ile
        115                 120                 125

Ala Gly Val Glu Asn Ser Val Lys Arg Leu Gly Thr Tyr Ile Asp Leu
    130                 135                 140

Leu Gln Ile His Arg Leu Asp His Glu Thr Pro Met Lys Glu Ile Met
145                 150                 155                 160

Lys Ala Leu Asn Asp Val Val Glu Ala Gly His Val Arg Tyr Ile Gly
                165                 170                 175

Ala Ser Ser Met Leu Ala Thr Glu Phe Ala Glu Leu Gln Phe Thr Ala
            180                 185                 190

Asp Lys Tyr Gly Trp Phe Gln Phe Ile Ser Ser Gln Ser Tyr Tyr Asn
        195                 200                 205

Leu Leu Tyr Arg Glu Asp Glu Arg Glu Leu Ile Pro Phe Ala Lys Arg
    210                 215                 220

His Asn Ile Gly Leu Leu Pro Trp Ser Pro Asn Ala Arg Gly Met Leu
225                 230                 235                 240

Thr Arg Pro Leu Asn Gln Ser Thr Asp Arg Ile Lys Ser Asp Pro Thr
                245                 250                 255

Phe Lys Ser Leu His Leu Asp Asn Leu Glu Glu Glu Gln Lys Glu Ile
            260                 265                 270

Ile Asn Arg Val Glu Lys Val Ser Lys Asp Lys Lys Val Ser Met Ala
        275                 280                 285

Met Leu Ser Ile Ala Trp Val Leu His Lys Gly Cys His Pro Ile Val
    290                 295                 300

Gly Leu Asn Thr Thr Ala Arg Val Asp Glu Ala Ile Ala Ala Leu Gln
305                 310                 315                 320

Val Thr Leu Thr Glu Glu Glu Ile Lys Tyr Leu Glu Glu Pro Tyr Lys
                325                 330                 335

Pro Gln Arg Gln Arg Cys
            340

<210> SEQ ID NO 146
<211> LENGTH: 359

<212> TYPE: PRT
<213> ORGANISM: Saccharomyces cerevisiae

<400> SEQUENCE: 146

```
Met Gly Val Glu Gln Ile Leu Lys Arg Lys Thr Gly Val Ile Val Gly
1               5                   10                  15

Glu Asp Val His Asn Leu Phe Thr Tyr Ala Lys Glu His Lys Phe Ala
            20                  25                  30

Ile Pro Ala Ile Asn Val Thr Ser Ser Thr Ala Val Ala Ala Leu
        35                  40                  45

Glu Ala Ala Arg Asp Ser Lys Ser Pro Ile Ile Leu Gln Thr Ser Asn
50                  55                  60

Gly Gly Ala Ala Tyr Phe Ala Gly Lys Gly Ile Ser Asn Glu Gly Gln
65                  70                  75                  80

Asn Ala Ser Ile Lys Gly Ala Ile Ala Ala His Tyr Ile Arg Ser
                85                  90                  95

Ile Ala Pro Ala Tyr Gly Ile Pro Val Val Leu His Ser Asp His Cys
            100                 105                 110

Ala Lys Lys Leu Leu Pro Trp Phe Asp Gly Met Leu Glu Ala Asp Glu
        115                 120                 125

Ala Tyr Phe Lys Glu His Gly Glu Pro Leu Phe Ser Ser His Met Leu
    130                 135                 140

Asp Leu Ser Glu Glu Thr Asp Glu Glu Asn Ile Ser Thr Cys Val Lys
145                 150                 155                 160

Tyr Phe Lys Arg Met Ala Ala Met Asp Gln Trp Leu Glu Met Glu Ile
                165                 170                 175

Gly Ile Thr Gly Gly Glu Glu Asp Gly Val Asn Asn Glu Asn Ala Asp
            180                 185                 190

Lys Glu Asp Leu Tyr Thr Lys Pro Glu Gln Val Tyr Asn Val Tyr Lys
        195                 200                 205

Ala Leu His Pro Ile Ser Pro Asn Phe Ser Ile Ala Ala Ala Phe Gly
    210                 215                 220

Asn Cys His Gly Leu Tyr Ala Gly Asp Ile Ala Leu Arg Pro Glu Ile
225                 230                 235                 240

Leu Ala Glu His Gln Lys Tyr Thr Arg Glu Gln Val Gly Cys Lys Glu
                245                 250                 255

Glu Lys Pro Leu Phe Leu Val Phe His Gly Gly Ser Gly Ser Thr Val
            260                 265                 270

Gln Glu Phe His Thr Gly Ile Asp Asn Gly Val Val Lys Val Asn Leu
        275                 280                 285

Asp Thr Asp Cys Gln Tyr Ala Tyr Leu Thr Gly Ile Arg Asp Tyr Val
    290                 295                 300

Leu Asn Lys Lys Asp Tyr Ile Met Ser Pro Val Gly Asn Pro Glu Gly
305                 310                 315                 320

Pro Glu Lys Pro Asn Lys Lys Phe Phe Asp Pro Arg Val Trp Val Arg
                325                 330                 335

Glu Gly Glu Lys Thr Met Gly Ala Lys Ile Thr Lys Ser Leu Glu Thr
            340                 345                 350

Phe Arg Thr Thr Asn Thr Leu
        355
```

<210> SEQ ID NO 147
<211> LENGTH: 248
<212> TYPE: PRT
<213> ORGANISM: Saccharomyces cerevisiae -continued

```
<400> SEQUENCE: 147

Met Ala Arg Thr Phe Phe Val Gly Gly Asn Phe Lys Leu Asn Gly Ser
1               5                   10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Ala Thr Tyr Leu Asp
            35                  40                  45

Tyr Ser Val Ser Leu Val Lys Lys Pro Gln Val Thr Val Gly Ala Gln
50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
            85                  90                  95

Glu Arg Arg Ser Tyr Phe His Glu Asp Asp Lys Phe Ile Ala Asp Lys
            100                 105                 110

Thr Lys Phe Ala Leu Gly Gln Gly Val Gly Val Ile Leu Cys Ile Gly
            115                 120                 125

Glu Thr Leu Glu Glu Lys Lys Ala Gly Lys Thr Leu Asp Val Val Glu
130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Thr Gly Leu Ala Ala
            165                 170                 175

Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
            195                 200                 205

Gly Gly Ser Ala Asn Gly Ser Asn Ala Val Thr Phe Lys Asp Lys Ala
            210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
            245

<210> SEQ ID NO 148
<211> LENGTH: 376
<212> TYPE: PRT
<213> ORGANISM: Saccharomyces cerevisiae

<400> SEQUENCE: 148

Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
            20                  25                  30

Ile Arg Asn Phe Ile Glu Glu Gln Gly Tyr Glu Leu Val Thr Thr Ile
            35                  40                  45

Asp Lys Asp Pro Glu Pro Thr Ser Thr Val Arg Glu Leu Lys Asp
            50                  55                  60

Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
            85                  90                  95

Val Gly Ser Asp His Val Asp Leu Glu Ala Ala Asn Glu Arg Lys Ile
            100                 105                 110
```

```
Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
        130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
    290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
    370                 375

<210> SEQ ID NO 149
<211> LENGTH: 327
<212> TYPE: PRT
<213> ORGANISM: Saccharomyces cerevisiae

<400> SEQUENCE: 149

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
```

100                 105                 110
Pro Ile Ala Phe Lys Tyr Val Pro Phe Glu Glu Lys Tyr Pro Pro Gly
            115                 120                 125

Phe Tyr Thr Gly Ala Asp Asp Glu Lys Lys Gly His Ile Thr Glu Ala
130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
        210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
        290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 150
<211> LENGTH: 350
<212> TYPE: PRT
<213> ORGANISM: Saccharomyces cerevisiae

<400> SEQUENCE: 150

Met Ser Lys Lys Pro Ile Val Leu Lys Leu Gly Lys Asp Ala Phe Gly
1               5                   10                  15

Asp Gln Ala Trp Gly Glu Leu Glu Lys Ile Ala Asp Val Ile Thr Ile
            20                  25                  30

Pro Glu Ser Thr Thr Arg Glu Gln Phe Leu Arg Glu Val Lys Asp Pro
        35                  40                  45

Gln Asn Lys Leu Ser Gln Val Gln Val Ile Thr Arg Thr Ala Arg Ser
    50                  55                  60

Val Lys Asn Thr Gly Arg Phe Asp Glu Glu Leu Ala Leu Ala Leu Pro
65                  70                  75                  80

Ser Ser Val Val Ala Val Cys His Thr Gly Ala Gly Tyr Asp Gln Ile
                85                  90                  95

Asp Val Glu Pro Phe Lys Lys Arg His Ile Gln Val Ala Asn Val Pro
            100                 105                 110

Asp Leu Val Ser Asn Ala Thr Ala Asp Thr His Val Phe Leu Leu Leu
        115                 120                 125

Gly Ala Leu Arg Asn Phe Gly Ile Gly Asn Arg Arg Leu Ile Glu Gly
        130                 135                 140

```
Asn Trp Pro Glu Ala Gly Pro Ala Cys Gly Ser Pro Phe Gly Tyr Asp
145                 150                 155                 160

Pro Glu Gly Lys Thr Val Gly Ile Leu Gly Leu Gly Arg Ile Gly Arg
                165                 170                 175

Cys Ile Leu Glu Arg Leu Lys Pro Phe Gly Phe Glu Asn Phe Ile Tyr
            180                 185                 190

His Asn Arg His Gln Leu Pro Ser Glu Glu His Gly Cys Glu Tyr
        195                 200                 205

Val Gly Phe Glu Glu Phe Leu Lys Arg Ser Asp Ile Val Ser Val Asn
    210                 215                 220

Val Pro Leu Asn His Asn Thr His His Leu Ile Asn Ala Glu Thr Ile
225                 230                 235                 240

Glu Lys Met Lys Asp Gly Val Val Ile Val Asn Thr Ala Arg Gly Ala
                245                 250                 255

Val Ile Asp Glu Gln Ala Met Thr Asp Ala Leu Arg Ser Gly Lys Ile
            260                 265                 270

Arg Ser Ala Gly Leu Asp Val Phe Glu Tyr Glu Pro Lys Ile Ser Lys
        275                 280                 285

Glu Leu Leu Ser Met Ser Gln Val Leu Gly Leu Pro His Met Gly Thr
    290                 295                 300

His Ser Val Glu Thr Arg Lys Lys Met Glu Glu Leu Val Val Glu Asn
305                 310                 315                 320

Ala Lys Asn Val Ile Leu Thr Gly Lys Val Leu Thr Ile Val Pro Glu
                325                 330                 335

Leu Gln Asn Glu Asp Trp Pro Asn Glu Ser Lys Pro Leu Val
            340                 345                 350

<210> SEQ ID NO 151
<211> LENGTH: 396
<212> TYPE: PRT
<213> ORGANISM: Saccharomyces cerevisiae

<400> SEQUENCE: 151

Met Ile Thr Ser Ile Asp Ile Ala Asp Val Thr Tyr Ser Ala Lys Pro
1               5                   10                  15

Arg Ile Leu Val Pro Tyr Lys Thr Gln Trp Glu Val Ala Ser His Leu
                20                  25                  30

Pro Glu Tyr Arg Lys Leu Ala Glu Arg Val Glu Phe Tyr Lys Tyr Glu
            35                  40                  45

Met Ser Thr Lys Asp Asp Phe Val Lys Phe Leu Glu Thr His Arg Ile
50                  55                  60

Asn Gly Phe Trp Leu Thr Glu Glu Phe Phe Thr Val Leu Gly Asn Pro
65                  70                  75                  80

Ser Ser Tyr Ile Glu Phe Phe Pro Ala Ser Leu Lys Val Ile Leu Val
                85                  90                  95

Pro Trp Val Gly Cys Asp Phe Ile Asp Gly Lys Leu Leu Arg Ser Lys
            100                 105                 110

Gly Ile Thr Leu Cys Asn Ile Gly Pro His Ala Ala Asp His Val Thr
        115                 120                 125

Glu Leu Ala Ile Phe Leu Ala Ile Ser Cys Phe Arg Met Thr Ser Phe
    130                 135                 140

Trp Glu Tyr Cys Phe Lys Tyr Val Glu Asn Gly Asn Val Glu Gln Cys
145                 150                 155                 160

Lys Lys Tyr Ile Ser Ser Asp Ser Tyr Glu Ile Val Thr Asp Ser Tyr
                165                 170                 175
```

His Gly Gln Glu Met Lys Phe Pro Ser Arg Thr Asp Lys Cys Lys Pro
            180                 185                 190

Asn Lys Asp Arg Lys Val Val His Leu Ala Glu Lys Tyr Thr Val Gly
            195                 200                 205

Gly Lys Lys Met Glu Ser Pro Met Asn Lys Val Leu Ile Leu Gly
210                 215                 220

Phe Gly Ser Ile Gly Gln Asn Ile Gly Ser Asn Leu His Lys Val Phe
225                 230                 235                 240

Asn Met Ser Ile Glu Tyr Tyr Lys Arg Thr Gly Pro Val Gln Lys Ser
            245                 250                 255

Leu Leu Asp Tyr Asn Ala Lys Tyr His Ser Asp Leu Asp Pro Asn
            260                 265                 270

Thr Trp Lys Asn Ala Asp Leu Ile Ile Leu Ala Leu Pro Ser Thr Ala
            275                 280                 285

Ser Thr Asn Asn Ile Ile Asn Arg Lys Ser Leu Ala Trp Cys Lys Asp
            290                 295                 300

Gly Val Arg Ile Val Asn Val Gly Arg Gly Thr Cys Ile Asp Glu Asp
305                 310                 315                 320

Val Leu Leu Asp Ala Leu Glu Ser Gly Lys Val Ala Ser Cys Gly Leu
            325                 330                 335

Asp Val Phe Lys Asn Glu Glu Thr Arg Val Lys Gln Glu Leu Leu Arg
            340                 345                 350

Arg Trp Asp Val Thr Ala Leu Pro His Ile Gly Ser Thr Val Ala Asp
            355                 360                 365

Met Val Ile Lys Gln Thr Leu Ile Thr Leu Glu Asn Val Gln Asp Ile
            370                 375                 380

Phe Val Glu Gly Gly Asp Gly Lys Tyr Val Leu Asn
385                 390                 395

<210> SEQ ID NO 152
<211> LENGTH: 312
<212> TYPE: PRT
<213> ORGANISM: Saccharomyces cerevisiae

<400> SEQUENCE: 152

Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
            20                  25                  30

Asn Asp Ala Tyr Lys Ala Val Leu Thr Ala Leu Lys Asp Gly Tyr Arg
            35                  40                  45

His Ile Asp Thr Ala Ala Ile Tyr Arg Asn Glu Asp Gln Val Gly Gln
            50                  55                  60

Ala Ile Lys Asp Ser Gly Val Pro Arg Glu Glu Ile Phe Val Thr Thr
65              70                  75                  80

Lys Leu Trp Cys Thr Gln His His Glu Pro Glu Val Ala Leu Asp Gln
            85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
            115                 120                 125

Ser Val Pro Thr Lys Lys Asp Gly Ser Arg Ala Val Asp Ile Thr Asn
            130                 135                 140

Trp Asn Phe Ile Lys Thr Trp Glu Leu Met Gln Glu Leu Pro Lys Thr

```
145                 150                 155                 160
Gly Lys Thr Lys Ala Val Gly Val Ser Asn Phe Ser Ile Asn Asn Leu
                165                 170                 175
Lys Asp Leu Leu Ala Ser Gln Gly Asn Lys Leu Thr Pro Ala Ala Asn
            180                 185                 190
Gln Val Glu Ile His Pro Leu Pro Gln Asp Glu Leu Ile Asn Phe
        195                 200                 205
Cys Lys Ser Lys Gly Ile Val Val Glu Ala Tyr Ser Pro Leu Gly Ser
    210                 215                 220
Thr Asp Ala Pro Leu Leu Lys Glu Pro Val Ile Leu Glu Ile Ala Lys
225                 230                 235                 240
Lys Asn Asn Val Gln Pro Gly His Val Val Ile Ser Trp His Val Gln
                245                 250                 255
Arg Gly Tyr Val Val Leu Pro Lys Ser Val Asn Pro Asp Arg Ile Lys
                260                 265                 270
Thr Asn Arg Lys Ile Phe Thr Leu Ser Thr Glu Asp Phe Glu Ala Ile
            275                 280                 285
Asn Asn Ile Ser Lys Glu Lys Gly Glu Lys Arg Val Val His Pro Asn
        290                 295                 300
Trp Ser Pro Phe Glu Val Phe Lys
305                 310
```

<210> SEQ ID NO 153
<211> LENGTH: 505
<212> TYPE: PRT
<213> ORGANISM: Saccharomyces cerevisiae

<400> SEQUENCE: 153

```
Met Pro Thr Leu Tyr Thr Asp Ile Glu Ile Pro Gln Leu Lys Ile Ser
1               5                   10                  15
Leu Lys Gln Pro Leu Gly Leu Phe Ile Asn Asn Glu Phe Cys Pro Ser
                20                  25                  30
Ser Asp Gly Lys Thr Ile Glu Thr Val Asn Pro Ala Thr Gly Glu Pro
            35                  40                  45
Ile Thr Ser Phe Gln Ala Ala Asn Glu Lys Asp Val Asp Lys Ala Val
        50                  55                  60
Lys Ala Ala Arg Ala Ala Phe Asp Asn Val Trp Ser Lys Thr Ser Ser
65                  70                  75                  80
Glu Gln Arg Gly Ile Tyr Leu Ser Asn Leu Leu Lys Leu Ile Glu Glu
                85                  90                  95
Glu Gln Asp Thr Leu Ala Ala Leu Glu Thr Leu Asp Ala Gly Lys Pro
            100                 105                 110
Tyr Ser Asn Ala Lys Gly Asp Leu Ala Gln Ile Leu Gln Leu Thr Arg
        115                 120                 125
Tyr Phe Ala Gly Ser Ala Asp Lys Phe Asp Lys Gly Ala Thr Ile Pro
    130                 135                 140
Leu Thr Phe Asn Lys Phe Ala Tyr Thr Leu Lys Val Pro Phe Gly Val
145                 150                 155                 160
Val Ala Gln Ile Val Pro Trp Asn Tyr Pro Leu Ala Met Ala Cys Trp
                165                 170                 175
Lys Leu Gln Gly Ala Leu Ala Ala Gly Asn Thr Val Ile Ile Lys Pro
            180                 185                 190
Ala Glu Asn Thr Ser Leu Ser Leu Leu Tyr Phe Ala Thr Leu Ile Lys
        195                 200                 205
```

```
Lys Ala Gly Phe Pro Pro Gly Val Asn Ile Val Pro Gly Tyr Gly
    210                 215                 220

Ser Leu Val Gly Gln Ala Leu Ala Ser His Met Asp Ile Asp Lys Ile
225                 230                 235                 240

Ser Phe Thr Gly Ser Thr Lys Val Gly Gly Phe Val Leu Glu Ala Ser
                245                 250                 255

Gly Gln Ser Asn Leu Lys Asp Val Thr Leu Glu Cys Gly Gly Lys Ser
                260                 265                 270

Pro Ala Leu Val Phe Glu Asp Ala Asp Leu Asp Lys Ala Ile Asp Trp
                275                 280                 285

Ile Ala Ala Gly Ile Phe Tyr Asn Ser Gly Gln Asn Cys Thr Ala Asn
290                 295                 300

Ser Arg Val Tyr Val Gln Ser Ser Ile Tyr Asp Lys Phe Val Glu Lys
305                 310                 315                 320

Phe Lys Glu Thr Ala Lys Lys Glu Trp Asp Val Ala Gly Lys Phe Asp
                325                 330                 335

Pro Phe Asp Glu Lys Cys Ile Val Gly Pro Val Ile Ser Ser Thr Gln
                340                 345                 350

Tyr Asp Arg Ile Lys Ser Tyr Ile Glu Arg Gly Lys Arg Glu Glu Lys
                355                 360                 365

Leu Asp Met Phe Gln Thr Ser Glu Phe Pro Ile Gly Gly Ala Lys Gly
370                 375                 380

Tyr Phe Ile Pro Pro Thr Ile Phe Thr Asp Val Pro Gln Thr Ser Lys
385                 390                 395                 400

Leu Leu Gln Asp Glu Ile Phe Gly Pro Val Val Val Ser Lys Phe
                405                 410                 415

Thr Asn Tyr Asp Asp Ala Leu Lys Leu Ala Asn Asp Thr Cys Tyr Gly
                420                 425                 430

Leu Ala Ser Ala Val Phe Thr Lys Asp Val Lys Lys Ala His Met Phe
                435                 440                 445

Ala Arg Asp Ile Lys Ala Gly Thr Val Trp Ile Asn Ser Ser Asn Asp
                450                 455                 460

Glu Asp Val Thr Val Pro Phe Gly Gly Phe Lys Met Ser Gly Ile Gly
465                 470                 475                 480

Arg Glu Leu Gly Gln Ser Gly Val Asp Thr Tyr Leu Gln Thr Lys Ala
                485                 490                 495

Val His Ile Asn Leu Ser Leu Asp Asn
                500                 505

<210> SEQ ID NO 154
<211> LENGTH: 506
<212> TYPE: PRT
<213> ORGANISM: Saccharomyces cerevisiae

<400> SEQUENCE: 154

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val
        50                  55                  60

Lys Ala Ala Arg Ala Ala Phe Asp Asn Val Trp Ser Lys Thr Ser Ser
65                  70                  75                  80
```

```
Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
            100                 105                 110

Phe His Ser Asn Ala Lys Gln Asp Leu Ala Gln Ile Ile Glu Leu Thr
            115                 120                 125

Arg Tyr Tyr Ala Gly Ala Val Asp Lys Phe Asn Met Gly Glu Thr Ile
            130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Arg Lys Met Gln Gly Ala Leu Ala Gly Asn Thr Val Ile Ile Lys
                180                 185                 190

Pro Ala Glu Asn Thr Ser Leu Ser Leu Leu Tyr Phe Ala Thr Leu Ile
            195                 200                 205

Lys Lys Ala Gly Phe Pro Pro Gly Val Val Asn Val Ile Pro Gly Tyr
            210                 215                 220

Gly Ser Val Val Gly Lys Ala Leu Gly Thr His Met Asp Ile Asp Lys
225                 230                 235                 240

Ile Ser Phe Thr Gly Ser Thr Lys Val Gly Gly Ser Val Leu Glu Ala
                245                 250                 255

Ser Gly Gln Ser Asn Leu Lys Asp Ile Thr Leu Glu Cys Gly Gly Lys
            260                 265                 270

Ser Pro Ala Leu Val Phe Glu Asp Ala Asp Leu Asp Lys Ala Ile Glu
            275                 280                 285

Trp Val Ala Asn Gly Ile Phe Phe Asn Ser Gly Gln Ile Cys Thr Ala
            290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Lys Glu Glu
            355                 360                 365

Lys Leu Asp Met Phe Gln Thr Ser Glu Phe Pro Ile Gly Gly Ala Lys
370                 375                 380

Gly Tyr Phe Ile Pro Pro Thr Ile Phe Thr Asp Val Pro Glu Thr Ser
385                 390                 395                 400

Lys Leu Leu Arg Asp Glu Ile Phe Gly Pro Val Val Val Ser Lys
                405                 410                 415

Phe Thr Asn Tyr Asp Asp Ala Leu Lys Leu Ala Asn Asp Thr Cys Tyr
            420                 425                 430

Gly Leu Ala Ser Ala Val Phe Thr Lys Asp Val Lys Lys Ala His Met
            435                 440                 445

Phe Ala Arg Asp Ile Lys Ala Gly Thr Val Trp Ile Asn Gln Thr Asn
450                 455                 460

Gln Glu Glu Ala Lys Val Pro Phe Gly Gly Phe Lys Met Ser Gly Ile
465                 470                 475                 480

Gly Arg Glu Ser Gly Asp Thr Gly Val Asp Asn Tyr Leu Gln Ile Lys
                485                 490                 495
```

Ser Val His Val Asp Leu Ser Leu Asp Lys
            500                 505

<210> SEQ ID NO 155
<211> LENGTH: 519
<212> TYPE: PRT
<213> ORGANISM: Saccharomyces cerevisiae

<400> SEQUENCE: 155

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
    290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

```
Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Thr Val Thr Lys Phe
                420                 425                 430

Lys Ser Ala Asp Glu Val Ile Asn Met Ala Asn Asp Ser Glu Tyr Gly
                435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
                500                 505                 510

Val Arg Ala Lys Leu Asp Glu
            515

<210> SEQ ID NO 156
<211> LENGTH: 520
<212> TYPE: PRT
<213> ORGANISM: Saccharomyces cerevisiae

<400> SEQUENCE: 156

Met Leu Ser Arg Thr Arg Ala Ala Ala Pro Asn Ser Arg Ile Phe Thr
1               5                   10                  15

Arg Ser Leu Leu Arg Leu Tyr Ser Gln Ala Pro Leu Arg Val Pro Ile
                20                  25                  30

Thr Leu Pro Asn Gly Phe Thr Tyr Glu Gln Pro Thr Gly Leu Phe Ile
                35                  40                  45

Asn Gly Glu Phe Val Ala Ser Lys Gln Lys Thr Phe Asp Val Ile
50                  55                  60

Asn Pro Ser Asn Glu Glu Lys Ile Thr Thr Val Tyr Lys Ala Met Glu
65                  70                  75                  80

Asp Asp Val Asp Glu Ala Val Ala Ala Lys Lys Ala Phe Glu Thr
                85                  90                  95

Lys Trp Ser Ile Val Glu Pro Gly Val Arg Ala Lys Ala Leu Phe Asn
                100                 105                 110

Leu Ala Asp Leu Val Glu Lys His Gln Glu Thr Leu Ala Ala Ile Glu
                115                 120                 125

Ser Met Asp Asn Gly Lys Ser Leu Phe Cys Ala Arg Gly Asp Val Ala
    130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
                165                 170                 175

Lys Glu Pro Leu Gly Val Cys Gly Gln Ile Ile Pro Trp Asn Phe Pro
                180                 185                 190

Leu Leu Met Trp Ser Trp Lys Ile Gly Pro Ala Leu Ala Thr Gly Asn
        195                 200                 205

Thr Val Val Leu Lys Pro Ala Glu Thr Thr Pro Leu Ser Ala Leu Phe
```

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
            245                 250                 255

Pro Asp Val Lys Lys Ile Ala Phe Thr Gly Ser Thr Ala Thr Gly Arg
            260                 265                 270

His Ile Met Lys Val Ala Ala Asp Thr Val Lys Val Thr Leu Glu
        275                 280                 285

Leu Gly Gly Lys Ser Pro Asn Ile Val Phe Ala Asp Ala Asp Leu Asp
        290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly
            340                 345                 350

Asp Pro Phe Asp Glu Glu Val Phe Gln Gly Ala Gln Thr Ser Asp Lys
            355                 360                 365

Gln Leu His Lys Ile Leu Asp Tyr Val Asp Val Ala Lys Ser Glu Gly
        370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Gly Asp Met Arg Ile Val
            405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
            435                 440                 445

Ala Gly Ile His Thr Asn Asp Ile Asn Lys Ala Val Asp Val Ser Lys
        450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
            485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
        515                 520

<210> SEQ ID NO 157
<211> LENGTH: 500
<212> TYPE: PRT
<213> ORGANISM: Saccharomyces cerevisiae

<400> SEQUENCE: 157

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

-continued

```
Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
```

-continued

```
                485                 490                 495

Arg Ile Lys Leu
            500

<210> SEQ ID NO 158
<211> LENGTH: 532
<212> TYPE: PRT
<213> ORGANISM: Saccharomyces cerevisiae

<400> SEQUENCE: 158

Met Ser Asn Asp Gly Ser Lys Ile Leu Asn Tyr Thr Pro Val Ser Lys
1               5                   10                  15

Ile Asp Glu Ile Val Glu Ile Ser Arg Asn Phe Phe Glu Lys Gln
            20                  25                  30

Leu Lys Leu Ser His Glu Asn Asn Pro Arg Lys Lys Asp Leu Glu Phe
        35                  40                  45

Arg Gln Leu Gln Leu Lys Lys Leu Tyr Tyr Ala Val Lys Asp His Glu
    50                  55                  60

Glu Glu Leu Ile Asp Ala Met Tyr Lys Asp Phe His Arg Asn Lys Ile
65                  70                  75                  80

Glu Ser Val Leu Asn Glu Thr Thr Lys Leu Met Asn Asp Ile Leu His
                85                  90                  95

Leu Ile Glu Ile Leu Pro Lys Leu Ile Lys Pro Arg Arg Val Ser Asp
            100                 105                 110

Ser Ser Pro Pro Phe Met Phe Gly Lys Thr Ile Val Glu Lys Ile Ser
        115                 120                 125

Arg Gly Ser Val Leu Ile Ile Ala Pro Phe Asn Phe Pro Leu Leu Leu
    130                 135                 140

Ala Phe Ala Pro Leu Ala Ala Ala Leu Ala Ala Gly Asn Thr Ile Val
145                 150                 155                 160

Leu Lys Pro Ser Glu Leu Thr Pro His Thr Ala Val Val Met Glu Asn
                165                 170                 175

Leu Leu Thr Thr Ala Gly Phe Pro Asp Gly Leu Ile Gln Val Val Gln
            180                 185                 190

Gly Ala Ile Asp Glu Thr Thr Arg Leu Leu Asp Cys Gly Lys Phe Asp
        195                 200                 205

Leu Ile Phe Tyr Thr Gly Ser Pro Arg Val Gly Ser Ile Val Ala Glu
    210                 215                 220

Lys Ala Ala Lys Ser Leu Thr Pro Cys Val Leu Glu Leu Gly Gly Lys
225                 230                 235                 240

Ser Pro Thr Phe Ile Thr Glu Asn Phe Lys Ala Ser Asn Ile Lys Ile
                245                 250                 255

Ala Leu Lys Arg Ile Phe Phe Gly Ala Phe Gly Asn Ser Gly Gln Ile
            260                 265                 270

Cys Val Ser Pro Asp Tyr Leu Leu Val His Lys Ser Ile Tyr Pro Lys
        275                 280                 285

Val Ile Lys Glu Cys Glu Ser Val Leu Asn Glu Phe Tyr Pro Ser Phe
    290                 295                 300

Asp Glu Gln Thr Asp Phe Thr Arg Met Ile His Glu Pro Ala Tyr Lys
305                 310                 315                 320

Lys Ala Val Ala Ser Ile Asn Ser Thr Asn Gly Ser Lys Ile Val Pro
                325                 330                 335

Ser Lys Ile Ser Ile Asn Ser Asp Thr Glu Asp Leu Cys Leu Val Pro
            340                 345                 350
```

```
Pro Thr Ile Val Tyr Asn Ile Gly Trp Asp Asp Pro Leu Met Lys Gln
            355                 360                 365

Glu Asn Phe Ala Pro Val Leu Pro Ile Ile Glu Tyr Glu Asp Leu Asp
        370                 375                 380

Glu Thr Ile Asn Lys Ile Ile Glu His Asp Thr Pro Leu Val Gln
385                 390                 395                 400

Tyr Ile Phe Ser Asp Ser Gln Thr Glu Ile Asn Arg Ile Leu Thr Arg
                405                 410                 415

Leu Arg Ser Gly Asp Cys Val Val Gly Asp Thr Val Ile His Val Gly
                420                 425                 430

Ile Thr Asp Ala Pro Phe Gly Gly Ile Gly Thr Ser Gly Tyr Gly Asn
            435                 440                 445

Tyr Gly Gly Tyr Tyr Gly Phe Asn Thr Phe Ser His Glu Arg Thr Ile
    450                 455                 460

Phe Lys Gln Pro Tyr Trp Asn Asp Phe Thr Leu Phe Met Arg Tyr Pro
465                 470                 475                 480

Pro Asn Ser Ala Gln Lys Glu Lys Leu Val Arg Phe Ala Met Glu Arg
                485                 490                 495

Lys Pro Trp Phe Asp Arg Asn Gly Asn Asn Lys Trp Gly Leu Arg Gln
                500                 505                 510

Tyr Phe Ser Leu Ser Ala Ala Val Ile Leu Ile Ser Thr Ile Tyr Ala
    515                 520                 525

His Cys Ser Ser
    530

<210> SEQ ID NO 159
<211> LENGTH: 500
<212> TYPE: PRT
<213> ORGANISM: Saccharomyces cerevisiae

<400> SEQUENCE: 159

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
            20                  25                  30

Asp Glu Leu Thr Ala Tyr Phe Ile Glu Gln Met Glu Lys Gly Leu Ala
        35                  40                  45

Pro Pro Lys Glu Gly His Thr Leu Ala Ser Asp Lys Gly Leu Pro Met
    50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
            100                 105                 110

Ile Pro Asp Asp Leu Leu Asp Asp Glu Asn Val Thr Ser Asp Asp Leu
        115                 120                 125

Phe Gly Phe Leu Ala Arg Arg Thr Leu Ala Phe Met Lys Lys Tyr His
    130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190
```

```
Asp Val Val Gln Leu Tyr Gln Glu Gln Leu Ser Ala Gln Gly Met Pro
            195                 200                 205
Met Ile Lys Val Val Ala Leu Thr Asn Asp Thr Val Gly Thr Tyr Leu
210                 215                 220
Ser His Cys Tyr Thr Ser Asp Asn Thr Asp Ser Met Thr Ser Gly Glu
225                 230                 235                 240
Ile Ser Glu Pro Val Ile Gly Cys Ile Phe Gly Thr Gly Thr Asn Gly
            245                 250                 255
Cys Tyr Met Glu Glu Ile Asn Lys Ile Thr Lys Leu Pro Gln Glu Leu
            260                 265                 270
Arg Asp Lys Leu Ile Lys Glu Gly Lys Thr His Met Ile Ile Asn Val
            275                 280                 285
Glu Trp Gly Ser Phe Asp Asn Glu Leu Lys His Leu Pro Thr Thr Lys
            290                 295                 300
Tyr Asp Val Val Ile Asp Gln Lys Leu Ser Thr Asn Pro Gly Phe His
305                 310                 315                 320
Leu Phe Glu Lys Arg Val Ser Gly Met Phe Leu Gly Glu Val Leu Arg
            325                 330                 335
Asn Ile Leu Val Asp Leu His Ser Gln Gly Leu Leu Leu Gln Gln Tyr
            340                 345                 350
Arg Ser Lys Glu Gln Leu Pro Arg His Leu Thr Thr Pro Phe Gln Leu
            355                 360                 365
Ser Ser Glu Val Leu Ser His Ile Glu Ile Asp Asp Ser Thr Gly Leu
370                 375                 380
Arg Glu Thr Glu Leu Ser Leu Leu Gln Ser Leu Arg Leu Pro Thr Thr
385                 390                 395                 400
Pro Thr Glu Arg Val Gln Ile Gln Lys Leu Val Arg Ala Ile Ser Arg
            405                 410                 415
Arg Ser Ala Tyr Leu Ala Ala Val Pro Leu Ala Ala Ile Leu Ile Lys
            420                 425                 430
Thr Asn Ala Leu Asn Lys Arg Tyr His Gly Glu Val Glu Ile Gly Cys
            435                 440                 445
Asp Gly Ser Val Val Glu Tyr Tyr Pro Gly Phe Arg Ser Met Leu Arg
450                 455                 460
His Ala Leu Ala Leu Ser Pro Leu Gly Ala Glu Gly Glu Arg Lys Val
465                 470                 475                 480
His Leu Lys Ile Ala Lys Asp Gly Ser Gly Val Gly Ala Ala Leu Cys
            485                 490                 495
Ala Leu Val Ala
            500

<210> SEQ ID NO 160
<211> LENGTH: 554
<212> TYPE: PRT
<213> ORGANISM: Saccharomyces cerevisiae

<400> SEQUENCE: 160

Met Ser Asn Asn Ser Phe Thr Asn Phe Lys Leu Ala Thr Glu Leu Pro
1               5                   10                  15
Ala Trp Ser Lys Leu Gln Lys Ile Tyr Glu Ser Gln Gly Lys Thr Leu
            20                  25                  30
Ser Val Lys Gln Glu Phe Gln Lys Asp Ala Lys Arg Phe Glu Lys Leu
            35                  40                  45
Asn Lys Thr Phe Thr Asn Tyr Asp Gly Ser Lys Ile Leu Phe Asp Tyr
```

```
            50                  55                  60
Ser Lys Asn Leu Val Asn Asp Glu Ile Ile Ala Ala Leu Ile Glu Leu
 65                  70                  75                  80

Ala Lys Glu Ala Asn Val Thr Gly Leu Arg Asp Ala Met Phe Lys Gly
                     85                  90                  95

Glu His Ile Asn Ser Thr Glu Asp Arg Ala Val Tyr His Val Ala Leu
                    100                 105                 110

Arg Asn Arg Ala Asn Lys Pro Met Tyr Val Asp Gly Val Asn Val Ala
                115                 120                 125

Pro Glu Val Asp Ser Val Leu Lys His Met Lys Glu Phe Ser Glu Gln
130                 135                 140

Val Arg Ser Gly Glu Trp Lys Gly Tyr Thr Gly Lys Lys Ile Thr Asp
145                 150                 155                 160

Val Val Asn Ile Gly Ile Gly Gly Ser Asp Leu Gly Pro Val Met Val
                165                 170                 175

Thr Glu Ala Leu Lys His Tyr Ala Gly Val Leu Asp Val His Phe Val
                180                 185                 190

Ser Asn Ile Asp Gly Thr His Ile Ala Glu Thr Leu Lys Val Val Asp
                195                 200                 205

Pro Glu Thr Thr Leu Phe Leu Ile Ala Ser Lys Thr Phe Thr Thr Ala
210                 215                 220

Glu Thr Ile Thr Asn Ala Asn Thr Ala Lys Asn Trp Phe Leu Ser Lys
225                 230                 235                 240

Thr Gly Asn Asp Pro Ser His Ile Ala Lys His Phe Ala Ala Leu Ser
                245                 250                 255

Thr Asn Glu Thr Glu Val Ala Lys Phe Gly Ile Asp Thr Lys Asn Met
                260                 265                 270

Phe Gly Phe Glu Ser Trp Val Gly Gly Arg Tyr Ser Val Trp Ser Ala
                275                 280                 285

Ile Gly Leu Ser Val Ala Leu Tyr Ile Gly Tyr Asp Asn Phe Glu Ala
                290                 295                 300

Phe Leu Lys Gly Ala Glu Ala Val Asp Asn His Phe Thr Gln Thr Pro
305                 310                 315                 320

Leu Glu Asp Asn Ile Pro Leu Leu Gly Gly Leu Leu Ser Val Trp Tyr
                325                 330                 335

Asn Asn Phe Phe Gly Ala Gln Thr His Leu Val Ala Pro Phe Asp Gln
                340                 345                 350

Tyr Leu His Arg Phe Pro Ala Tyr Leu Gln Gln Leu Ser Met Glu Ser
                355                 360                 365

Asn Gly Lys Ser Val Thr Arg Gly Asn Val Phe Thr Asp Tyr Ser Thr
                370                 375                 380

Gly Ser Ile Leu Phe Gly Glu Pro Ala Thr Asn Ala Gln His Ser Phe
385                 390                 395                 400

Phe Gln Leu Val His Gln Gly Thr Lys Leu Ile Pro Ser Asp Phe Ile
                405                 410                 415

Leu Ala Ala Gln Ser His Asn Pro Ile Glu Asn Lys Leu His Gln Lys
                420                 425                 430

Met Leu Ala Ser Asn Phe Phe Ala Gln Ala Glu Ala Leu Met Val Gly
                435                 440                 445

Lys Asp Glu Glu Gln Val Lys Ala Glu Gly Ala Thr Gly Gly Leu Val
450                 455                 460

Pro His Lys Val Phe Ser Gly Asn Arg Pro Thr Thr Ser Ile Leu Ala
465                 470                 475                 480
```

```
Gln Lys Ile Thr Pro Ala Thr Leu Gly Ala Leu Ile Ala Tyr Tyr Glu
                485                 490                 495

His Val Thr Phe Thr Glu Gly Ala Ile Trp Asn Ile Asn Ser Phe Asp
            500                 505                 510

Gln Trp Gly Val Glu Leu Gly Lys Val Leu Ala Lys Val Ile Gly Lys
        515                 520                 525

Glu Leu Asp Asn Ser Ser Thr Ile Ser Thr His Asp Ala Ser Thr Asn
    530                 535                 540

Gly Leu Ile Asn Gln Phe Lys Glu Trp Met
545                 550

<210> SEQ ID NO 161
<211> LENGTH: 987
<212> TYPE: PRT
<213> ORGANISM: Saccharomyces cerevisiae

<400> SEQUENCE: 161

Met Gln Ser Gln Asp Ser Cys Tyr Gly Val Ala Phe Arg Ser Ile Ile
1               5                   10                  15

Thr Asn Asp Glu Ala Leu Phe Lys Lys Thr Ile His Phe Tyr His Thr
            20                  25                  30

Leu Gly Phe Ala Thr Val Lys Asp Phe Asn Lys Phe Lys His Gly Glu
        35                  40                  45

Asn Ser Leu Leu Ser Ser Gly Thr Ser Gln Asp Ser Leu Arg Glu Val
    50                  55                  60

Trp Leu Glu Ser Phe Lys Leu Ser Glu Val Asp Ala Ser Gly Phe Arg
65                  70                  75                  80

Ile Pro Gln Gln Glu Ala Thr Asn Lys Ala Gln Ser Gln Gly Ala Leu
                85                  90                  95

Leu Lys Ile Arg Leu Val Met Ser Ala Pro Ile Asp Glu Thr Phe Asp
            100                 105                 110

Thr Asn Glu Thr Ala Thr Ile Thr Tyr Phe Ser Thr Asp Leu Asn Lys
        115                 120                 125

Ile Val Glu Lys Phe Pro Lys Gln Ala Glu Lys Leu Ser Asp Thr Leu
    130                 135                 140

Val Phe Leu Lys Asp Pro Met Gly Asn Asn Ile Thr Phe Ser Gly Leu
145                 150                 155                 160

Ala Asn Ala Thr Asp Ser Ala Pro Thr Ser Lys Asp Ala Phe Leu Glu
                165                 170                 175

Ala Thr Ser Glu Asp Glu Ile Ile Ser Arg Ala Ser Ser Asp Ala Ser
            180                 185                 190

Asp Leu Leu Arg Gln Thr Leu Gly Ser Ser Gln Lys Lys Lys Lys Ile
        195                 200                 205

Ala Val Met Thr Ser Gly Gly Asp Ser Pro Gly Met Asn Ala Ala Val
    210                 215                 220

Arg Ala Val Val Arg Thr Gly Ile His Phe Gly Cys Asp Val Phe Ala
225                 230                 235                 240

Val Tyr Glu Gly Tyr Glu Gly Leu Leu Arg Gly Gly Lys Tyr Leu Lys
                245                 250                 255

Lys Met Ala Trp Glu Asp Val Arg Gly Trp Leu Ser Glu Gly Gly Thr
            260                 265                 270

Leu Ile Gly Thr Ala Arg Ser Met Glu Phe Arg Lys Arg Glu Gly Arg
        275                 280                 285

Arg Gln Ala Ala Gly Asn Leu Ile Ser Gln Gly Ile Asp Ala Leu Val
```

```
                290                 295                 300
Val Cys Gly Gly Asp Gly Ser Leu Thr Gly Ala Asp Leu Phe Arg His
305                 310                 315                 320

Glu Trp Pro Ser Leu Val Asp Glu Leu Val Ala Glu Gly Arg Phe Thr
                325                 330                 335

Lys Glu Glu Val Ala Pro Tyr Lys Asn Leu Ser Ile Val Gly Leu Val
                340                 345                 350

Gly Ser Ile Asp Asn Asp Met Ser Gly Thr Asp Ser Thr Ile Gly Ala
                355                 360                 365

Tyr Ser Ala Leu Glu Arg Ile Cys Glu Met Val Asp Tyr Ile Asp Ala
                370                 375                 380

Thr Ala Lys Ser His Ser Arg Ala Phe Val Val Glu Val Met Gly Arg
385                 390                 395                 400

His Cys Gly Trp Leu Ala Leu Met Ala Gly Ile Ala Thr Gly Ala Asp
                405                 410                 415

Tyr Ile Phe Ile Pro Glu Arg Ala Val Pro His Gly Lys Trp Gln Asp
                420                 425                 430

Glu Leu Lys Glu Val Cys Gln Arg His Arg Ser Lys Gly Arg Arg Asn
                435                 440                 445

Asn Thr Ile Ile Val Ala Glu Gly Ala Leu Asp Asp Gln Leu Asn Pro
450                 455                 460

Val Thr Ala Asn Asp Val Lys Asp Ala Leu Ile Glu Leu Gly Leu Asp
465                 470                 475                 480

Thr Lys Val Thr Ile Leu Gly His Val Gln Arg Gly Gly Thr Ala Val
                485                 490                 495

Ala His Asp Arg Trp Leu Ala Thr Leu Gln Gly Val Asp Ala Val Lys
                500                 505                 510

Ala Val Leu Glu Phe Thr Pro Glu Thr Pro Ser Pro Leu Ile Gly Ile
                515                 520                 525

Leu Glu Asn Lys Ile Ile Arg Met Pro Leu Val Glu Ser Val Lys Leu
                530                 535                 540

Thr Lys Ser Val Ala Thr Ala Ile Glu Asn Lys Asp Phe Asp Lys Ala
545                 550                 555                 560

Ile Ser Leu Arg Asp Thr Glu Phe Ile Glu Leu Tyr Glu Asn Phe Leu
                565                 570                 575

Ser Thr Thr Val Lys Asp Asp Gly Ser Glu Leu Leu Pro Val Ser Asp
                580                 585                 590

Arg Leu Asn Ile Gly Ile Val His Val Gly Ala Pro Ser Ala Ala Leu
                595                 600                 605

Asn Ala Ala Thr Arg Ala Ala Thr Leu Tyr Cys Leu Ser His Gly His
                610                 615                 620

Lys Pro Tyr Ala Ile Met Asn Gly Phe Ser Gly Leu Ile Gln Thr Gly
625                 630                 635                 640

Glu Val Lys Glu Leu Ser Trp Ile Asp Val Glu Asn Trp His Asn Leu
                645                 650                 655

Gly Gly Ser Glu Ile Gly Thr Asn Arg Ser Val Ala Ser Glu Asp Leu
                660                 665                 670

Gly Thr Ile Ala Tyr Tyr Phe Gln Lys Asn Lys Leu Asp Gly Leu Ile
                675                 680                 685

Ile Leu Gly Gly Phe Glu Gly Phe Arg Ser Leu Lys Gln Leu Arg Asp
                690                 695                 700

Gly Arg Thr Gln His Pro Ile Phe Asn Ile Pro Met Cys Leu Ile Pro
705                 710                 715                 720
```

-continued

```
Ala Thr Val Ser Asn Val Pro Gly Thr Glu Tyr Ser Leu Gly Val
                725                 730                 735

Asp Thr Cys Leu Asn Ala Leu Val Asn Tyr Thr Asp Asp Ile Lys Gln
            740                 745                 750

Ser Ala Ser Ala Thr Arg Arg Val Phe Val Cys Glu Val Gln Gly
        755                 760                 765

Gly His Ser Gly Tyr Ile Ala Ser Phe Thr Gly Leu Ile Thr Gly Ala
    770                 775                 780

Val Ser Val Tyr Thr Pro Glu Lys Lys Ile Asp Leu Ala Ser Ile Arg
785                 790                 795                 800

Glu Asp Ile Thr Leu Leu Lys Glu Asn Phe Arg His Asp Lys Gly Glu
                805                 810                 815

Asn Arg Asn Gly Lys Leu Leu Val Arg Asn Glu Gln Ala Ser Ser Val
            820                 825                 830

Tyr Ser Thr Gln Leu Leu Ala Asp Ile Ile Ser Glu Ala Ser Lys Gly
        835                 840                 845

Lys Phe Gly Val Arg Thr Ala Ile Pro Gly His Val Gln Gln Gly Gly
    850                 855                 860

Val Pro Ser Ser Lys Asp Arg Val Thr Ala Ser Arg Phe Ala Val Lys
865                 870                 875                 880

Cys Ile Lys Phe Ile Glu Gln Trp Asn Lys Lys Asn Glu Ala Ser Pro
                885                 890                 895

Asn Thr Asp Ala Lys Val Leu Arg Phe Lys Phe Asp Thr His Gly Glu
            900                 905                 910

Lys Val Pro Thr Val Glu His Glu Asp Asp Ser Ala Ala Val Ile Cys
        915                 920                 925

Val Asn Gly Ser His Val Ser Phe Lys Pro Ile Ala Asn Leu Trp Glu
    930                 935                 940

Asn Glu Thr Asn Val Glu Leu Arg Lys Gly Phe Glu Val His Trp Ala
945                 950                 955                 960

Glu Tyr Asn Lys Ile Gly Asp Ile Leu Ser Gly Arg Leu Lys Leu Arg
                965                 970                 975

Ala Glu Val Ala Ala Leu Ala Ala Glu Asn Lys
            980                 985

<210> SEQ ID NO 162
<211> LENGTH: 959
<212> TYPE: PRT
<213> ORGANISM: Saccharomyces cerevisiae

<400> SEQUENCE: 162

Met Thr Val Thr Thr Pro Phe Val Asn Gly Thr Ser Tyr Cys Thr Val
1               5                   10                  15

Thr Ala Tyr Ser Val Gln Ser Tyr Lys Ala Ala Ile Asp Phe Tyr Thr
            20                  25                  30

Lys Phe Leu Ser Leu Glu Asn Arg Ser Ser Pro Asp Glu Asn Ser Thr
        35                  40                  45

Leu Leu Ser Asn Asp Ser Ile Ser Leu Lys Ile Leu Leu Arg Pro Asp
    50                  55                  60

Glu Lys Ile Asn Lys Asn Val Glu Ala His Leu Lys Glu Leu Asn Ser
65                  70                  75                  80

Ile Thr Lys Thr Gln Asp Trp Arg Ser His Ala Thr Gln Ser Leu Val
                85                  90                  95

Phe Asn Thr Ser Asp Ile Leu Ala Val Lys Asp Thr Leu Asn Ala Met
```

```
                100                 105                 110
Asn Ala Pro Leu Gln Gly Tyr Pro Thr Glu Leu Phe Pro Met Gln Leu
            115                 120                 125

Tyr Thr Leu Asp Pro Leu Gly Asn Val Val Gly Val Thr Ser Thr Lys
130                 135                 140

Asn Ala Val Ser Thr Lys Pro Thr Pro Pro Ala Pro Glu Ala Ser
145                 150                 155                 160

Ala Glu Ser Gly Leu Ser Ser Lys Val His Ser Tyr Thr Asp Leu Ala
            165                 170                 175

Tyr Arg Met Lys Thr Thr Asp Thr Tyr Pro Ser Leu Pro Lys Pro Leu
            180                 185                 190

Asn Arg Pro Gln Lys Ala Ile Ala Val Met Thr Ser Gly Gly Asp Ala
            195                 200                 205

Pro Gly Met Asn Ser Asn Val Arg Ala Ile Val Arg Ser Ala Ile Phe
210                 215                 220

Lys Gly Cys Arg Ala Phe Val Val Met Glu Gly Tyr Glu Gly Leu Val
225                 230                 235                 240

Arg Gly Gly Pro Glu Tyr Ile Lys Glu Phe His Trp Glu Asp Val Arg
            245                 250                 255

Gly Trp Ser Ala Glu Gly Gly Thr Asn Ile Gly Thr Ala Arg Cys Met
            260                 265                 270

Glu Phe Lys Lys Arg Glu Gly Arg Leu Leu Gly Ala Gln His Leu Ile
            275                 280                 285

Glu Ala Gly Val Asp Ala Leu Ile Val Cys Gly Gly Asp Gly Ser Leu
            290                 295                 300

Thr Gly Ala Asp Leu Phe Arg Ser Glu Trp Pro Ser Leu Ile Glu Glu
305                 310                 315                 320

Leu Leu Lys Thr Asn Arg Ile Ser Asn Glu Gln Tyr Glu Arg Met Lys
            325                 330                 335

His Leu Asn Ile Cys Gly Thr Val Gly Ser Ile Asp Asn Asp Met Ser
            340                 345                 350

Thr Thr Asp Ala Thr Ile Gly Ala Tyr Ser Ala Leu Asp Arg Ile Cys
            355                 360                 365

Lys Ala Ile Asp Tyr Val Glu Ala Thr Ala Asn Ser His Ser Arg Ala
            370                 375                 380

Phe Val Val Glu Val Met Gly Arg Asn Cys Gly Trp Leu Ala Leu Leu
385                 390                 395                 400

Ala Gly Ile Ala Thr Ser Ala Asp Tyr Ile Phe Ile Pro Glu Lys Pro
            405                 410                 415

Ala Thr Ser Ser Glu Trp Gln Asp Gln Met Cys Asp Ile Val Ser Lys
            420                 425                 430

His Arg Ser Arg Gly Lys Arg Thr Thr Ile Val Val Ala Glu Gly
            435                 440                 445

Ala Ile Ala Ala Asp Leu Thr Pro Ile Ser Pro Ser Asp Val His Lys
            450                 455                 460

Val Leu Val Asp Arg Leu Gly Leu Asp Thr Arg Ile Thr Thr Leu Gly
465                 470                 475                 480

His Val Gln Arg Gly Gly Thr Ala Val Ala Tyr Asp Arg Ile Leu Ala
            485                 490                 495

Thr Leu Gln Gly Leu Glu Ala Val Asn Ala Val Leu Glu Ser Thr Pro
            500                 505                 510

Asp Thr Pro Ser Pro Leu Ile Ala Val Asn Glu Asn Lys Ile Val Arg
            515                 520                 525
```

```
Lys Pro Leu Met Glu Ser Val Lys Leu Thr Lys Ala Val Ala Glu Ala
    530                 535                 540

Ile Gln Ala Lys Asp Phe Lys Arg Ala Met Ser Leu Arg Asp Thr Glu
545                 550                 555                 560

Phe Ile Glu His Leu Asn Asn Phe Met Ala Ile Asn Ser Ala Asp His
                565                 570                 575

Asn Glu Pro Lys Leu Pro Lys Asp Lys Arg Leu Lys Ile Ala Ile Val
                580                 585                 590

Asn Val Gly Ala Pro Ala Gly Gly Ile Asn Ser Ala Val Tyr Ser Met
            595                 600                 605

Ala Thr Tyr Cys Met Ser Gln Gly His Arg Pro Tyr Ala Ile Tyr Asn
        610                 615                 620

Gly Trp Ser Gly Leu Ala Arg His Glu Ser Val Arg Ser Leu Asn Trp
625                 630                 635                 640

Lys Asp Met Leu Gly Trp Gln Ser Arg Gly Gly Ser Glu Ile Gly Thr
                645                 650                 655

Asn Arg Val Thr Pro Glu Glu Ala Asp Leu Gly Met Ile Ala Tyr Tyr
                660                 665                 670

Phe Gln Lys Tyr Glu Phe Asp Gly Leu Ile Ile Val Gly Gly Phe Glu
            675                 680                 685

Ala Phe Glu Ser Leu His Gln Leu Glu Arg Ala Arg Glu Ser Tyr Pro
    690                 695                 700

Ala Phe Arg Ile Pro Met Val Leu Ile Pro Ala Thr Leu Ser Asn Asn
705                 710                 715                 720

Val Pro Gly Thr Glu Tyr Ser Leu Gly Ser Asp Thr Ala Leu Asn Ala
                725                 730                 735

Leu Met Glu Tyr Cys Asp Val Val Lys Gln Ser Ala Ser Ser Thr Arg
                740                 745                 750

Gly Arg Ala Phe Val Val Asp Cys Gln Gly Gly Asn Ser Gly Tyr Leu
            755                 760                 765

Ala Thr Tyr Ala Ser Leu Ala Val Gly Ala Gln Val Ser Tyr Val Pro
    770                 775                 780

Glu Glu Gly Ile Ser Leu Glu Gln Leu Ser Glu Asp Ile Glu Tyr Leu
785                 790                 795                 800

Ala Gln Ser Phe Glu Lys Ala Glu Gly Arg Gly Arg Phe Gly Lys Leu
                805                 810                 815

Ile Leu Lys Ser Thr Asn Ala Ser Lys Ala Leu Ser Ala Thr Lys Leu
                820                 825                 830

Ala Glu Val Ile Thr Ala Glu Ala Asp Gly Arg Phe Asp Ala Lys Pro
            835                 840                 845

Ala Tyr Pro Gly His Val Gln Gln Gly Gly Leu Pro Ser Pro Ile Asp
    850                 855                 860

Arg Thr Arg Ala Thr Arg Met Ala Ile Lys Ala Val Gly Phe Ile Lys
865                 870                 875                 880

Asp Asn Gln Ala Ala Ile Ala Glu Ala Arg Ala Ala Glu Glu Asn Phe
                885                 890                 895

Asn Ala Asp Asp Lys Thr Ile Ser Asp Thr Ala Ala Val Val Gly Val
                900                 905                 910

Lys Gly Ser His Val Val Tyr Asn Ser Ile Arg Gln Leu Tyr Asp Tyr
            915                 920                 925

Glu Thr Glu Val Ser Met Arg Met Pro Lys Val Ile His Trp Gln Ala
    930                 935                 940
```

```
Thr Arg Leu Ile Ala Asp His Leu Val Gly Arg Lys Arg Val Asp
945                 950                 955
```

<210> SEQ ID NO 163
<211> LENGTH: 563
<212> TYPE: PRT
<213> ORGANISM: Saccharomyces cerevisiae

<400> SEQUENCE: 163

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr
        130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365
```

-continued

```
Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 164
<211> LENGTH: 563
<212> TYPE: PRT
<213> ORGANISM: Saccharomyces cerevisiae

<400> SEQUENCE: 164

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
                20                  25                  30

Leu Leu Asp Lys Leu Tyr Glu Val Lys Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175
```

```
Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
        195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
            370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln

<210> SEQ ID NO 165
<211> LENGTH: 563
<212> TYPE: PRT
```

<213> ORGANISM: Saccharomyces cerevisiae

<400> SEQUENCE: 165

```
Met Ser Glu Ile Thr Leu Gly Lys Tyr Leu Phe Glu Arg Leu Lys Gln
1               5                   10                  15
Val Asn Val Asn Thr Ile Phe Gly Leu Pro Gly Asp Phe Asn Leu Ser
            20                  25                  30
Leu Leu Asp Lys Ile Tyr Glu Val Asp Gly Leu Arg Trp Ala Gly Asn
        35                  40                  45
Ala Asn Glu Leu Asn Ala Ala Tyr Ala Ala Asp Gly Tyr Ala Arg Ile
    50                  55                  60
Lys Gly Leu Ser Val Leu Val Thr Thr Phe Gly Val Gly Glu Leu Ser
65                  70                  75                  80
Ala Leu Asn Gly Ile Ala Gly Ser Tyr Ala Glu His Val Gly Val Leu
                85                  90                  95
His Val Val Gly Val Pro Ser Ile Ser Ala Gln Ala Lys Gln Leu Leu
            100                 105                 110
Leu His His Thr Leu Gly Asn Gly Asp Phe Thr Val Phe His Arg Met
        115                 120                 125
Ser Ala Asn Ile Ser Glu Thr Thr Ser Met Ile Thr Asp Ile Ala Thr
    130                 135                 140
Ala Pro Ser Glu Ile Asp Arg Leu Ile Arg Thr Thr Phe Ile Thr Gln
145                 150                 155                 160
Arg Pro Ser Tyr Leu Gly Leu Pro Ala Asn Leu Val Asp Leu Lys Val
                165                 170                 175
Pro Gly Ser Leu Leu Glu Lys Pro Ile Asp Leu Ser Leu Lys Pro Asn
            180                 185                 190
Asp Pro Glu Ala Glu Lys Glu Val Ile Asp Thr Val Leu Glu Leu Ile
        195                 200                 205
Gln Asn Ser Lys Asn Pro Val Ile Leu Ser Asp Ala Cys Ala Ser Arg
    210                 215                 220
His Asn Val Lys Lys Glu Thr Gln Lys Leu Ile Asp Leu Thr Gln Phe
225                 230                 235                 240
Pro Ala Phe Val Thr Pro Leu Gly Lys Gly Ser Ile Asp Glu Gln His
                245                 250                 255
Pro Arg Tyr Gly Gly Val Tyr Val Gly Thr Leu Ser Lys Gln Asp Val
            260                 265                 270
Lys Gln Ala Val Glu Ser Ala Asp Leu Ile Leu Ser Val Gly Ala Leu
        275                 280                 285
Leu Ser Asp Phe Asn Thr Gly Ser Phe Ser Tyr Ser Tyr Lys Thr Lys
    290                 295                 300
Asn Val Val Glu Phe His Ser Asp Tyr Val Lys Val Lys Asn Ala Thr
305                 310                 315                 320
Phe Leu Gly Val Gln Met Lys Phe Ala Leu Gln Asn Leu Leu Lys Val
                325                 330                 335
Ile Pro Asp Val Val Lys Gly Tyr Lys Ser Val Pro Val Pro Thr Lys
            340                 345                 350
Thr Pro Ala Asn Lys Gly Val Pro Ala Ser Thr Pro Leu Lys Gln Glu
        355                 360                 365
Trp Leu Trp Asn Glu Leu Ser Lys Phe Leu Gln Glu Gly Asp Val Ile
    370                 375                 380
Ile Ser Glu Thr Gly Thr Ser Ala Phe Gly Ile Asn Gln Thr Ile Phe
385                 390                 395                 400
```

```
Pro Lys Asp Ala Tyr Gly Ile Ser Gln Val Leu Trp Gly Ser Ile Gly
                    405                 410                 415
Phe Thr Thr Gly Ala Thr Leu Gly Ala Ala Phe Ala Ala Glu Glu Ile
            420                 425                 430
Asp Pro Asn Lys Arg Val Ile Leu Phe Ile Gly Asp Gly Ser Leu Gln
        435                 440                 445
Leu Thr Val Gln Glu Ile Ser Thr Met Ile Arg Trp Gly Leu Lys Pro
450                 455                 460
Tyr Leu Phe Val Leu Asn Asn Asp Gly Tyr Thr Ile Glu Lys Leu Ile
465                 470                 475                 480
His Gly Pro His Ala Glu Tyr Asn Glu Ile Gln Thr Trp Asp His Leu
                485                 490                 495
Ala Leu Leu Pro Ala Phe Gly Ala Lys Lys Tyr Glu Asn His Lys Ile
            500                 505                 510
Ala Thr Thr Gly Glu Trp Asp Ala Leu Thr Thr Asp Ser Glu Phe Gln
        515                 520                 525
Lys Asn Ser Val Ile Arg Leu Ile Glu Leu Lys Leu Pro Val Phe Asp
530                 535                 540
Ala Pro Glu Ser Leu Ile Lys Gln Ala Gln Leu Thr Ala Ala Thr Asn
545                 550                 555                 560
Ala Lys Gln

<210> SEQ ID NO 166
<211> LENGTH: 440
<212> TYPE: PRT
<213> ORGANISM: Saccharomyces cerevisiae

<400> SEQUENCE: 166

Met Leu Ala Val Arg Arg Leu Thr Arg Tyr Thr Phe Leu Lys Arg Thr
1               5                   10                  15
His Pro Val Leu Tyr Thr Arg Arg Ala Tyr Lys Ile Leu Pro Ser Arg
            20                  25                  30
Ser Thr Phe Leu Arg Arg Ser Leu Leu Gln Thr Gln Leu His Ser Lys
        35                  40                  45
Met Thr Ala His Thr Asn Ile Lys Gln His Lys His Cys His Glu Asp
    50                  55                  60
His Pro Ile Arg Arg Ser Asp Ser Ala Val Ser Ile Val His Leu Lys
65                  70                  75                  80
Arg Ala Pro Phe Lys Val Thr Val Ile Gly Ser Gly Asn Trp Gly Thr
                85                  90                  95
Thr Ile Ala Lys Val Ile Ala Glu Asn Thr Glu Leu His Ser His Ile
            100                 105                 110
Phe Glu Pro Glu Val Arg Met Trp Val Phe Asp Glu Lys Ile Gly Asp
        115                 120                 125
Glu Asn Leu Thr Asp Ile Ile Asn Thr Arg His Gln Asn Val Lys Tyr
    130                 135                 140
Leu Pro Asn Ile Asp Leu Pro His Asn Leu Val Ala Asp Pro Asp Leu
145                 150                 155                 160
Leu His Ser Ile Lys Gly Ala Asp Ile Leu Val Phe Asn Ile Pro His
                165                 170                 175
Gln Phe Leu Pro Asn Ile Val Lys Gln Leu Gln Gly His Val Ala Pro
            180                 185                 190
His Val Arg Ala Ile Ser Cys Leu Lys Gly Phe Glu Leu Gly Ser Lys
        195                 200                 205
```

Gly Val Gln Leu Leu Ser Ser Tyr Val Thr Asp Glu Leu Gly Ile Gln
            210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
            275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
                340                 345                 350

Thr Thr Cys Ser Gly Gly Arg Asn Val Lys Val Ala Thr Tyr Met Ala
            355                 360                 365

Lys Thr Gly Lys Ser Ala Leu Glu Ala Glu Lys Glu Leu Leu Asn Gly
            370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
            435                 440

<210> SEQ ID NO 167
<211> LENGTH: 250
<212> TYPE: PRT
<213> ORGANISM: Saccharomyces cerevisiae

<400> SEQUENCE: 167

Met Pro Leu Thr Thr Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

```
Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
            210             215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250
```